(12) United States Patent
Song et al.

(10) Patent No.: US 8,034,994 B2
(45) Date of Patent: Oct. 11, 2011

(54) STARCHY-ENDOSPERM AND/OR GERMINATING EMBRYO-SPECIFIC EXPRESSION IN MONO-COTYLEDONOUS PLANTS

(75) Inventors: Hee-Sook Song, Raleigh, NC (US); Christina E. Roche, Youngsville, NC (US); Christian Dammann, Durham, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 957 days.

(21) Appl. No.: 11/918,553

(22) PCT Filed: Apr. 13, 2006

(86) PCT No.: PCT/EP2006/061585
§ 371 (c)(1), (2), (4) Date: Oct. 15, 2007

(87) PCT Pub. No.: WO2006/133983
PCT Pub. Date: Dec. 21, 2006

(65) Prior Publication Data
US 2009/0113572 A1 Apr. 30, 2009

Related U.S. Application Data

(60) Provisional application No. 60/672,977, filed on Apr. 19, 2005.

(51) Int. Cl.
*A01H 5/00* (2006.01)
*C12N 15/09* (2006.01)
*C12N 15/82* (2006.01)

(52) U.S. Cl. ............ 800/287; 800/278; 800/320.1; 800/298; 800/279; 435/468; 435/419

(58) Field of Classification Search .................. None
See application file for complete search history.

(56) References Cited

U.S. PATENT DOCUMENTS

| | | | |
|---|---|---|---|
| 4,885,357 A | 12/1989 | Larkins et al. |
| 4,886,878 A | 12/1989 | Larkins et al. |
| 5,003,045 A | 3/1991 | Hoffman |
| 5,057,419 A | 10/1991 | Martin et al. |
| 5,093,249 A | 3/1992 | Nakajima et al. |
| 5,147,792 A | 9/1992 | Perchorowicz et al. |
| 5,214,912 A | 6/1993 | Farrauto et al. |
| 5,229,114 A | 7/1993 | Cregan et al. |
| 5,231,020 A | 7/1993 | Jorgensen et al. |
| 5,258,300 A | 11/1993 | Glassman et al. |
| 5,270,200 A | 12/1993 | Sun et al. |
| 5,283,184 A | 2/1994 | Jorgensen et al. |
| 5,298,421 A | 3/1994 | Davies et al. |
| 5,304,481 A | 4/1994 | Davies et al. |
| 5,344,771 A | 9/1994 | Davies et al. |
| 5,367,110 A | 11/1994 | Galili et al. |
| 5,443,974 A | 8/1995 | Hitz et al. |
| 5,508,468 A | 4/1996 | Lundquist et al. |
| 5,512,466 A | 4/1996 | Klee et al. |
| 5,512,482 A | 4/1996 | Voelker et al. |
| 5,530,186 A | 6/1996 | Hitz et al. |
| 5,534,421 A | 7/1996 | Livshits et al. |
| 5,543,576 A | 8/1996 | van Ooijen et al. |
| 5,552,306 A | 9/1996 | Thomas et al. |
| 5,576,203 A | 11/1996 | Hoffman |
| 5,589,616 A | 12/1996 | Hoffman |
| 5,608,149 A | 3/1997 | Barry et al. |
| 5,614,393 A | 3/1997 | Thomas et al. |
| 5,633,436 A | 5/1997 | Wandelt |
| 5,639,790 A | 6/1997 | Voelker et al. |
| 5,641,876 A | 6/1997 | McElroy et al. |
| 5,654,402 A | 8/1997 | Cahoon et al. |
| 5,659,645 A | 8/1997 | Satake |
| 5,663,068 A | 9/1997 | Thomas et al. |
| 5,689,041 A | 11/1997 | Mariani et al. |
| 5,689,050 A | 11/1997 | Thomas et al. |
| 5,705,391 A | 1/1998 | Cahoon et al. |
| 5,750,876 A | 5/1998 | Barry et al. |
| 5,759,829 A | 6/1998 | Shewmaker et al. |
| 5,760,206 A | 6/1998 | Hitz et al. |
| 5,789,220 A | 8/1998 | Thomas et al. |
| 5,807,893 A | 9/1998 | Voelker et al. |
| 5,850,024 A | 12/1998 | Beach et al. |
| 5,856,157 A | 1/1999 | Craig et al. |
| 5,858,749 A | 1/1999 | Matthews et al. |
| 5,866,789 A | 2/1999 | Hildebrand et al. |
| 5,885,801 A | 3/1999 | Rao |
| 5,885,802 A | 3/1999 | Rao |
| 5,888,732 A | 3/1999 | Hartley et al. |

(Continued)

FOREIGN PATENT DOCUMENTS

WO WO-90/01869 A1 3/1990

(Continued)

OTHER PUBLICATIONS

Fourgoux-Nicol et al (1999), Plant Molecular Biology 40: 857-872.*
Atkinson, H. J., et al., "Prototype demonstration of transgenic resistance to the nematode *Radopholus similis* conferred on banana by a cystatin", Transgenic Research, 2004, vol. 13, pp. 135-142.
Gelvin, S. B., "III. Characterization of the expression of novel promoters in monocot plants" in Summaries of "1999 Annual Research Report", Revised Jul. 14, 1999.
Narasimhulu, S., et al., "Early transcription of Agrobacterium T-DNA genes in tobacco and maize", Plant Cell, 1996, vol. 8, pp. 873-886.
Ni, M., et al., "Strength and tissue specificity of chimeric promoters derived from the octopine and mannopine synthase genes", The Plant Journal, 1995, vol. 7, No. 4, pp. 661-676.
Kasuga, M., et al., "Improving plant drought, salt, and freezing tolerance by gene transfer of a single stress-inducible transcription factor", Nature Biotechnology, 1999, vol. 17, pp. 287-291.
Ow, D. W., et al., "Transient and stable expression of the firefly luciferase gene in plant cells and transgenic plants", Science, 1986, vol. 234, pp. 856-859.

(Continued)

*Primary Examiner* — Medina A Ibrahim
(74) *Attorney, Agent, or Firm* — Connolly Bove Lodge & Hutz, LLP

(57) ABSTRACT

The present invention relates to the field of agricultural biotechnology. Disclosed herein are expression constructs with expression specificity for the starchy endosperm and/or the germinating embryo, transgenic plants comprising such expression constructs, and methods of making and using such DNA constructs and transgenic plants.

15 Claims, 3 Drawing Sheets

U.S. PATENT DOCUMENTS

| | | | |
|---|---|---|---|
| 5,914,450 A | 6/1999 | Blechl et al. |
| 5,939,599 A | 8/1999 | Chui et al. |
| 5,942,660 A | 8/1999 | Gruys et al. |
| 5,945,585 A | 8/1999 | Hitz et al. |
| 5,952,544 A | 9/1999 | Browse et al. |
| 5,955,329 A | 9/1999 | Yuan et al. |
| 5,955,646 A | 9/1999 | Gelvin et al. |
| 5,955,650 A | 9/1999 | Hitz |
| 5,958,745 A | 9/1999 | Gruys et al. |
| 5,965,727 A | 10/1999 | Song et al. |
| 5,985,605 A | 11/1999 | Cheng et al. |
| 5,990,384 A | 11/1999 | Bagga et al. |
| 5,990,389 A | 11/1999 | Rao et al. |
| 5,998,700 A | 12/1999 | Lightfoot et al. |
| 5,998,701 A | 12/1999 | Kawchuk et al. |
| 6,011,199 A | 1/2000 | Speirs et al. |
| 6,040,160 A | 3/2000 | Kojima et al. |
| 6,051,754 A | 4/2000 | Knutzon |
| 6,072,103 A | 6/2000 | Wu et al. |
| 6,075,183 A | 6/2000 | Knutzon et al. |
| 6,080,560 A | 6/2000 | Russell et al. |
| 6,100,091 A | 8/2000 | Cahoon et al. |
| 6,107,051 A | 8/2000 | Job et al. |
| 6,110,891 A | 8/2000 | Pusztai et al. |
| 6,117,677 A | 9/2000 | Thompson et al. |
| 6,147,279 A | 11/2000 | Poulsen |
| 6,166,292 A | 12/2000 | Osumi et al. |
| 6,171,640 B1 | 1/2001 | Bringe |
| 6,172,106 B1 | 1/2001 | Forse et al. |
| 6,194,167 B1 | 2/2001 | Browse et al. |
| 6,194,636 B1 | 2/2001 | McElroy et al. |
| 6,207,879 B1 | 3/2001 | McElroy et al. |
| 6,232,122 B1 | 5/2001 | Poulsen |
| 6,232,526 B1 | 5/2001 | McElroy et al. |
| 6,277,608 B1 | 8/2001 | Hartley et al. |
| 6,359,196 B1 | 3/2002 | Lok et al. |
| 6,380,466 B1 | 4/2002 | Facciotti |
| 6,388,174 B1 | 5/2002 | Wakasa et al. |
| 6,426,446 B1 | 7/2002 | McElroy et al. |
| 6,429,357 B1 | 8/2002 | McElroy et al. |
| 6,433,252 B1 | 8/2002 | Kriz et al. |
| 6,437,217 B1 | 8/2002 | McElroy et al. |
| 6,444,876 B1 | 9/2002 | Lassner et al. |
| 6,476,295 B2 | 11/2002 | Barry et al. |
| 6,515,201 B2 | 2/2003 | Anderson et al. |
| 6,531,648 B1 | 3/2003 | Lanahan et al. |
| 6,537,750 B1 | 3/2003 | Shorrosh |
| 6,583,338 B2 | 6/2003 | McElroy et al. |
| 6,835,868 B1 | 12/2004 | Misra et al. |
| 6,858,717 B1* | 2/2005 | Ball .................... 536/23.2 |
| 7,297,847 B1 | 11/2007 | Ludevid et al. |
| 2002/0007051 A1 | 1/2002 | Cheo et al. |
| 2003/0028917 A1 | 2/2003 | Gruys et al. |
| 2003/0028923 A1 | 2/2003 | Lardizabal et al. |
| 2003/0115632 A1 | 6/2003 | Lardizabal et al. |
| 2004/0088754 A1 | 5/2004 | Cho et al. |
| 2004/0154051 A1* | 8/2004 | Cade et al. .................... 800/279 |
| 2004/0163144 A1 | 8/2004 | Kriz et al. |
| 2005/0172365 A1 | 8/2005 | Puchta et al. |
| 2006/0218658 A1 | 9/2006 | Kock et al. |

FOREIGN PATENT DOCUMENTS

| | | |
|---|---|---|
| WO | WO-91/13993 A1 | 9/1991 |
| WO | WO-92/14822 A1 | 9/1992 |
| WO | WO-93/08682 A1 | 5/1993 |
| WO | WO-94/20628 A2 | 9/1994 |
| WO | WO-95/14098 A1 | 5/1995 |
| WO | WO-96/17064 A1 | 6/1996 |
| WO | WO-97/22703 A2 | 6/1997 |
| WO | WO-97/26366 A1 | 7/1997 |
| WO | WO-97/28247 | 8/1997 |
| WO | WO-97/35023 A2 | 9/1997 |
| WO | WO-98/26064 A2 | 6/1998 |
| WO | WO-98/55601 A2 | 12/1998 |
| WO | WO-99/02656 A1 | 1/1999 |
| WO | WO-99/06581 A1 | 2/1999 |
| WO | WO-99/11800 | 3/1999 |
| WO | WO-99/40209 A1 | 8/1999 |
| WO | WO-99/49058 A2 | 9/1999 |
| WO | WO-00/10380 A1 | 3/2000 |
| WO | WO-00/19839 A2 | 4/2000 |
| WO | WO-00/32757 A2 | 6/2000 |
| WO | WO-01/77161 A2 | 10/2001 |
| WO | WO-02/57471 A2 | 7/2002 |
| WO | WO-02/81711 | 10/2002 |
| WO | WO-03/004659 | 1/2003 |
| WO | WO-2004/013333 | 2/2004 |
| WO | WO-2005/028656 A2 | 3/2005 |

OTHER PUBLICATIONS

Gleave, A. P., et al., "Selectable marker-free transgenic plants without sexual crossing: transient expression of *cre*recombinase and use of a conditional lethal dominant gene", Plant Mol. Biol., 1999, vol. 40, pp. 223-235.

Dale, E. C., et al., "Gene transfer with subsequent removal of the selection gene from the host genome", Proc. Natl. Acad. Sci. USA, 1991, vol. 88, pp. 10558-10562.

Russell, S. H., et al., "Directed excision of a transgene from the plant genome", Mol. Genet. Genet., 1992, vol. 234, pp. 49-59.

Osborne, B. I., et al., "A system for insertional mutagenesis and chromosomal rearrangement using the Ds transposon and Cre-*lox*", The Plant Journal, 1995, vol. 7, No. 4, pp. 687-701.

Kilby, N. J., et al., "FLP recombinase in transgenic plants: constitutive activity in stably transformed tobacco and generation of marked cell clones in *Arabidopsis*", The Plant Journal, 1995, vol. 8, No. 5, pp. 637-652.

Lyznik, L. A., et al., "FLP-mediated recombination of *FRT*sites in the maize genome", Nucleic Acids Res., 1996, vol. 24, No. 19, pp. 3784-3789.

Onouchi, H., et al., "Visualization of site-specific recombination catalyzed by a recombinase from *Zygosaccharomyces rouxii* in *Arabidopsis thaliana*", Mol. Gen. Genet., 1995, vol. 247, pp. 653-660.

Sugita, K., et al., "A transformation vector for the production of marker-free transgenic plants containing a single copy transgene at high frequency", The Plant Journal, 2000, vol. 22, No. 5, pp. 461-469.

Zubko, E., et al., "Intrachromosomal recombination between attP regions as a tool to remove selectable marker genes from tobacco transgenes", Nature Biotechnology, 2000, vol. 18, pp. 442-445.

Colot, V., et al., "Localization of sequences in wheat endosperm protein genes which confer tissue-specific expression in tobacco", The EMBO Journal, 1987, vol. 6, No. 12, pp. 3559-3564.

Kridi, J. C., et al., "Isolation and characterization of an expressed napin gene from *Brassica raga*", Seed Science Research, 1991, vol. 1, pp. 209-219.

DiRita, V. J., et al., "Deletion analysis of the mannopine synthase gene promoter in sunflower crown gall tumors and *Agrobacterium tumefaciens*", Mol. Gen. Genet., 1987, vol. 207, pp. 233-241.

Harpster, M. H., et al., "Relative strengths of the 35S califlower mosaic virus, 1',2', and nopaline synthase promoters in transformed tobacco sugarbeet and oilseed rape callus tissue", Mol. Gen. Genet., 1988, vol. 212, pp. 182-190.

Sanger, M., et al., "Characteristics of a strong promoter from figwort mosaic virus: comparison with the analogous 35S promoter from cauliflower mosaic virus and the regulated mannpoine synthase promoter", Plant Molecular Biology, 1990, vol. 14, pp. 433-443.

Kononowicz, H., et al., "Subdomains of the octopine synthase upstream activating element direct cell-specific expression in transgenic tobacco plants", Plant Cell, 1992, vol. 4, pp. 17-27.

Langridge, W. H. R., at al., "Dual promoter of *Agrobacterium tumefaciens*mannopine synthase genes is regulated by plant growth hormones", Proc. Natl. Acad. Sci. USA, 1989, vol. 86, pp. 3219-3223.

Teeri, T. H., et al., "Gene fusions to *lacZ*reveal new expression patterns of chimeric genes in transgenic plants", The EMBO Journal, 1989, vol. 8, No. 2, pp. 343-350.

Saito, K., et al., "Tissue-specific and stress-enhancing expression of the TR promoter for mannopine synthase in transgenic medicinal plants", Planta, 1991, vol. 184, pp. 40-46.

Guevara-Garciá, A., et al., "Tissue-specific and wound-inducible pattern of expression of the mannopine synthase promoter is determined by the interaction between positive and negative *cis*-regulatory elements", The Plant Journal, 1993, vol. 4, No. 3, pp. 495-505.

Kononov, M. E., et al., "A comparative study of the activity of the *super-promoter* with other promoters in maize", presented in the 19th Annual Crown-Gall Meeting, 1998, Purdue University, West Lafayette, Indiana.

Ellis, J. G., et al., "*Agrobacterium tumefaciens*$T_R$-DNA encodes a pathway for agropine biosynthesis", Mol. Gen. Genet., 1984, vol. 195, pp. 466-473.

Komro, C. T., et al., "Site-specific mutagenesis in the TR-DNA region of octopine-type Ti plasmids", Plant Mol. Biol., 1985, vol. 4, pp. 253-263.

Fox, P. C., et al., "Multiple *ocs*-like elements required for efficient transcription of the mannopine synthase gene of T-DNA in maize protoplasts", Plant Mol. Biol., 1992, vol. 20, pp. 219-233.

Leung, J., et al., "Functional analysis of *cis*-elements, auxin response and early developmental profiles of the mannopine synthase bidirectional promoter", Mol. Gen. Genet., 1991, vol. 230, pp. 463-474.

Jenes, B., et al., "Techniques for gene transfer", Transgenic Plants, 1993, vol. 1, pp. 125-146.

Ellis, J. G., et al., "The *ocs* element: a 16 base pair palindrome essential for activity of the octopine synthase enhancer", The EMBO Journal, 1987, vol. 6, No. 11, pp. 3203-3208.

Leisner, S. M., et al., "Structure of the octopine synthase upstream activator sequence", Proc. Natl. Acad. Sci. USA, 1988, vol. 85, pp. 2553-2557.

Leisner, S. M., et al., "Multiple domains exist within the upstream activator sequence of the octopine synthase gene", The Plant Cell, 1989, vol. 1, pp. 925-936.

Callis, J., et al., "Introns increase gene expression in cultured maize cells", Genes & Development, 1987, vol. 1, pp. 1183-1200.

Vasil, M. L., et al., "Regulation of exotoxin a synthesis in *Pseudomonas aeruginosa*: characterization of *toxA-lacZ* fusions in wild-type and mutant strains", Mol. Microbiol., 1989, vol. 3, No. 3, pp. 371-381.

Mette, M. F., et al., "Production of aberrant promoter transcripts contributes to methylation and silencing of unlinked homologous promoters in *trans*", The EMBO Journal, 1999, vol. 18, No. 1, pp. 241-248.

Mette, M. F., et al., "Transcriptional silencing and promoter methylation triggered by double-stranded RNA", The EMBO Journal, 2000, vol. 19, No. 19, pp. 5194-5201.

Keegstra, K., "Transport and routing of proteins into chloroplasts", Cell, 1989, vol. 56, pp. 247-253.

Nawrath, C., et al., "Targeting of the polyhydroxybutyrate biosynthetic pathway to the plastids of *Arabidopsis thaliana* results in high levels of polymer accumulation", Proc. Natl. Acad. Sci. USA, 1994, vol. 91, pp. 12760-12764.

Xia, T., et al., "A monofunctional prephenate dehydrogenase created by cleavage of the 5' 109 bp of the *tyrA* gene from *Erwinia herbicola*", J. of General Microbiol., 1992, vol. 138, pp. 1309-1316.

Lois, L. M., et al., "Cloning and characterization of a gene from *Escherichia coli* encoding a transketolase-like enzyme that catalyzes the synthesis of $_D$-1-deoxyxylulose 5-phosphate, a common precursor for isoprenoid, thiamin, and pyridoxol biosynthesis", Proc. Natl. Acad. Sci. USA, 1992, vol. 95, pp. 2105-2110.

Takahashi, S., et al., "A 1-deoxy-$_D$-xylulose 5 phosphate reductoisomerase catalyzing the formation of 2-C-methyl-D-erythritol 4-phosphate in an alternative nonmevalonate pathway for teraenoid biosynthesis", Proc. Natl. Acad. Sci. USA, 1998, vol. 95, pp. 9879-9884.

Norris, S. R., et al., "Complementation of the Arabidopis *pds1* mutation with the gene encoding *p*-hydroxyphenylpyruvate dioxygenase", Plant Physiology, 1998, vol. 117, pp. 1317-1323.

Scolnik, P. A., et al., "Nucleotide sequence of an *Arabidopsis* cDNA for geranylgeranyl pyrophosphate synthase", Plant Physiol., 1994, vol. 104, pp. 1469-1470.

Smith, F. W., et al., "The cloning of two *Arabidopsis* genes belonging to a phosphate transporter family", The Plant Journal, 1997, vol. 11, No. 1, pp. 83-92.

Saint-Guily, A., et al., "Complementary DNA sequence of an adenylate translocator from *Arabidopsis thaliana*", Plant Physiol., 1992, vol. 100, pp. 1069-1071.

Sato, S., et al., "Structural analysis of *Arabidopsis thaliana* chromosome 5. X. Sequence features of the regions of 3,076,755 bp covered by sixty P1 and TAC clones", DNA Research, 2000, vol. 7, pp. 31-63.

Girke, T., et al, "Identification of a novel Δ6-acyl-group desaturase by targeted gene disruption in *Physcomitrella patens*", The Plant Journal, 1998, vol. 15, No. 1, pp. 39-48.

Sakuradani, E., et al., "Δ6-Fatty acid desaturase from an arachidonic acid-producing *Mortierella* fungus—Gene cloning and its heterologous expression in fungus, *Aspergillus*", Gene, 1999, vol. 238, pp. 445-453.

Michaelson, L. V., et al., "Functional identification of a fatty acid Δ$^6$ desaturase gene from *Caenorhabditis elegans*", FEBS Letters, 1998, vol. 439, pp. 215-218.

Beaudoin, F., et al., "Heterologous reconstitution in yeast of the polyunsaturated fatty acid biosynthetic pathway", PNAS, 2000, vol. 97, No. 12, pp. 6421-6426.

Zank, T. K., et al., "Cloning and functional expression of the first plant fatty acid elongase specific for Δ$^6$-polyunsaturdated fatty acids", Biochemical Society Transactions, 2000, vol. 28, pp. 654-658.

Hood, E. E., et al., "Plant-based production of xenogenic proteins", Current Opinion in Biotechnology, 1999, vol. 10, pp. 382-386.

Ma, J. K.-C., et al., "Plant expression systems for the production of vaccines", Curr. Topics Microbiol. Immunol., 1999, vol. 236, pp. 275-292.

Hood, E. E., et al., "Molecular farming of industrial proteins from transgenic maize", Adv. Exp. Med. Biol., 1999, vol. 464, pp. 127-147.

Dunwell, J. M., "Transgenic approaches to crop improvement", Journal of Experimental Botany, 2000, vol. 51, pp. 487-496.

"Phytase gene locus of plasmids pAF 2-3, pAF 2-6, pAF 2-7", The EMBL Database, Accession No. A19451, Jun. 10, 1994.

"N. pseudonarcissus mRNA for phytoene desaturase", The EMBL Database, Accession No. X78815, Apr. 18, 1995.

"Bertholletia exceisa gene for 2S albumin, complete cds.", The EMBL Database, Accession No. AB044391, Jun. 10, 2000.

"Physcomitrella patens mRNA for delta6-acyl-lipid desaturase", The EMBL Database, Accession No. AJ222980, Oct. 23, 1998.

"*Caenorhabditis elegans* delta 5 fatty acid desaturase (des-5) mRNA, complete cds.", The EMBL Database, Accession No. AF078796, Dec. 14, 1998.

\* cited by examiner

SEQUENCE LISTING

```
<160> NUMBER OF SEQ ID NOS: 160

<210> SEQ ID NO 1
<211> LENGTH: 219
<212> TYPE: DNA
<213> ORGANISM: Agrobacterium tumefaciens
<220> FEATURE:
<221> NAME/KEY: misc_feature
<222> LOCATION: (1)..(219)
<223> OTHER INFORMATION: upstream activating sequence derived from an
      octopine synthase gene of Agrobacterium tumefaciens

<400> SEQUENCE: 1
ggatccctga aagcgacgtt ggatgttaac atctacaaat tgccttttct tatcgaccat      60
gtacgtaagc gcttacgttt ttggtggacc cttgaggaaa ctggtagctg ttgtgggcct     120
gtggtctcaa gatggatcat taatttccac cttcacctac gatgggggc atcgcaccgg      180 tgagtaatat tgtacggcta agagcgaatt tggcctgta                            219

<210> SEQ ID NO 2
<211> LENGTH: 387
```

```
<212> TYPE: DNA
<213> ORGANISM: Agrobacterium tumefaciens
<220> FEATURE:
<221> NAME/KEY: promoter
<222> LOCATION: (1)..(387)
<223> OTHER INFORMATION: transcription regulating nucleotide sequence
      derived from the promoter of an Agrobacterium tumefaciens
      mannopine synthase gene

<400> SEQUENCE: 2
gagatttttc aaatcagtgc gcaagacgtg acgtaagtat ccgagtcagt ttttattttt     60
ctactaattt ggtcgtttat ttcggcgtgt aggacatggc aaccgggcct gaatttcgcg    120
ggtattctgt ttctattcca acttttcttt gatccgcagc cattaacgac ttttgaatag    180
atacgctgac acgccaagcc tcgctagtca aaagtgtacc aaacaacgct ttacagcaag    240
aacggaatgc gcgtgacgct cgcggtgacg ccatttcgcc ttttcagaaa tggataaata    300
gccttgcttc ctattatatc ttcccaaatt accaatacat tacactagca tctgaatttc    360
ataaccaatc tcgatacacc aaatcga                                         387

<210> SEQ ID NO 3
<211> LENGTH: 455
<212> TYPE: DNA
<213> ORGANISM: Artificial sequence
<220> FEATURE:
<223> OTHER INFORMATION: artificial construct comprising transcription
      regulating nucleotide sequence derived from the promoter of an
      Agrobacterium tumefaciens mannopine synthase gene
<220> FEATURE:
<221> NAME/KEY: misc_feature
<222> LOCATION: (1)..(18)
<223> OTHER INFORMATION: stuffer comprising BamH1 site
<220> FEATURE:
<221> NAME/KEY: misc_feature
<222> LOCATION: (19)..(68)
<223> OTHER INFORMATION: stuffer (part of mannopine synthase cDNA)
<220> FEATURE:
<221> NAME/KEY: promoter
<222> LOCATION: (69)..(455)
<223> OTHER INFORMATION: transcription regulating nucleotide sequence
      derived from the promoter of an Agrobacterium tumefaciens
      mannopine synthase gene

<400> SEQUENCE: 3
ggatccgcga gctggtcaat cccattgctt ttgaagcagc tcaacattga tctctttctc     60
gatcgaggga gatttttcaa atcagtgcgc aagacgtgac gtaagtatcc gagtcagttt    120
ttatttttct actaatttgg tcgtttattt cggcgtgtag gacatggcaa ccgggcctga    180
atttcgcggg tattctgttt ctattccaac tttttcttga tccgcagcca ttaacgactt    240
ttgaatagat acgctgacac gccaagcctc gctagtcaaa agtgtaccaa acaacgcttt    300
acagcaagaa cggaatgcgc gtgacgctcg cggtgacgcc atttcgcctt ttcagaaatg    360
gataaatagc cttgcttcct attatatctt cccaaattac caatacatta cactagcatc    420
tgaatttcat aaccaatctc gatacaccaa atcga                                455

<210> SEQ ID NO 4
<211> LENGTH: 1112
<212> TYPE: DNA
<213> ORGANISM: Artificial sequence
<220> FEATURE:
<223> OTHER INFORMATION: super promoter (chimeric transcription
      regulating sequence comprising 3 upstream activating sequences
      from A. tumefaciens octopine synthase gene operably linked to a
      transcription regulating nucleotide sequence from A. tumefaciens
      mannopine
<220> FEATURE:
<221> NAME/KEY: misc_feature
```

```
<222> LOCATION: (1)..(219)
<223> OTHER INFORMATION: first upstream activating sequence derived from
      an octopine synthase gene of Agrobacterium tumefaciens
<220> FEATURE:
<221> NAME/KEY: misc_feature
<222> LOCATION: (220)..(438)
<223> OTHER INFORMATION: second upstream activating sequence derived
      from an octopine synthase gene of Agrobacterium tumefaciens
<220> FEATURE:
<221> NAME/KEY: misc_feature
<222> LOCATION: (439)..(657)
<223> OTHER INFORMATION: third upstream activating sequence derived from
      an octopine synthase gene of Agrobacterium tumefaciens
<220> FEATURE:
<221> NAME/KEY: misc_feature
<222> LOCATION: (658)..(675)
<223> OTHER INFORMATION: stuffer comrpising BamH1 site
<220> FEATURE:
<221> NAME/KEY: misc_feature
<222> LOCATION: (676)..(725)
<223> OTHER INFORMATION: stuffer comrpising part of mannopine synthase
      cDNA
<220> FEATURE:
<221> NAME/KEY: promoter
<222> LOCATION: (726)..(1112)
<223> OTHER INFORMATION: transcription regulating nucleotide sequence
      derived from the promoter of an Agrobacterium tumefaciens
      mannopine synthase gene

<400> SEQUENCE: 4
ggatccctga aagcgacgtt ggatgttaac atctacaaat tgcctttct tatcgaccat      60 gtacgtaagc gcttacgttt ttggtggacc cttgaggaaa ctggtagctg ttgtgggcct    120
gtggtctcaa gatggatcat taatttccac cttcacctac gatggggggc atcgcaccgg    180
tgagtaatat tgtacggcta agagcgaatt tggcctgtag gatccctgaa agcgacgttg    240
gatgttaaca tctacaaatt gcctttctt atcgaccatg tacgtaagcg cttacgtttt    300
tggtggaccc ttgaggaaac tggtagctgt tgtgggcctg tggtctcaag atggatcatt    360
aatttccacc ttcacctacg atgggggca tcgcaccggt gagtaatatt gtacggctaa    420
gagcgaattt ggcctgtagg atccctgaaa gcgacgttgg atgttaacat ctacaaattg    480
ccttttctta tcgaccatgt acgtaagcgc ttacgttttt ggtggaccct tgaggaaact    540
ggtagctgtt gtgggcctgt ggtctcaaga tggatcatta atttccacct tcacctacga    600 tgggggcat cgcaccggtg agtaatattg tacggctaag agcgaatttg gcctgtagga    660
tccgcgagct ggtcaatccc attgcttttg aagcagctca acattgatct ctttctcgat    720
cgagggagat ttttcaaatc agtgcgcaag acgtgacgta agtatccgag tcagttttta    780
tttttctact aatttggtcg tttatttcgg cgtgtaggac atggcaaccg ggcctgaatt    840
tcgcgggtat tctgtttcta ttccaacttt ttcttgatcc gcagccatta acgacttttg    900
aatagatacg ctgacacgcc aagcctcgct agtcaaaagt gtaccaaaca acgctttaca    960
gcaagaacgg aatgcgcgtg acgctcgcgg tgacgccatt tcgccttttc agaaatggat   1020
aaatagcctt gcttcctatt atatcttccc aaattaccaa tacattacac tagcatctga   1080
atttcataac caatctcgat acaccaaatc ga                                 1112

<210> SEQ ID NO 5
<211> LENGTH: 916
<212> TYPE: DNA
<213> ORGANISM: Physcomitrella patens
<220> FEATURE:
<221> NAME/KEY: CDS
<222> LOCATION: (40)..(816)
<223> OTHER INFORMATION: coding for Physcomitrella patens 14-3-3 protein
      (gb AX281102)
```

<400> SEQUENCE: 5

```
atcccgggcg gactgtcgtg gacgatgtgc taggccaag atg agt acg gag aag       54
                                            Met Ser Thr Glu Lys
                                             1               5 gag cgc gag agc tat gtg tac atg gcc aag ctc gcc gag cag gcg gag      102
Glu Arg Glu Ser Tyr Val Tyr Met Ala Lys Leu Ala Glu Gln Ala Glu
            10                  15                  20 cgt tac gat gag atg gtg gaa tcg atg aag aag gtt gcc aag ctt gat      150
Arg Tyr Asp Glu Met Val Glu Ser Met Lys Lys Val Ala Lys Leu Asp
         25                  30                  35 gtg gag ctg aca gta gag gag cga aat ctc ttg tcc gtg ggt tat aag      198
Val Glu Leu Thr Val Glu Glu Arg Asn Leu Leu Ser Val Gly Tyr Lys
     40                  45                  50 aat gtc atc gga gcc cgg agg gcg tca tgg cgg atc atg tca tcc atc      246
Asn Val Ile Gly Ala Arg Arg Ala Ser Trp Arg Ile Met Ser Ser Ile
 55                  60                  65 gaa cag aag gag gag agc aaa ggt aac gaa cag aat gtt aaa cgc atc      294
Glu Gln Lys Glu Glu Ser Lys Gly Asn Glu Gln Asn Val Lys Arg Ile
 70                  75                  80                  85 aag gac tac aga cac aag gtg gag gag gag ctg tcg aag atc tgc aat      342
Lys Asp Tyr Arg His Lys Val Glu Glu Glu Leu Ser Lys Ile Cys Asn
                 90                  95                 100 gat atc ctg tct atc atc gac gga cac ctg att ccg tcg tcc agc acg      390
Asp Ile Leu Ser Ile Ile Asp Gly His Leu Ile Pro Ser Ser Ser Thr
            105                 110                 115 gga gag tcc act gtg ttc tac tat aaa atg aag gga gat tac tat cgg      438
Gly Glu Ser Thr Val Phe Tyr Tyr Lys Met Lys Gly Asp Tyr Tyr Arg
        120                 125                 130 tac ctg gcg gag ttc aag acc ggg aat gag agg aaa gag gcc gct gac      486
Tyr Leu Ala Glu Phe Lys Thr Gly Asn Glu Arg Lys Glu Ala Ala Asp
    135                 140                 145 caa tct ttg aag gca tac cag gct gca tcc agc act gca gtg acg gac      534
Gln Ser Leu Lys Ala Tyr Gln Ala Ala Ser Ser Thr Ala Val Thr Asp
150                 155                 160                 165 ctg gca ccg acg cat cct atc cga ctg gga tta gct ttg aac ttc tcg      582
Leu Ala Pro Thr His Pro Ile Arg Leu Gly Leu Ala Leu Asn Phe Ser
                170                 175                 180 gtc ttt tat tat gaa att ttg aac tct cct gag agg gca tgc cat ttg      630
Val Phe Tyr Tyr Glu Ile Leu Asn Ser Pro Glu Arg Ala Cys His Leu
            185                 190                 195 gcg aaa caa gca ttt gac gag gcg att gct gag ttg gat acg tta agt      678
Ala Lys Gln Ala Phe Asp Glu Ala Ile Ala Glu Leu Asp Thr Leu Ser
        200                 205                 210 gag gag tcg tac aag gac agc aca ttg atc atg cag cta ctt aga gat      726
Glu Glu Ser Tyr Lys Asp Ser Thr Leu Ile Met Gln Leu Leu Arg Asp
    215                 220                 225 aat ctg acc ctg tgg aca tct gac ctt cag gac gag gga ggt gac gac      774
Asn Leu Thr Leu Trp Thr Ser Asp Leu Gln Asp Glu Gly Gly Asp Asp
230                 235                 240                 245 cag gga aag gga gat gat atg agg ccc gag gag gct gag tga            816
Gln Gly Lys Gly Asp Asp Met Arg Pro Glu Glu Ala Glu
                250                 255 tgacgattag gtcttttatg tggagacgaa tttgcaaatc acttcactca attggtggtg    876
ggccggggca agaagatgtg cagttgcgtg ccgagctcgc                          916
```

<210> SEQ ID NO 6
<211> LENGTH: 258
<212> TYPE: PRT
<213> ORGANISM: Physcomitrella patens -continued

```
<400> SEQUENCE: 6

Met Ser Thr Glu Lys Glu Arg Glu Ser Tyr Val Tyr Met Ala Lys Leu
1               5                   10                  15

Ala Glu Gln Ala Glu Arg Tyr Asp Glu Met Val Glu Ser Met Lys Lys
            20                  25                  30

Val Ala Lys Leu Asp Val Glu Leu Thr Val Glu Glu Arg Asn Leu Leu
        35                  40                  45

Ser Val Gly Tyr Lys Asn Val Ile Gly Ala Arg Arg Ala Ser Trp Arg
    50                  55                  60

Ile Met Ser Ser Ile Glu Gln Lys Glu Glu Ser Lys Gly Asn Glu Gln
65                  70                  75                  80

Asn Val Lys Arg Ile Lys Asp Tyr Arg His Lys Val Glu Glu Glu Leu
                85                  90                  95

Ser Lys Ile Cys Asn Asp Ile Leu Ser Ile Ile Asp Gly His Leu Ile
            100                 105                 110

Pro Ser Ser Ser Thr Gly Glu Ser Thr Val Phe Tyr Tyr Lys Met Lys
        115                 120                 125

Gly Asp Tyr Tyr Arg Tyr Leu Ala Glu Phe Lys Thr Gly Asn Glu Arg
    130                 135                 140

Lys Glu Ala Ala Asp Gln Ser Leu Lys Ala Tyr Gln Ala Ala Ser Ser
145                 150                 155                 160

Thr Ala Val Thr Asp Leu Ala Pro Thr His Pro Ile Arg Leu Gly Leu
                165                 170                 175

Ala Leu Asn Phe Ser Val Phe Tyr Tyr Glu Ile Leu Asn Ser Pro Glu
            180                 185                 190

Arg Ala Cys His Leu Ala Lys Gln Ala Phe Asp Glu Ala Ile Ala Glu
        195                 200                 205

Leu Asp Thr Leu Ser Glu Glu Ser Tyr Lys Asp Ser Thr Leu Ile Met
    210                 215                 220

Gln Leu Leu Arg Asp Asn Leu Thr Leu Trp Thr Ser Asp Leu Gln Asp
225                 230                 235                 240

Glu Gly Gly Asp Asp Gln Gly Lys Gly Asp Asp Met Arg Pro Glu Glu
                245                 250                 255

Ala Glu

<210> SEQ ID NO 7
<211> LENGTH: 2139
<212> TYPE: DNA
<213> ORGANISM: Physcomitrella patens
<220> FEATURE:
<221> NAME/KEY: CDS
<222> LOCATION: (123)..(2009)
<223> OTHER INFORMATION: coding fro Physcomitrella patens
      phosphoinositide-specific phospholipase C (gb AX281101)

<400> SEQUENCE: 7
atcccgggct tcgggagttt aagaggatgt cacggcgtgg gaagacgagg cggtgatgca      60
ggtttgggtg gagcttaagg ttgacggagt gtaagggatc ggctcgtcac tgggtttgca     120 aa atg tgt tcc ata gca tgt tgt cga agt gga acc ccg aaa ggg gat        167
   Met Cys Ser Ile Ala Cys Cys Arg Ser Gly Thr Pro Lys Gly Asp
   1               5                   10                  15 ccg gag caa gac ctg gtg ggg gag gtg ttc aca ata tac agc gag aat       215
Pro Glu Gln Asp Leu Val Gly Glu Val Phe Thr Ile Tyr Ser Glu Asn
                20                  25                  30 gag agg atg agt gcg gag ggg ttg ctg aaa ttc ttg cat aca gag caa       263
Glu Arg Met Ser Ala Glu Gly Leu Leu Lys Phe Leu His Thr Glu Gln
        35                  40                  45
```

```
ggg gat gtc gac ttc acc ctt gat gac gcc aag cag atc atg gag cgc      311
Gly Asp Val Asp Phe Thr Leu Asp Asp Ala Lys Gln Ile Met Glu Arg
         50                  55                  60 att cgc aag gac tgg aag aaa tcc ttc gga ctc gcc tct atc aac tca      359
Ile Arg Lys Asp Trp Lys Lys Ser Phe Gly Leu Ala Ser Ile Asn Ser
 65                  70                  75 gac ttg tcg aag gag gct ttt cgg aag tac ttg atg aat ccc gac ttg      407
Asp Leu Ser Lys Glu Ala Phe Arg Lys Tyr Leu Met Asn Pro Asp Leu
 80                  85                  90                  95 aat ggc gtc tta cac aac gtt gtt cac caa gac atg acg cag ccg atg      455
Asn Gly Val Leu His Asn Val Val His Gln Asp Met Thr Gln Pro Met
                100                 105                 110 tcg cac tat ttc ata ttc acg ggc cat aac tcg tac ctg acc ggc aac      503
Ser His Tyr Phe Ile Phe Thr Gly His Asn Ser Tyr Leu Thr Gly Asn
            115                 120                 125 cag ctg agc agc gac agc agc gac aca ccc atc gct gcg gca ctg cgg      551
Gln Leu Ser Ser Asp Ser Ser Asp Thr Pro Ile Ala Ala Ala Leu Arg
        130                 135                 140 cgc ggc gtg cgg gtt gtg gaa ttg gac ttg tgg cct gat gac aaa ggc      599
Arg Gly Val Arg Val Val Glu Leu Asp Leu Trp Pro Asp Asp Lys Gly
145                 150                 155 ggc atg aag gtc aca cac gga aac aca ctt acc aat ccg gtg tcg ttc      647
Gly Met Lys Val Thr His Gly Asn Thr Leu Thr Asn Pro Val Ser Phe
160                 165                 170                 175 caa aag tgt gtc aca gcc atc aag aat aac gcc ttc ttc acc tcg gag      695
Gln Lys Cys Val Thr Ala Ile Lys Asn Asn Ala Phe Phe Thr Ser Glu
                180                 185                 190 tac cca gtt tgc gtt act att gag gat cat ctt aca agc gaa tta cag      743
Tyr Pro Val Cys Val Thr Ile Glu Asp His Leu Thr Ser Glu Leu Gln
            195                 200                 205 ggc cat gct gca gag att tta gag caa att ctc gga gac gcc ctg tat      791
Gly His Ala Ala Glu Ile Leu Glu Gln Ile Leu Gly Asp Ala Leu Tyr
        210                 215                 220 tat cca ccc aca act gat gca tta gtg gag ttt cct tca ccg gag tca      839
Tyr Pro Pro Thr Thr Asp Ala Leu Val Glu Phe Pro Ser Pro Glu Ser
225                 230                 235 ctg aag agg aag atc ata atc tcc acc aaa ccg ccg aag gag tat ctc      887
Leu Lys Arg Lys Ile Ile Ile Ser Thr Lys Pro Pro Lys Glu Tyr Leu
240                 245                 250                 255 gaa gca tgt tcc acg cag aaa ttg gcc atg gag aac agg aat ctg gtg      935
Glu Ala Cys Ser Thr Gln Lys Leu Ala Met Glu Asn Arg Asn Leu Val
                260                 265                 270 gag gag ctt gag aag gaa gac aaa ttg gag cag acc aca ttc gct ccc      983
Glu Glu Leu Glu Lys Glu Asp Lys Leu Glu Gln Thr Thr Phe Ala Pro
            275                 280                 285 ctt gaa gag aac cac atc ctg gga gaa aat aca cca tcg ctg cgt aag     1031
Leu Glu Glu Asn His Ile Leu Gly Glu Asn Thr Pro Ser Leu Arg Lys
        290                 295                 300 gaa gtc gag gtt tta agc caa aag gaa atg tca aca cca gct gag ctt     1079
Glu Val Glu Val Leu Ser Gln Lys Glu Met Ser Thr Pro Ala Glu Leu
305                 310                 315 aac tct aga agt ccc tct gac ctc ggg gaa gca aca tcc aca agg tat     1127
Asn Ser Arg Ser Pro Ser Asp Leu Gly Glu Ala Thr Ser Thr Arg Tyr
320                 325                 330                 335 agc aag agc aac gat ggc aat gac aac cct aaa cat ttc aag tat gcc     1175
Ser Lys Ser Asn Asp Gly Asn Asp Asn Pro Lys His Phe Lys Tyr Ala
                340                 345                 350 cgg ctc atc aca atc cgg cta gca aag cac gca aag ggg aca tcg atg     1223
Arg Leu Ile Thr Ile Arg Leu Ala Lys His Ala Lys Gly Thr Ser Met
            355                 360                 365
```

| | | | | | | | | | | | | | | | | |
|---|---|---|---|---|---|---|---|---|---|---|---|---|---|---|---|---|
| gag | cat | cga | ctg | caa | gtc | gat | gaa | tca | gtg | aaa | cgg | atc | agt | ctg | tcg | 1271 |
| Glu | His | Arg | Leu | Gln | Val | Asp | Glu | Ser | Val | Lys | Arg | Ile | Ser | Leu | Ser | |
| | | 370 | | | | | 375 | | | | | 380 | | | | |
| gaa | tcg | aag | ctg | gaa | aaa | gtg | gtg | gaa | aag | tgg | ccc | gaa | gct | ctg | gtc | 1319 |
| Glu | Ser | Lys | Leu | Glu | Lys | Val | Val | Glu | Lys | Trp | Pro | Glu | Ala | Leu | Val | |
| 385 | | | | | 390 | | | | | 395 | | | | | | |
| aaa | ttc | acg | cag | aag | aac | att | tta | cgt | gtg | tat | cct | gct | gct | aat | cgt | 1367 |
| Lys | Phe | Thr | Gln | Lys | Asn | Ile | Leu | Arg | Val | Tyr | Pro | Ala | Ala | Asn | Arg | |
| 400 | | | | | 405 | | | | | 410 | | | | | 415 | |
| gta | aac | tcc | tcc | aac | ttc | tgc | cct | act | ctg | gct | tgg | aac | tac | gga | gct | 1415 |
| Val | Asn | Ser | Ser | Asn | Phe | Cys | Pro | Thr | Leu | Ala | Trp | Asn | Tyr | Gly | Ala | |
| | | | | 420 | | | | | 425 | | | | | 430 | | |
| caa | atg | gtg | gct | caa | aac | atg | cag | ggc | tat | ggt | aaa | gag | ctt | tgg | cag | 1463 |
| Gln | Met | Val | Ala | Gln | Asn | Met | Gln | Gly | Tyr | Gly | Lys | Glu | Leu | Trp | Gln | |
| | | | 435 | | | | | 440 | | | | | 445 | | | |
| gca | ttt | ggc | aag | ttc | aag | gga | aat | ggg | gga | tgt | ggg | tat | gtt | ttg | aag | 1511 |
| Ala | Phe | Gly | Lys | Phe | Lys | Gly | Asn | Gly | Gly | Cys | Gly | Tyr | Val | Leu | Lys | |
| | | 450 | | | | | 455 | | | | | 460 | | | | |
| cca | cag | tat | ctg | ttg | gaa | aac | ttg | cct | tct | ggt | gtg | cct | ttc | aac | ccc | 1559 |
| Pro | Gln | Tyr | Leu | Leu | Glu | Asn | Leu | Pro | Ser | Gly | Val | Pro | Phe | Asn | Pro | |
| 465 | | | | | 470 | | | | | 475 | | | | | | |
| aca | tca | ccc | aga | aac | aca | acc | cta | att | ctc | aag | att | aaa | gtt | atg | act | 1607 |
| Thr | Ser | Pro | Arg | Asn | Thr | Thr | Leu | Ile | Leu | Lys | Ile | Lys | Val | Met | Thr | |
| 480 | | | | | 485 | | | | | 490 | | | | | 495 | |
| acc | ttg | gga | tgg | gac | aag | gcc | ttt | tcc | aaa | cgc | cat | ttt | gac | cta | ttc | 1655 |
| Thr | Leu | Gly | Trp | Asp | Lys | Ala | Phe | Ser | Lys | Arg | His | Phe | Asp | Leu | Phe | |
| | | | | 500 | | | | | 505 | | | | | 510 | | |
| tca | cct | cca | gat | ttc | ttc | act | agg | gtg | att | gtg | gtg | gga | gtg | cct | gct | 1703 |
| Ser | Pro | Pro | Asp | Phe | Phe | Thr | Arg | Val | Ile | Val | Val | Gly | Val | Pro | Ala | |
| | | | 515 | | | | | 520 | | | | | 525 | | | |
| gac | gag | gcc | aag | tgg | aag | aca | tct | gtg | gtg | gac | aat | tca | tgg | gca | ccc | 1751 |
| Asp | Glu | Ala | Lys | Trp | Lys | Thr | Ser | Val | Val | Asp | Asn | Ser | Trp | Ala | Pro | |
| | | | 530 | | | | | 535 | | | | | 540 | | | |
| cat | tgg | aat | gag | gac | cat | gag | ttt | gcc | cta | aaa | tgc | cct | gag | ctc | gca | 1799 |
| His | Trp | Asn | Glu | Asp | His | Glu | Phe | Ala | Leu | Lys | Cys | Pro | Glu | Leu | Ala | |
| | | 545 | | | | | 550 | | | | | 555 | | | | |
| cta | ctt | cgc | atc | gag | gtc | cga | gac | cat | gat | gat | gat | agc | aaa | gat | gag | 1847 |
| Leu | Leu | Arg | Ile | Glu | Val | Arg | Asp | His | Asp | Asp | Asp | Ser | Lys | Asp | Glu | |
| 560 | | | | | 565 | | | | | 570 | | | | | 575 | |
| ttt | gaa | ggg | cag | aca | tgc | ctt | ccc | atc | cat | gaa | gtc | cgg | gat | ggg | tat | 1895 |
| Phe | Glu | Gly | Gln | Thr | Cys | Leu | Pro | Ile | His | Glu | Val | Arg | Asp | Gly | Tyr | |
| | | | | 580 | | | | | 585 | | | | | 590 | | |
| cgg | tgc | atg | caa | atg | tac | gac | aag | aag | ggc | aat | gta | ctg | aaa | ggc | gtg | 1943 |
| Arg | Cys | Met | Gln | Met | Tyr | Asp | Lys | Lys | Gly | Asn | Val | Leu | Lys | Gly | Val | |
| | | | 595 | | | | | 600 | | | | | 605 | | | |
| ctg | atg | ttg | ttt | cat | ttt | caa | aag | tgc | aaa | tgc | acc | ttt | caa | gac | aca | 1991 |
| Leu | Met | Leu | Phe | His | Phe | Gln | Lys | Cys | Lys | Cys | Thr | Phe | Gln | Asp | Thr | |
| | | 610 | | | | | 615 | | | | | 620 | | | | |
| gct | cct | ata | tcc | tct | taa | actcaacccg | cccacacatg | gccccattat | | | | | | | | 2039 |
| Ala | Pro | Ile | Ser | Ser | | | | | | | | | | | | |
| | | 625 | | | | | | | | | | | | | | | caattactaa tgctgctttt tatgttgcca ttgtcatata attgttggtt tgtgggggg    2099 aagactgacc agtttagtgt gtgcacccaa ggttaacgcc                         2139

<210> SEQ ID NO 8
<211> LENGTH: 628
<212> TYPE: PRT
<213> ORGANISM: Physcomitrella patens

<400> SEQUENCE: 8

-continued

```
Met Cys Ser Ile Ala Cys Cys Arg Ser Gly Thr Pro Lys Gly Asp Pro
1               5                   10                  15

Glu Gln Asp Leu Val Gly Val Phe Thr Ile Tyr Ser Glu Asn Glu
            20                  25                  30

Arg Met Ser Ala Glu Gly Leu Leu Lys Phe Leu His Thr Glu Gln Gly
        35                  40                  45

Asp Val Asp Phe Thr Leu Asp Asp Ala Lys Gln Ile Met Glu Arg Ile
    50                  55                  60

Arg Lys Asp Trp Lys Lys Ser Phe Gly Leu Ala Ser Ile Asn Ser Asp
65                  70                  75                  80

Leu Ser Lys Glu Ala Phe Arg Lys Tyr Leu Met Asn Pro Asp Leu Asn
                85                  90                  95

Gly Val Leu His Asn Val Val His Gln Asp Met Thr Gln Pro Met Ser
            100                 105                 110

His Tyr Phe Ile Phe Thr Gly His Asn Ser Tyr Leu Thr Gly Asn Gln
        115                 120                 125

Leu Ser Ser Asp Ser Ser Asp Thr Pro Ile Ala Ala Leu Arg Arg
    130                 135                 140

Gly Val Arg Val Val Glu Leu Asp Leu Trp Pro Asp Asp Lys Gly Gly
145                 150                 155                 160

Met Lys Val Thr His Gly Asn Thr Leu Thr Asn Pro Val Ser Phe Gln
                165                 170                 175

Lys Cys Val Thr Ala Ile Lys Asn Asn Ala Phe Phe Thr Ser Glu Tyr
            180                 185                 190

Pro Val Cys Val Thr Ile Glu Asp His Leu Thr Ser Glu Leu Gln Gly
        195                 200                 205

His Ala Ala Glu Ile Leu Glu Gln Ile Leu Gly Asp Ala Leu Tyr Tyr
    210                 215                 220

Pro Pro Thr Thr Asp Ala Leu Val Glu Phe Pro Ser Pro Glu Ser Leu
225                 230                 235                 240

Lys Arg Lys Ile Ile Ile Ser Thr Lys Pro Pro Lys Glu Tyr Leu Glu
                245                 250                 255

Ala Cys Ser Thr Gln Lys Leu Ala Met Glu Asn Arg Asn Leu Val Glu
            260                 265                 270

Glu Leu Glu Lys Glu Asp Lys Leu Glu Gln Thr Thr Phe Ala Pro Leu
        275                 280                 285

Glu Glu Asn His Ile Leu Gly Glu Asn Thr Pro Ser Leu Arg Lys Glu
    290                 295                 300

Val Glu Val Leu Ser Gln Lys Glu Met Ser Thr Pro Ala Glu Leu Asn
305                 310                 315                 320

Ser Arg Ser Pro Ser Asp Leu Gly Glu Ala Thr Ser Thr Arg Tyr Ser
                325                 330                 335

Lys Ser Asn Asp Gly Asn Asp Asn Pro Lys His Phe Lys Tyr Ala Arg
            340                 345                 350

Leu Ile Thr Ile Arg Leu Ala Lys His Ala Lys Gly Thr Ser Met Glu
        355                 360                 365

His Arg Leu Gln Val Asp Glu Ser Val Lys Arg Ile Ser Leu Ser Glu
    370                 375                 380

Ser Lys Leu Glu Lys Val Val Glu Lys Trp Pro Glu Ala Leu Val Lys
385                 390                 395                 400

Phe Thr Gln Lys Asn Ile Leu Arg Val Tyr Pro Ala Ala Asn Arg Val
                405                 410                 415

Asn Ser Ser Asn Phe Cys Pro Thr Leu Ala Trp Asn Tyr Gly Ala Gln
```

```
                    420             425             430
Met Val Ala Gln Asn Met Gln Gly Tyr Gly Lys Glu Leu Trp Gln Ala
        435                 440                 445

Phe Gly Lys Phe Lys Gly Asn Gly Gly Cys Gly Tyr Val Leu Lys Pro
    450                 455                 460

Gln Tyr Leu Leu Glu Asn Leu Pro Ser Gly Val Pro Phe Asn Pro Thr
465                 470                 475                 480

Ser Pro Arg Asn Thr Thr Leu Ile Leu Lys Ile Lys Val Met Thr Thr
                485                 490                 495

Leu Gly Trp Asp Lys Ala Phe Ser Lys Arg His Phe Asp Leu Phe Ser
            500                 505                 510

Pro Pro Asp Phe Phe Thr Arg Val Ile Val Val Gly Val Pro Ala Asp
        515                 520                 525

Glu Ala Lys Trp Lys Thr Ser Val Val Asp Asn Ser Trp Ala Pro His
    530                 535                 540

Trp Asn Glu Asp His Glu Phe Ala Leu Lys Cys Pro Glu Leu Ala Leu
545                 550                 555                 560

Leu Arg Ile Glu Val Arg Asp His Asp Asp Ser Lys Asp Glu Phe
                565                 570                 575

Glu Gly Gln Thr Cys Leu Pro Ile His Glu Val Arg Asp Gly Tyr Arg
            580                 585                 590

Cys Met Gln Met Tyr Asp Lys Lys Gly Asn Val Leu Lys Gly Val Leu
        595                 600                 605

Met Leu Phe His Phe Gln Lys Cys Lys Cys Thr Phe Gln Asp Thr Ala
    610                 615                 620

Pro Ile Ser Ser
625

<210> SEQ ID NO 9
<211> LENGTH: 1554
<212> TYPE: DNA
<213> ORGANISM: Arabidopsis thaliana
<220> FEATURE:
<221> NAME/KEY: CDS
<222> LOCATION: (127)..(1371)
<223> OTHER INFORMATION: coding for Arabidopsis thaliana, putative
      tyrosine aminotransferase (At5g53970) gb BT000782

<400> SEQUENCE: 9
aaaatcaaaa ccttctcttc ttcttcttct tgcgagttgc accgaaacac tcaacaaaac      60
caaatcatcc aaattgggta aaacaaaaga aactaacaag aagaagatcg aattcaagaa     120 gaagag atg gag aat gga gca acg acg acg agc aca att acc atc aaa       168
       Met Glu Asn Gly Ala Thr Thr Thr Ser Thr Ile Thr Ile Lys
       1               5                   10 ggg att ctg agt ttg cta atg gaa agc atc aca aca gag gaa gat gaa       216
Gly Ile Leu Ser Leu Leu Met Glu Ser Ile Thr Thr Glu Glu Asp Glu
15              20                  25                  30 gga gga aag aga gta ata tct ctg gga atg gga gac cca aca ctc tac       264
Gly Gly Lys Arg Val Ile Ser Leu Gly Met Gly Asp Pro Thr Leu Tyr
                35                  40                  45 tcg tgt ttt cgt aca aca caa gtc tct ctt caa gct gtt tct gat tct       312
Ser Cys Phe Arg Thr Thr Gln Val Ser Leu Gln Ala Val Ser Asp Ser
            50                  55                  60 ctt ctc tcc aac aag ttc cat ggt tac tct cat acc gtc ggt ctt ccc       360
Leu Leu Ser Asn Lys Phe His Gly Tyr Ser His Thr Val Gly Leu Pro
        65                  70                  75 caa gct cga agg gca ata gca gag tat cta tcg cgt gat ctt cca tac       408
Gln Ala Arg Arg Ala Ile Ala Glu Tyr Leu Ser Arg Asp Leu Pro Tyr
```

```
                  80                  85                  90
aaa ctt tca cag gat gat gtg ttt atc aca tcg ggt tgc acg caa gcg    456
Lys Leu Ser Gln Asp Asp Val Phe Ile Thr Ser Gly Cys Thr Gln Ala
 95                 100                 105                 110 atc gat gta gca ttg tcg atg tta gct cgt ccc agg gct aat ata ctt    504
Ile Asp Val Ala Leu Ser Met Leu Ala Arg Pro Arg Ala Asn Ile Leu
                115                 120                 125 ctt cca agg cct ggt ttc cca atc tat gaa ctc tgt gct aag ttt aga    552
Leu Pro Arg Pro Gly Phe Pro Ile Tyr Glu Leu Cys Ala Lys Phe Arg
        130                 135                 140 cac ctt gaa gtt cgc tac gtc gat ctt ctt ccg gaa aat gga tgg gag    600
His Leu Glu Val Arg Tyr Val Asp Leu Leu Pro Glu Asn Gly Trp Glu
            145                 150                 155 atc gat ctt gat gct gtc gag gct ctt gca gac gaa aac acg gtt gct    648
Ile Asp Leu Asp Ala Val Glu Ala Leu Ala Asp Glu Asn Thr Val Ala
160                 165                 170 ttg gtt gtt ata aac cct ggt aat cct tgc ggg aat gtc tat agc tac    696
Leu Val Val Ile Asn Pro Gly Asn Pro Cys Gly Asn Val Tyr Ser Tyr
175                 180                 185                 190 cag cat ttg atg aag att gcg gaa tcg gcg aaa aaa cta ggg ttt ctt    744
Gln His Leu Met Lys Ile Ala Glu Ser Ala Lys Lys Leu Gly Phe Leu
                195                 200                 205 gtg att gct gat gag gtt tac ggt cat ctt gct ttt ggt agc aaa ccg    792
Val Ile Ala Asp Glu Val Tyr Gly His Leu Ala Phe Gly Ser Lys Pro
        210                 215                 220 ttt gtg cca atg ggt gtg ttt gga tct att gtt cct gtg ctt act ctt    840
Phe Val Pro Met Gly Val Phe Gly Ser Ile Val Pro Val Leu Thr Leu
            225                 230                 235 ggc tct tta tca aag aga tgg ata gtt cca ggt tgg cga ctc ggg tgg    888
Gly Ser Leu Ser Lys Arg Trp Ile Val Pro Gly Trp Arg Leu Gly Trp
240                 245                 250 ttt gtc acc act gat cct tct ggt tcc ttt aag gac cct aag atc att    936
Phe Val Thr Thr Asp Pro Ser Gly Ser Phe Lys Asp Pro Lys Ile Ile
255                 260                 265                 270 gag agg ttt aag aaa tac ttt gat att ctt ggt gga cca gct aca ttt    984
Glu Arg Phe Lys Lys Tyr Phe Asp Ile Leu Gly Gly Pro Ala Thr Phe
                275                 280                 285 att cag gct gca gtt ccc act att ttg gaa cag acg gat gag tct ttc   1032
Ile Gln Ala Ala Val Pro Thr Ile Leu Glu Gln Thr Asp Glu Ser Phe
        290                 295                 300 ttc aag aaa acc ttg aac tcg ttg aag aac tct tcg gat att tgt tgt   1080
Phe Lys Lys Thr Leu Asn Ser Leu Lys Asn Ser Ser Asp Ile Cys Cys
            305                 310                 315 gac tgg atc aag gag att cct tgc att gat tcc tcg cat cga cca gaa   1128
Asp Trp Ile Lys Glu Ile Pro Cys Ile Asp Ser Ser His Arg Pro Glu
320                 325                 330 gga tcc atg gca atg atg gtt aag ctg aat ctc tca tta ctt gaa gat   1176
Gly Ser Met Ala Met Met Val Lys Leu Asn Leu Ser Leu Leu Glu Asp
335                 340                 345                 350 gta agt gac gat atc gac ttc tgt ttc aag tta gct agg gaa gaa tca   1224
Val Ser Asp Asp Ile Asp Phe Cys Phe Lys Leu Ala Arg Glu Glu Ser
                355                 360                 365 gtc atc ctt ctt cct ggg acc gcg gtg ggg ctg aag aac tgg ctg agg   1272
Val Ile Leu Leu Pro Gly Thr Ala Val Gly Leu Lys Asn Trp Leu Arg
        370                 375                 380 ata acg ttt gca gca gat gca act tcg att gaa gaa gct ttt aaa agg   1320
Ile Thr Phe Ala Ala Asp Ala Thr Ser Ile Glu Glu Ala Phe Lys Arg
            385                 390                 395 atc aaa tgt ttc tat ctt aga cat gcc aag act caa tat cca acc ata   1368
Ile Lys Cys Phe Tyr Leu Arg His Ala Lys Thr Gln Tyr Pro Thr Ile
```

```
                    400              405              410
tag ttgatttctg attttggtat ggtcataaat tgttcttaaa ttacatgttt        1421
aaaaacacag atacagtaca gtgtcttttt gttctcccta tataagtgtt gatataaaat  1481
ttctttattg taataagatt aactcttaat taaaaacatc aactaaacga ataaacagaa  1541
aaatgttaac ttg                                                     1554
```

<210> SEQ ID NO 10
<211> LENGTH: 414
<212> TYPE: PRT
<213> ORGANISM: Arabidopsis thaliana

<400> SEQUENCE: 10

```
Met Glu Asn Gly Ala Thr Thr Ser Thr Ile Thr Ile Lys Gly Ile
1               5                   10                  15

Leu Ser Leu Leu Met Glu Ser Ile Thr Thr Glu Glu Asp Glu Gly Gly
                20                  25                  30

Lys Arg Val Ile Ser Leu Gly Met Gly Asp Pro Thr Leu Tyr Ser Cys
            35                  40                  45

Phe Arg Thr Thr Gln Val Ser Leu Gln Ala Val Ser Asp Ser Leu Leu
50                  55                  60

Ser Asn Lys Phe His Gly Tyr Ser His Thr Val Gly Leu Pro Gln Ala
65                  70                  75                  80

Arg Arg Ala Ile Ala Glu Tyr Leu Ser Arg Asp Leu Pro Tyr Lys Leu
                85                  90                  95

Ser Gln Asp Asp Val Phe Ile Thr Ser Gly Cys Thr Gln Ala Ile Asp
            100                 105                 110

Val Ala Leu Ser Met Leu Ala Arg Pro Arg Ala Asn Ile Leu Leu Pro
        115                 120                 125

Arg Pro Gly Phe Pro Ile Tyr Glu Leu Cys Ala Lys Phe Arg His Leu
    130                 135                 140

Glu Val Arg Tyr Val Asp Leu Leu Pro Glu Asn Gly Trp Glu Ile Asp
145                 150                 155                 160

Leu Asp Ala Val Glu Ala Leu Ala Asp Glu Asn Thr Val Ala Leu Val
                165                 170                 175

Val Ile Asn Pro Gly Asn Pro Cys Gly Asn Val Tyr Ser Tyr Gln His
            180                 185                 190

Leu Met Lys Ile Ala Glu Ser Ala Lys Lys Leu Gly Phe Leu Val Ile
        195                 200                 205

Ala Asp Glu Val Tyr Gly His Leu Ala Phe Gly Ser Lys Pro Phe Val
    210                 215                 220

Pro Met Gly Val Phe Gly Ser Ile Val Pro Val Leu Thr Leu Gly Ser
225                 230                 235                 240

Leu Ser Lys Arg Trp Ile Val Pro Gly Trp Arg Leu Gly Trp Phe Val
                245                 250                 255

Thr Thr Asp Pro Ser Gly Ser Phe Lys Asp Pro Lys Ile Ile Glu Arg
            260                 265                 270

Phe Lys Lys Tyr Phe Asp Ile Leu Gly Gly Pro Ala Thr Phe Ile Gln
        275                 280                 285

Ala Ala Val Pro Thr Ile Leu Glu Gln Thr Asp Glu Ser Phe Phe Lys
    290                 295                 300

Lys Thr Leu Asn Ser Leu Lys Asn Ser Ser Asp Ile Cys Cys Asp Trp
305                 310                 315                 320

Ile Lys Glu Ile Pro Cys Ile Asp Ser Ser His Arg Pro Glu Gly Ser
                325                 330                 335
```

```
Met Ala Met Met Val Lys Leu Asn Leu Ser Leu Leu Glu Asp Val Ser
            340                 345                 350

Asp Asp Ile Asp Phe Cys Phe Lys Leu Ala Arg Glu Glu Ser Val Ile
            355                 360                 365

Leu Leu Pro Gly Thr Ala Val Gly Leu Lys Asn Trp Leu Arg Ile Thr
370                 375                 380

Phe Ala Ala Asp Ala Thr Ser Ile Glu Glu Ala Phe Lys Arg Ile Lys
385                 390                 395                 400

Cys Phe Tyr Leu Arg His Ala Lys Thr Gln Tyr Pro Thr Ile
                405                 410

<210> SEQ ID NO 11
<211> LENGTH: 1077
<212> TYPE: DNA
<213> ORGANISM: Oryza sativa
<220> FEATURE:
<221> NAME/KEY: CDS
<222> LOCATION: (1)..(1077)
<223> OTHER INFORMATION: coding for Oryza sativa putative
      porphobilinogen deaminase [gb XM_464262]

<400> SEQUENCE: 11 atg ccg ccg ccg ccg aga tgc gcc gcc acc acc gcc cac cac tcc ctc      48
Met Pro Pro Pro Pro Arg Cys Ala Ala Thr Thr Ala His His Ser Leu
1               5                   10                  15 ctc ggc tcg ccc acc tgc ctc gcg cgc ccg cgg cgg cgg tgc tgc ccc      96
Leu Gly Ser Pro Thr Cys Leu Ala Arg Pro Arg Arg Arg Cys Cys Pro
            20                  25                  30 gtg cgc gcc gcc gtc gcc gtc cag gcc gag gcg cag gcc aag gtc tcg     144
Val Arg Ala Ala Val Ala Val Gln Ala Glu Ala Gln Ala Lys Val Ser
        35                  40                  45 ctc atc cgg att ggc acc cgc ggg agt cct ctt gca ctg gca caa gct     192
Leu Ile Arg Ile Gly Thr Arg Gly Ser Pro Leu Ala Leu Ala Gln Ala
    50                  55                  60 cat gaa acc cga gac aag ctg aag gct gca cac tca gag tta gcc gag     240
His Glu Thr Arg Asp Lys Leu Lys Ala Ala His Ser Glu Leu Ala Glu
65              70                  75                  80 gag ggg gcc gtt gag att gtc atc att aag acc aca gga gac atg atc     288
Glu Gly Ala Val Glu Ile Val Ile Ile Lys Thr Thr Gly Asp Met Ile
            85                  90                  95 ttg gac aaa ccc ctg gca gat ata ggt ggc aag ggt tta ttc acc aag     336
Leu Asp Lys Pro Leu Ala Asp Ile Gly Gly Lys Gly Leu Phe Thr Lys
            100                 105                 110 gag atc gat gat gca ctt ttg cag gga agg att gac att gcc gtc cac     384
Glu Ile Asp Asp Ala Leu Leu Gln Gly Arg Ile Asp Ile Ala Val His
            115                 120                 125 tcg atg aaa gat gtt cca aca tat tta cca gaa ggc acg ata ttg cct     432
Ser Met Lys Asp Val Pro Thr Tyr Leu Pro Glu Gly Thr Ile Leu Pro
130             135                 140 tgt aat ctc cca cgg gaa gat gtg aga gat gca ttc ata tgc ttg act     480
Cys Asn Leu Pro Arg Glu Asp Val Arg Asp Ala Phe Ile Cys Leu Thr
145             150                 155                 160 gca agt tcc ctt gcg gag ctt cct gct ggc agt gtt gtt gga agt gct     528
Ala Ser Ser Leu Ala Glu Leu Pro Ala Gly Ser Val Val Gly Ser Ala
            165                 170                 175 tct ctg cgt aga caa tct caa att ctc tac aaa tat cca tca ctc aaa     576
Ser Leu Arg Arg Gln Ser Gln Ile Leu Tyr Lys Tyr Pro Ser Leu Lys
            180                 185                 190 gtt gtt aac ttc aga gga aat gtt caa aca cga ttg agg aaa ctc aaa     624
Val Val Asn Phe Arg Gly Asn Val Gln Thr Arg Leu Arg Lys Leu Lys
            195                 200                 205
```

-continued

| | |
|---|---|
| gaa gga gat gtc cat gct aca ttg ttg gct cta gct gga cta aaa cgc<br>Glu Gly Asp Val His Ala Thr Leu Leu Ala Leu Ala Gly Leu Lys Arg<br>210                               215                            220 | 672 |
| tta aac atg gca gaa act gcg aca tct gta ttg tca gtg gac gaa atg<br>Leu Asn Met Ala Glu Thr Ala Thr Ser Val Leu Ser Val Asp Glu Met<br>225                          230                            235                 240 | 720 |
| ctt cca gca gtt gct caa ggt gct att gga ata gct tgc aga agc agt<br>Leu Pro Ala Val Ala Gln Gly Ala Ile Gly Ile Ala Cys Arg Ser Ser<br>                       245                            250                          255 | 768 |
| gat gac aca atg atg aat tac ttg tcc tca ttg aac cat gaa gat acc<br>Asp Asp Thr Met Met Asn Tyr Leu Ser Ser Leu Asn His Glu Asp Thr<br>               260                            265                          270 | 816 |
| aga tta gct gtt gca tgt gaa aga gaa ttc ttg tca gtt ctt gat ggc<br>Arg Leu Ala Val Ala Cys Glu Arg Glu Phe Leu Ser Val Leu Asp Gly<br>275                          280                            285 | 864 |
| aac tgc cga act cca att gcg gca tat gct tct cgt gac aag gat ggg<br>Asn Cys Arg Thr Pro Ile Ala Ala Tyr Ala Ser Arg Asp Lys Asp Gly<br>               290                            295                          300 | 912 |
| aat tgt tca ttc cga ggg cta ttg gct tca cct gat gga tct aca gta<br>Asn Cys Ser Phe Arg Gly Leu Leu Ala Ser Pro Asp Gly Ser Thr Val<br>305                          310                            315                 320 | 960 |
| tat gag act tcg aga act gga cct tat gat ttc gat atc atg gtt gag<br>Tyr Glu Thr Ser Arg Thr Gly Pro Tyr Asp Phe Asp Ile Met Val Glu<br>                       325                            330                          335 | 1008 |
| atg ggt aaa gat gct ggc cac gag ctg aaa gca aag gct ggc cct ggc<br>Met Gly Lys Asp Ala Gly His Glu Leu Lys Ala Lys Ala Gly Pro Gly<br>               340                            345                          350 | 1056 |
| ttc ttt gat agc ttg caa tga<br>Phe Phe Asp Ser Leu Gln<br>               355 | 1077 |

<210> SEQ ID NO 12
<211> LENGTH: 358
<212> TYPE: PRT
<213> ORGANISM: Oryza sativa

<400> SEQUENCE: 12

Met Pro Pro Pro Arg Cys Ala Ala Thr Thr Ala His His Ser Leu
1               5                   10                  15

Leu Gly Ser Pro Thr Cys Leu Ala Arg Pro Arg Arg Cys Cys Pro
            20                  25                  30

Val Arg Ala Ala Val Ala Val Gln Ala Glu Ala Gln Ala Lys Val Ser
        35                  40                  45

Leu Ile Arg Ile Gly Thr Arg Gly Ser Pro Leu Ala Leu Ala Gln Ala
    50                  55                  60

His Glu Thr Arg Asp Lys Leu Lys Ala Ala His Ser Glu Leu Ala Glu
65                  70                  75                  80

Glu Gly Ala Val Glu Ile Val Ile Ile Lys Thr Thr Gly Asp Met Ile
                85                  90                  95

Leu Asp Lys Pro Leu Ala Asp Ile Gly Gly Lys Gly Leu Phe Thr Lys
            100                 105                 110

Glu Ile Asp Asp Ala Leu Leu Gln Gly Arg Ile Asp Ile Ala Val His
        115                 120                 125

Ser Met Lys Asp Val Pro Thr Tyr Leu Pro Glu Gly Thr Ile Leu Pro
    130                 135                 140

Cys Asn Leu Pro Arg Glu Asp Val Arg Asp Ala Phe Ile Cys Leu Thr
145                 150                 155                 160

Ala Ser Ser Leu Ala Glu Leu Pro Ala Gly Ser Val Val Gly Ser Ala

```
                    165                 170                 175
Ser Leu Arg Arg Gln Ser Gln Ile Leu Tyr Lys Tyr Pro Ser Leu Lys
            180                 185                 190

Val Val Asn Phe Arg Gly Asn Val Gln Thr Arg Leu Arg Lys Leu Lys
            195                 200                 205

Glu Gly Asp Val His Ala Thr Leu Leu Ala Leu Ala Gly Leu Lys Arg
        210                 215                 220

Leu Asn Met Ala Glu Thr Ala Thr Ser Val Leu Ser Val Asp Glu Met
225                 230                 235                 240

Leu Pro Ala Val Ala Gln Gly Ala Ile Gly Ile Ala Cys Arg Ser Ser
                245                 250                 255

Asp Asp Thr Met Met Asn Tyr Leu Ser Ser Leu Asn His Glu Asp Thr
            260                 265                 270

Arg Leu Ala Val Ala Cys Glu Arg Glu Phe Leu Ser Val Leu Asp Gly
        275                 280                 285

Asn Cys Arg Thr Pro Ile Ala Ala Tyr Ala Ser Arg Asp Lys Asp Gly
    290                 295                 300

Asn Cys Ser Phe Arg Gly Leu Leu Ala Ser Pro Asp Gly Ser Thr Val
305                 310                 315                 320

Tyr Glu Thr Ser Arg Thr Gly Pro Tyr Asp Phe Asp Ile Met Val Glu
                325                 330                 335

Met Gly Lys Asp Ala Gly His Glu Leu Lys Ala Lys Ala Gly Pro Gly
            340                 345                 350

Phe Phe Asp Ser Leu Gln
        355

<210> SEQ ID NO 13
<211> LENGTH: 1242
<212> TYPE: DNA
<213> ORGANISM: Oryza sativa
<220> FEATURE:
<221> NAME/KEY: CDS
<222> LOCATION: (1)..(1242)
<223> OTHER INFORMATION: coding for Oryza sativa putative omega-3 fatty
      acid desaturase [gb NM_185577]

<400> SEQUENCE: 13 atg gcc cgg ctg cta ctc tcc ggc gtc gcg ccg ctc ccc ctc ctc ccc    48
Met Ala Arg Leu Leu Leu Ser Gly Val Ala Pro Leu Pro Leu Leu Pro
1               5                   10                  15 tgc cgc cgt cgc gcc att gca ttt gcg ctc cca ctt ggg aat gtc cgc    96
Cys Arg Arg Arg Ala Ile Ala Phe Ala Leu Pro Leu Gly Asn Val Arg
                20                  25                  30 ctc cgc ctc cgt gtg gcc gca ccc acc agc cgc gtg gcc acc gtg gag   144
Leu Arg Leu Arg Val Ala Ala Pro Thr Ser Arg Val Ala Thr Val Glu
            35                  40                  45 gag gac gac aat gaa aat aat gct cct cct cct cct tgt gag gac ttc   192
Glu Asp Asp Asn Glu Asn Asn Ala Pro Pro Pro Pro Cys Glu Asp Phe
        50                  55                  60 gac ccg ggc gcg gcg ccc ccg ttt ggt ctg gcc gac atc cgc gcc gct   240
Asp Pro Gly Ala Ala Pro Pro Phe Gly Leu Ala Asp Ile Arg Ala Ala
65                  70                  75                  80 atc ccc aag cac tgt tgg gtg aag gac ccc tgg cga tcc atg ggg tac   288
Ile Pro Lys His Cys Trp Val Lys Asp Pro Trp Arg Ser Met Gly Tyr
                85                  90                  95 gtg ctg cgc gac gtg gtg gtg ttc gcc ctc gct gcc gcc gcg            336
Val Leu Arg Asp Val Val Val Phe Ala Leu Ala Ala Ala Ala
                100                 105                 110 cgc ctc cac agc tgc ctc gcc tgg ccg ctc tac tgg gcg gcg cag gga   384
```

```
Arg Leu His Ser Cys Leu Ala Trp Pro Leu Tyr Trp Ala Ala Gln Gly
        115                 120                 125 acc atg ttc tgg gcg ctc ttc gtc ctc ggc cac gac tgc ggg cac ggg       432
Thr Met Phe Trp Ala Leu Phe Val Leu Gly His Asp Cys Gly His Gly
    130                 135                 140 agc ttc tcc aac aac tcg agg ctc aac agc gtg atg ggc cac ata ctc       480
Ser Phe Ser Asn Asn Ser Arg Leu Asn Ser Val Met Gly His Ile Leu
145                 150                 155                 160 cac tcc tcc atc ctc gta ccc tac cat ggc tgg agg att agc cac agg       528
His Ser Ser Ile Leu Val Pro Tyr His Gly Trp Arg Ile Ser His Arg
                165                 170                 175 acg cat cat cag aac cat ggc cat gtc gac aag gat gag tcc tgg cat       576
Thr His His Gln Asn His Gly His Val Asp Lys Asp Glu Ser Trp His
            180                 185                 190 ccc ctc ccc gag cgg ctg tac agg agc ctt aac aga gcc acc cgg atg       624
Pro Leu Pro Glu Arg Leu Tyr Arg Ser Leu Asn Arg Ala Thr Arg Met
        195                 200                 205 ctc cgc ttc tcc ata ccc ttc ccc atg ctc gcc tac cca ttc tac ctg       672
Leu Arg Phe Ser Ile Pro Phe Pro Met Leu Ala Tyr Pro Phe Tyr Leu
    210                 215                 220 tgg tct cgg agc cca gga aag tct ggt tcg cat ttc cat ccc agc agc       720
Trp Ser Arg Ser Pro Gly Lys Ser Gly Ser His Phe His Pro Ser Ser
225                 230                 235                 240 gac ctg ttc cag ccc aac gaa agg aac gat gtg ctg aca tcc aca gcg       768
Asp Leu Phe Gln Pro Asn Glu Arg Asn Asp Val Leu Thr Ser Thr Ala
                245                 250                 255 tgc tgg gtg gcc atg gct gcc ctc ctc gca ggc ctc acc ttc ctc atg       816
Cys Trp Val Ala Met Ala Ala Leu Leu Ala Gly Leu Thr Phe Leu Met
            260                 265                 270 gga ccc ctc ctc atg ctc aac ctc tac ttt gtc cct tac tgg att ttt       864
Gly Pro Leu Leu Met Leu Asn Leu Tyr Phe Val Pro Tyr Trp Ile Phe
        275                 280                 285 gtt atg tgg ctg gac ttc gtc acc tac ttg cac cat cac ggc cac aac       912
Val Met Trp Leu Asp Phe Val Thr Tyr Leu His His His Gly His Asn
    290                 295                 300 gac aag ctg ccc tgg tac cgt ggc aag gaa tgg agc tat ttg cgg gga       960
Asp Lys Leu Pro Trp Tyr Arg Gly Lys Glu Trp Ser Tyr Leu Arg Gly
305                 310                 315                 320 gga ctg acg aca gtg gac agg gac tat ggg tgg atc aac aac atc cac      1008
Gly Leu Thr Thr Val Asp Arg Asp Tyr Gly Trp Ile Asn Asn Ile His
                325                 330                 335 cac gac atc ggg aca cat gtc att cac cat ctt ttc ccc caa atc ccg      1056
His Asp Ile Gly Thr His Val Ile His His Leu Phe Pro Gln Ile Pro
            340                 345                 350 cat tac cat cta att gag gcg acg gaa gca gca aag ggt gtg atg ggg      1104
His Tyr His Leu Ile Glu Ala Thr Glu Ala Ala Lys Gly Val Met Gly
        355                 360                 365 aaa tac tac agg gag ccg gac aag tct ggg cct ttt ccc tta cac ctg      1152
Lys Tyr Tyr Arg Glu Pro Asp Lys Ser Gly Pro Phe Pro Leu His Leu
    370                 375                 380 ttt gga gcg ctg tcc cgg agc ttg aaa cgc gac cac tat gtc agc gac      1200
Phe Gly Ala Leu Ser Arg Ser Leu Lys Arg Asp His Tyr Val Ser Asp
385                 390                 395                 400 acc gga gat gtg gtc tac tac cag acc gac cct gct aac taa              1242
Thr Gly Asp Val Val Tyr Tyr Gln Thr Asp Pro Ala Asn
                405                 410

<210> SEQ ID NO 14
<211> LENGTH: 413
<212> TYPE: PRT
<213> ORGANISM: Oryza sativa
```

<400> SEQUENCE: 14

```
Met Ala Arg Leu Leu Leu Ser Gly Val Ala Pro Leu Pro Leu Leu Pro
1               5                   10                  15
Cys Arg Arg Arg Ala Ile Ala Phe Ala Leu Pro Leu Gly Asn Val Arg
                20                  25                  30
Leu Arg Leu Arg Val Ala Ala Pro Thr Ser Arg Val Ala Thr Val Glu
            35                  40                  45
Glu Asp Asp Asn Glu Asn Asn Ala Pro Pro Pro Cys Glu Asp Phe
    50                  55                  60
Asp Pro Gly Ala Ala Pro Pro Phe Gly Leu Ala Asp Ile Arg Ala Ala
65                  70                  75                  80
Ile Pro Lys His Cys Trp Val Lys Asp Pro Trp Arg Ser Met Gly Tyr
                85                  90                  95
Val Leu Arg Asp Val Val Val Phe Ala Leu Ala Ala Ala Ala
                100                 105                 110
Arg Leu His Ser Cys Leu Ala Trp Pro Leu Tyr Trp Ala Ala Gln Gly
            115                 120                 125
Thr Met Phe Trp Ala Leu Phe Val Leu Gly His Asp Cys Gly His Gly
    130                 135                 140
Ser Phe Ser Asn Asn Ser Arg Leu Asn Ser Val Met Gly His Ile Leu
145                 150                 155                 160
His Ser Ser Ile Leu Val Pro Tyr His Gly Trp Arg Ile Ser His Arg
                165                 170                 175
Thr His His Gln Asn His Gly His Val Asp Lys Asp Glu Ser Trp His
            180                 185                 190
Pro Leu Pro Glu Arg Leu Tyr Arg Ser Leu Asn Arg Ala Thr Arg Met
        195                 200                 205
Leu Arg Phe Ser Ile Pro Phe Pro Met Leu Ala Tyr Pro Phe Tyr Leu
210                 215                 220
Trp Ser Arg Ser Pro Gly Lys Ser Gly Ser His Phe His Pro Ser Ser
225                 230                 235                 240
Asp Leu Phe Gln Pro Asn Glu Arg Asn Asp Val Leu Thr Ser Thr Ala
                245                 250                 255
Cys Trp Val Ala Met Ala Ala Leu Leu Ala Gly Leu Thr Phe Leu Met
            260                 265                 270
Gly Pro Leu Leu Met Leu Asn Leu Tyr Phe Val Pro Tyr Trp Ile Phe
        275                 280                 285
Val Met Trp Leu Asp Phe Val Thr Tyr Leu His His His Gly His Asn
290                 295                 300
Asp Lys Leu Pro Trp Tyr Arg Gly Lys Glu Trp Ser Tyr Leu Arg Gly
305                 310                 315                 320
Gly Leu Thr Thr Val Asp Arg Asp Tyr Gly Trp Ile Asn Asn Ile His
                325                 330                 335
His Asp Ile Gly Thr His Val Ile His His Leu Phe Pro Gln Ile Pro
            340                 345                 350
His Tyr His Leu Ile Glu Ala Thr Glu Ala Ala Lys Gly Val Met Gly
        355                 360                 365
Lys Tyr Tyr Arg Glu Pro Asp Lys Ser Gly Pro Phe Pro Leu His Leu
370                 375                 380
Phe Gly Ala Leu Ser Arg Ser Leu Lys Arg Asp His Tyr Val Ser Asp
385                 390                 395                 400
Thr Gly Asp Val Val Tyr Tyr Gln Thr Asp Pro Ala Asn
                405                 410
```

<210> SEQ ID NO 15
<211> LENGTH: 1668
<212> TYPE: DNA
<213> ORGANISM: Oryza sativa
<220> FEATURE:
<221> NAME/KEY: CDS
<222> LOCATION: (1)..(1668)
<223> OTHER INFORMATION: coding for Oryza sativa Fusarium resistance
  protein I2C-5-like [gb NM_194161]

<400> SEQUENCE: 15

| | | | | | | | | | | | | | | | | |
|---|---|---|---|---|---|---|---|---|---|---|---|---|---|---|---|---|
| atg | gat | aac | acg | ttg | gtg | gca | acg | tca | gct | agg | gtt | ctt | cca | aca | atg | 48 |
| Met | Asp | Asn | Thr | Leu | Val | Ala | Thr | Ser | Ala | Arg | Val | Leu | Pro | Thr | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | gca | ccg | gat | ggc | gat | gcc | tcc | ttg | ctg | tct | gtg | tct | gct | ctt | gat | 96 |
| Leu | Ala | Pro | Asp | Gly | Asp | Ala | Ser | Leu | Leu | Ser | Val | Ser | Ala | Leu | Asp | |
| | | 20 | | | | | 25 | | | | | 30 | | | | |

| | | | | | | | | | | | | | | | | |
|---|---|---|---|---|---|---|---|---|---|---|---|---|---|---|---|---|
| cca | gtt | ctt | gtt | gat | cca | ttg | agt | gat | cta | cag | aac | ttc | aga | tta | cat | 144 |
| Pro | Val | Leu | Val | Asp | Pro | Leu | Ser | Asp | Leu | Gln | Asn | Phe | Arg | Leu | His | |
| | 35 | | | | | 40 | | | | | 45 | | | | | |

| | | | | | | | | | | | | | | | | |
|---|---|---|---|---|---|---|---|---|---|---|---|---|---|---|---|---|
| act | tca | ctt | atg | gag | aca | ttt | ttg | tct | gtg | att | ctg | agt | gat | ctt | gcc | 192 |
| Thr | Ser | Leu | Met | Glu | Thr | Phe | Leu | Ser | Val | Ile | Leu | Ser | Asp | Leu | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| act | aaa | tcc | ata | tct | ttc | ctg | atc | aac | aag | tgc | tcg | aaa | ccg | aca | gca | 240 |
| Thr | Lys | Ser | Ile | Ser | Phe | Leu | Ile | Asn | Lys | Cys | Ser | Lys | Pro | Thr | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tca | aac | atg | gag | gag | aga | ctg | caa | cgg | ctg | ctg | ctc | cgt | gcc | cag | atc | 288 |
| Ser | Asn | Met | Glu | Glu | Arg | Leu | Gln | Arg | Leu | Leu | Leu | Arg | Ala | Gln | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | gtg | gag | gag | gca | gag | gac | cgg | ctc | atc | aca | aac | caa | cgc | atg | ctg | 336 |
| Ile | Val | Glu | Glu | Ala | Glu | Asp | Arg | Leu | Ile | Thr | Asn | Gln | Arg | Met | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | caa | ctg | aat | ata | ctg | agg | aag | gag | atg | ttc | aga | ggg | tat | tac | gct | 384 |
| Leu | Gln | Leu | Asn | Ile | Leu | Arg | Lys | Glu | Met | Phe | Arg | Gly | Tyr | Tyr | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| ctt | gac | aga | ttc | aga | tgc | cgt | ggc | cat | gaa | gaa | gat | gat | gca | aaa | gat | 432 |
| Leu | Asp | Arg | Phe | Arg | Cys | Arg | Gly | His | Glu | Glu | Asp | Asp | Ala | Lys | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| cac | cag | gtg | agt | aac | tct | ttc | gcg | caa | tcc | aag | ttc | aat | cct | gct | aag | 480 |
| His | Gln | Val | Ser | Asn | Ser | Phe | Ala | Gln | Ser | Lys | Phe | Asn | Pro | Ala | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agt | gtc | cgg | ttc | ttc | agg | atc | agt | ggc | cat | agt | tta | caa | gag | cag | ttg | 528 |
| Ser | Val | Arg | Phe | Phe | Arg | Ile | Ser | Gly | His | Ser | Leu | Gln | Glu | Gln | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | caa | gtt | gtt | ggc | agc | ata | gaa | gtc | acc | ctt | gaa | gat | atg | agc | gtt | 576 |
| Gln | Gln | Val | Val | Gly | Ser | Ile | Glu | Val | Thr | Leu | Glu | Asp | Met | Ser | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ttt | gtc | atg | ttc | ttg | aac | agt | tgt | ccc | cat | ttg | tgc | cgt | cag | cca | tat | 624 |
| Phe | Val | Met | Phe | Leu | Asn | Ser | Cys | Pro | His | Leu | Cys | Arg | Gln | Pro | Tyr | |
| | | 195 | | | | | 200 | | | | | 205 | | | | |

| | | | | | | | | | | | | | | | | |
|---|---|---|---|---|---|---|---|---|---|---|---|---|---|---|---|---|
| agc | atg | cac | ttg | ctt | cta | gac | aaa | tgt | ttg | ttt | ggt | cgc | caa | atg | gag | 672 |
| Ser | Met | His | Leu | Leu | Leu | Asp | Lys | Cys | Leu | Phe | Gly | Arg | Gln | Met | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| atc | gag | cgc | atc | atg | aac | ttc | ctg | ctc | aaa | gtg | gat | tct | cca | ggt | tct | 720 |
| Ile | Glu | Arg | Ile | Met | Asn | Phe | Leu | Leu | Lys | Val | Asp | Ser | Pro | Gly | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gaa | aat | ccg | ggt | gtc | ctg | ccg | atc | att | ggt | cga | cgg | aaa | gct | ggg | aag | 768 |
| Glu | Asn | Pro | Gly | Val | Leu | Pro | Ile | Ile | Gly | Arg | Arg | Lys | Ala | Gly | Lys | |
| | | | | 245 | | | | | 250 | | | | | 255 | | |

| | | | | | | | | | | | | | | | | |
|---|---|---|---|---|---|---|---|---|---|---|---|---|---|---|---|---|
| agc | acc | ttg | atc | gag | cat | gcc | tgt | aac | gat | gaa | agg | gtg | cgt | aac | cac | 816 |
| Ser | Thr | Leu | Ile | Glu | His | Ala | Cys | Asn | Asp | Glu | Arg | Val | Arg | Asn | His | |

```
                   260             265                 270
ttc tct caa att gtg tgt ttc agt gac gat gat ctt aaa gat gca gac     864
Phe Ser Gln Ile Val Cys Phe Ser Asp Asp Asp Leu Lys Asp Ala Asp
        275                 280                 285 atg gta act ctt cga cat tgt ggt tca atc aag aat gga aac caa tgc     912
Met Val Thr Leu Arg His Cys Gly Ser Ile Lys Asn Gly Asn Gln Cys
290                 295                 300 act ggt gga gaa aga ata ttg atc gtt atc gag cta atc aga gac atc     960
Thr Gly Gly Glu Arg Ile Leu Ile Val Ile Glu Leu Ile Arg Asp Ile
305                 310                 315                 320 gat gag gtt gta tgg aca aga ttg tac tca gct tcc aag agt tat gtt    1008
Asp Glu Val Val Trp Thr Arg Leu Tyr Ser Ala Ser Lys Ser Tyr Val
                325                 330                 335 cca aat ggc agt aaa att atc gtc gca agc caa tct gat aag att gca    1056
Pro Asn Gly Ser Lys Ile Ile Val Ala Ser Gln Ser Asp Lys Ile Ala
            340                 345                 350 aga ttt gga aca aca caa gct ctt aga gta gaa tta ttt act gaa gaa    1104
Arg Phe Gly Thr Thr Gln Ala Leu Arg Val Glu Leu Phe Thr Glu Glu
        355                 360                 365 gca tac tgg tac ttt ttc aag gtg cgc aca ttc gga agc atg gat gca    1152
Ala Tyr Trp Tyr Phe Phe Lys Val Arg Thr Phe Gly Ser Met Asp Ala
370                 375                 380 cag gag cac cca aag atg gca tca atg gcc atg gaa atg gcc agg gag    1200
Gln Glu His Pro Lys Met Ala Ser Met Ala Met Glu Met Ala Arg Glu
385                 390                 395                 400 ttg caa ggg tgc ttc atg ggt gca agc atc tac agt gga ctt ttg aaa    1248
Leu Gln Gly Cys Phe Met Gly Ala Ser Ile Tyr Ser Gly Leu Leu Lys
                405                 410                 415 gca aat ttc aat gct cgg ttt tgg aac atg gct ctg gca agc atc aga    1296
Ala Asn Phe Asn Ala Arg Phe Trp Asn Met Ala Leu Ala Ser Ile Arg
            420                 425                 430 gaa tac aag cag acg aat ctc cta gta tac ggt aca tat ttt gag aat    1344
Glu Tyr Lys Gln Thr Asn Leu Leu Val Tyr Gly Thr Tyr Phe Glu Asn
        435                 440                 445 cca tgg cag gcg tct gaa cct cca tat gtt agg aca gta aac aaa att    1392
Pro Trp Gln Ala Ser Glu Pro Pro Tyr Val Arg Thr Val Asn Lys Ile
450                 455                 460 tcc tcc gaa tac ctt gtg att cat gat gag tat cac aca tgt tct gtt    1440
Ser Ser Glu Tyr Leu Val Ile His Asp Glu Tyr His Thr Cys Ser Val
465                 470                 475                 480 cag aac atg gtt ctt tgt cgc aca aac ttt act cgg agt gaa gct gaa    1488
Gln Asn Met Val Leu Cys Arg Thr Asn Phe Thr Arg Ser Glu Ala Glu
                485                 490                 495 gtt ccc atg ttg agc atg caa gat ttt ctc ttt gga agt gtt aga cct    1536
Val Pro Met Leu Ser Met Gln Asp Phe Leu Phe Gly Ser Val Arg Pro
            500                 505                 510 caa gga aaa ttc aag gtt ctt gcg tgg aag tct cac ctt ccg cct tac    1584
Gln Gly Lys Phe Lys Val Leu Ala Trp Lys Ser His Leu Pro Pro Tyr
        515                 520                 525 tac aac cac atg ttc aac tgt gag ttt gaa gat gtc aac atg cta aga    1632
Tyr Asn His Met Phe Asn Cys Glu Phe Glu Asp Val Asn Met Leu Arg
530                 535                 540 cgc aag gat att agt tca gaa gtc gat gac aac tga                    1668
Arg Lys Asp Ile Ser Ser Glu Val Asp Asp Asn
545                 550                 555

<210> SEQ ID NO 16
<211> LENGTH: 555
<212> TYPE: PRT
<213> ORGANISM: Oryza sativa
```

<400> SEQUENCE: 16

Met Asp Asn Thr Leu Val Ala Thr Ser Ala Arg Val Leu Pro Thr Met
1               5                   10                  15

Leu Ala Pro Asp Gly Asp Ala Ser Leu Leu Ser Val Ser Ala Leu Asp
            20                  25                  30

Pro Val Leu Val Asp Pro Leu Ser Asp Leu Gln Asn Phe Arg Leu His
                35                  40                  45

Thr Ser Leu Met Glu Thr Phe Leu Ser Val Ile Leu Ser Asp Leu Ala
    50                  55                  60

Thr Lys Ser Ile Ser Phe Leu Ile Asn Lys Cys Ser Lys Pro Thr Ala
65                  70                  75                  80

Ser Asn Met Glu Glu Arg Leu Gln Arg Leu Leu Arg Ala Gln Ile
                85                  90                  95

Ile Val Glu Glu Ala Glu Asp Arg Leu Ile Thr Asn Gln Arg Met Leu
                100                 105                 110

Leu Gln Leu Asn Ile Leu Arg Lys Glu Met Phe Arg Gly Tyr Tyr Ala
            115                 120                 125

Leu Asp Arg Phe Arg Cys Arg Gly His Glu Asp Asp Ala Lys Asp
130                 135                 140

His Gln Val Ser Asn Ser Phe Ala Gln Ser Lys Phe Asn Pro Ala Lys
145                 150                 155                 160

Ser Val Arg Phe Phe Arg Ile Ser Gly His Ser Leu Gln Glu Gln Leu
                165                 170                 175

Gln Gln Val Val Gly Ser Ile Glu Val Thr Leu Glu Asp Met Ser Val
            180                 185                 190

Phe Val Met Phe Leu Asn Ser Cys Pro His Leu Cys Arg Gln Pro Tyr
        195                 200                 205

Ser Met His Leu Leu Leu Asp Lys Cys Leu Phe Gly Arg Gln Met Glu
    210                 215                 220

Ile Glu Arg Ile Met Asn Phe Leu Leu Lys Val Asp Ser Pro Gly Ser
225                 230                 235                 240

Glu Asn Pro Gly Val Leu Pro Ile Ile Gly Arg Arg Lys Ala Gly Lys
                245                 250                 255

Ser Thr Leu Ile Glu His Ala Cys Asn Asp Glu Arg Val Arg Asn His
            260                 265                 270

Phe Ser Gln Ile Val Cys Phe Ser Asp Asp Asp Leu Lys Asp Ala Asp
        275                 280                 285

Met Val Thr Leu Arg His Cys Gly Ser Ile Lys Asn Gly Asn Gln Cys
    290                 295                 300

Thr Gly Gly Glu Arg Ile Leu Ile Val Ile Glu Leu Ile Arg Asp Ile
305                 310                 315                 320

Asp Glu Val Val Trp Thr Arg Leu Tyr Ser Ala Ser Lys Ser Tyr Val
                325                 330                 335

Pro Asn Gly Ser Lys Ile Ile Val Ala Ser Gln Ser Asp Lys Ile Ala
            340                 345                 350

Arg Phe Gly Thr Thr Gln Ala Leu Arg Val Glu Leu Phe Thr Glu Glu
        355                 360                 365

Ala Tyr Trp Tyr Phe Phe Lys Val Arg Thr Phe Gly Ser Met Asp Ala
    370                 375                 380

Gln Glu His Pro Lys Met Ala Ser Met Ala Met Glu Met Ala Arg Glu
385                 390                 395                 400

Leu Gln Gly Cys Phe Met Gly Ala Ser Ile Tyr Ser Gly Leu Leu Lys
                405                 410                 415

```
Ala Asn Phe Asn Ala Arg Phe Trp Asn Met Ala Leu Ala Ser Ile Arg
            420                 425                 430

Glu Tyr Lys Gln Thr Asn Leu Leu Val Tyr Gly Thr Tyr Phe Glu Asn
            435                 440                 445

Pro Trp Gln Ala Ser Glu Pro Pro Tyr Val Arg Thr Val Asn Lys Ile
450                 455                 460

Ser Ser Glu Tyr Leu Val Ile His Asp Glu Tyr His Thr Cys Ser Val
465                 470                 475                 480

Gln Asn Met Val Leu Cys Arg Thr Asn Phe Thr Arg Ser Glu Ala Glu
            485                 490                 495

Val Pro Met Leu Ser Met Gln Asp Phe Leu Phe Gly Ser Val Arg Pro
            500                 505                 510

Gln Gly Lys Phe Lys Val Leu Ala Trp Lys Ser His Leu Pro Pro Tyr
            515                 520                 525

Tyr Asn His Met Phe Asn Cys Glu Phe Glu Asp Val Asn Met Leu Arg
            530                 535                 540

Arg Lys Asp Ile Ser Ser Glu Val Asp Asp Asn
545                 550                 555

<210> SEQ ID NO 17
<211> LENGTH: 1695
<212> TYPE: DNA
<213> ORGANISM: Arabidopsis thaliana
<220> FEATURE:
<221> NAME/KEY: CDS
<222> LOCATION: (1)..(1695)
<223> OTHER INFORMATION: coding for Arabidopsis thaliana, constitutive
      expressor of pathogenesis related genes 5 (cpr5, At5g64930; gb
      AY033229)

<400> SEQUENCE: 17 atg gaa gcc ctc ctc ctc cct cct tcg ccg gaa ccc caa aat caa atc      48
Met Glu Ala Leu Leu Leu Pro Pro Ser Pro Glu Pro Gln Asn Gln Ile
1               5                   10                  15 acc aat ccg gcg aat tca aag cca aat cat caa tct ggt gac gta cat      96
Thr Asn Pro Ala Asn Ser Lys Pro Asn His Gln Ser Gly Asp Val His
            20                  25                  30 aaa gat gag acg atg atg atg aag aag aag aag gat acg aat cca tcg     144
Lys Asp Glu Thr Met Met Met Lys Lys Lys Lys Asp Thr Asn Pro Ser
        35                  40                  45 aat ttg gaa aag aga aaa ctc aag gga aag aag aaa gag att atg gac     192
Asn Leu Glu Lys Arg Lys Leu Lys Gly Lys Lys Lys Glu Ile Met Asp
    50                  55                  60 aac gac gaa gct tct tcg tcc tat tgt tct aca tct tct acc tct aat     240
Asn Asp Glu Ala Ser Ser Ser Tyr Cys Ser Thr Ser Ser Thr Ser Asn
65                  70                  75                  80 tca aat tct act aaa agg gtt acg aga gtg gtt cat aga tta cga aac     288
Ser Asn Ser Thr Lys Arg Val Thr Arg Val Val His Arg Leu Arg Asn
                85                  90                  95 cct atg cgg tta ggt atg gct cga cga agc gtt ggt gaa cga caa gct     336
Pro Met Arg Leu Gly Met Ala Arg Arg Ser Val Gly Glu Arg Gln Ala
            100                 105                 110 gaa aaa ttg gcg aag cct ctg ggc ttt tca ctt gcc gct ttt gct aat     384
Glu Lys Leu Ala Lys Pro Leu Gly Phe Ser Leu Ala Ala Phe Ala Asn
        115                 120                 125 atg gtt att gca aga aag aat gcc gca ggt cag aat gtt tat gtt gat     432
Met Val Ile Ala Arg Lys Asn Ala Ala Gly Gln Asn Val Tyr Val Asp
    130                 135                 140 gat ctt gtt gag atc ttt gct act ctt gtc gaa gaa tca tta gcc aat     480
Asp Leu Val Glu Ile Phe Ala Thr Leu Val Glu Glu Ser Leu Ala Asn
145                 150                 155                 160
```

| | | |
|---|---|---|
| gtt tat ggt aat aag ctt ggt tcc ttt gcg acc aac ttt gag caa aca<br>Val Tyr Gly Asn Lys Leu Gly Ser Phe Ala Thr Asn Phe Glu Gln Thr<br>                165                          170                        175 | 528 |
| ttc agc agt act cta aag atc ctt aaa ttg acc aat gaa tgt gca aat<br>Phe Ser Ser Thr Leu Lys Ile Leu Lys Leu Thr Asn Glu Cys Ala Asn<br>            180                        185                        190 | 576 |
| cca cat cag tca aac aat aat gat ggt ggg agt tgt aat tta gat cgc<br>Pro His Gln Ser Asn Asn Asn Asp Gly Gly Ser Cys Asn Leu Asp Arg<br>                195                          200                        205 | 624 |
| tct acc ata gac gga tgc tca gac acc gag cta ttt gag agg gag act<br>Ser Thr Ile Asp Gly Cys Ser Asp Thr Glu Leu Phe Glu Arg Glu Thr<br>    210                          215                        220 | 672 |
| tca tct gct acg tct gct tat gaa gtg atg caa ggc agt gca aca gca<br>Ser Ser Ala Thr Ser Ala Tyr Glu Val Met Gln Gly Ser Ala Thr Ala<br>225                        230                        235                        240 | 720 |
| acc tct ttg atg aat gag ctt gcc ctt ttc gaa gag act cta caa ctc<br>Thr Ser Leu Met Asn Glu Leu Ala Leu Phe Glu Glu Thr Leu Gln Leu<br>                245                          250                        255 | 768 |
| tct tgt gtc cct cct aga agt tca gca atg gct ttg acc aca gac gaa<br>Ser Cys Val Pro Pro Arg Ser Ser Ala Met Ala Leu Thr Thr Asp Glu<br>            260                        265                        270 | 816 |
| agg ttt tta aaa gag caa aca cga gca aac gac cta aag acc gtg gag<br>Arg Phe Leu Lys Glu Gln Thr Arg Ala Asn Asp Leu Lys Thr Val Glu<br>        275                        280                        285 | 864 |
| att ggt ctt caa ata aga gag tta agg tgc aaa gag acg gcg cta gga<br>Ile Gly Leu Gln Ile Arg Glu Leu Arg Cys Lys Glu Thr Ala Leu Gly<br>    290                          295                        300 | 912 |
| tta aaa ttt gaa tca aac aac ctg ggg aaa gcg gcg cta gag ttg gat<br>Leu Lys Phe Glu Ser Asn Asn Leu Gly Lys Ala Ala Leu Glu Leu Asp<br>305                        310                        315                        320 | 960 |
| gtt tcg aaa gct gca ttc aga gcg gag aaa ttc aaa acc gaa tta gaa<br>Val Ser Lys Ala Ala Phe Arg Ala Glu Lys Phe Lys Thr Glu Leu Glu<br>                325                          330                        335 | 1008 |
| gat aca aga aaa gaa gag atg gtc aca aga atc atg gat tgg ctc ctc<br>Asp Thr Arg Lys Glu Glu Met Val Thr Arg Ile Met Asp Trp Leu Leu<br>            340                        345                        350 | 1056 |
| gta agt gtc ttc agc atg ttg gct tct atg gta ctt ggc gtt tac aat<br>Val Ser Val Phe Ser Met Leu Ala Ser Met Val Leu Gly Val Tyr Asn<br>    355                          360                        365 | 1104 |
| ttt tca ata aag aga atc gag gat gct acc tca gta tgc gac caa tcc<br>Phe Ser Ile Lys Arg Ile Glu Asp Ala Thr Ser Val Cys Asp Gln Ser<br>370                        375                        380 | 1152 |
| gag gag aaa agt tcg tcg tgg tgg gtt cct aaa caa gtt tca tcg att<br>Glu Glu Lys Ser Ser Ser Trp Trp Val Pro Lys Gln Val Ser Ser Ile<br>385                        390                        395                        400 | 1200 |
| aac tca ggc ttc aac acc ttc atc tgc cgg gtt cga gtt tgg gtg cag<br>Asn Ser Gly Phe Asn Thr Phe Ile Cys Arg Val Arg Val Trp Val Gln<br>                405                          410                        415 | 1248 |
| ata ttt ttc ggt gtg tta atg atc att gtc ttc act tac ttt cta aac<br>Ile Phe Phe Gly Val Leu Met Ile Ile Val Phe Thr Tyr Phe Leu Asn<br>            420                        425                        430 | 1296 |
| aaa cga tca tca ggt acg aag cag aca atg ccg ata agt ttc atc gtt<br>Lys Arg Ser Ser Gly Thr Lys Gln Thr Met Pro Ile Ser Phe Ile Val<br>        435                        440                        445 | 1344 |
| ctt ttc ctc ggt ata ttt tgc ggt gta tcg ggt aaa ttg tgt gtg gac<br>Leu Phe Leu Gly Ile Phe Cys Gly Val Ser Gly Lys Leu Cys Val Asp<br>    450                          455                        460 | 1392 |
| aca ttg ggc ggt gat ggc aaa ctc tgg cta ata gtt tgg gaa gtg ttt<br>Thr Leu Gly Gly Asp Gly Lys Leu Trp Leu Ile Val Trp Glu Val Phe<br>465                        470                        475                        480 | 1440 |

```
tgc ctt ttg caa ttc gtt gca aat gtc ttc aca ttg gct ttg tat ggt      1488
Cys Leu Leu Gln Phe Val Ala Asn Val Phe Thr Leu Ala Leu Tyr Gly
            485                 490                 495 cta atg ttc ggt cct ata aac gtg act caa gag acc aga tcg aac cgt      1536
Leu Met Phe Gly Pro Ile Asn Val Thr Gln Glu Thr Arg Ser Asn Arg
            500                 505                 510 tgt aac agt atg ttt cca tat tgg gca agg cgc agt gtc gtg tat gtg      1584
Cys Asn Ser Met Phe Pro Tyr Trp Ala Arg Arg Ser Val Val Tyr Val
            515                 520                 525 gtg att ctg ttt gtt ctt cca gtc ata aac ggt ctt ttg cca ttt gca      1632
Val Ile Leu Phe Val Leu Pro Val Ile Asn Gly Leu Leu Pro Phe Ala
        530                 535                 540 aca ttt ggt gaa tgg aga gac ttc gct atg tat cac ctt cat ggt ggg      1680
Thr Phe Gly Glu Trp Arg Asp Phe Ala Met Tyr His Leu His Gly Gly
545                 550                 555                 560 tct gac tat gct tga                                                  1695
Ser Asp Tyr Ala <210> SEQ ID NO 18
<211> LENGTH: 564
<212> TYPE: PRT
<213> ORGANISM: Arabidopsis thaliana

<400> SEQUENCE: 18

Met Glu Ala Leu Leu Pro Pro Ser Pro Gln Asn Gln Ile
1               5                   10              15

Thr Asn Pro Ala Asn Ser Lys Pro Asn His Gln Ser Gly Asp Val His
            20                  25                  30

Lys Asp Glu Thr Met Met Met Lys Lys Lys Asp Thr Asn Pro Ser
        35                  40                  45

Asn Leu Glu Lys Arg Lys Leu Lys Gly Lys Lys Lys Glu Ile Met Asp
    50                  55                  60

Asn Asp Glu Ala Ser Ser Ser Tyr Cys Ser Thr Ser Thr Ser Asn
65                  70                  75                  80

Ser Asn Ser Thr Lys Arg Val Thr Arg Val Val His Arg Leu Arg Asn
                85                  90                  95

Pro Met Arg Leu Gly Met Ala Arg Arg Ser Val Gly Glu Arg Gln Ala
            100                 105                 110

Glu Lys Leu Ala Lys Pro Leu Gly Phe Ser Leu Ala Ala Phe Ala Asn
        115                 120                 125

Met Val Ile Ala Arg Lys Asn Ala Ala Gly Gln Asn Val Tyr Val Asp
    130                 135                 140

Asp Leu Val Glu Ile Phe Ala Thr Leu Val Glu Glu Ser Leu Ala Asn
145                 150                 155                 160

Val Tyr Gly Asn Lys Leu Gly Ser Phe Ala Thr Asn Phe Glu Gln Thr
                165                 170                 175

Phe Ser Ser Thr Leu Lys Ile Leu Lys Leu Thr Asn Glu Cys Ala Asn
            180                 185                 190

Pro His Gln Ser Asn Asn Asn Asp Gly Gly Ser Cys Asn Leu Asp Arg
        195                 200                 205

Ser Thr Ile Asp Gly Cys Ser Asp Thr Glu Leu Phe Glu Arg Glu Thr
    210                 215                 220

Ser Ser Ala Thr Ser Ala Tyr Glu Val Met Gln Gly Ser Ala Thr Ala
225                 230                 235                 240

Thr Ser Leu Met Asn Glu Leu Ala Leu Phe Glu Glu Thr Leu Gln Leu
                245                 250                 255
```

-continued

```
Ser Cys Val Pro Pro Arg Ser Ser Ala Met Ala Leu Thr Thr Asp Glu
            260                 265                 270

Arg Phe Leu Lys Glu Gln Thr Arg Ala Asn Asp Leu Lys Thr Val Glu
    275                 280                 285

Ile Gly Leu Gln Ile Arg Glu Leu Arg Cys Lys Glu Thr Ala Leu Gly
290                 295                 300

Leu Lys Phe Glu Ser Asn Asn Leu Gly Lys Ala Ala Leu Glu Leu Asp
305                 310                 315                 320

Val Ser Lys Ala Ala Phe Arg Ala Glu Lys Phe Lys Thr Glu Leu Glu
                325                 330                 335

Asp Thr Arg Lys Glu Glu Met Val Thr Arg Ile Met Asp Trp Leu Leu
            340                 345                 350

Val Ser Val Phe Ser Met Leu Ala Ser Met Val Leu Gly Val Tyr Asn
        355                 360                 365

Phe Ser Ile Lys Arg Ile Glu Asp Ala Thr Ser Val Cys Asp Gln Ser
    370                 375                 380

Glu Glu Lys Ser Ser Ser Trp Trp Val Pro Lys Gln Val Ser Ser Ile
385                 390                 395                 400

Asn Ser Gly Phe Asn Thr Phe Ile Cys Arg Val Arg Val Trp Val Gln
                405                 410                 415

Ile Phe Phe Gly Val Leu Met Ile Ile Val Phe Thr Tyr Phe Leu Asn
            420                 425                 430

Lys Arg Ser Ser Gly Thr Lys Gln Thr Met Pro Ile Ser Phe Ile Val
        435                 440                 445

Leu Phe Leu Gly Ile Phe Cys Gly Val Ser Gly Lys Leu Cys Val Asp
    450                 455                 460

Thr Leu Gly Gly Asp Gly Lys Leu Trp Leu Ile Val Trp Glu Val Phe
465                 470                 475                 480

Cys Leu Leu Gln Phe Val Ala Asn Val Phe Thr Leu Ala Leu Tyr Gly
                485                 490                 495

Leu Met Phe Gly Pro Ile Asn Val Thr Gln Glu Thr Arg Ser Asn Arg
            500                 505                 510

Cys Asn Ser Met Phe Pro Tyr Trp Ala Arg Arg Ser Val Val Tyr Val
        515                 520                 525

Val Ile Leu Phe Val Leu Pro Val Ile Asn Gly Leu Leu Pro Phe Ala
    530                 535                 540

Thr Phe Gly Glu Trp Arg Asp Phe Ala Met Tyr His Leu His Gly Gly
545                 550                 555                 560

Ser Asp Tyr Ala
```

```
<210> SEQ ID NO 19
<211> LENGTH: 321
<212> TYPE: DNA
<213> ORGANISM: Oryza sativa
<220> FEATURE:
<221> NAME/KEY: CDS
<222> LOCATION: (1)..(321)
<223> OTHER INFORMATION: coding for Oryza sativa, Plant disease
      resistance polyprotein-like [gb XM_465297]

<400> SEQUENCE: 19 atg ggg aag aaa agg aaa ggg gag gga gtc ctc acc gga ggg gac ggc      48
Met Gly Lys Lys Arg Lys Gly Glu Gly Val Leu Thr Gly Gly Asp Gly
1               5                   10                  15 ggc gtc cgg cga cga gga acg acg gag gga ggt cga cac gcg gcg gac      96
Gly Val Arg Arg Arg Gly Thr Thr Glu Gly Gly Arg His Ala Ala Asp
            20                  25                  30
```

```
ggc gac cgg gac gac cta aag agc gaa aag aaa gag gtt aga gag gaa    144
Gly Asp Arg Asp Asp Leu Lys Ser Glu Lys Lys Glu Val Arg Glu Glu
         35                  40                  45 gag agg ggc cat agg aga cgg gaa tgc cgg ccg aaa gcg gcg gac atg    192
Glu Arg Gly His Arg Arg Arg Glu Cys Arg Pro Lys Ala Ala Asp Met
 50                  55                  60 gcg acc ctc acc tac gca cga tgg gaa tgg cgc tcc ggc gac gaa cct    240
Ala Thr Leu Thr Tyr Ala Arg Trp Glu Trp Arg Ser Gly Asp Glu Pro
 65                  70                  75                  80 cga cga agg agg ggt gga cgg ggt gga tct cgg cca cgc gaa ccc gac    288
Arg Arg Arg Arg Gly Gly Arg Gly Gly Ser Arg Pro Arg Glu Pro Asp
                 85                  90                  95 ggc ggc gac ggc gcg gtg cgg cgg cga gcc tag                         321
Gly Gly Asp Gly Ala Val Arg Arg Arg Ala
            100                 105

<210> SEQ ID NO 20
<211> LENGTH: 106
<212> TYPE: PRT
<213> ORGANISM: Oryza sativa

<400> SEQUENCE: 20

Met Gly Lys Lys Arg Lys Gly Glu Gly Val Leu Thr Gly Gly Asp Gly
 1               5                  10                  15

Gly Val Arg Arg Arg Gly Thr Thr Glu Gly Gly Arg His Ala Ala Asp
             20                  25                  30

Gly Asp Arg Asp Asp Leu Lys Ser Glu Lys Lys Glu Val Arg Glu Glu
         35                  40                  45

Glu Arg Gly His Arg Arg Arg Glu Cys Arg Pro Lys Ala Ala Asp Met
 50                  55                  60

Ala Thr Leu Thr Tyr Ala Arg Trp Glu Trp Arg Ser Gly Asp Glu Pro
 65                  70                  75                  80

Arg Arg Arg Arg Gly Gly Arg Gly Gly Ser Arg Pro Arg Glu Pro Asp
                 85                  90                  95

Gly Gly Asp Gly Ala Val Arg Arg Arg Ala
            100                 105

<210> SEQ ID NO 21
<211> LENGTH: 714
<212> TYPE: DNA
<213> ORGANISM: Saccharomyces cerevisiae
<220> FEATURE:
<221> NAME/KEY: CDS
<222> LOCATION: (1)..(714)
<223> OTHER INFORMATION: coding for Saccharomyces cerevisiae homing
      endonuclease I-SceI

<400> SEQUENCE: 21 atg cat atg aaa aac atc aaa aaa aac cag gta atg aac ctc ggt ccg     48
Met His Met Lys Asn Ile Lys Lys Asn Gln Val Met Asn Leu Gly Pro
 1               5                  10                  15 aac tct aaa ctg ctg aaa gaa tac aaa tcc cag ctg atc gaa ctg aac     96
Asn Ser Lys Leu Leu Lys Glu Tyr Lys Ser Gln Leu Ile Glu Leu Asn
             20                  25                  30 atc gaa cag ttc gaa gca ggt atc ggt ctg atc ctg ggt gat gct tac    144
Ile Glu Gln Phe Glu Ala Gly Ile Gly Leu Ile Leu Gly Asp Ala Tyr
         35                  40                  45 atc cgt tct cgt gat gaa ggt aaa acc tac tgt atg cag ttc gag tgg    192
Ile Arg Ser Arg Asp Glu Gly Lys Thr Tyr Cys Met Gln Phe Glu Trp
 50                  55                  60 aaa aac aaa gca tac atg gac cac gta tgt ctg ctg tac gat cag tgg    240
Lys Asn Lys Ala Tyr Met Asp His Val Cys Leu Leu Tyr Asp Gln Trp
```

```
                65                  70                  75                  80 gta ctg tcc ccg ccg cac aaa aaa gaa cgt gtt aac cac ctg ggt aac        288
Val Leu Ser Pro Pro His Lys Lys Glu Arg Val Asn His Leu Gly Asn
                    85                  90                  95 ctg gta atc acc tgg ggc gcc cag act ttc aaa cac caa gct ttc aac        336
Leu Val Ile Thr Trp Gly Ala Gln Thr Phe Lys His Gln Ala Phe Asn
                    100                 105                 110 aaa ctg gct aac ctg ttc atc gtt aac aac aaa aaa acc atc ccg aac        384
Lys Leu Ala Asn Leu Phe Ile Val Asn Asn Lys Lys Thr Ile Pro Asn
                    115                 120                 125 aac ctg gtt gaa aac tac ctg acc ccg atg tct ctg gca tac tgg ttc        432
Asn Leu Val Glu Asn Tyr Leu Thr Pro Met Ser Leu Ala Tyr Trp Phe
                    130                 135                 140 atg gat gat ggt ggt aaa tgg gat tac aac aaa aac tct acc aac aaa        480
Met Asp Asp Gly Gly Lys Trp Asp Tyr Asn Lys Asn Ser Thr Asn Lys
145                 150                 155                 160 tcg atc gta ctg aac acc cag tct ttc act ttc gaa gaa gta gaa tac        528
Ser Ile Val Leu Asn Thr Gln Ser Phe Thr Phe Glu Glu Val Glu Tyr
                    165                 170                 175 ctg gtt aag ggt ctg cgt aac aaa ttc caa ctg aac tgt tac gta aaa        576
Leu Val Lys Gly Leu Arg Asn Lys Phe Gln Leu Asn Cys Tyr Val Lys
                    180                 185                 190 atc aac aaa aac aaa ccg atc atc tac atc gat tct atg tct tac ctg        624
Ile Asn Lys Asn Lys Pro Ile Ile Tyr Ile Asp Ser Met Ser Tyr Leu
                    195                 200                 205 atc ttc tac aac ctg atc aaa ccg tac ctg atc ccg cag atg atg tac        672
Ile Phe Tyr Asn Leu Ile Lys Pro Tyr Leu Ile Pro Gln Met Met Tyr
                    210                 215                 220 aaa ctg ccg aac act atc tcc tcc gaa act ttc ctg aaa taa              714
Lys Leu Pro Asn Thr Ile Ser Ser Glu Thr Phe Leu Lys
225                 230                 235

<210> SEQ ID NO 22
<211> LENGTH: 237
<212> TYPE: PRT
<213> ORGANISM: Saccharomyces cerevisiae

<400> SEQUENCE: 22

Met His Met Lys Asn Ile Lys Lys Asn Gln Val Met Asn Leu Gly Pro
1               5                   10                  15

Asn Ser Lys Leu Leu Lys Glu Tyr Lys Ser Gln Leu Ile Glu Leu Asn
                20                  25                  30

Ile Glu Gln Phe Glu Ala Gly Ile Gly Leu Ile Leu Gly Asp Ala Tyr
            35                  40                  45

Ile Arg Ser Arg Asp Glu Gly Lys Thr Tyr Cys Met Gln Phe Glu Trp
        50                  55                  60

Lys Asn Lys Ala Tyr Met Asp His Val Cys Leu Leu Tyr Asp Gln Trp
65                  70                  75                  80

Val Leu Ser Pro Pro His Lys Lys Glu Arg Val Asn His Leu Gly Asn
                85                  90                  95

Leu Val Ile Thr Trp Gly Ala Gln Thr Phe Lys His Gln Ala Phe Asn
                100                 105                 110

Lys Leu Ala Asn Leu Phe Ile Val Asn Asn Lys Lys Thr Ile Pro Asn
                115                 120                 125

Asn Leu Val Glu Asn Tyr Leu Thr Pro Met Ser Leu Ala Tyr Trp Phe
                130                 135                 140

Met Asp Asp Gly Gly Lys Trp Asp Tyr Asn Lys Asn Ser Thr Asn Lys
145                 150                 155                 160
```

```
Ser Ile Val Leu Asn Thr Gln Ser Phe Thr Phe Glu Glu Val Glu Tyr
            165                 170                 175

Leu Val Lys Gly Leu Arg Asn Lys Phe Gln Leu Asn Cys Tyr Val Lys
        180                 185                 190

Ile Asn Lys Asn Lys Pro Ile Ile Tyr Ile Asp Ser Met Ser Tyr Leu
        195                 200                 205

Ile Phe Tyr Asn Leu Ile Lys Pro Tyr Leu Ile Pro Gln Met Met Tyr
        210                 215                 220

Lys Leu Pro Asn Thr Ile Ser Ser Glu Thr Phe Leu Lys
225                 230                 235

<210> SEQ ID NO 23
<211> LENGTH: 897
<212> TYPE: DNA
<213> ORGANISM: Artificial sequence
<220> FEATURE:
<223> OTHER INFORMATION: encoding Saccharomyces cerevisiae himing
      endonuclease I-SceI comprising an intron
<220> FEATURE:
<221> NAME/KEY: misc_feature
<222> LOCATION: (1)..(897)
<223> OTHER INFORMATION: coding for Saccharomyces cerevisiae homing
      endonuclease I-SceI

<400> SEQUENCE: 23
atgaaaaaca tcaaaaaaaa ccaggtaatg aacctgggtc cgaactctaa actgctgaaa      60
gaatacaaat cccagctgat cgaactgaac atcgaacagt tcgaagcagg tatcggtctg     120
atcctgggtg atgcttacat ccgttctcgt gatgaaggta aaacctactg tatgcagttc    180
gagtggaaaa acaaagcata catggaccac gtatgtctgc tgtacgatca gtgggtactg    240
tccccgccgc acaaaaaaga acgtgttaac cacctgggta acctggtaat cacctggggc    300
gcccagactt tcaaacacca agctttcaac aaactggcta gcctgttcat cgttaacaac    360
aaaaaaacca tcccgaacaa cctggttgaa aactacctga cccgatgtc tctggcatac     420 tggttcatgg atgatggtgg taaatgggat tacaacaaaa actctaccaa caaatcgatc    480
gtactgaaca cccagtcttt cactttcgaa gaagtagaat acctggttaa gggtctgcgt    540
aacaaattcc aactgaactg ttacgtaagt ttctgcttct acctttgata tatatataat    600
aattatcatt aattagtagt aatataatat ttcaaatatt tttttcaaaa taaaagaatg    660
tagtatatag caattgcttt tctgtagttt ataagtgtgt atattttaat ttataacttt    720
tctaatatat gaccaaaatt tgttgatgtg caggtaaaaa tcaacaaaaa caaaccgatc    780
atctacatcg attctatgtc ttacctgatc ttctacaacc tgatcaaacc gtacctgatc    840
ccgcagatga tgtacaaact gccgaacact atctcctccg aaactttcct gaaataa      897

<210> SEQ ID NO 24
<211> LENGTH: 21
<212> TYPE: DNA
<213> ORGANISM: Artificial sequence
<220> FEATURE:
<223> OTHER INFORMATION: oligonucleotide primer

<400> SEQUENCE: 24
atcccgggcg gactgtcgtg g                                               21

<210> SEQ ID NO 25
<211> LENGTH: 21
<212> TYPE: DNA
<213> ORGANISM: Artificial sequence
<220> FEATURE:
<223> OTHER INFORMATION: oligonucleotide primer
```

```
<400> SEQUENCE: 25
gcgagctcgg cacgcaactg c                                              21

<210> SEQ ID NO 26
<211> LENGTH: 21
<212> TYPE: DNA
<213> ORGANISM: Artificial sequence
<220> FEATURE:
<223> OTHER INFORMATION: oligonucleotide primer

<400> SEQUENCE: 26
atcccgggct tcgggagttt a                                              21

<210> SEQ ID NO 27
<211> LENGTH: 21
<212> TYPE: DNA
<213> ORGANISM: Artificial sequence
<220> FEATURE:
<223> OTHER INFORMATION: oligonucleotide primer

<400> SEQUENCE: 27
ggcgttaacc ttgggtgcac a                                              21

<210> SEQ ID NO 28
<211> LENGTH: 21
<212> TYPE: DNA
<213> ORGANISM: Artificial sequence
<220> FEATURE:
<223> OTHER INFORMATION: oligonucleotide primer

<400> SEQUENCE: 28
aaaatcaaaa ccttctcttc t                                              21

<210> SEQ ID NO 29
<211> LENGTH: 21
<212> TYPE: DNA
<213> ORGANISM: Artificial sequence
<220> FEATURE:
<223> OTHER INFORMATION: oligonucleotide primer

<400> SEQUENCE: 29
caagttaaca ttttctgtt t                                               21

<210> SEQ ID NO 30
<211> LENGTH: 21
<212> TYPE: DNA
<213> ORGANISM: Artificial sequence
<220> FEATURE:
<223> OTHER INFORMATION: oligonucleotide primer

<400> SEQUENCE: 30
atgccgccgc cgccgagatg c                                              21

<210> SEQ ID NO 31
<211> LENGTH: 21
<212> TYPE: DNA
<213> ORGANISM: Artificial sequence
<220> FEATURE:
<223> OTHER INFORMATION: oligonucleotide primer

<400> SEQUENCE: 31
tcattgcaag ctatcaaaga a                                              21

<210> SEQ ID NO 32
<211> LENGTH: 21
```

```
<212> TYPE: DNA
<213> ORGANISM: Artificial sequence
<220> FEATURE:
<223> OTHER INFORMATION: oligonucleotide primer

<400> SEQUENCE: 32
atggcccggc tgctactctc c                                              21

<210> SEQ ID NO 33
<211> LENGTH: 21
<212> TYPE: DNA
<213> ORGANISM: Artificial sequence
<220> FEATURE:
<223> OTHER INFORMATION: oligonucleotide primer

<400> SEQUENCE: 33
ttagttagca gggtcggtct g                                              21

<210> SEQ ID NO 34
<211> LENGTH: 21
<212> TYPE: DNA
<213> ORGANISM: Artificial sequence
<220> FEATURE:
<223> OTHER INFORMATION: oligonucleotide primer

<400> SEQUENCE: 34
atggataaca cgttggtggc a                                              21

<210> SEQ ID NO 35
<211> LENGTH: 21
<212> TYPE: DNA
<213> ORGANISM: Artificial sequence
<220> FEATURE:
<223> OTHER INFORMATION: oligonucleotide primer

<400> SEQUENCE: 35
tcagttgtca tcgacttctg a                                              21

<210> SEQ ID NO 36
<211> LENGTH: 21
<212> TYPE: DNA
<213> ORGANISM: Artificial sequence
<220> FEATURE:
<223> OTHER INFORMATION: oligonucleotide primer

<400> SEQUENCE: 36
atggaagccc tcctcctccc t                                              21

<210> SEQ ID NO 37
<211> LENGTH: 21
<212> TYPE: DNA
<213> ORGANISM: Artificial sequence
<220> FEATURE:
<223> OTHER INFORMATION: oligonucleotide primer

<400> SEQUENCE: 37
tcaagcatag tcagacccac c                                              21

<210> SEQ ID NO 38
<211> LENGTH: 22
<212> TYPE: DNA
<213> ORGANISM: Artificial sequence
<220> FEATURE:
<223> OTHER INFORMATION: oligonucleotide primer

<400> SEQUENCE: 38
atggggaaga aaaggaaagg gg                                             22
```

<210> SEQ ID NO 39
<211> LENGTH: 22
<212> TYPE: DNA
<213> ORGANISM: Artificial sequence
<220> FEATURE:
<223> OTHER INFORMATION: oligonucleotide primer

<400> SEQUENCE: 39
ctaggctcgc cgccgcaccg cg                                              22

<210> SEQ ID NO 40
<211> LENGTH: 21
<212> TYPE: DNA
<213> ORGANISM: Artificial sequence
<220> FEATURE:
<223> OTHER INFORMATION: oligonucleotide primer

<400> SEQUENCE: 40
atgcatatga aaacatcaa a                                                21

<210> SEQ ID NO 41
<211> LENGTH: 21
<212> TYPE: DNA
<213> ORGANISM: Artificial sequence
<220> FEATURE:
<223> OTHER INFORMATION: oligonucleotide primer

<400> SEQUENCE: 41
ttatttcagg aaagtttcgg a                                               21

<210> SEQ ID NO 42
<211> LENGTH: 594
<212> TYPE: DNA
<213> ORGANISM: Hordeum vulgare
<220> FEATURE:
<221> NAME/KEY: CDS
<222> LOCATION: (1)..(594)
<223> OTHER INFORMATION: Nucleotide sequence encoding HvRACB (RACB, a
      GTPase from barley)

<400> SEQUENCE: 42

| atg | agc | gcg | tcc | agg | ttc | ata | aag | tgc | gtc | acc | gtg | ggg | gac | ggc | gcc | 48 |
| Met | Ser | Ala | Ser | Arg | Phe | Ile | Lys | Cys | Val | Thr | Val | Gly | Asp | Gly | Ala | |
| 1 | | | | 5 | | | | | 10 | | | | | 15 | | |

| gtc | ggc | aag | acc | tgc | atg | ctc | atc | tcc | tac | acc | tcc | aac | acc | ttc | ccc | 96 |
| Val | Gly | Lys | Thr | Cys | Met | Leu | Ile | Ser | Tyr | Thr | Ser | Asn | Thr | Phe | Pro | |
| | | | 20 | | | | | 25 | | | | | 30 | | | |

| acc | gac | tat | gtg | ccc | acg | gtg | ttt | gac | aac | ttc | agt | gct | aat | gtt | gtg | 144 |
| Thr | Asp | Tyr | Val | Pro | Thr | Val | Phe | Asp | Asn | Phe | Ser | Ala | Asn | Val | Val | |
| | | 35 | | | | | 40 | | | | | 45 | | | | |

| gtt | gat | ggc | aac | act | gtc | aac | ctt | ggg | cta | tgg | gat | act | gca | ggt | cag | 192 |
| Val | Asp | Gly | Asn | Thr | Val | Asn | Leu | Gly | Leu | Trp | Asp | Thr | Ala | Gly | Gln | |
| 50 | | | | | 55 | | | | | 60 | | | | | | |

| gaa | gac | tac | aac | aga | ctg | aga | ccg | ctg | agt | tat | cgt | gga | gct | gat | gtc | 240 |
| Glu | Asp | Tyr | Asn | Arg | Leu | Arg | Pro | Leu | Ser | Tyr | Arg | Gly | Ala | Asp | Val | |
| 65 | | | | 70 | | | | | 75 | | | | | 80 | | |

| ttc | ctt | ctg | gcc | ttc | tcg | ctt | atc | agc | aag | gct | agc | tat | gag | aat | gtt | 288 |
| Phe | Leu | Leu | Ala | Phe | Ser | Leu | Ile | Ser | Lys | Ala | Ser | Tyr | Glu | Asn | Val | |
| | | | | 85 | | | | | 90 | | | | | 95 | | |

| tca | aag | aag | tgg | ata | cct | gaa | ctg | aag | cat | tat | gca | cca | ggt | gtg | cct | 336 |
| Ser | Lys | Lys | Trp | Ile | Pro | Glu | Leu | Lys | His | Tyr | Ala | Pro | Gly | Val | Pro | |
| | | | 100 | | | | | 105 | | | | | 110 | | | |

| att | atc | ctc | gtg | gga | aca | aag | ctt | gat | ctt | cga | gat | gac | aag | cag | ttc | 384 |
| Ile | Ile | Leu | Val | Gly | Thr | Lys | Leu | Asp | Leu | Arg | Asp | Asp | Lys | Gln | Phe | |

```
                115                  120                   125
ttt gtg gac cat cct ggt gct gtt cct atc act act gct cag ggg gag      432
Phe Val Asp His Pro Gly Ala Val Pro Ile Thr Thr Ala Gln Gly Glu
    130                 135                 140 gaa cta aaa aag tta ata ggc gca ccc tac tac atc gaa tgc agc tcg      480
Glu Leu Lys Lys Leu Ile Gly Ala Pro Tyr Tyr Ile Glu Cys Ser Ser
145                 150                 155                 160 aag acc caa cta aat gtc aag ggt gta ttt gat gcg gca ata aag gtg      528
Lys Thr Gln Leu Asn Val Lys Gly Val Phe Asp Ala Ala Ile Lys Val
                165                 170                 175 gta ctg cag cca cca aag gca aag aag aag aaa aag gcg cag agg ggg      576
Val Leu Gln Pro Pro Lys Ala Lys Lys Lys Lys Ala Gln Arg Gly
        180                 185                 190 gct tgc tcc atc ttg tga                                              594
Ala Cys Ser Ile Leu
        195

<210> SEQ ID NO 43
<211> LENGTH: 197
<212> TYPE: PRT
<213> ORGANISM: Hordeum vulgare

<400> SEQUENCE: 43

Met Ser Ala Ser Arg Phe Ile Lys Cys Val Thr Val Gly Asp Gly Ala
1               5                   10                  15

Val Gly Lys Thr Cys Met Leu Ile Ser Tyr Thr Ser Asn Thr Phe Pro
            20                  25                  30

Thr Asp Tyr Val Pro Thr Val Phe Asp Asn Phe Ser Ala Asn Val Val
        35                  40                  45

Val Asp Gly Asn Thr Val Asn Leu Gly Leu Trp Asp Thr Ala Gly Gln
    50                  55                  60

Glu Asp Tyr Asn Arg Leu Arg Pro Leu Ser Tyr Arg Gly Ala Asp Val
65                  70                  75                  80

Phe Leu Leu Ala Phe Ser Leu Ile Ser Lys Ala Ser Tyr Glu Asn Val
                85                  90                  95

Ser Lys Lys Trp Ile Pro Glu Leu Lys His Tyr Ala Pro Gly Val Pro
            100                 105                 110

Ile Ile Leu Val Gly Thr Lys Leu Asp Leu Arg Asp Asp Lys Gln Phe
        115                 120                 125

Phe Val Asp His Pro Gly Ala Val Pro Ile Thr Thr Ala Gln Gly Glu
    130                 135                 140

Glu Leu Lys Lys Leu Ile Gly Ala Pro Tyr Tyr Ile Glu Cys Ser Ser
145                 150                 155                 160

Lys Thr Gln Leu Asn Val Lys Gly Val Phe Asp Ala Ala Ile Lys Val
                165                 170                 175

Val Leu Gln Pro Pro Lys Ala Lys Lys Lys Lys Ala Gln Arg Gly
            180                 185                 190

Ala Cys Ser Ile Leu
        195

<210> SEQ ID NO 44
<211> LENGTH: 564
<212> TYPE: DNA
<213> ORGANISM: Hordeum vulgare
<220> FEATURE:
<221> NAME/KEY: CDS
<222> LOCATION: (1)..(564)
<223> OTHER INFORMATION: Nucleotide sequence encoding BAX INhibitor1
      (Barley antiapoptotic gene)
```

<400> SEQUENCE: 44

```
atg cgc ttg aat atc ggt gga acc att act aag ctt gga tgg gtt tta     48
Met Arg Leu Asn Ile Gly Gly Thr Ile Thr Lys Leu Gly Trp Val Leu
1               5                   10                  15 agt tta ttg gag cat gtg gtt tct tgt cct cca tat aaa cat aaa ata     96
Ser Leu Leu Glu His Val Val Ser Cys Pro Pro Tyr Lys His Lys Ile
                20                  25                  30 agg ttt tca ctt ctg ctt ctc ttt ggt gtt ctt cat ggg gct tca gtt    144
Arg Phe Ser Leu Leu Leu Leu Phe Gly Val Leu His Gly Ala Ser Val
            35                  40                  45 ggt cca tgt atc aag tcc aca atc gat att gat tca agc atc ctt atc    192
Gly Pro Cys Ile Lys Ser Thr Ile Asp Ile Asp Ser Ser Ile Leu Ile
        50                  55                  60 acc gcg ttc tta gga act gcg gtg ata ttt ttc tgt ttc tcg gca gtg    240
Thr Ala Phe Leu Gly Thr Ala Val Ile Phe Phe Cys Phe Ser Ala Val
65                  70                  75                  80 gca atg ctg gca aga cgc agg gag tat atc tac ctc gga gga ctg ctt    288
Ala Met Leu Ala Arg Arg Arg Glu Tyr Ile Tyr Leu Gly Gly Leu Leu
                85                  90                  95 tcg tct ggc ttt tcc ttg cta acg tgg ctc aag aat tct gat cag ttt    336
Ser Ser Gly Phe Ser Leu Leu Thr Trp Leu Lys Asn Ser Asp Gln Phe
            100                 105                 110 gcc tct gcg aca gtt gag att cag atg tac ctt gga ctc ctg ctc ttc    384
Ala Ser Ala Thr Val Glu Ile Gln Met Tyr Leu Gly Leu Leu Leu Phe
        115                 120                 125 gtg gga tgt ata gtg gtg aac aca cag gag ata ata gag aaa gca cac    432
Val Gly Cys Ile Val Val Asn Thr Gln Glu Ile Ile Glu Lys Ala His
130                 135                 140 tgt ggt gac atg gac tac gcg gta cat tcg ctg atc ctt tac att ggc    480
Cys Gly Asp Met Asp Tyr Ala Val His Ser Leu Ile Leu Tyr Ile Gly
145                 150                 155                 160 ttt gta cgt gtg ttc ctt caa att ctc agt ata atg tgg aat acc tct    528
Phe Val Arg Val Phe Leu Gln Ile Leu Ser Ile Met Trp Asn Thr Ser
                165                 170                 175 gcc gat aga ata aga aga aat aat gaa gaa act tag                    564
Ala Asp Arg Ile Arg Arg Asn Asn Glu Glu Thr
            180                 185
```

<210> SEQ ID NO 45
<211> LENGTH: 187
<212> TYPE: PRT
<213> ORGANISM: Hordeum vulgare

<400> SEQUENCE: 45

```
Met Arg Leu Asn Ile Gly Gly Thr Ile Thr Lys Leu Gly Trp Val Leu
1               5                   10                  15

Ser Leu Leu Glu His Val Val Ser Cys Pro Pro Tyr Lys His Lys Ile
                20                  25                  30

Arg Phe Ser Leu Leu Leu Leu Phe Gly Val Leu His Gly Ala Ser Val
            35                  40                  45

Gly Pro Cys Ile Lys Ser Thr Ile Asp Ile Asp Ser Ser Ile Leu Ile
        50                  55                  60

Thr Ala Phe Leu Gly Thr Ala Val Ile Phe Phe Cys Phe Ser Ala Val
65                  70                  75                  80

Ala Met Leu Ala Arg Arg Arg Glu Tyr Ile Tyr Leu Gly Gly Leu Leu
                85                  90                  95

Ser Ser Gly Phe Ser Leu Leu Thr Trp Leu Lys Asn Ser Asp Gln Phe
            100                 105                 110

Ala Ser Ala Thr Val Glu Ile Gln Met Tyr Leu Gly Leu Leu Leu Phe
```

```
            115                 120                 125
Val Gly Cys Ile Val Val Asn Thr Gln Glu Ile Ile Glu Lys Ala His
        130                 135                 140

Cys Gly Asp Met Asp Tyr Ala Val His Ser Leu Ile Leu Tyr Ile Gly
145                 150                 155                 160

Phe Val Arg Val Phe Leu Gln Ile Leu Ser Ile Met Trp Asn Thr Ser
                165                 170                 175

Ala Asp Arg Ile Arg Arg Asn Asn Glu Glu Thr
            180                 185

<210> SEQ ID NO 46
<211> LENGTH: 375
<212> TYPE: DNA
<213> ORGANISM: Hordeum vulgare
<220> FEATURE:
<221> NAME/KEY: CDS
<222> LOCATION: (1)..(375)
<223> OTHER INFORMATION: Nucleotide sequence encoding HvADF3 (Actin
      Depolymerization Factor 3)

<400> SEQUENCE: 46 atg gct aat gca gca tca gga atg gca gtc cat gat gac tgc aag ctg      48
Met Ala Asn Ala Ala Ser Gly Met Ala Val His Asp Asp Cys Lys Leu
1               5                  10                  15 aaa ttt atg gaa ttg aag acg aaa agg aca cac cgt ttc atc att tac      96
Lys Phe Met Glu Leu Lys Thr Lys Arg Thr His Arg Phe Ile Ile Tyr
            20                  25                  30 aag att gag gag ctg cag aaa caa gtg att gtt gag aaa atc ggt gaa     144
Lys Ile Glu Glu Leu Gln Lys Gln Val Ile Val Glu Lys Ile Gly Glu
        35                  40                  45 ccg ggt caa acc cat gag gac ctt gct gca agt ctt cca gct gat gaa     192
Pro Gly Gln Thr His Glu Asp Leu Ala Ala Ser Leu Pro Ala Asp Glu
    50                  55                  60 tgc cgc tat gcc att ttc gat ttt gat ttt gtc agt tct gag ggt gtc     240
Cys Arg Tyr Ala Ile Phe Asp Phe Asp Phe Val Ser Ser Glu Gly Val
65                  70                  75                  80 cca agg agc agg att ttt ttc gtg gca tgg tct ccg gac aca gca aga     288
Pro Arg Ser Arg Ile Phe Phe Val Ala Trp Ser Pro Asp Thr Ala Arg
                85                  90                  95 aga gaa cta gac gga att cag gtc gag ctt cag gca acc gat cca acc     336
Arg Glu Leu Asp Gly Ile Gln Val Glu Leu Gln Ala Thr Asp Pro Thr
            100                 105                 110 gag atg gat ctt gat gtt ttc aaa agc cga gcc aat tga                 375
Glu Met Asp Leu Asp Val Phe Lys Ser Arg Ala Asn
        115                 120

<210> SEQ ID NO 47
<211> LENGTH: 124
<212> TYPE: PRT
<213> ORGANISM: Hordeum vulgare

<400> SEQUENCE: 47

Met Ala Asn Ala Ala Ser Gly Met Ala Val His Asp Asp Cys Lys Leu
1               5                  10                  15

Lys Phe Met Glu Leu Lys Thr Lys Arg Thr His Arg Phe Ile Ile Tyr
            20                  25                  30

Lys Ile Glu Glu Leu Gln Lys Gln Val Ile Val Glu Lys Ile Gly Glu
        35                  40                  45

Pro Gly Gln Thr His Glu Asp Leu Ala Ala Ser Leu Pro Ala Asp Glu
    50                  55                  60

Cys Arg Tyr Ala Ile Phe Asp Phe Asp Phe Val Ser Ser Glu Gly Val
```

<210> SEQ ID NO 48
<211> LENGTH: 930
<212> TYPE: DNA
<213> ORGANISM: Hordeum vulgare
<220> FEATURE:
<221> NAME/KEY: CDS
<222> LOCATION: (1)..(930)
<223> OTHER INFORMATION: Nucleotide sequence encoding HvSNAP34 (t-SNARE interactor of ROR2, involved in vesicle transport)

<400> SEQUENCE: 48

```
atg agc gcc acc agg ccc tcc ttc ttc ccc tcc aac aac aac agg aac      48
Met Ser Ala Thr Arg Pro Ser Phe Phe Pro Ser Asn Asn Asn Arg Asn
1               5                   10                  15 aag ccc gcc acc cgg aac ccc ttc gac tcc gac tcg gac gac gac ggc      96
Lys Pro Ala Thr Arg Asn Pro Phe Asp Ser Asp Ser Asp Asp Asp Gly
            20                  25                  30 ggc atg gcc cgg cgc ggc ccg gcg cgg gcc tcg tcc gtc ccg acc ccc     144
Gly Met Ala Arg Arg Gly Pro Ala Arg Ala Ser Ser Val Pro Thr Pro
        35                  40                  45 gcc gcg ggg ccg gcc agg gcc tcc tcg gcc ccg atc ccc gcc gac gag     192
Ala Ala Gly Pro Ala Arg Ala Ser Ser Ala Pro Ile Pro Ala Asp Glu
    50                  55                  60 gcg gac cag cgg ggc gcc ctg ttc ggc gcg ggc ccc gcg ccg tcc ggc     240
Ala Asp Gln Arg Gly Ala Leu Phe Gly Ala Gly Pro Ala Pro Ser Gly
65                  70                  75                  80 ttc gcg tcc tcc tcc tcc gcg gcc gcc agg ggc cgg tac agg aac gac     288
Phe Ala Ser Ser Ser Ser Ala Ala Ala Arg Gly Arg Tyr Arg Asn Asp
                85                  90                  95 ttc cgc gac tcg ggc ggc gtg gag gcg cag tcc gtg cag gag ctc gag     336
Phe Arg Asp Ser Gly Gly Val Glu Ala Gln Ser Val Gln Glu Leu Glu
            100                 105                 110 ggc tac gcg gcc tac aag gcc gag gag acc acg cgc cgg gtc gac ggc     384
Gly Tyr Ala Ala Tyr Lys Ala Glu Glu Thr Thr Arg Arg Val Asp Gly
        115                 120                 125 tgc ctc cgg gtc gcc gag gag atg cgg gac acc gcg tca aag acc ctg     432
Cys Leu Arg Val Ala Glu Glu Met Arg Asp Thr Ala Ser Lys Thr Leu
    130                 135                 140 ctc cag gtg cac cag cag ggc cag cag atc agg cgc acc cac gcc atg     480
Leu Gln Val His Gln Gln Gly Gln Gln Ile Arg Arg Thr His Ala Met
145                 150                 155                 160 gcc gtc gac atc gac cag gat ctc tcc agg ggg gaa aag cta cta ggt     528
Ala Val Asp Ile Asp Gln Asp Leu Ser Arg Gly Glu Lys Leu Leu Gly
                165                 170                 175 gat ctt ggt ggt ttg ttt tcc aag aag tgg aag cca aag aag aac ggc     576
Asp Leu Gly Gly Leu Phe Ser Lys Lys Trp Lys Pro Lys Lys Asn Gly
            180                 185                 190 gca atc agg ggc cct atg ctg acc aga gac gat tcc ttc ata cgc aag     624
Ala Ile Arg Gly Pro Met Leu Thr Arg Asp Asp Ser Phe Ile Arg Lys
        195                 200                 205 ggc agc cat atg gag cag agg cat aaa ctg ggg ctg tca gat cgt ccg     672
Gly Ser His Met Glu Gln Arg His Lys Leu Gly Leu Ser Asp Arg Pro
    210                 215                 220
```

```
cat cga tcc aat gca cgc cag ttc cta tct gaa ccc aca tca ggc ctt    720
His Arg Ser Asn Ala Arg Gln Phe Leu Ser Glu Pro Thr Ser Gly Leu
225                 230                 235                 240 gag aaa gtc gag gtg gag aag gca aag cag gat gat ggc ctg tct gac    768
Glu Lys Val Glu Val Glu Lys Ala Lys Gln Asp Asp Gly Leu Ser Asp
            245                 250                 255 ctt agc gac ata ctg aca gag ttg aaa gga atg gcc att gac atg gga    816
Leu Ser Asp Ile Leu Thr Glu Leu Lys Gly Met Ala Ile Asp Met Gly
                260                 265                 270 act gag att gag ggg caa aca aag gat ctt ggt cat gcg gag aag gac    864
Thr Glu Ile Glu Gly Gln Thr Lys Asp Leu Gly His Ala Glu Lys Asp
            275                 280                 285 ttt gac gaa ctt aac tac agg gtc aag ggg gca aac gct cga aca cgt    912
Phe Asp Glu Leu Asn Tyr Arg Val Lys Gly Ala Asn Ala Arg Thr Arg
290                 295                 300 cgc ctg ctt ggc aga tag                                            930
Arg Leu Leu Gly Arg
305

<210> SEQ ID NO 49
<211> LENGTH: 309
<212> TYPE: PRT
<213> ORGANISM: Hordeum vulgare

<400> SEQUENCE: 49

Met Ser Ala Thr Arg Pro Ser Phe Phe Pro Ser Asn Asn Asn Arg Asn
1               5                   10                  15

Lys Pro Ala Thr Arg Asn Pro Phe Asp Ser Asp Ser Asp Asp Asp Gly
            20                  25                  30

Gly Met Ala Arg Arg Gly Pro Ala Arg Ala Ser Ser Val Pro Thr Pro
        35                  40                  45

Ala Ala Gly Pro Ala Arg Ala Ser Ser Ala Pro Ile Pro Ala Asp Glu
    50                  55                  60

Ala Asp Gln Arg Gly Ala Leu Phe Gly Ala Gly Pro Ala Pro Ser Gly
65                  70                  75                  80

Phe Ala Ser Ser Ser Ala Ala Ala Arg Gly Arg Tyr Arg Asn Asp
                85                  90                  95

Phe Arg Asp Ser Gly Gly Val Glu Ala Gln Ser Val Gln Glu Leu Glu
            100                 105                 110

Gly Tyr Ala Ala Tyr Lys Ala Glu Glu Thr Thr Arg Val Asp Gly
        115                 120                 125

Cys Leu Arg Val Ala Glu Glu Met Arg Asp Thr Ala Ser Lys Thr Leu
130                 135                 140

Leu Gln Val His Gln Gln Gly Gln Gln Ile Arg Arg Thr His Ala Met
145                 150                 155                 160

Ala Val Asp Ile Asp Gln Asp Leu Ser Arg Gly Glu Lys Leu Leu Gly
                165                 170                 175

Asp Leu Gly Gly Leu Phe Ser Lys Lys Trp Lys Pro Lys Asn Gly
            180                 185                 190

Ala Ile Arg Gly Pro Met Leu Thr Arg Asp Asp Ser Phe Ile Arg Lys
        195                 200                 205

Gly Ser His Met Glu Gln Arg His Lys Leu Gly Leu Ser Asp Arg Pro
210                 215                 220

His Arg Ser Asn Ala Arg Gln Phe Leu Ser Glu Pro Thr Ser Gly Leu
225                 230                 235                 240

Glu Lys Val Glu Val Glu Lys Ala Lys Gln Asp Asp Gly Leu Ser Asp
            245                 250                 255
```

```
Leu Ser Asp Ile Leu Thr Glu Leu Lys Gly Met Ala Ile Asp Met Gly
            260                 265                 270

Thr Glu Ile Glu Gly Gln Thr Lys Asp Leu Gly His Ala Glu Lys Asp
            275                 280                 285

Phe Asp Glu Leu Asn Tyr Arg Val Lys Gly Ala Asn Ala Arg Thr Arg
            290                 295                 300

Arg Leu Leu Gly Arg
305

<210> SEQ ID NO 50
<211> LENGTH: 957
<212> TYPE: DNA
<213> ORGANISM: Hordeum vulgare
<220> FEATURE:
<221> NAME/KEY: CDS
<222> LOCATION: (1)..(957)
<223> OTHER INFORMATION: Nucleotide sequence encoding HvROR2 (Syntaxin,
      interactor of SNAP34)

<400> SEQUENCE: 50 atg aac aac ctc ttc tcg agc tcg tgg aag cgg gcg ggc gcg ggg ggc       48
Met Asn Asn Leu Phe Ser Ser Ser Trp Lys Arg Ala Gly Ala Gly Gly
1               5                   10                  15 gac ggg gac ctg gag tcg ggc ggc ggc gtg gag atg acg gcg ccg            96
Asp Gly Asp Leu Glu Ser Gly Gly Gly Val Glu Met Thr Ala Pro
            20                  25                  30 ccg ggc gcc gcg gcg ggg gcg agc ctg gac cgc ttc ttc gag gac gtg      144
Pro Gly Ala Ala Ala Gly Ala Ser Leu Asp Arg Phe Phe Glu Asp Val
        35                  40                  45 gag tcg atc aag gac gac ctg cgg gag ctg gag cgg atc cag cgc tcc      192
Glu Ser Ile Lys Asp Asp Leu Arg Glu Leu Glu Arg Ile Gln Arg Ser
 50                  55                  60 ctc cac gac ggc aac gag tcg ggc aag tcg ctc cac gac gcg tcg gcg      240
Leu His Asp Gly Asn Glu Ser Gly Lys Ser Leu His Asp Ala Ser Ala
65                  70                  75                  80 gtg cgc gcg ctc cgc tcc cgc atg gac gcc gac gtg gcc gcc gcc atc      288
Val Arg Ala Leu Arg Ser Arg Met Asp Ala Asp Val Ala Ala Ala Ile
                85                  90                  95 aag aag gcc aag gtg gtg aag ttg cgg ctc gag tcg ctc gac cgc gcc      336
Lys Lys Ala Lys Val Val Lys Leu Arg Leu Glu Ser Leu Asp Arg Ala
            100                 105                 110 aac gcc gcc aac cgg tcc gtg gcc ggg tgc ggg ccg ggg tcg tcc acg      384
Asn Ala Ala Asn Arg Ser Val Ala Gly Cys Gly Pro Gly Ser Ser Thr
        115                 120                 125 gac cgc acc cgc acc tcc gtc gtg gcc ggg ctg cgc aag aag ctg cgg      432
Asp Arg Thr Arg Thr Ser Val Val Ala Gly Leu Arg Lys Lys Leu Arg
    130                 135                 140 gat gcc atg gag tcc ttc tcc tcc ctc cgc tcc cgc atc acc tcc gag      480
Asp Ala Met Glu Ser Phe Ser Ser Leu Arg Ser Arg Ile Thr Ser Glu
145                 150                 155                 160 tac cgg gaa acc gtg gcc cgc cgc tac ttc acg gtg acg ggg tcc cag      528
Tyr Arg Glu Thr Val Ala Arg Arg Tyr Phe Thr Val Thr Gly Ser Gln
                165                 170                 175 ccc gac gag gcc acg ctg gac acg ctg gcg gag acg ggg gag ggg gag      576
Pro Asp Glu Ala Thr Leu Asp Thr Leu Ala Glu Thr Gly Glu Gly Glu
            180                 185                 190 cgg ctc ctg cag cgc gcc atc gcg gag cag cag ggg aga ggg gag gtg      624
Arg Leu Leu Gln Arg Ala Ile Ala Glu Gln Gln Gly Arg Gly Glu Val
        195                 200                 205 ctg ggc gtg gtg gcg gag atc cag gag cgg cac ggc gcc gtg gcg gac      672
Leu Gly Val Val Ala Glu Ile Gln Glu Arg His Gly Ala Val Ala Asp
    210                 215                 220
```

```
ctg gag cgg tcc ctg ctg gag ctg cag cag gtg ttc aac gac atg gcc    720
Leu Glu Arg Ser Leu Leu Glu Leu Gln Gln Val Phe Asn Asp Met Ala
225                 230                 235                 240 gtg ctg gtg gcg gcg cag ggg gag cag ctg gac gac atc gag ggc cac    768
Val Leu Val Ala Ala Gln Gly Glu Gln Leu Asp Asp Ile Glu Gly His
                245                 250                 255 gtc ggg cgg gcg agg tcg ttc gtc gac cgc ggg cgc gag cag ctg cag    816
Val Gly Arg Ala Arg Ser Phe Val Asp Arg Gly Arg Glu Gln Leu Gln
            260                 265                 270 gtg gca cgc aag cac cag aag agc tcc cgc aag tgg acc ttc atc ggc    864
Val Ala Arg Lys His Gln Lys Ser Ser Arg Lys Trp Thr Phe Ile Gly
        275                 280                 285 atc ggc atc ctg ctc gtc gtc atc ctc atc atc gtc atc ccc atc gtg    912
Ile Gly Ile Leu Leu Val Val Ile Leu Ile Ile Val Ile Pro Ile Val
    290                 295                 300 ctc aag aac acc aac aag agc aac aac aac aac agc cag cag tag        957
Leu Lys Asn Thr Asn Lys Ser Asn Asn Asn Asn Ser Gln Gln
305                 310                 315

<210> SEQ ID NO 51
<211> LENGTH: 318
<212> TYPE: PRT
<213> ORGANISM: Hordeum vulgare

<400> SEQUENCE: 51

Met Asn Asn Leu Phe Ser Ser Trp Lys Arg Ala Gly Ala Gly Gly
1               5                   10                  15

Asp Gly Asp Leu Glu Ser Gly Gly Gly Val Glu Met Thr Ala Pro
            20                  25                  30

Pro Gly Ala Ala Gly Ala Ser Leu Asp Arg Phe Phe Glu Asp Val
        35                  40                  45

Glu Ser Ile Lys Asp Asp Leu Arg Glu Leu Glu Arg Ile Gln Arg Ser
    50                  55                  60

Leu His Asp Gly Asn Glu Ser Gly Lys Ser Leu His Asp Ala Ser Ala
65                  70                  75                  80

Val Arg Ala Leu Arg Ser Arg Met Asp Ala Asp Val Ala Ala Ala Ile
                85                  90                  95

Lys Lys Ala Lys Val Val Lys Leu Arg Leu Glu Ser Leu Asp Arg Ala
            100                 105                 110

Asn Ala Ala Asn Arg Ser Val Ala Gly Cys Gly Pro Gly Ser Ser Thr
        115                 120                 125

Asp Arg Thr Arg Thr Ser Val Val Ala Gly Leu Arg Lys Lys Leu Arg
    130                 135                 140

Asp Ala Met Glu Ser Phe Ser Ser Leu Arg Ser Arg Ile Thr Ser Glu
145                 150                 155                 160

Tyr Arg Glu Thr Val Ala Arg Arg Tyr Phe Thr Val Thr Gly Ser Gln
                165                 170                 175

Pro Asp Glu Ala Thr Leu Asp Thr Leu Ala Glu Thr Gly Glu Gly Glu
            180                 185                 190

Arg Leu Leu Gln Arg Ala Ile Ala Glu Gln Gly Arg Gly Glu Val
        195                 200                 205

Leu Gly Val Val Ala Glu Ile Gln Glu Arg His Gly Ala Val Ala Asp
    210                 215                 220

Leu Glu Arg Ser Leu Leu Glu Leu Gln Gln Val Phe Asn Asp Met Ala
225                 230                 235                 240

Val Leu Val Ala Ala Gln Gly Glu Gln Leu Asp Asp Ile Glu Gly His
                245                 250                 255
```

```
Val Gly Arg Ala Arg Ser Phe Val Asp Arg Gly Arg Glu Gln Leu Gln
            260                 265                 270

Val Ala Arg Lys His Gln Lys Ser Ser Arg Lys Trp Thr Phe Ile Gly
        275                 280                 285

Ile Gly Ile Leu Leu Val Val Ile Leu Ile Ile Val Ile Pro Ile Val
        290                 295                 300

Leu Lys Asn Thr Asn Lys Ser Asn Asn Asn Ser Gln Gln
305                 310                 315

<210> SEQ ID NO 52
<211> LENGTH: 945
<212> TYPE: DNA
<213> ORGANISM: Hordeum vulgare
<220> FEATURE:
<221> NAME/KEY: CDS
<222> LOCATION: (1)..(945)
<223> OTHER INFORMATION: Nucleotide sequence encoding HvPOX8.1
      (Peroxidase)

<400> SEQUENCE: 52 atg gcc tct act tcg tcc cta tca gtg gtg ttg ctc ttg tgc ctg gcc      48
Met Ala Ser Thr Ser Ser Leu Ser Val Val Leu Leu Leu Cys Leu Ala
1               5                   10                  15 gtg gcg gcg tcg gcg cag ctg tcg ccg acg ttc tac caa acg acg tgc      96
Val Ala Ala Ser Ala Gln Leu Ser Pro Thr Phe Tyr Gln Thr Thr Cys
                20                  25                  30 ccg aac gct ctg tcc acc atc aag gcc gcc gtg acg gcc gcc gtg aac     144
Pro Asn Ala Leu Ser Thr Ile Lys Ala Ala Val Thr Ala Ala Val Asn
            35                  40                  45 aat gag aac cgc atg ggc gcg tcg ctg ctc cgg ctg cac ttc cac gac     192
Asn Glu Asn Arg Met Gly Ala Ser Leu Leu Arg Leu His Phe His Asp
        50                  55                  60 tgc ttc gtc caa ggt tgt gac gcg tct gtt ctg ctg tct ggc atg gaa     240
Cys Phe Val Gln Gly Cys Asp Ala Ser Val Leu Leu Ser Gly Met Glu
65                  70                  75                  80 caa aac gcg gcg ccg aac gtc atg tcc ctg cga ggc ttc gaa gtc ata     288
Gln Asn Ala Ala Pro Asn Val Met Ser Leu Arg Gly Phe Glu Val Ile
                85                  90                  95 gac agc atc aag gcg aag ctc gag acc atg tgc aag cag acc gtc tcc     336
Asp Ser Ile Lys Ala Lys Leu Glu Thr Met Cys Lys Gln Thr Val Ser
                100                 105                 110 tgc gcc gac atc ctc acc gtc gct gcc cgc gat tcc gtc gtc gcc ttg     384
Cys Ala Asp Ile Leu Thr Val Ala Ala Arg Asp Ser Val Val Ala Leu
            115                 120                 125 gga ggg cca tcg tgg acg gtt ccg cta gga agg agg gac tcc acc aat     432
Gly Gly Pro Ser Trp Thr Val Pro Leu Gly Arg Arg Asp Ser Thr Asn
        130                 135                 140 gca aac gaa gca gcg gcg aac tcc gac cta cct ccc ccg ttc ttc gac     480
Ala Asn Glu Ala Ala Ala Asn Ser Asp Leu Pro Pro Pro Phe Phe Asp
145                 150                 155                 160 ctc gtc aac ctc acc caa tcc ttc ggc gac aag ggc ttc acc gtc acc     528
Leu Val Asn Leu Thr Gln Ser Phe Gly Asp Lys Gly Phe Thr Val Thr
                165                 170                 175 gac atg gtc gcg ctc tcc ggt gcc cac acc atc gga cag gcg cag tgc     576
Asp Met Val Ala Leu Ser Gly Ala His Thr Ile Gly Gln Ala Gln Cys
                180                 185                 190 cag aac ttc agg gat agg ctc tac aac gag act aac atc aac tcc ggc     624
Gln Asn Phe Arg Asp Arg Leu Tyr Asn Glu Thr Asn Ile Asn Ser Gly
            195                 200                 205 ttc gcg acg tcg ctc aag gcc aac tgc ccc cgg ccg acc ggc tcc ggc     672
Phe Ala Thr Ser Leu Lys Ala Asn Cys Pro Arg Pro Thr Gly Ser Gly
```

```
              210                 215                 220
gac cgc aac ctg gcc aat ctg gac gtg tct acc ccg tac tca ttc gac    720
Asp Arg Asn Leu Ala Asn Leu Asp Val Ser Thr Pro Tyr Ser Phe Asp
225                 230                 235                 240 aac gcc tac tac agc aac ctc aag tcc cag aag ggg ctc ctg cac tct    768
Asn Ala Tyr Tyr Ser Asn Leu Lys Ser Gln Lys Gly Leu Leu His Ser
                245                 250                 255 gac cag gtg ctc ttc acc ggc acg ggc ggc acg gac aac atc gtc        816
Asp Gln Val Leu Phe Thr Gly Thr Gly Gly Thr Asp Asn Ile Val
            260                 265                 270 aac aac ttc gcg agc aac cca gct gcg ttc agc ggc gcc ttt gcc tcg    864
Asn Asn Phe Ala Ser Asn Pro Ala Ala Phe Ser Gly Ala Phe Ala Ser
            275                 280                 285 gcc atg gtg aag atg ggg aac ctc agc cca ttg act ggc tct cag ggg    912
Ala Met Val Lys Met Gly Asn Leu Ser Pro Leu Thr Gly Ser Gln Gly
290                 295                 300 cag gtc agg ctg agc tgc tcc aag gtg aat taa                        945
Gln Val Arg Leu Ser Cys Ser Lys Val Asn
305                 310

<210> SEQ ID NO 53
<211> LENGTH: 314
<212> TYPE: PRT
<213> ORGANISM: Hordeum vulgare

<400> SEQUENCE: 53

Met Ala Ser Thr Ser Ser Leu Ser Val Leu Leu Leu Cys Leu Ala
1               5                   10                  15

Val Ala Ala Ser Ala Gln Leu Ser Pro Thr Phe Tyr Gln Thr Thr Cys
                20                  25                  30

Pro Asn Ala Leu Ser Thr Ile Lys Ala Ala Val Thr Ala Ala Val Asn
            35                  40                  45

Asn Glu Asn Arg Met Gly Ala Ser Leu Leu Arg Leu His Phe His Asp
        50                  55                  60

Cys Phe Val Gln Gly Cys Asp Ala Ser Val Leu Leu Ser Gly Met Glu
65                  70                  75                  80

Gln Asn Ala Ala Pro Asn Val Met Ser Leu Arg Gly Phe Glu Val Ile
                85                  90                  95

Asp Ser Ile Lys Ala Lys Leu Glu Thr Met Cys Lys Gln Thr Val Ser
            100                 105                 110

Cys Ala Asp Ile Leu Thr Val Ala Ala Arg Asp Ser Val Val Ala Leu
        115                 120                 125

Gly Gly Pro Ser Trp Thr Val Pro Leu Gly Arg Arg Asp Ser Thr Asn
130                 135                 140

Ala Asn Glu Ala Ala Ala Asn Ser Asp Leu Pro Pro Phe Phe Asp
145                 150                 155                 160

Leu Val Asn Leu Thr Gln Ser Phe Gly Asp Lys Gly Phe Thr Val Thr
                165                 170                 175

Asp Met Val Ala Leu Ser Gly Ala His Thr Ile Gly Gln Ala Gln Cys
            180                 185                 190

Gln Asn Phe Arg Asp Arg Leu Tyr Asn Glu Thr Asn Ile Asn Ser Gly
        195                 200                 205

Phe Ala Thr Ser Leu Lys Ala Asn Cys Pro Arg Pro Thr Gly Ser Gly
    210                 215                 220

Asp Arg Asn Leu Ala Asn Leu Asp Val Ser Thr Pro Tyr Ser Phe Asp
225                 230                 235                 240

Asn Ala Tyr Tyr Ser Asn Leu Lys Ser Gln Lys Gly Leu Leu His Ser
```

-continued

```
                    245                 250                 255
Asp Gln Val Leu Phe Thr Gly Thr Gly Gly Thr Asp Asn Ile Val
            260                 265                 270

Asn Asn Phe Ala Ser Asn Pro Ala Ala Phe Ser Gly Ala Phe Ala Ser
        275                 280                 285

Ala Met Val Lys Met Gly Asn Leu Ser Pro Leu Thr Gly Ser Gln Gly
    290                 295                 300

Gln Val Arg Leu Ser Cys Ser Lys Val Asn
305                 310
```

<210> SEQ ID NO 54
<211> LENGTH: 21
<212> TYPE: DNA
<213> ORGANISM: Artificial sequence
<220> FEATURE:
<223> OTHER INFORMATION: oligonucleotide primer

<400> SEQUENCE: 54
atgagcgcgt ccaggttcat a                                         21

<210> SEQ ID NO 55
<211> LENGTH: 21
<212> TYPE: DNA
<213> ORGANISM: Artificial sequence
<220> FEATURE:
<223> OTHER INFORMATION: oligonucleotide primer

<400> SEQUENCE: 55
tcacaagatg gagcaagccc c                                         21

<210> SEQ ID NO 56
<211> LENGTH: 21
<212> TYPE: DNA
<213> ORGANISM: Artificial sequence
<220> FEATURE:
<223> OTHER INFORMATION: oligonucleotide primer

<400> SEQUENCE: 56
atgcgcttga atatcggtgg a                                         21

<210> SEQ ID NO 57
<211> LENGTH: 21
<212> TYPE: DNA
<213> ORGANISM: Artificial sequence
<220> FEATURE:
<223> OTHER INFORMATION: oligonucleotide primer

<400> SEQUENCE: 57
ctaagtttct tcattatttc t                                         21

<210> SEQ ID NO 58
<211> LENGTH: 21
<212> TYPE: DNA
<213> ORGANISM: Artificial sequence
<220> FEATURE:
<223> OTHER INFORMATION: oligonucleotide primer

<400> SEQUENCE: 58
atggctaatg cagcatcagg a                                         21

<210> SEQ ID NO 59
<211> LENGTH: 21
<212> TYPE: DNA
<213> ORGANISM: Artificial sequence
<220> FEATURE:

<223> OTHER INFORMATION: oligonucleotide primer

<400> SEQUENCE: 59
tcaattggct cggcttttga a                                              21

<210> SEQ ID NO 60
<211> LENGTH: 21
<212> TYPE: DNA
<213> ORGANISM: Artificial sequence
<220> FEATURE:
<223> OTHER INFORMATION: oligonucleotide primer

<400> SEQUENCE: 60
atgagcgcca ccaggccctc c                                              21

<210> SEQ ID NO 61
<211> LENGTH: 21
<212> TYPE: DNA
<213> ORGANISM: Artificial sequence
<220> FEATURE:
<223> OTHER INFORMATION: oligonucleotide primer

<400> SEQUENCE: 61
ctatctgcca agcaggcgac g                                              21

<210> SEQ ID NO 62
<211> LENGTH: 24
<212> TYPE: DNA
<213> ORGANISM: Artificial sequence
<220> FEATURE:
<223> OTHER INFORMATION: oligonucleotide primer

<400> SEQUENCE: 62
atgaacaacc tcttctcgag ctcg                                           24

<210> SEQ ID NO 63
<211> LENGTH: 21
<212> TYPE: DNA
<213> ORGANISM: Artificial sequence
<220> FEATURE:
<223> OTHER INFORMATION: oligonucleotide primer

<400> SEQUENCE: 63
ctactgctgg ctgttgttgt t                                              21

<210> SEQ ID NO 64
<211> LENGTH: 21
<212> TYPE: DNA
<213> ORGANISM: Artificial sequence
<220> FEATURE:
<223> OTHER INFORMATION: oligonucleotide primer

<400> SEQUENCE: 64
atggcctcta cttcgtccct a                                              21

<210> SEQ ID NO 65
<211> LENGTH: 21
<212> TYPE: DNA
<213> ORGANISM: Artificial sequence
<220> FEATURE:
<223> OTHER INFORMATION: oligonucleotide primer

<400> SEQUENCE: 65
ttaattcacc ttggagcagc t                                              21

<210> SEQ ID NO 66

```
<211> LENGTH: 85
<212> TYPE: DNA
<213> ORGANISM: Artificial sequence
<220> FEATURE:
<223> OTHER INFORMATION: Recombination site for CRE recombinase

<400> SEQUENCE: 66
aactctcatc gcttcggata acttcctgtt atccgaaaca tatcactcac tttggtgatt      60
tcaccgtaac tgtctatgat taatg                                           85

<210> SEQ ID NO 67
<211> LENGTH: 48
<212> TYPE: DNA
<213> ORGANISM: Artificial sequence
<220> FEATURE:
<223> OTHER INFORMATION: Recombination site for FLP recombinase

<400> SEQUENCE: 67
gaagttccta ttccgaagtt cctattctct agaaagtata ggaacttc                  48

<210> SEQ ID NO 68
<211> LENGTH: 58
<212> TYPE: DNA
<213> ORGANISM: Artificial sequence
<220> FEATURE:
<223> OTHER INFORMATION: Recombination site for R recombinase

<400> SEQUENCE: 68
cgagatcata tcactgtgga cgttgatgaa agaatacgtt attctttcat caaatcgt       58

<210> SEQ ID NO 69
<211> LENGTH: 23
<212> TYPE: DNA
<213> ORGANISM: Artificial sequence
<220> FEATURE:
<223> OTHER INFORMATION: P-Element transposase recognition sequence

<400> SEQUENCE: 69
ctagatgaaa taacataagg tgg                                             23

<210> SEQ ID NO 70
<211> LENGTH: 39
<212> TYPE: DNA
<213> ORGANISM: Artificial sequence
<220> FEATURE:
<223> OTHER INFORMATION: I-AniI recognition sequence
<220> FEATURE:
<221> NAME/KEY: misc_feature
<222> LOCATION: (25)..(39)
<223> OTHER INFORMATION: N is A, T, C, or G.

<400> SEQUENCE: 70
ttgaggaggt ttctctgtaa ataannnnnn nnnnnnnn                              39

<210> SEQ ID NO 71
<211> LENGTH: 24
<212> TYPE: DNA
<213> ORGANISM: Artificial sequence
<220> FEATURE:
<223> OTHER INFORMATION: I-DdiI recognition site

<400> SEQUENCE: 71 tttttttggtc atccagaagt atat                                           24

<210> SEQ ID NO 72
<211> LENGTH: 30
<212> TYPE: DNA
```

```
<213> ORGANISM: Artificial sequence
<220> FEATURE:
<223> OTHER INFORMATION: I-CvuI recognition site

<400> SEQUENCE: 72
ctgggttcaa aacgtcgtga gacagtttgg                                              30

<210> SEQ ID NO 73
<211> LENGTH: 30
<212> TYPE: DNA
<213> ORGANISM: Artificial sequence
<220> FEATURE:
<223> OTHER INFORMATION: I-CsmI  recognition site

<400> SEQUENCE: 73
gtactagcat ggggtcaaat gtctttctgg                                              30

<210> SEQ ID NO 74
<211> LENGTH: 18
<212> TYPE: DNA
<213> ORGANISM: Artificial sequence
<220> FEATURE:
<223> OTHER INFORMATION: I-CmoeI recognition site

<400> SEQUENCE: 74
tcgtagcagc tcacggtt                                                           18

<210> SEQ ID NO 75
<211> LENGTH: 30
<212> TYPE: DNA
<213> ORGANISM: Artificial sequence
<220> FEATURE:
<223> OTHER INFORMATION: I-CreI  recognition site

<400> SEQUENCE: 75
ctgggttcaa aacgtcgtga gacagtttgg                                              30

<210> SEQ ID NO 76
<211> LENGTH: 30
<212> TYPE: DNA
<213> ORGANISM: Artificial sequence
<220> FEATURE:
<223> OTHER INFORMATION: I-ChuI recognition site

<400> SEQUENCE: 76
gaaggtttgg cacctcgatg tcggctcatc                                              30

<210> SEQ ID NO 77
<211> LENGTH: 23
<212> TYPE: DNA
<213> ORGANISM: Artificial sequence
<220> FEATURE:
<223> OTHER INFORMATION: I-CpaI recognition site

<400> SEQUENCE: 77
cgatcctaag gtagcgaaat tca                                                     23

<210> SEQ ID NO 78
<211> LENGTH: 20
<212> TYPE: DNA
<213> ORGANISM: Artificial sequence
<220> FEATURE:
<223> OTHER INFORMATION: I-CpaII recognition site

<400> SEQUENCE: 78
cccggctaac tctgtgccag                                                         20
```

```
<210> SEQ ID NO 79
<211> LENGTH: 29
<212> TYPE: DNA
<213> ORGANISM: Artificial sequence
<220> FEATURE:
<223> OTHER INFORMATION: I-CeuI recognition site

<400> SEQUENCE: 79
cgtaactata acggtcctaa ggtagcgaa                                    29

<210> SEQ ID NO 80
<211> LENGTH: 30
<212> TYPE: DNA
<213> ORGANISM: Artificial sequence
<220> FEATURE:
<223> OTHER INFORMATION: I-DmoI recognition site

<400> SEQUENCE: 80
atgccttgcc gggtaagttc cggcgcgcat                                   30

<210> SEQ ID NO 81
<211> LENGTH: 30
<212> TYPE: DNA
<213> ORGANISM: Artificial sequence
<220> FEATURE:
<223> OTHER INFORMATION: I-SceI recognition site

<400> SEQUENCE: 81
agttacgcta gggataacag ggtaatatag                                   30

<210> SEQ ID NO 82
<211> LENGTH: 18
<212> TYPE: DNA
<213> ORGANISM: Artificial sequence
<220> FEATURE:
<223> OTHER INFORMATION: "Core" sequence of I-SceI recognition site

<400> SEQUENCE: 82
tagggataac agggtaat                                                18

<210> SEQ ID NO 83
<211> LENGTH: 29
<212> TYPE: DNA
<213> ORGANISM: Artificial sequence
<220> FEATURE:
<223> OTHER INFORMATION: I-SceII recognition site

<400> SEQUENCE: 83
ttttgattct ttggtcaccc tgaagtata                                    29

<210> SEQ ID NO 84
<211> LENGTH: 29
<212> TYPE: DNA
<213> ORGANISM: Artificial sequence
<220> FEATURE:
<223> OTHER INFORMATION: I-SceIII recognition site

<400> SEQUENCE: 84
attggaggtt ttggtaacta tttattacc                                    29

<210> SEQ ID NO 85
<211> LENGTH: 29
<212> TYPE: DNA
<213> ORGANISM: Artificial sequence
<220> FEATURE:
<223> OTHER INFORMATION: I-SceIV recognition site
```

<400> SEQUENCE: 85
tcttttctct tgattagccc taatctacg                              29

<210> SEQ ID NO 86
<211> LENGTH: 24
<212> TYPE: DNA
<213> ORGANISM: Artificial sequence
<220> FEATURE:
<223> OTHER INFORMATION: I-SceV recognition site

<400> SEQUENCE: 86
aataattttc ttcttagtaa tgcc                                   24

<210> SEQ ID NO 87
<211> LENGTH: 24
<212> TYPE: DNA
<213> ORGANISM: Artificial sequence
<220> FEATURE:
<223> OTHER INFORMATION: I-SceVI recognition site

<400> SEQUENCE: 87
gttatttaat gttttagtag ttgg                                   24

<210> SEQ ID NO 88
<211> LENGTH: 28
<212> TYPE: DNA
<213> ORGANISM: Artificial sequence
<220> FEATURE:
<223> OTHER INFORMATION: I-SceVII recognition site

<400> SEQUENCE: 88
tgtcacattg aggtgcacta gttattac                               28

<210> SEQ ID NO 89
<211> LENGTH: 30
<212> TYPE: DNA
<213> ORGANISM: Artificial sequence
<220> FEATURE:
<223> OTHER INFORMATION: PI-SceI recognition site

<400> SEQUENCE: 89
atctatgtcg ggtgcggaga aagaggtaat                             30

<210> SEQ ID NO 90
<211> LENGTH: 24
<212> TYPE: DNA
<213> ORGANISM: Artificial sequence
<220> FEATURE:
<223> OTHER INFORMATION: F-SceI recognition site

<400> SEQUENCE: 90
gatgctgtag gcataggctt ggtt                                   24

<210> SEQ ID NO 91
<211> LENGTH: 20
<212> TYPE: DNA
<213> ORGANISM: Artificial sequence
<220> FEATURE:
<223> OTHER INFORMATION: F-SceII recognition site

<400> SEQUENCE: 91
ctttccgcaa cagtaaaatt                                        20

<210> SEQ ID NO 92
<211> LENGTH: 24
<212> TYPE: DNA

```
<213> ORGANISM: Artificial sequence
<220> FEATURE:
<223> OTHER INFORMATION: I-HmuI recognition site

<400> SEQUENCE: 92
agtaatgagc ctaacgctca gcaa                                          24

<210> SEQ ID NO 93
<211> LENGTH: 63
<212> TYPE: DNA
<213> ORGANISM: Artificial sequence
<220> FEATURE:
<223> OTHER INFORMATION: I-HmuII recognition site
<220> FEATURE:
<221> NAME/KEY: misc_feature
<222> LOCATION: (25)..(63)
<223> OTHER INFORMATION: N is A, T, C, or G.

<400> SEQUENCE: 93
agtaatgagc ctaacgctca acaannnnn nnnnnnnnnn nnnnnnnnnn nnnnnnnnnn      60 nnn                                                                  63

<210> SEQ ID NO 94
<211> LENGTH: 24
<212> TYPE: DNA
<213> ORGANISM: Artificial sequence
<220> FEATURE:
<223> OTHER INFORMATION: I-LlaI recognition site

<400> SEQUENCE: 94
cacatccata accatatcat tttt                                          24

<210> SEQ ID NO 95
<211> LENGTH: 30
<212> TYPE: DNA
<213> ORGANISM: Artificial sequence
<220> FEATURE:
<223> OTHER INFORMATION: I-MsoI recognition site

<400> SEQUENCE: 95
ctgggttcaa aacgtcgtga gacagtttgg                                    30

<210> SEQ ID NO 96
<211> LENGTH: 21
<212> TYPE: DNA
<213> ORGANISM: Artificial sequence
<220> FEATURE:
<223> OTHER INFORMATION: I-NanI recognition site

<400> SEQUENCE: 96
aagtctggtg ccagcacccg c                                             21

<210> SEQ ID NO 97
<211> LENGTH: 21
<212> TYPE: DNA
<213> ORGANISM: Artificial sequence
<220> FEATURE:
<223> OTHER INFORMATION: I-NitI recognition site

<400> SEQUENCE: 97
aagtctggtg ccagcacccg c                                             21

<210> SEQ ID NO 98
<211> LENGTH: 21
<212> TYPE: DNA
<213> ORGANISM: Artificial sequence
<220> FEATURE:
```

<223> OTHER INFORMATION: I-NjaI recognition site

<400> SEQUENCE: 98
aagtctggtg ccagcacccg c                                           21

<210> SEQ ID NO 99
<211> LENGTH: 30
<212> TYPE: DNA
<213> ORGANISM: Artificial sequence
<220> FEATURE:
<223> OTHER INFORMATION: I-PakI recognition site

<400> SEQUENCE: 99
ctgggttcaa aacgtcgtga gacagtttgg                                  30

<210> SEQ ID NO 100
<211> LENGTH: 25
<212> TYPE: DNA
<213> ORGANISM: Artificial sequence
<220> FEATURE:
<223> OTHER INFORMATION: I-PorI recognition site

<400> SEQUENCE: 100
gcgagcccgt aagggtgtgt acggg                                       25

<210> SEQ ID NO 101
<211> LENGTH: 29
<212> TYPE: DNA
<213> ORGANISM: Artificial sequence
<220> FEATURE:
<223> OTHER INFORMATION: I-PpoI recognition site

<400> SEQUENCE: 101
taactatgac tctcttaagg tagccaaat                                   29

<210> SEQ ID NO 102
<211> LENGTH: 28
<212> TYPE: DNA
<213> ORGANISM: Artificial sequence
<220> FEATURE:
<223> OTHER INFORMATION: I-ScaI recognition site

<400> SEQUENCE: 102
tgtcacattg aggtgcacta gttattac                                    28

<210> SEQ ID NO 103
<211> LENGTH: 19
<212> TYPE: DNA
<213> ORGANISM: Artificial sequence
<220> FEATURE:
<223> OTHER INFORMATION: I-Ssp6803I recognition site

<400> SEQUENCE: 103
gtcgggctca tacccgaa                                               19

<210> SEQ ID NO 104
<211> LENGTH: 30
<212> TYPE: DNA
<213> ORGANISM: Artificial sequence
<220> FEATURE:
<223> OTHER INFORMATION: PI-PfuI recognition site

<400> SEQUENCE: 104
gaagatggga ggagggaccg gactcaactt                                  30

<210> SEQ ID NO 105

```
<211> LENGTH: 29
<212> TYPE: DNA
<213> ORGANISM: Artificial sequence
<220> FEATURE:
<223> OTHER INFORMATION: PI-PfuII recognition site

<400> SEQUENCE: 105
acgaatccat gtggagaaga gcctctata                                     29

<210> SEQ ID NO 106
<211> LENGTH: 19
<212> TYPE: DNA
<213> ORGANISM: Artificial sequence
<220> FEATURE:
<223> OTHER INFORMATION: PI-PkoI recognition site

<400> SEQUENCE: 106
gattttagat ccctgtacc                                                19

<210> SEQ ID NO 107
<211> LENGTH: 15
<212> TYPE: DNA
<213> ORGANISM: Artificial sequence
<220> FEATURE:
<223> OTHER INFORMATION: PI-PkoII recognition site

<400> SEQUENCE: 107
cagtactacg gttac                                                    15

<210> SEQ ID NO 108
<211> LENGTH: 30
<212> TYPE: DNA
<213> ORGANISM: Artificial sequence
<220> FEATURE:
<223> OTHER INFORMATION: PI-PspI recognition site

<400> SEQUENCE: 108
aaaatcctgg caaacagcta ttatgggtat                                    30

<210> SEQ ID NO 109
<211> LENGTH: 26
<212> TYPE: DNA
<213> ORGANISM: Artificial sequence
<220> FEATURE:
<223> OTHER INFORMATION: PI-TfuI recognition site

<400> SEQUENCE: 109
tagattttag gtcgctatat ccttcc                                        26

<210> SEQ ID NO 110
<211> LENGTH: 22
<212> TYPE: DNA
<213> ORGANISM: Artificial sequence
<220> FEATURE:
<223> OTHER INFORMATION: PI-TfuII recognition site
<220> FEATURE:
<221> NAME/KEY: misc_feature
<222> LOCATION: (6)..(12)
<223> OTHER INFORMATION: N at positions 6 and 12 is A, T, C, or G.

<400> SEQUENCE: 110
taygcngaya cngacggytt yt                                            22

<210> SEQ ID NO 111
<211> LENGTH: 22
<212> TYPE: DNA
<213> ORGANISM: Artificial sequence
<220> FEATURE:
```

```
<223> OTHER INFORMATION: PI-ThyI recognition site
<220> FEATURE:
<221> NAME/KEY: misc_feature
<222> LOCATION: (6)..(12)
<223> OTHER INFORMATION: N at positions 6 and 12 is A, T, C, or G.

<400> SEQUENCE: 111
taygcngaya cngacggytt yt                                              22

<210> SEQ ID NO 112
<211> LENGTH: 22
<212> TYPE: DNA
<213> ORGANISM: Artificial sequence
<220> FEATURE:
<223> OTHER INFORMATION: PI-TliI recognition site
<220> FEATURE:
<221> NAME/KEY: misc_feature
<222> LOCATION: (6)..(12)
<223> OTHER INFORMATION: N at positions 6 and 12 is A, T, C, or G.

<400> SEQUENCE: 112
taygcngaya cngacggytt yt                                              22

<210> SEQ ID NO 113
<211> LENGTH: 30
<212> TYPE: DNA
<213> ORGANISM: Artificial sequence
<220> FEATURE:
<223> OTHER INFORMATION: PI-TliII recognition site

<400> SEQUENCE: 113
aaattgcttg caaacagcta ttacggctat                                      30

<210> SEQ ID NO 114
<211> LENGTH: 24
<212> TYPE: DNA
<213> ORGANISM: Artificial sequence
<220> FEATURE:
<223> OTHER INFORMATION: I-TevI recognition site

<400> SEQUENCE: 114
agtggtatca acgctcagta gatg                                            24

<210> SEQ ID NO 115
<211> LENGTH: 30
<212> TYPE: DNA
<213> ORGANISM: Artificial sequence
<220> FEATURE:
<223> OTHER INFORMATION: I-TevII recognition site

<400> SEQUENCE: 115
gcttatgagt atgaagtgaa cacgttattc                                      30

<210> SEQ ID NO 116
<211> LENGTH: 38
<212> TYPE: DNA
<213> ORGANISM: Artificial sequence
<220> FEATURE:
<223> OTHER INFORMATION: F-TevI recognition site
<220> FEATURE:
<221> NAME/KEY: misc_feature
<222> LOCATION: (25)..(38)
<223> OTHER INFORMATION: N is A, T, C, or G.

<400> SEQUENCE: 116
gaaacacaag aaatgtttag taaannnnnn nnnnnnnn                             38

<210> SEQ ID NO 117
```

```
<211> LENGTH: 29
<212> TYPE: DNA
<213> ORGANISM: Artificial sequence
<220> FEATURE:
<223> OTHER INFORMATION: F-TevII recognition site

<400> SEQUENCE: 117
tttaatcctc gcttcagata tggcaactg                                    29

<210> SEQ ID NO 118
<211> LENGTH: 24
<212> TYPE: DNA
<213> ORGANISM: Artificial sequence
<220> FEATURE:
<223> OTHER INFORMATION: H-DreI recognition site

<400> SEQUENCE: 118
caaaacgtcg taagttccgg cgcg                                         24

<210> SEQ ID NO 119
<211> LENGTH: 24
<212> TYPE: DNA
<213> ORGANISM: Artificial sequence
<220> FEATURE:
<223> OTHER INFORMATION: I-BasI recognition site

<400> SEQUENCE: 119
agtaatgagc ctaacgctca gcaa                                         24

<210> SEQ ID NO 120
<211> LENGTH: 24
<212> TYPE: DNA
<213> ORGANISM: Artificial sequence
<220> FEATURE:
<223> OTHER INFORMATION: I-BasI recognition site

<400> SEQUENCE: 120
gttaggctca agctgagcat tact                                         24

<210> SEQ ID NO 121
<211> LENGTH: 28
<212> TYPE: DNA
<213> ORGANISM: Artificial sequence
<220> FEATURE:
<223> OTHER INFORMATION: I-BmoI recognition site

<400> SEQUENCE: 121
gagtaagagc ccgtagtaat gacatggc                                     28

<210> SEQ ID NO 122
<211> LENGTH: 19
<212> TYPE: DNA
<213> ORGANISM: Artificial sequence
<220> FEATURE:
<223> OTHER INFORMATION: I-PogI recognition site

<400> SEQUENCE: 122
cttcagtatg ccccgaaac                                               19

<210> SEQ ID NO 123
<211> LENGTH: 20
<212> TYPE: DNA
<213> ORGANISM: Artificial sequence
<220> FEATURE:
<223> OTHER INFORMATION: I-TwoI recognition site

<400> SEQUENCE: 123
```

-continued

```
tcttgcacct acacaatcca                                                  20

<210> SEQ ID NO 124
<211> LENGTH: 22
<212> TYPE: DNA
<213> ORGANISM: Artificial sequence
<220> FEATURE:
<223> OTHER INFORMATION: PI-MgaI recognition site

<400> SEQUENCE: 124
cgtagctgcc cagtatgagt ca                                               22

<210> SEQ ID NO 125
<211> LENGTH: 22
<212> TYPE: DNA
<213> ORGANISM: Artificial sequence
<220> FEATURE:
<223> OTHER INFORMATION: PI-PabI recognition site

<400> SEQUENCE: 125
gggggcagcc agtggtcccg tt                                               22

<210> SEQ ID NO 126
<211> LENGTH: 23
<212> TYPE: DNA
<213> ORGANISM: Artificial sequence
<220> FEATURE:
<223> OTHER INFORMATION: PI-PabII recognition site

<400> SEQUENCE: 126
acccctgtgg agaggagccc ctc                                              23

<210> SEQ ID NO 127
<211> LENGTH: 19
<212> TYPE: PRT
<213> ORGANISM: Artificial sequence
<220> FEATURE:
<223> OTHER INFORMATION: Consensus motif
<220> FEATURE:
<221> NAME/KEY: MISC_FEATURE
<222> LOCATION: (1)..(2)
<223> OTHER INFORMATION: Xaa is Leu, Ile, Val, or Met
<220> FEATURE:
<221> NAME/KEY: MISC_FEATURE
<222> LOCATION: (4)..(4)
<223> OTHER INFORMATION: Xaa is Asn, His, or Ala
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is Gly, Ser, or Ala
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (12)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid

<400> SEQUENCE: 127

Xaa Xaa His Xaa Tyr Gly Xaa Xaa Xaa Xaa Gly Xaa Xaa Xaa Xaa Xaa
1               5                   10                  15

Gly Xaa Ala
```

<210> SEQ ID NO 128
<211> LENGTH: 5
<212> TYPE: DNA
<213> ORGANISM: Artificial sequence
<220> FEATURE:
<223> OTHER INFORMATION: Regulatory protein binding DNA motif

<400> SEQUENCE: 128 cgacg                                                                    5

<210> SEQ ID NO 129
<211> LENGTH: 9
<212> TYPE: DNA
<213> ORGANISM: Artificial sequence
<220> FEATURE:
<223> OTHER INFORMATION: Regulatory protein binding DNA motif

<400> SEQUENCE: 129 catccaacg                                                                9

<210> SEQ ID NO 130
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 130 cctttt                                                                   6

<210> SEQ ID NO 131
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 131 gataaga                                                                  7

<210> SEQ ID NO 132
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 132 tacgta                                                                   6

<210> SEQ ID NO 133
<211> LENGTH: 16
<212> TYPE: DNA
<213> ORGANISM: Artificial sequence
<220> FEATURE:
<223> OTHER INFORMATION: Regulatory protein binding DNA motif

<400> SEQUENCE: 133
acgtaagcgc ttacgt                                                       16

<210> SEQ ID NO 134
<211> LENGTH: 5
<212> TYPE: DNA
<213> ORGANISM: Artificial sequence
<220> FEATURE:
<223> OTHER INFORMATION: Regulatory protein binding DNA motif

```
<400> SEQUENCE: 134 caaca                                                               5

<210> SEQ ID NO 135
<211> LENGTH: 8
<212> TYPE: DNA
<213> ORGANISM: Artificial sequence
<220> FEATURE:
<223> OTHER INFORMATION: Regulatory protein binding DNA motif

<400> SEQUENCE: 135 cgcggatc                                                            8

<210> SEQ ID NO 136
<211> LENGTH: 15
<212> TYPE: DNA
<213> ORGANISM: Artificial sequence
<220> FEATURE:
<223> OTHER INFORMATION: Regulatory protein binding DNA motif

<400> SEQUENCE: 136
attgaccagc tcgcg                                                   15

<210> SEQ ID NO 137
<211> LENGTH: 8
<212> TYPE: DNA
<213> ORGANISM: Artificial sequence
<220> FEATURE:
<223> OTHER INFORMATION: Regulatory protein binding DNA motif

<400> SEQUENCE: 137 aaaaatct                                                            8

<210> SEQ ID NO 138
<211> LENGTH: 9
<212> TYPE: DNA
<213> ORGANISM: Artificial sequence
<220> FEATURE:
<223> OTHER INFORMATION: Regulatory protein binding DNA motif

<400> SEQUENCE: 138 tgaaaaatc                                                           9

<210> SEQ ID NO 139
<211> LENGTH: 13
<212> TYPE: DNA
<213> ORGANISM: Artificial sequence
<220> FEATURE:
<223> OTHER INFORMATION: Regulatory protein binding DNA motif

<400> SEQUENCE: 139
caagacgtga cgt                                                     13

<210> SEQ ID NO 140
<211> LENGTH: 13
<212> TYPE: DNA
<213> ORGANISM: Artificial sequence
<220> FEATURE:
<223> OTHER INFORMATION: Regulatory protein binding DNA motif

<400> SEQUENCE: 140
agacgtgacg taa                                                     13

<210> SEQ ID NO 141
<211> LENGTH: 13
```

```
<212> TYPE: DNA
<213> ORGANISM: Artificial sequence
<220> FEATURE:
<223> OTHER INFORMATION: Regulatory protein binding DNA motif

<400> SEQUENCE: 141
acttacgtca cgt                                                         13

<210> SEQ ID NO 142
<211> LENGTH: 13
<212> TYPE: DNA
<213> ORGANISM: Artificial sequence
<220> FEATURE:
<223> OTHER INFORMATION: Regulatory protein binding DNA motif

<400> SEQUENCE: 142
cgtgacgtaa gta                                                         13

<210> SEQ ID NO 143
<211> LENGTH: 15
<212> TYPE: DNA
<213> ORGANISM: Artificial sequence
<220> FEATURE:
<223> OTHER INFORMATION: Regulatory protein binding DNA motif

<400> SEQUENCE: 143
actgactcgg atact                                                       15

<210> SEQ ID NO 144
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 144 cggatac                                                                 7

<210> SEQ ID NO 145
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 145 ccgaaa                                                                  6

<210> SEQ ID NO 146
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 146 tattct                                                                  6

<210> SEQ ID NO 147
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 147 atagaa                                                                  6
```

<210> SEQ ID NO 148
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 148 ttaatgg                                                                   7

<210> SEQ ID NO 149
<211> LENGTH: 15
<212> TYPE: DNA
<213> ORGANISM: Artificial sequence
<220> FEATURE:
<223> OTHER INFORMATION: Regulatory protein binding DNA motif

<400> SEQUENCE: 149
tttgactagc gaggc                                                          15

<210> SEQ ID NO 150
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 150 tgtaaag                                                                   7

<210> SEQ ID NO 151
<211> LENGTH: 13
<212> TYPE: DNA
<213> ORGANISM: Artificial sequence
<220> FEATURE:
<223> OTHER INFORMATION: Regulatory protein binding DNA motif

<400> SEQUENCE: 151
gcgcgtgacg ctc                                                            13

<210> SEQ ID NO 152
<211> LENGTH: 13
<212> TYPE: DNA
<213> ORGANISM: Artificial sequence
<220> FEATURE:
<223> OTHER INFORMATION: Regulatory protein binding DNA motif

<400> SEQUENCE: 152
cgcggtgacg cca                                                            13

<210> SEQ ID NO 153
<211> LENGTH: 9
<212> TYPE: DNA
<213> ORGANISM: Artificial sequence
<220> FEATURE:
<223> OTHER INFORMATION: Regulatory protein binding DNA motif

<400> SEQUENCE: 153 tgaaaaggc                                                                 9

<210> SEQ ID NO 154
<211> LENGTH: 7
<212> TYPE: DNA
<213> ORGANISM: Artificial sequence
<220> FEATURE:
<223> OTHER INFORMATION: Regulatory protein binding DNA motif

```
<400> SEQUENCE: 154 tatccat                                                            7

<210> SEQ ID NO 155
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 155 tggataa                                                            7

<210> SEQ ID NO 156
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 156 gataaat                                                            7

<210> SEQ ID NO 157
<211> LENGTH: 5
<212> TYPE: DNA
<213> ORGANISM: Artificial sequence
<220> FEATURE:
<223> OTHER INFORMATION: Regulatory protein binding DNA motif

<400> SEQUENCE: 157 ccaat                                                              5

<210> SEQ ID NO 158
<211> LENGTH: 7
<212> TYPE: DNA
<213> ORGANISM: Artificial sequence
<220> FEATURE:
<223> OTHER INFORMATION: Regulatory protein binding DNA motif

<400> SEQUENCE: 158 acactag                                                            7

<210> SEQ ID NO 159
<211> LENGTH: 6
<212> TYPE: DNA
<213> ORGANISM: Artificial sequence
<220> FEATURE:
<223> OTHER INFORMATION: Regulatory protein binding DNA motif

<400> SEQUENCE: 159 taacca                                                             6

<210> SEQ ID NO 160
<211> LENGTH: 11
<212> TYPE: DNA
<213> ORGANISM: Artificial sequence
<220> FEATURE:
<223> OTHER INFORMATION: Regulatory protein binding DNA motif

<400> SEQUENCE: 160
aaccaatctc g                                                      11
```

STARCHY-ENDOSPERM AND/OR GERMINATING EMBRYO-SPECIFIC EXPRESSION IN MONO-COTYLEDONOUS PLANTS

RELATED APPLICATIONS

This application is a national stage application (under 35 U.S.C. 371) of PCT/EP2006/061585 filed Apr. 13, 2006, which claims benefit of U.S. application 60/672,977 filed Apr. 19, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_13987_00071. The size of the text file is 149 KB, and the text file was created on Jan. 18, 2011.

FIELD OF THE INVENTION

The present invention relates to the field of agricultural biotechnology. Disclosed herein are expression constructs with expression specificity for the starchy endosperm and/or the germinating embryo, transgenic plants comprising such expression constructs, and methods of making and using such DNA constructs and transgenic plants.

BACKGROUND OF THE INVENTION

In grain crops of agronomic importance, seed formation is the ultimate goal of plant development. Seeds are harvested for use in food, feed, and industrial products. The utility and value of those seeds are determined by the quantity and quality of protein, oil, and starch contained therein. In turn, the quality and quantity of seed produced may be affected by environmental conditions at any point prior to fertilization through seed maturation. In particular, stress at or around the time of fertilization may have substantial impact on seed development. Members of the grass family (Poaceae), which include the cereal grains, produce dry, one-seeded fruits. This type of fruit is, strictly speaking, a caryopsis but is commonly called a kernel or grain. The caryopsis of a fruit coat or pericarp surrounds the seed and adheres tightly to a seed coat. The seed consists of an embryo or germ and an endosperm enclosed by a nucellar epidermis and a seed coat. Accordingly the grain comprises the seed and its coat or pericarp. The seed comprises the embryo and the endosperm. (R. Carl Hoseney in "Principles of Cereal Science and Technology" expressly incorporated by reference in its entirety).

A fertile corn plant contains both male and female reproductive tissues, commonly known as the tassel and the ear, respectively. The tassel tissues form the haploid pollen grains with two nuclei in each grain, which, when shed at anthesis, contact the silks of a female ear. The ear may be on the same plant as that which shed the pollen, or on a different plant. The pollen cell develops a structure known as a pollen tube, which extends down through an individual female silk to the ovule. The two male nuclei travel through this tube to reach the haploid female egg at the base of the silk. One of the male nuclei fuses with and fertilizes the female haploid egg nuclei to form the zygote, which is diploid in chromosome number and will become the embryo within the kernel. The remaining male nucleus fuses with and fertilizes a second female nucleus to form the primary endosperm nucleus, which is triploid in number and will become the endosperm of the kernel, or seed, of the corn plant. Non-fertilized ovules do not produce kernels and the unfertilized tissues eventually degenerate.

The kernel consists of a number of parts, some derived from maternal tissue and others from the fertilization process. Maternally, the kernel inherits a number of tissues, including a protective, surrounding pericarp and a pedicel. The pedicel is a short stalk-like tissue which attaches the kernel to the cob and provides nutrient transfer from maternal tissue into the kernel. The kernel contains tissues resulting from the fertilization activities, including the new embryo as well as the endosperm. The embryo is the miniature progenitor of the next generation, containing cells for root and shoot growth of a new, young corn plant. It is also one tissue in which oils and proteins are stored in the kernel. The endosperm functions more as a nutritive tissue and provides the energy in the form of stored starch, proteins and oil, needed for the germination and initial growth of the embryo.

Considering the complex regulation that occurs during embryo and kernel development in higher plants, and considering that it is commonly grain that is a primary source of nutrition for animals and humans, key tools needed to improve such a nutritional source include genetic promoters that can drive the expression of nutrition enhancing genes. On the other hand the embryo is highly sensitive toward stresses. Stresses to plants may be caused by both biotic and abiotic agents. For example, biotic causes of stress include infection with a pathogen, insect feeding, and parasitism by another plant such as mistletoe, and grazing by ruminant animals. Abiotic stresses include, for example, excessive or insufficient available water, insufficient light, temperature extremes, synthetic chemicals such as herbicides, excessive wind, extremes of soil pH, limited nutrient availability, and air pollution. Yet plants survive and often flourish, even under unfavorable conditions, using a variety of internal and external mechanisms for avoiding or tolerating stress. Plants' physiological responses to stress reflect changes in gene expression.

While manipulation of stress-induced genes may play an important role in improving plant tolerance to stresses, it has been shown that constitutive expression of stress-inducible genes has a severe negative impact on plant growth and development when the stress is not present. (Kasuga 1999) Therefore, there is a need in the art for promoters driving expression which is temporally- and/or spatially-differentiated, to provide a means to control and direct gene expression in specific cells or tissues at critical times, especially to provide stress tolerance or avoidance. In particular, drought and/or density stress of maize often results in reduced yield, typically from plant failure to set and fill seed in the apical portion of the ear, a condition known as "tip kernel abortion" or colloquially as "nosing back." To stabilize plant development and grain yield under unfavorable environments, manipulation of hormones and carbon supply to the developing ear and its kernels is of interest. Thus there is a need for promoters which drive gene expression in female reproductive tissues under abiotic stress conditions.

One other well-known problem in the art of plant biotechnology is marker-deletion. Selectable marker are useful during the transformation process to select for, and identify, transformed organisms, but typically provide no useful function once the transformed organism has been identified and contributes substantially to the lack of acceptance of these "gene food" products among consumers (Kuiper 2001), and few markers are available that are not based on these mechanisms (Hare 2002). Thus, there are multiple attempts to develop techniques by means of which marker DNA can be excised from plant genome (Ow 1995; Gleave 1999). The person skilled in the art is familiar with a variety of systems for the site-directed removal of recombinantly introduced nucleic acid sequences. They are mainly based on the use of sequence specific recombinases. Various sequence-specific recombination systems are described, such as the Cre/lox system of the bacteriophage P1 (Dale 1991; Russell 1992; Osborne 1995), the yeast FLP/FRT system (Kilby 1995; Lyznik 1996), the Mu phage Gin recombinase, the *E. coli* Pin recombinase, the R/RS system of the plasmid pSR1 (Onouchi 1995; Sugita2000), the attP/bacteriophage Lambda system (Zubko 2000). It is one known disadvantage of these methods known in the prior art that excision is not homogenous through the entire plants thereby leading to mosaic-like excision patterns, which require laborious additional rounds of selection and regeneration.

Promoters that confer enhanced expression during seed or grain maturation are also described (such as the barley hordein promoters; see US patent application 20040088754). Promoters which direct embryo-specific or seed-specific expression in dicots (e.g., the soybean conglycinin promoter; Chen 1988; the napin promoter, Kridl 1991) are in general not capable to direct similar expression in monocots. Unfortunately, relatively few promoters specifically directing this aspect of physiology have been identified (see for example US20040163144).

The octopine synthase (ocs) and mannopine synthase (mas) gene promoters have been used to direct the expression of linked genes in transgenic plants. However, the application of these promoters has been restricted by weak expression levels in certain tissues of transgenic plants (DiRita 1987; Harpster 1988; Sanger 1990). For example, the ocs promoter directs a distinct cell-specific pattern of expression in transgenic tobacco (Kononowicz 1992). The mas gene exhibits weak expression in leaves and stems, but has stronger expression in roots and exhibits a degree of wound and auxin inducibility (Langridge 1989; Teeri 1989; Saito 1991; Guevara-Garcia 1993). Chimeric promoters for expressing genes in plants comprising *Agrobacterium tumefaciens* opine synthase upstream activating sequences operably linked to a *Agrobacterium tumefaciens* opine synthase promoter are described (Ni 1995; U.S. Pat. No. 5,955,646). The most characterized sequence is the so called "super-promoter", a chimeric construct of three upstream activating sequences derived from an *Agrobacterium tumefaciens* octopine synthase gene operably linked to a transcription regulating nucleotide sequence derived from the promoter of an *Agrobacterium tumefaciens* mannopine synthase gene. Although the promoter is widely used in dicotyledonous plants, its experiences from application to monocotyledonous plants are very limited. Kononov et al. (A Comparative Study of the Activity of the Super-promoter with Other Promoters in Maize (1999) 20th annual crown gall conference, University of Texas-Houston Medical School; abstract book, p. 36; Comparative Study of the Activity of the Super-promoter and Other Promoters in Maize (1998) 19th annual crown gall meeting, Purdue University, West Lafayette, Ind.]) showed expression a broad range of tissues. Expression was nearly the same in all tissues but was elevated in roots. In contrast to the ubiquitin promoter the presence or absence of an intron sequence was reported to have no effect on transcription activity of the super-promoter.

Accordingly there is a first need in the art for promoter sequences which allow for expression in starch endosperm during seed development and in embryo during the early germinating seed. Further more there is a strong second need in the art for promoter sequences which allow for strong expression of excision mediating enzymes in a way that the resulting plant is substantially marker-free.

For the first need in the art some seed- or grain-specific promoters are described include those associated with genes that encode plant seed storage proteins such as genes encoding: barley hordeins, rice glutelins, oryzins, prolamines, or globulins; wheat gliadins or glutenins; maize zeins or glutelins; oat glutelins; sorghum kafirins; millet pennisetins; or rye secalins. However, on the one hand expression of these promoters is often leaky or of low expression level. Furthermore, it has been noted that improvement of crop plants with multiple transgenes ("stacking") is of increasing interest. For example, a single maize hybrid may comprise recombinant DNA constructs conferring not only insect resistance, but also resistance to a specific herbicide. Importantly, appropriate regulatory sequences are needed to drive the desired expression of each of these or other transgenes of interest. Furthermore, it is important that regulatory elements be distinct from each other. Concerns associated with the utilization of similar regulatory sequences to drive expression of multiple genes include, but are not restricted to: (a) pairing along homologous regions, crossing-over and loss of the intervening region either within a plasmid prior to integration, or within the plant genome, post-integration; (b) hairpin loops caused by two copies of the sequence in opposite orientation adjacent to each other, again with possibilities of excision and loss of these regulatory regions; (c) competition among different copies of the same promoter region for binding of promoter-specific transcription factors or other regulatory DNA-binding proteins.

There is, therefore, a great need in the art for the identification of novel sequences that can be used for expression of selected transgenes in economically important plants, especially in monocotyledonous plants. It is thus an objective of the present invention to provide new and alternative expression cassettes for endosperm- and/or embryo-preferential or specific expression. The objective is solved by the present invention.

SUMMARY OF THE INVENTION

One first embodiment of the invention relates to a monocotyledonous plant comprising an expression cassette, said expression cassette comprising
a) a chimeric transcription regulating nucleotide sequence comprising
   i) at least one transcription regulating nucleotide sequence derived from the promoter of an *Agrobacterium* mannopine synthase gene,
   ii) at least one upstream activating sequence derived from an *Agrobacterium* octopine synthase gene, and operably linked thereto
b) at least one nucleic acid sequence which is heterologous in relation to said chimeric transcription regulating nucleotide sequence and is suitable to confer to a plant a trait or property selected from the group consisting of
   i) enhanced resistance against at least one stress factor,
   ii) increased nutritional quality of a seed or a sprout,
   iii) increased yield, and
   iv) targeted sequence excision.

Preferably, the transcription regulating nucleotide sequence derived from the promoter of an *Agrobacterium* mannopine synthase gene and/or the upstream activating sequence derived from an *Agrobacterium* octopine synthase gene, are derived from an *Agrobacterium tumefaciens* strain.

Preferably, the chimeric transcription regulating nucleotide sequence causes said heterologous DNA to be predominantly expressed in the starchy endosperm or the germinating embryo.

Various forms are possible to form a chimeric transcription regulating nucleotide sequence of the invention. Preferably said chimeric transcription regulating nucleotide sequence comprises at least three upstream activating sequences derived from an *Agrobacterium tumefaciens* octopine synthase gene operably linked to at least one transcription regulating nucleotide sequence derived from the promoter of an *Agrobacterium tumefaciens* mannopine synthase gene. More preferably said chimeric transcription regulating nucleotide sequence further comprises at least one upstream activating sequence derived from a mannopine synthase gene of *Agrobacterium tumefaciens*.

In one preferred embodiment the transcription regulating nucleotide sequence derived from the promoter of an *Agrobacterium tumefaciens* mannopine synthase gene is described by a sequence selected from the group consisting of
i) the sequence described by SEQ ID NOs: 2 or 3,
ii) a fragment of at least 50 consecutive bases of the sequence described by SEQ ID NOs: 2 or 3,
iii) a nucleotide sequence having a sequence identity of at least 60% to the sequence described by SEQ ID NO: 2 or 3,
iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 2 or 3, or the complement thereof;
v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a sequence described by SEQ ID NO: 2 or 3, or the complement thereof;
vi) a nucleotide sequence which is the complement or reverse complement of any of the previously mentioned nucleotide sequences under i) to v).

In another preferred embodiment the upstream activating sequence derived from an octopine synthase gene of *Agrobacterium tumefaciens* is described by a sequence selected from the group consisting of
i) the sequence described by SEQ ID NOs: 1,
ii) a fragment of at least 50 consecutive bases of the sequence described by SEQ ID NOs: 1,
iii) a nucleotide sequence having a sequence identity of at least 60% to the sequence described by SEQ ID NO: 1,
iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 1, or the complement thereof;
v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a sequence described by SEQ ID NO: 1, or the complement thereof;
vi) a nucleotide sequence which is the complement or reverse complement of any of the previously mentioned nucleotide sequences under i) to v).

In a more preferred embodiment the chimeric transcription regulating nucleotide sequence comprises a specific combination of the upstream activating sequences from an octopine synthase and the transcription regulating nucleotide sequence from a mannopine gene.

In a more preferred embodiment the chimeric transcription regulating nucleotide sequence is described by a sequence selected from the group consisting of
i) the sequence described by SEQ ID NOs: 4,
ii) a fragment of at least 50 consecutive bases of the sequence described by SEQ ID NOs: 4,
iii) a nucleotide sequence having a sequence identity of at least 60% to the sequence described by SEQ ID NO: 4,
iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 4, or the complement thereof;
v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a sequence described by SEQ ID NO: 4, or the complement thereof;

vi) a nucleotide sequence which is the complement or reverse complement of any of the previously mentioned nucleotide sequences under i) to v).

The sequences specified under ii), iii), iv) v) and vi) are preferably capable to modify transcription in a monocotyledonous plant cell or organism, more preferably they are capable to induce starchy endosperm and/or embryo specific expression. Preferably, the sequences specified under iv) or v) are hybridizing under stringent conditions with the specified target sequence.

In another preferred embodiment the expression cassette of the invention does not comprise an intron with expression enhancing properties operably linked to said chimeric transcription regulating sequence. The operably linked polynucleotide may encode a polypeptide as described by any of SEQ ID NO: 6, 8, 10, 12, 14, 16, 18, 20, 22, 43, 45, 47, 49, 50, 51, or 53, or a functional equivalent thereof, which is capable to bring about the same phenotype than any of said polypeptides. More examples are given below.

Expression of the nucleic acid sequence under the chimeric transcription regulating sequence may result in expression of a protein, or expression of an antisense RNA, sense or double-stranded RNA.

The stress resistance, which can be advantageously obtained, is preferably against an abiotic or biotic stress factor. The biotic stress factor may be selected from the group consisting of fungal resistance, nematode resistance, insect resistance, virus resistance, and bacteria resistance. Preferably, the biotic stress factor is a seed-borne disease (mainly fungal diseases e.g. common bunt (*Tilletia tritici*) mainly in wheat; leaf stripe (*Pyrenophora graminea*), and loose smut (*Ustilago nuda*) mainly in barley).

The abiotic stress factor may be selected from the group consisting of water stress resistance, drought resistance, cold resistance, salt resistance, high plant population density, and UV light resistance. Preferably, the stress resistance is achieved by inducing early vigor.

Various nucleic acids sequences are known to the person skilled in the art to obtain such stress resistance. Said sequences may include but are not limited to polynucleotides encoding a polypeptide involved in phytohormone biosynthesis, phytohormone regulation, cell cycle regulation, or carbohydrate metabolism.

The invention is applicable to all monocotyledonous plants such as maize, wheat, rice, barley, oat, rye, sorghum, millet, tricalate, banana, ryegrass or coix, but is preferably applicable to kernel producing cereal plants of the Pooideae family such as maize, wheat, rice, barley, oat, rye, sorghum, millet, or tricalate, preferably to maize, barley and wheat, most preferably to maize.

Further embodiments of the invention relate to seeds, parts and cells of the monocotyledonous plant of the invention.

Preferably, the plant parts are selected from the group consisting of: cells, protoplasts, cell tissue cultures, callus, cell clumps, embryos, pollen, ovules, seeds, flowers, kernels, ears, cobs, leaves, husks, stalks, roots, root tips, anthers, and silk.

Another embodiment of the invention relates to a method for conferring enhanced stress resistance to a monocotyledonous plant, said method comprising the steps of
a) constructing an expression cassette by operably linking at least one chimeric transcription regulating nucleotide sequence comprising
   i) at least one transcription regulating nucleotide sequence derived from the promoter of an *Agrobacterium* mannopine synthase gene, and
   ii) at least one upstream activating sequence derived from an *Agrobacterium* octopine synthase gene,
   to at least one nucleic acid sequence which is heterologous in relation to said chimeric transcription regulating nucleotide sequence and is suitable to confer to a plant an enhanced resistance against stress, and
b) inserting said expression cassette into a monocotyledonous plant to provide a transgenic plant, wherein said plant expresses said heterologous nucleic acid sequence, and
c) selecting transgenic plants, which demonstrate enhanced resistance against at least one stress factor in comparison to plants, which are not comprising said expression cassette but are otherwise identical to said transgenic plant.

Various nucleic acids sequences are known to the person skilled in the art to obtain such stress resistance. Said sequences may include but are not limited to polynucleotides encoding a polypeptide involved in phytohormone biosynthesis, phytohormone regulation, cell cycle regulation, or carbohydrate metabolism. The stress factor is preferably defined as above. The heterologous nucleic acid sequence to be expressed (e.g., either as a sense, antisense or double-stranded RNA) may encode a polypeptide (or a part thereof; preferably a part of at least 5, more preferably at least 10, most preferably at least 30 consecutive amino acids) as described by any of SEQ ID NO: 6, 8, 16, 18, 20, 43, 45, 47, 49, 50, 51, or 53, or a functional equivalent thereof, which is capable to bring about the same phenotype than any of said polypeptide. Preferred chimeric transcription regulating nucleotide sequence are described above, most preferred is the superpromoter.

Yet another embodiment of the invention relates to a method for conferring increased nutritional quality of a seed or a sprout to a monocotyledonous plant, said method comprising the steps of
a) constructing an expression cassette by operably linking at least one chimeric transcription regulating nucleotide sequence comprising
   i) at least one transcription regulating nucleotide sequence derived from the promoter of an *Agrobacterium* mannopine synthase gene, and
   ii) at least one upstream activating sequence derived from an *Agrobacterium* octopine synthase gene,
   to at least one nucleic acid sequence which is heterologous in relation to said chimeric transcription regulating nucleotide sequence and is suitable to confer to a plant increased nutritional quality of a seed or a sprout, and
b) inserting said expression cassette into a monocotyledonous plant to provide a transgenic plant, wherein said plant expresses said heterologous nucleic acid sequence, and
c) selecting transgenic plants, which demonstrate increased nutritional quality of a seed or a sprout in comparison to plants, which are not comprising said expression cassette but are otherwise identical to said transgenic plant.

The nutritional quality may comprise an increased content of at least one compound selected from the group consisting of vitamins, carotinoids, antioxidants, unsaturated fatty acids, and poly-unsaturated fatty acids. The heterologous nucleic acid sequence to be expressed (e.g., either as a sense, antisense or double-stranded RNA) may encode a polypeptide (or a part thereof; preferably a part of at least 5, more preferably at least 10, most preferably at least 30 consecutive amino acids) as described by any of SEQ ID NO: 10, 12, or 14, or a functional equivalent thereof, which is capable to bring about the same phenotype than any of said polypeptide.

The nutritional quality and the corresponding heterologous nucleic acid sequence to be expressed are defined as above. More specific example are given herein below. Preferred chimeric transcription regulating nucleotide sequence are described above, most preferred is the super-promoter.

Another embodiment of the invention relates to a method for conferring increased yield to a monocotyledonous plant, said method comprising the steps of a) constructing an expression cassette by operably linking at least one chimeric transcription regulating nucleotide sequence comprising
  i) at least one transcription regulating nucleotide sequence derived from the promoter of an *Agrobacterium* mannopine synthase gene, and
  ii) at least one upstream activating sequence derived from an *Agrobacterium* octopine synthase gene,
  to at least one nucleic acid sequence which is heterologous in relation to said chimeric transcription regulating nucleotide sequence and is suitable to confer to a plant increased yield, and
b) inserting said expression cassette into a monocotyledonous plant to provide a transgenic plant, wherein said plant expresses said heterologous nucleic acid sequence, and
c) selecting transgenic plants, which demonstrate increased yield in comparison to plants, which are not comprising said expression cassette but are otherwise identical to said transgenic plant.

The increased yield and the corresponding heterologous nucleic acid sequence to be expressed are defined as above. The increased yield may be caused by a higher stress-resistance. Accordingly, the heterologous nucleic acid sequence to be expressed may encode a polypeptide (or a part thereof; preferably a part of at least 5, more preferably at least 10, most preferably at least 30 consecutive amino acids) as described by any of SEQ ID NO: 6, 8, 16, 18, 20, 43, 45, 47, 49, 50, 51, or 53, or a functional equivalent thereof, which is capable to bring about the same phenotype than any of said polypeptide. Preferred chimeric transcription regulating nucleotide sequence are described above, most preferred is the super-promoter.

Another embodiment of the invention relates to a method for excision of target sequences (e.g., marker sequences) from a monocotyledonous plant, said method comprising the steps of a) constructing an expression cassette by operably linking at least one chimeric transcription regulating nucleotide sequence comprising
  i) at least one transcription regulating nucleotide sequence derived from the promoter of an *Agrobacterium* mannopine synthase gene, and
  ii) at least one upstream activating sequence derived from an *Agrobacterium* octopine synthase gene,
  to at least one nucleic acid sequence which is heterologous in relation to said chimeric transcription regulating nucleotide sequence and is suitable to induce excision of marker sequences from a monocotyledonous plant, and
b) inserting said expression cassette into a monocotyledonous plant comprising at least one marker sequence to provide a transgenic plant, wherein said plant expresses said heterologous nucleic acid sequence, and
c) selecting transgenic plants, which demonstrate excision of said marker.

The excision is realized by various means, including but not limited to:
  induction of sequence deletion by side specific recombination using site-specific recombinases, wherein said site-specific recombinase is expressed by the chimeric transcription regulating nucleotide sequence of the invention,
  induction of sequence deletion by induced homologous recombination, wherein the sequences to be deleted are flanked by sequences, said sequences having an orientation, a sufficient length and a homology to each other to allow for homologous recombination between them, wherein homologous recombination is induced by a site-specific double-strand break made by a site-specific endonuclease (preferably a homing endonuclease, more preferably the homing endonuclease I-SceI), wherein said site-specific endonuclease is expressed by the chimeric transcription regulating nucleotide sequence of the invention.

The heterologous nucleic acid sequence to be expressed encodes a polypeptide (or a part thereof; preferably a part of at least 5, more preferably at least 10, most preferably at least 30 consecutive amino acids) as described by any of SEQ ID NO: 22, or a functional equivalent thereof, which is capable to bring about the same phenotype than any of said polypeptide. Preferred chimeric transcription regulating nucleotide sequences are described above, most preferred is the super-promoter. Preferred heterologous nucleic acid sequences to be expressed to achieve sequence excision (e.g., encoding for a site-specific recombinase or endonuclease) are described herein below.

Yet another embodiment of the invention relates to a method for starchy-endosperm and/or germinating embryo-specific or -preferred expression of nucleic acid sequences in monocotyledonous plants, said method comprising the steps of a) constructing an expression cassette by operably linking at least one chimeric transcription regulating nucleotide sequence comprising
  i) at least one transcription regulating nucleotide sequence derived from the promoter of an *Agrobacterium tumefaciens* mannopine synthase gene,
  ii) at least one upstream activating sequence derived from an octopine synthase gene of *Agrobacterium tumefaciens*,
  to at least one nucleic acid sequence which is heterologous in relation to said chimeric transcription regulating nucleotide sequence, and
b) inserting said expression cassette into a monocotyledonous plant to provide a transgenic plant, and
c) selecting transgenic plants, which demonstrate starchy-endosperm and/or germinating embryo-specific or -preferred expression of said heterologous nucleic acid sequence.

The method for starchy-endosperm and/or germinating embryo-specific or -preferred expression of the invention is resulting in expression a heterologous nucleic acid sequence which confers to a monocotyledonous plant at least one trait or property selected from the group consisting of i) enhanced resistance against at least one stress factor,
ii) increased nutritional quality of a seed or a sprout,
iii) increased yield, and
iv) selection marker excision.

Preferred specified traits and sequences to achieve them are specified herein below.

The monocotyledonous plant to which the methods of this invention are preferably applied to may be selected from the group consisting of maize, wheat, rice, barley, oat, rye, sorghum, banana, ryegrass or coix. Preferably the plant is a cereal plant selected from the group consisting of maize, wheat, barley, rice, oat, rye, and sorghum, even more preferably from maize, wheat, and rice, most preferably the plant is a maize plant.

In one preferred embodiment of the invention the nucleotide sequence expressed from the chimeric transcription regulating sequence of the invention is not encoding a beta-glucuronidase (GUS), or is not a method for expression of a GUS gene for the purpose of achieving a GUS-mediating staining.

DEFINITIONS

Figure 1:
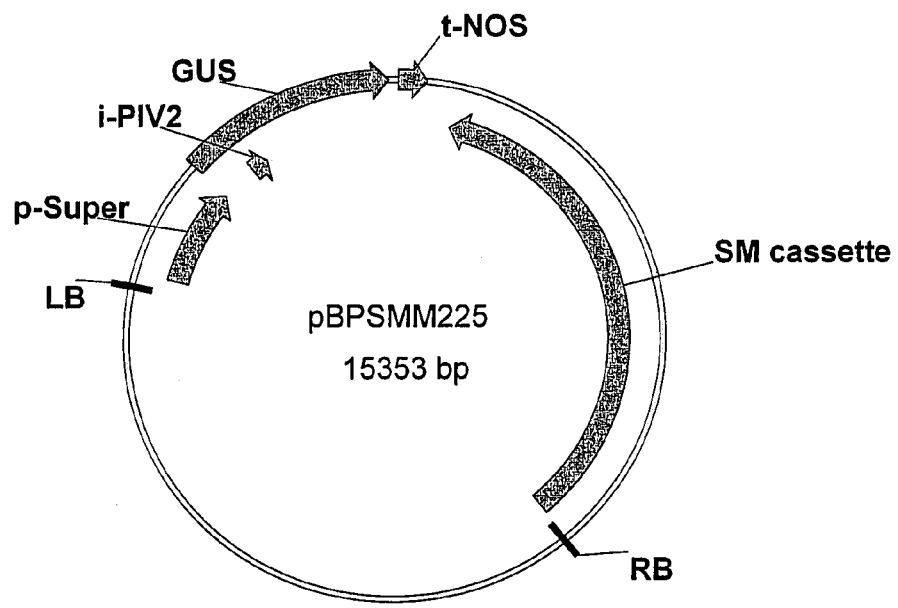
FIG. 1 Map of super-promoter::GUS::terminator fusion construct (pBPSMM225).
The plasmid comprises an expression construct containing a super-promoter operably linked to a β-glucuronidase gene (GUS including the potato invertase [PIV]2 intron), and nopaline synthase (NOS) terminator. SM cassette is representing a selection marker (ahas) cassette.
Figure 2:
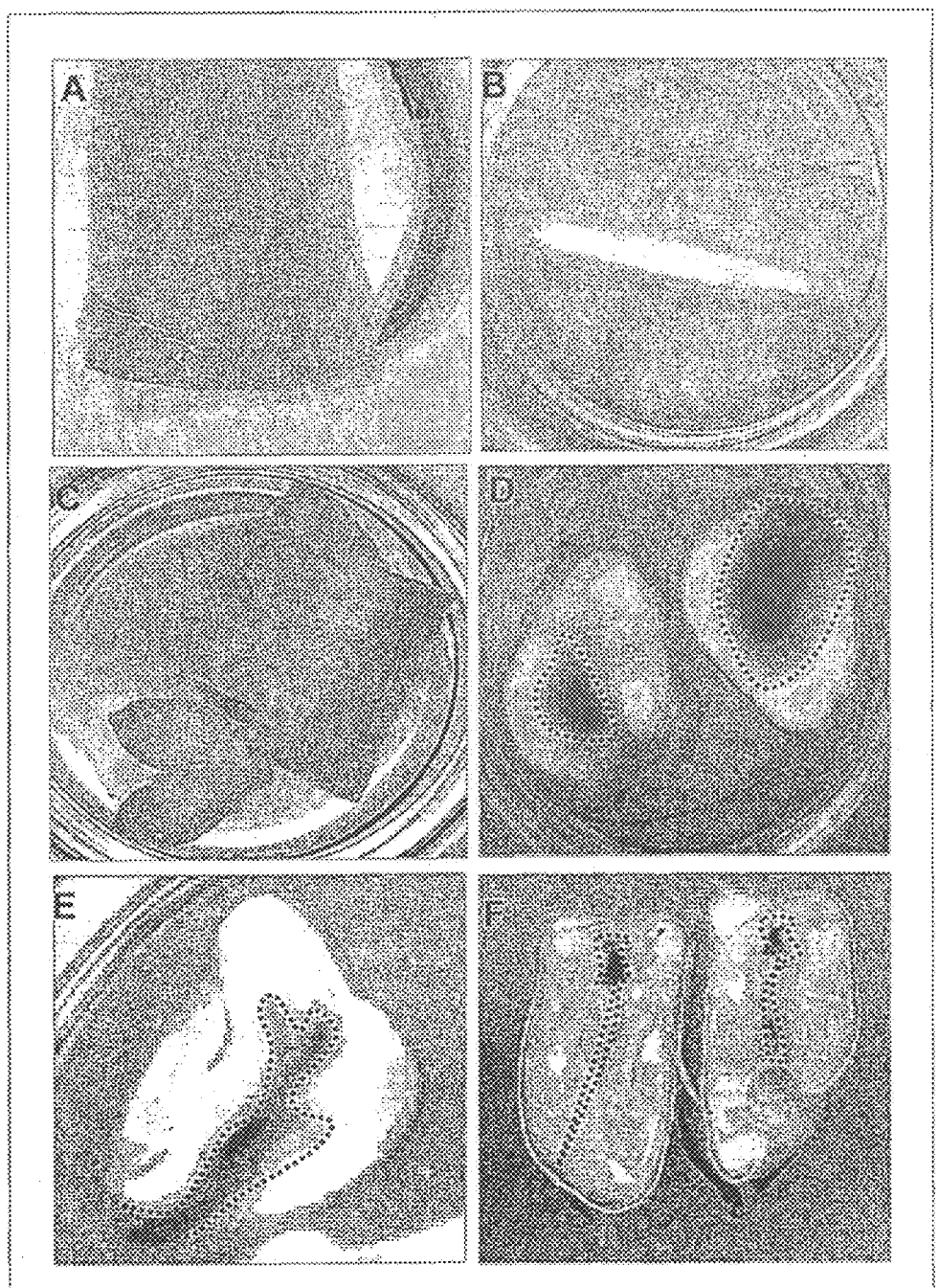
FIG. 2 GUS expression controlled by super-promoter in maize at different developmental stages (A-F). The areas with significant GUS staining are marked with a dotted line.
(A) Leaf and root at the 5 leaf stage
(B) Ear (prepollination)
(C) Kernel on ear (5 days after pollination)
(D) Kernel (20 days after pollination)
(E) Kernel (30 days after pollination)
(F) Kernel (dried)
Pictures represent reproducible expression patterns from 15 $T_1$ single copy lines.
Figure 3:
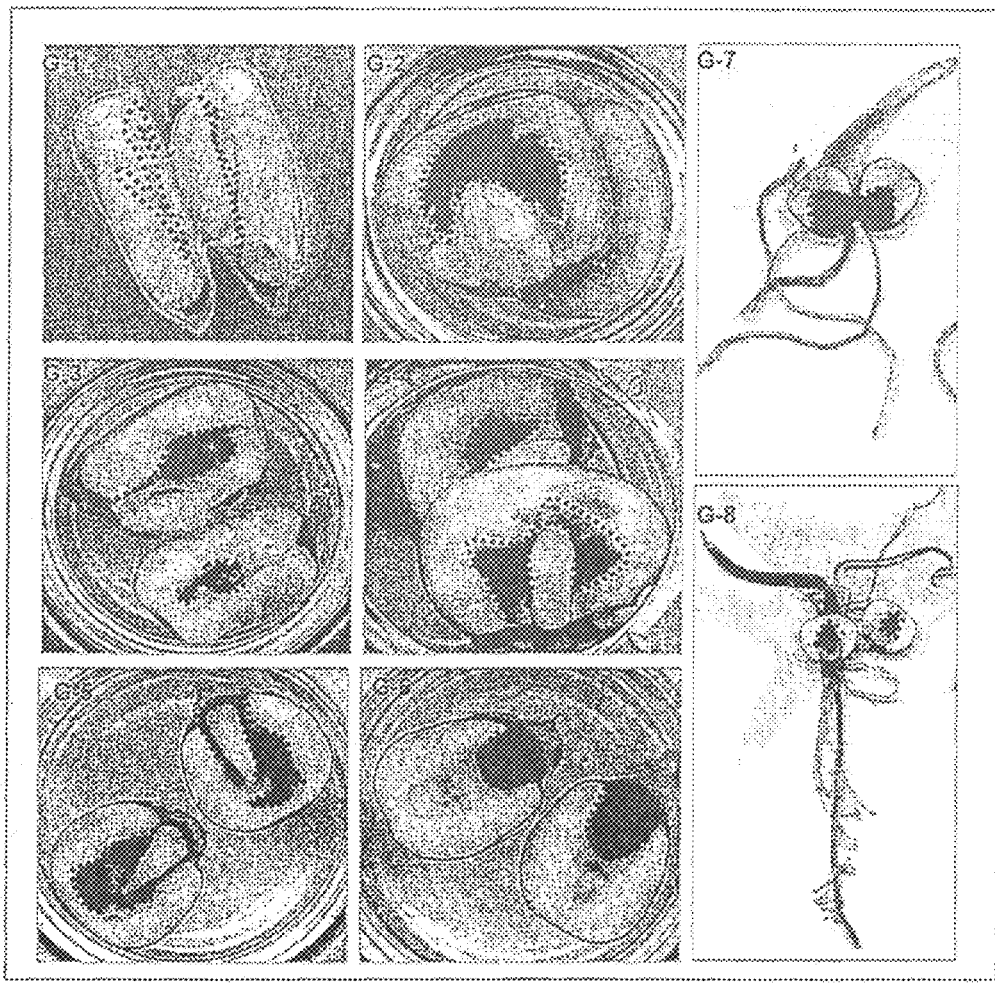
FIG. 3 GUS expression controlled by super-promoter in maize kernels at different stages of germination. Kernels of the transgenic plants are evaluated after incubation on wet filters. The areas with significant GUS staining are marked with a dotted line.
(G) kernels after incubation on wet filter paper (water imbibition); G–1 to G8: 0, 3, 5, 8, 16, 24, 120, and 168 hours of water imbibition.
Pictures represent reproducible expression patterns from 15 $T_1$ single copy lines.

Unless otherwise noted, technical terms are used according to conventional usage. Definitions of common terms in molecular biology may be found in Lewin, Genes V published by Oxford University Press, 1994 (ISBN 0-19-854187-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.
The term "chimeric gene" refers to any gene that contains
1) DNA sequences, including regulatory and coding sequences, that are not found together in nature, or
2) sequences encoding parts of proteins not naturally adjoined, or
3) parts of promoters that are not naturally adjoined.
Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1,000's of nucleotides in length.

The terms "polypeptide", "peptide", "oligopeptide", "polypeptide", "gene product", "expression product" and "protein" are used interchangeably herein to refer to a polymer or oligomer of consecutive amino acid residues. As used herein, the term "amino acid sequence" or a "polypeptide sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W.H. Freeman and Company, New York. The letter "x" as used herein within an amino acid sequence can stand for any amino acid residue.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

"Promoter" refers to a nucleotide sequence, usually upstream (5') to its coding sequence, which controls the expression of the coding sequence by providing the recognition for RNA polymerase and other factors (e.g., trans-acting transcription factors) required for proper transcription. "Promoter" includes a minimal promoter that is a short DNA sequence comprised of a TATA box and other sequences that serve to specify the site of transcription initiation, to which regulatory elements (e.g., cis-elements) are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors which control the effectiveness of transcription initiation in response to physiological or developmental conditions. As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

The term "intron" refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: intron 14 of the RecA-like protein gene and intron 7 of the G5 gene from *Arabidopsis thaliana* are AT-AC introns, Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branchpoint The branchpoint sequence is important in splicing and splice-site selection in plants. The branchpoint sequence is usually located 10-60 nucleotides upstream of the 3' splice site. Plant sequences exhibit sequence deviations in the branchpoint, the consensus sequences being CURAY or YURAY.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements does not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression.

However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates. The rate of degradation can however be considered to proceed at a fixed rate when the transcribed sequences are identical, and thus this value can serve as a measure of synthesis rates. When promoters are compared in this way, techniques available to those skilled in the art are hybridization, S1-RNAse analysis, northern blots and competitive RT-PCR. This list of techniques in no way represents all available techniques, but rather describes commonly used procedures to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"5' non-coding sequence" or "5'-untranslated sequence" or "-region" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" or "3'-untranslated sequence" or "-region" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of a expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents or orthologs of *Arabidopsis thaliana* or *Brassica napus* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 60% or greater to the instant sequences. Modifications that result in equivalent nucleotide or amino acid sequences are well within the routine skill in the art. The percentage of amino acid sequence identity between the substantially similar and the reference polypeptide is at least 60%, 61%, 62%, 63%, 64%, 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%. One indication that two polypeptides are substantially similar to each other, besides having substantially the same function, is that an agent, e.g., an antibody, which specifically binds to one of the polypeptides, also specifically binds to the other.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 60%, 61%, 62%, 63%, 64%, 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as Agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue, which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

The term "nucleic acid" refers to deoxyribonucleotides or ribonucleotides and polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals. The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. No. 5,605,797, 9, 11, 13, 15, and 17,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred. Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" or "expression construct" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) down-stream of an endogenous promoter sequence thereby forming an expression cassette. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., the seed-specific or seed-preferential promoters of the invention). In a preferred embodiment, such expression cassettes will comprise the transcriptional initiation region of the invention linked to a nucleotide sequence of interest. Such an expression cassette is preferably provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such, as the octopine synthase and nopaline synthase termination regions and others described below (see also, Guerineau 1991; Proudfoot 1991; Sanfacon 1991; Mogen 1990; Munroe 1990; Ballas 1989; Joshi 1987).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra. Multiple alignments (i.e. of more than 2 sequences) are preferably performed using the Clustal W algorithm (Thompson 1994; e.g., in the software VectorNTI™, version 9; Invitrogen Inc.) with the scoring matrix BLOSUM62MT2 with the default settings (gap opening penalty 15/19, gap extension penalty 6.66/0.05; gap separation penalty range 8; % identity for alignment delay 40; using residue specific gaps and hydrophilic residue gaps).

Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See ncbi.nlm nih gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 60%, 61%, 62%, 63%, 64%, 65%, 66%, 67%, 68%, 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60% or 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 60%, 61%, 62%, 63%, 64%, 65%, 66%, 67%, 68%, 69%, 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5° C. + 16.6(\log_{10} M) + 0.41(\% GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The present invention is especially useful for applications in monocotyledonous plants. The term "monocotyledonous plant" includes plants of a variety of ploidy levels, including aneuploid, polyploid, diploid, haploid and hemizygous. Included are furthermore the mature plants, seed, shoots and seedlings, and parts, propagation material (for example seeds and fruit) and cultures, for example cell cultures, derived therefrom. Annual and perennial monocotyledonous plants are preferred host organisms for the generation of transgenic plants. Preferably the monocotyledonous plant of the invention is a Gramineae.

The terms "Gramineae" or "Graminaceae" as used herein intents to comprise all plants species of the Gramineae (Poaceae) family, especially those employed as foodstuffs or feeding stuffs such as rice, maize, wheat or other cereal species such as barley, millet and sorghum, rye, triticale or oats, and sugar cane, and all grass species. Furthermore included are the mature plants, seed, shoots and seedlings, and parts, propagation material and cultures derived therefrom, for example cell cultures. Mature plants refers to plants at any developmental stage beyond that of the seedling. The term seedling refers to a young immature plant in an early developmental stage, at which it is still dependent upon assimilates stored within the seed (e.g. in the endosperm, perisperm or cotyledons. Included are all genera of the subfamilies Bambusoideae (e.g., the genus bamboo), Andropogonoideae (e.g., the genera *Saccharum, Sorghum*, or *Zea*), Arundineae (e.g., the genus *Phragmites*), Oryzoideae (e.g., the genus *Oryza*), Panicoideae (e.g., the genera *Panicum, Pennisetum*, and *Setaria*), Pooideae (Festuciadeae) (e.g., the genera *Poa, Festuca, Lolium, Trisetum, Agrostis, Phleum, Dactylis, Alopecurus, Avena, Triticum, Secale*, and *Hordeum*). Preferred are *Avena sativa* (oats), *Bambusa* sp. and *Bambusa bambos* (bamboo), *Saccharum officinarum* (sugarcane), *Triticum dicoccum* (Emmer wheat), *Triticum monococcum* (Einkorn wheat), *Triticum spelta* (spelt wheat), *Triticum durum* (wheat), *Triticum turgidum, Triticum aestivum* (wheat), *Zea mays* (maize/corn), *Panicum miliaceum* (common millet), *Pennisetum thiphoides* (Bulrush millet), *Hordeum vulgare* or *H. sativum* (barley), *Oryza sativa* (rice), *Zizania aquatica* (wild rice), *Secale cereale* (rye), *Sorghum bicolor* (*S. vulgare*) (sorghum). More preferred are wheat (*Triticum* spp.), rice (*Oryza* spp.), barley (*Hordeum* spp.), oats (*Avena* spp.), rye (*Secale* spp.), corn (*Zea mays*), sorghum and millet (*Pennisettum* spp). Preferred are all wheat species especially of the Triticum family (including both winter and spring wheat), more especially *Triticum* spp.: common (*T. aestivum*), durum (*T. durum*), spelt (*T. spelta*), *Triticum dicoccum* (Emmer wheat), *Triticum turgidum*, and *Triticum monococcum* (Einkorn wheat), with *T. aestivum* being particularly preferred. The method of the invention can be used to produce transgenic plants from spring wheats, such as, for example, Bobwhite, Marshall, PIVOT1, UC702, and Panewawa as well as from winter wheats, such as, for example, HY368, Neeley, FL302, RH91, R332, R1269 and R585. Other suitable wheat genotypes are including, but not limited to Yecora Rojo, Karl and Anza. However, it should be pointed out, that the invention is not limited to certain varities but is highly genotype-independent.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention provides for methods and subject matter to achieve starchy endosperm and embryo specific expression profiles in monocotyledonous plants, especially in corn (*Zea mays*).

One first embodiment of the invention relates to a monocotyledonous plant comprising an expression cassette, said expression cassette comprising a) a chimeric transcription regulating nucleotide sequence comprising
   i) at least one transcription regulating nucleotide sequence derived from the promoter of an *Agrobacterium* mannopine synthase gene,
   ii) at least one upstream activating sequence derived from an *Agrobacterium* octopine synthase gene, and operably linked thereto
b) at least one nucleic acid sequence which is heterologous in relation to said chimeric transcription regulating nucleotide sequence and is suitable to confer to a plant a trait or property selected from the group consisting of i) enhanced resistance against at least one stress factor,
ii) increased nutritional quality of a seed or a sprout,
iii) increased yield, and
iv) targeted sequence excision.

The chimeric transcription regulating nucleic acid sequences (e.g., the super-promoter) employed in the expression constructs surprisingly demonstrated a high specificity in seed (kernel) development and germination. This is in sharp contrast to the profiles reported in the art both in dicotyledonous and monocotyledonous plants where constitutive expression profiles in all tissues were reported (Ni M et al. (1995) Plant J 7(4): 661-676; U.S. Pat. No. 5,955,646; Kononov et al. A Comparative Study of the Activity of the Super-promoter with Other Promoters in Maize (1999) 20th annual crown gall conference, University of Texas-Houston Medical School; abstract book, p. 36; Comparative Study of the Activity of the Super-promoter and Other Promoters in Maize (1998) 19th annual crown gall meeting, Purdue University, West Lafayette, Ind.]). However, for monocotyledonous plants expression was previously only tested with the GUS gene.

Preferably, the chimeric transcription regulating nucleotide sequence causes said heterologous DNA to be predominantly expressed in the starchy endosperm or the germinating embryo. Expression regulated by the chimeric transcription regulating nucleic acid sequences (e.g., the super-promoter) is present in the starchy endosperm during seed kernel (development) starting between 5 and 20 days after pollination and becoming nearly silent during the dormancy period. By this, the sequences have seed- or grain-maturation specificity. By "seed or grain-maturation" herein refers to the period starting with fertilization in which metabolizable food reserves (e.g., proteins, lipids, starch, etc.) are deposited in the developing seed, particularly in storage organs of the seed, including the endosperm, resulting in enlargement and filling of the seed and ending with seed desiccation. Transcription activity then starts to very high levels during the germination period, first again in the starchy endosperm and then "switching" between 16 and 24 hours imbibition nearly entirely to the germinating embryo with very high expression levels. Expression then stops at about 7 days after start of germination. No significant expression was detected in any tissue beside the starchy endosperm and the embryo during germination. This expression profile is especially useful for the following applications:

i) enhanced resistance against stress factors: as described above in the prior art section the embryo is very sensitive against all kinds of biotic and abiotc stress factors (drought, cold, diseases etc.). These stress factors have an immediate effect on yield and crop quality. Most promoters known in the art have no or low expression capacity during this stage. The transcription regulating specificity disclosed herein is especially useful to express stress-resistance genes "on-demand" i.e. at the right time to high levels. Furthermore, because of the specificity in the starchy endosperm it is possible to pursue new ways of stress-resistance. Because the starchy endosperm is the tissue, which nourishes the embryo, one can increase stress-resistance via improved supplementation of the embryo with nutrients.

ii) increased nutritional quality of a seed or a sprout: The expression profile of the chimeric transcription regulating nucleic acid sequences (e.g., the super-promoter) allows for conversion of seed (kernel) ingredients or for changing the distribution of the ingredients in the seed. For example one can convert carbohydrates (starch) into oil or other high-value ingredients (e.g., vitamins) or can shift localization of ingredients from the endosperm towards the embryo thereby providing sprouts with improved nutritional value.

iii) increased yield: Increased yield is partially related to stress resistance (see above under i)). However, the expression profile of the chimeric transcription regulating nucleic acid sequences (e.g., the super-promoter) allows even without stress factors to increase yield by optimizing growth of the embryo, which will directly affect growth of the seedling. One can also achieve earlier germination under field conditions and other traits, which will lead to higher or earlier yield.

iv) targeted sequence excision. As described above homogenous excision of sequences, especially marker sequences, is a yet unsolved issue in the field of biotechnology. Most plants demonstrate mosaic-like excision patterns, which areas of successful excision and areas of no excision. To achieve homogenous or substantially homogenous excision, the excision mechanism needs to be activated preferably at an early stage of development, when the organism does not consist of many plants. Furthermore the activation (i.e. expression of the excision mediating enzyme) needs to be strong. Both requirements are met by the expression profile of the chimeric transcription regulating nucleic acid sequences (e.g., the super-promoter) disclosed herein. The strong transcription activity in early embryo germination allows for efficient marker excision in this stage, from which a target sequence free (e.g., marker-free) plant is generated.

The expression profile of the chimeric transcription regulating nucleic acid sequences (e.g., the super-promoter) is—depending on the development time—either specific for the starchy endosperm or the embryo, respectively.

"Germinating embryo-specific transcription" in the context of this invention means the transcription of a nucleic acid sequence by a transcription regulating element in a way that transcription of said nucleic acid sequence in the germinating plant, preferably the germinating embryo contribute to more than 90%, preferably more than 95%, more preferably more than 99% of the entire quantity of the RNA transcribed from said nucleic acid sequence in the entire plant, seed or sprout during the specified developmental stage.

"Starchy endosperm-specific transcription" in the context of this invention means the transcription of a nucleic acid sequence by a transcription regulating element in a way that transcription of said nucleic acid sequence in the starchy endosperm contribute to more than 90%, preferably more than 95%, more preferably more than 99% of the entire quantity of the RNA transcribed from said nucleic acid sequence in the entire plant, seed or sprout during the specified developmental stage.

1. The Chimeric Transcription Regulating Nucleic Acid Sequence

In its most general form the chimeric transcription regulating nucleotide sequence comprises
i) at least one transcription regulating nucleotide sequence derived from the promoter of an *Agrobacterium* mannopine synthase gene, and
ii) at least one upstream activating sequence derived from an *Agrobacterium* octopine synthase gene.

The term "transcription regulating nucleotide sequence derived from the promoter of an *Agrobacterium* mannopine synthase gene" means a sequence comprising at least the functional elements responsible for regulating expression of mannopine synthase in *Agrobacterium*, preferably in *Agrobacterium tumefaciens*.

Preferably, the transcription regulating nucleotide sequence derived from the promoter of an *Agrobacterium* mannopine synthase gene and/or the upstream activating sequence derived from an *Agrobacterium* octopine synthase gene, are derived from an *Agrobacterium tumefaciens* strain.

Promoter sequences of mannopine synthase genes are well known in the art. For example the mannopine synthase genes mas 1' and 2' share a dual bidirectional promoter and a 479 bp intergenic region. These genes encode enzymes for a two-step pathway for the synthesis of mannopine (Ellis 1984; Komro 1985). The transcription of the mas genes is divergent, and the intergenic region contains all the cis-acting elements necessary for the transcription of both genes (DiRita 1987; Fox 1992; Leung 1991; Guevara-Garcia 1993). Transcriptional elements for the mannopine synthase genes are disclosed in DiRita 1987, Gelvin, supra, Fox 1992; Leung 1991; Langridge 1989. Additionally, the overall sequence of a T-DNA is disclosed in Barker 1983.

The term "upstream activating sequence" (UAS) refers to a sequence which in the native state is preferably at least 100 base pairs in advance of the native transcriptional start site, and can exert influence on expression. T-DNA genes contain regions that are functional in plant environments and possess similarities to plant regulatory regions. For example, most plant promoters contain cis-acting elements such as upstream activating sequences ("UAS") (often called "enhancers") that, by binding trans-acting factors, define or influence the promoter strength and tissue-specific expression pattern. Atchison, (1988) Annu. Rev. Cell Biol. 4:127-53. The overall strength of a given promoter, as well as its pattern of expression, can be influenced by the combination and spatial orientation of cis-acting elements and the presence of the nuclear factors that interact with these elements. Dynan, (1989) Cell 58:1-4. Although initially resident on a prokaryotic plasmid, T-DNA genes possess all of the sequence elements (promoters and UAS) required for transcription in plants. For instance, T-DNA genes contain TATA boxes that set the site of transcription initiation, and often contain upstream elements, located more than 100 bp from the transcription initiation site, that modulate the levels of transcription. See Gelvin, TRANSGENIC PLANTS (Academic Press 1993). The UAS of octopine and mannopine synthase genes are particularly useful in this regard. These UAS can then be operably linked to a promoter sequence or to an upstream activating sequence and promoter sequence derived from a different *Agrobacterium tumefaciens* opine synthase gene. Two T-DNA genes that possess upstream activating sequences are the octopine synthase (ocs) and mannopine synthase (mas) genes. The ocs gene encodes a product that condenses arginine and pyruvate to form octopine. Hack and Kemp, (1980) Plant Physiol. 65:949-55. A 16-base pair palindrome located upstream of the ocs gene is capable of activating a heterologous maize adhl promoter in a transient expression system. Ellis et al., (1987) EMBO J. 6:11-16; Ellis et al., (1987) EMBO J. 6:3203-08. This palindrome is also essential for ocs promoter activity in stably transformed tobacco calli. Leisner and Gelvin, (1988) Proc. Nat'l Acad. Sci. USA 85:2553-57; Leisner and Gelvin, (1989) Plant Cell 1:925-36.

Transcriptional elements, such as promoters and upstream activating sequences, of the opine synthase genes can be readily obtained based upon available sequence information. For example, transcriptional elements for the octopine synthase genes are disclosed in Leisner et al., (1988) Proc. Nat'l Acad. Sci. USA 85:2553-57; Leisner et al., (1989) Plant Cell 1:925-936.

Various forms are possible to form a chimeric transcription regulating nucleotide sequence of the invention. Preferably said chimeric transcription regulating nucleotide sequence comprises at least three upstream activating sequences derived from an *Agrobacterium tumefaciens* octopine synthase gene operably linked to at least one transcription regulating nucleotide sequence derived from the promoter of an *Agrobacterium tumefaciens* mannopine synthase gene. More preferably said chimeric transcription regulating nucleotide sequence further comprises at least one upstream activating sequence derived from a mannopine synthase gene of *Agrobacterium tumefaciens*.

In a more preferred embodiment the chimeric transcription regulating nucleotide sequence comprises a specific combination of the upstream activating sequences from an octopine synthase and the transcription regulating nucleotide sequence from a mannopine gene. In a more preferred embodiment the chimeric transcription regulating nucleotide sequence is the super-promoter. The term "super-promoter" as used herein means the specific combination of the upstream activating sequences from an octopine synthase and the transcription regulating nucleotide sequence from a mannopine gene as described by SEQ ID NO: 4. As used herein the term also comprises derivatives and variants of the super-promoter as described by SEQ ID NO: 4.

The term "derived" when used in the context of DNA regions like promoters, transcription regulating nucleic acid sequences, or upstream activating sequences refers to situations where the DNA region that is "derived" is obtained from or based upon a naturally-occurring DNA region or other source DNA region. The DNA region that is "derived" can differ, usually through deliberate mutation, from the naturally-occurring DNA region or other source DNA region.

The phrase "operably linked" refers to a first sequence(s) being positioned sufficiently proximal to a second sequence(s) so that the first sequence(s) can exert influence over the second sequence(s) or a region under control of that second sequence. For instance, an UAS can be operably linked to a transcription regulating nucleic acid sequences (e.g., a promoter), whereby the UAS enhances the transcriptional strength of the promoter. In this situation, the UAS would typically be 5' to the promoter. The UAS and promoter can, in turn, be operably linked to a gene so that the gene will be expressed under the control of the UAS/promoter combination, which would typically be 5' to the gene. Usually, a promoter would be within about 30-50 base pairs from the start site of transcription and within a few hundred base pairs from the start site of translation. An activating sequence is usually within a few hundred base pairs of a promoter. For example, most activating sequence are within about 300 to 400 base pairs of the promoter that is enhanced. In embodiments of the invention where more than one activating sequence is employed, the activating sequences are usually within about 100 to 200 base pairs of each other.

1.1 Derivatives and Variants of the Chimeric Transcription Regulating Nucleotide Sequence of the Invention and Its Functional Elements The invention disclosed herein contemplates that beside the specific chimeric transcription regulating nucleotide sequences (e.g., the super-promoter) and their specific elements (e.g., UAS sequences and promoter sequences) disclosed herein, derivatives and variants of said sequences can be employed.

By "variants" or "derivatives" is intended substantially similar sequences wherein one or more bases have been modified, removed or added. Such derivatives and variants include sequences, which are modified in comparison to the original sequence (e.g., the sequence as described by SEQ ID NO: 4) or derived from similar but different organisms.

Accordingly a variant or derivative may comprise one or more mutations (including but not limited to insertions, deletions, substitutions, alterations, inversions etc. of one or more nucleotides). For nucleotide sequences, naturally-occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 60%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein, using default parameters.

Derivatives of the specific chimeric transcription regulating nucleotide sequences (e.g., the super-promoter) and their specific elements (e.g., UAS sequences and promoter sequences) may include, but are not limited to, deletions of sequence, single or multiple point mutations, alterations at a particular restriction enzyme site, addition of functional elements, or other means of molecular modification. This modification may or may not enhance, or otherwise alter the transcription regulating activity of said sequences.

For example, one of skill in the art may delimit the functional elements within the sequences and delete any non-essential elements. Functional elements may be modified or combined to increase the utility or expression of the sequences of the invention for any particular application. Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the B10BASE database "Transfac" (Biologische Datenbanken GmbH, Braunschweig; Wingender 2001) or the database PlantCARE (Lescot 2002). Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences (see Table 2 below).

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter construct, which contains a deleted segment to a selectable or screenable marker, and to isolate only those cells expressing the marker gene. In this way, a number of different, deleted promoter constructs are identified which still retain the desired, or even enhanced, activity. The smallest segment, which is required for activity, is thereby identified through comparison of the selected constructs. This segment may then be used for the construction of vectors for the expression of exogenous genes.

The means for mutagenizing or creating deletions in a DNA segment encoding any promoter sequence are well known to those of skill in the art and are disclosed, for example, in U.S. Pat. No. 6,583,338, incorporated herein by reference in its entirety. Certain variant nucleotide sequences of the present invention retain biological activity (i.e. regulate transcription with a profile as defined above). One example of a regulatory sequence variant is a promoter formed by one or more deletions from a larger promoter. The 5' portion of a promoter up to the TATA box near the transcription start site can sometimes be deleted without abolishing promoter activity, as described by Zhu et al., (1995) The Plant Cell 7:1681-1689. A routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Biologically active variants also include, for example, the native promoter sequences of the invention having one or more nucleotide substitutions, deletions or insertions.

Derivatives and variants also include homologs, paralogs and orthologs from Agrobacterium (e.g., Agrobacterium tumefaciens) and other species, such as other soil-borne bacteria. "Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Paralog" refers to a polynucleotide or polypeptide that within the same species which is functionally similar. "Ortholog" refers to a polynucleotide or polypeptide that is the functional equivalent of the polynucleotide or polypeptide in another species. An orthologous gene means preferably a gene, which is encoding a orthologous protein. More specifically, the term "ortholog" denotes a polypeptide or protein obtained from one species that is the functional counterpart of a polypeptide or protein from a different species. Sequence differences among orthologs are the result of speciation.

Preferably, the transcription regulating activity of a variant or derivative of a chimeric transcription regulating nucleotide sequences (e.g., the super-promoter) is substantially the same (or equivalent) than for the chimeric transcription regulating nucleotide sequences (e.g., the super-promoter) specifically disclosed herein, i.e. that expression is regulated in the starchy-endosperm and germinating embryo-specific fashion as described above. Beside this the transcription regulating activity of a derivative or variant may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences, which—in comparison with its parent sequence—does, not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%. Such expression profile is preferably demonstrated using reporter genes operably linked to said transcription regulating nucleotide sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987). Other methods to assay transcriptional regulation are well known in the art and include Northern blots, and RT-PCR (see, for example, Sambrook et al., supra, herein incorporated by reference).

In one preferred embodiment the transcription regulating nucleotide sequence derived from the promoter of an *Agrobacterium tumefaciens* mannopine synthase gene is described by a sequence selected from the group consisting of i) the sequence described by SEQ ID NOs: 2 or 3, ii) a fragment of at least 50 consecutive bases, preferably at least 100 consecutive bases, more preferably 200 consecutive bases of the sequence described by SEQ ID NOs: 2 or 3, iii) a nucleotide sequence having a sequence identity of at least 60%, preferably at least 70% or 80%, more preferably at least 85% or 90%, most preferably at least 95% or 98% to the sequence described by SEQ ID NO: 2 or 3, iv) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 2 or 3, or the complement thereof;

v) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides (such as 50 or 100, preferably 150 or 200, more preferably 250 or 400 consecutive nucleotides, most preferably the entire sequence) of a sequence described by SEQ ID NO: 2 or 3, or the complement thereof;

vi) a nucleotide sequence which is the complement or reverse complement of any of the previously mentioned nucleotide sequences under i) to v).

In another preferred embodiment the upstream activating sequence derived from an octopine synthase gene of *Agrobacterium tumefaciens* is described by a sequence selected from the group consisting of i) the sequence described by SEQ ID NOs: 1, ii) a fragment of at least 50 consecutive bases, preferably at least 100 consecutive bases, more preferably 200 consecutive bases of the sequence described by SEQ ID NOs: 1, iii) a nucleotide sequence having a sequence identity of at least 60%, preferably at least 70% or 80%, more preferably at least 85% or 90%, most preferably at least 95% or 98% to the sequence described by SEQ ID NO: 1, iv) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 1, or the complement thereof;

v) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides (such as 50 or 100, preferably 150 or 200, more preferably 250 or 400 consecutive nucleotides, most preferably the entire sequence) of a sequence described by SEQ ID NO: 1, or the complement thereof;

vi) a nucleotide sequence which is the complement or reverse complement of any of the previously mentioned nucleotide sequences under i) to v).

Thus, in a more preferred embodiment the chimeric transcription regulating nucleotide sequence is described by a sequence selected from the group consisting of i) the sequence described by SEQ ID NOs: 4, ii) a fragment of at least 50 consecutive bases, preferably at least 100 consecutive bases, more preferably 200 consecutive bases of the sequence described by SEQ ID NOs: 4, iii) a nucleotide sequence having a sequence identity of at least 60%, preferably at least 70% or 80%, more preferably at least 85% or 90%, most preferably at least 95% or 98% to the sequence described by SEQ ID NO: 4, iv) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to the sequence described by SEQ ID NO: 4, or the complement thereof;

v) a nucleotide sequence capable of hybridizing (preferably under low stringency conditions, more preferably under medium stringency conditions, most preferably under high stringency conditions as define above in the DEFINITION section; for example under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides (such as 50 or 100, preferably 150 or 200, more preferably 250 or 400 consecutive nucleotides, most preferably the entire sequence) of a sequence described by SEQ ID NO: 4, or the complement thereof;

vi) a nucleotide sequence which is the complement or reverse complement of any of the previously mentioned nucleotide sequences under i) to v).

The sequences specified under ii), iii), iv) v) and vi) of any of the specified chimeric transcription regulating sequences defined above are preferably capable to modify transcription in a monocotyledonous plant cell or organism, more preferably they are capable to induce starchy endosperm and/or embryo specific expression. Preferably, the sequences specified under iv) or v) are hybridizing under stringent conditions with the specified target sequence.

Preferably, the nucleotide sequences identify is determined by using the BlastN program (version 1.4.7 or later) with its default parameters (wordlength (W) of 11, an expectation (E) of 10, a cutoff of 100, M=5, N=−4, and a comparison of both strands) or any equivalent program.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least about 60% to 70% and even about 80% 85%, 90%, 95% to 98% or more identity with the disclosed sequences. That is, the sequence similarity of sequences may range, sharing at least about 60% to 70%, and even about 80%, 85%, 90%, 95% to 98% sequence similarity.

1.2 Inducible Variants of the Chimeric Transcription Regulating Nucleotide Sequence of the Invention In one preferred embodiment the chimeric transcription regulating nucleotide sequence of the invention (e.g., the super-promoter) is modified in a way that it becomes inducible by application of an external compound or other stimulus.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Whatever the level of expression is in the absence of the stimulus, expression from any inducible promoter is increased in the presence of the correct stimulus. The preferable situation is where the level of expression increases upon in the presence of the relevant stimulus by an amount effective to alter a phenotypic characteristic. Thus an inducible (or "switchable") promoter may be used which causes a basic level of expression in the absence of the stimulus which level is too low to bring about the desired phenotype (and may in fact be zero). Upon application of the stimulus, expression is increased (or switched on) to a level that causes expression. Many examples of inducible promoters will be known to those skilled in the art, which can be combined with the chimeric transcription regulating nucleotide sequence of the invention (e.g., the super-promoter).

The inducer can be a physical stimulus like light, heat, drought (low moisture), wounding etc. However, preferably, the inducer is an externally applied chemical substance. It is preferred that the inducible excision promoter only causes functional expression of the endonuclease operably linked if this chemical inducer is externally applied. This leads to a controlled, governable expression and deletion.

Inducible and repressible promoters have been developed for use in plants (Review: Gatz, Annu Rev Plant Physiol Plant Mol Biol 1997, 48:89-108), based on—for example—bacterial repressor (Gatz C & Quail P H (1988) Proc. Natl. Acad. Sci. USA 85:1394-1397), animal steroid (Aoyarna T & Chua N H (1997) Plant J. 11:605-612; Martinez A et al. (1999) Plant J. 19:97-106) or fungal regulatory elements (Caddick M X et al. (1998) Nature Biotechnol 16:177-180). Promoter systems that are positively regulated by chemical ligands (inducible systems) include the tetracycline(doxycycline)-induced 'Triple-Op' promoter (Gatz C & Quail P H (1988) Proc Natl Acad Sci USA 85:1394-1397; Gatz C et al. (1991) Mol Gen Genet. 277:229-237; Gatz C et al. (1992) Plant J. 2:397-404), the glucocorticoid-inducible 'GAL4-UAS' promoter (Aoyarna T & Chua N H (1997) Plant J. 11:605-612), the ecdysone-inducible 'GRHEcR' promoter (Martinez A et al. (1999) Plant J. 19:97-106) and the ethanol-inducible 'alcA' promoter (Caddick M X et al. (1998) Nature Biotechnol 16:177-180). Hormones that have been used to regulate gene expression include, for example, estrogen, tomoxifen, toremifen and ecdysone (Ramkumar and Adler (1995) Endocrinology 136:536-542). See, also, Gossen and Bujard (1992) Proc. Natl. Acad. Sci. USA 89:5547; Gossen et al. (1995) Science 268:1766. In tetracycline-inducible systems, tetracycline or doxycycline modulates the binding of a repressor to the promoter, thereby modulating expression from the promoter.

Inducible expression system can be distinguished into positively and negatively regulated systems. For positively regulated system, expression is induced by adding the corresponding inducer, for negatively regulated systems expression is induced by removing the inducer (better named repressor in this case). An example for a negatively regulated (repressible) system is the tetracycline-inactivated 'Top10' promoter and derivatives (Bohner S et al. (1999) Plant J. 19:87-95; Weinmann P et al. (1994) Plant J 5:559-569). The Top10 promoter sequence contains a tandem repeat of seven copies of the Tn10 tet operator (tet-OP) DNA sequence that tightly bind the tetracycline repressor polypeptide TetR (Lederer T et al. (1995) Anal Biochem 232:190-196). This element is fused to a truncated version of e.g., the CaMV 35s promoter (nucleotide positions −53 to 0). The Top10 promoter sequence is recognized by a transactivator that effectively acts as an artificial transcription factor. The transactivator is a chimeric protein fusion between amino acids 1-207 of TetR (Postle K et al. (1984) Nucl Acids Res 12:4849-4963) and amino acids 363-490 of the transcriptional activation domain (VP16) from the Herpes simplex virus (Triezenberg S J et al. (1988) Genes Dev. 2:718-729), and is labelled 'TetR/VP16' or 'tTA' (tetracycline transactivator). In the absence of tetracycline, the TetR portion of the tTA binds the tet-OP DNA sequences within the Top10 promoter with high affinity (Hinrichs W et al. (1994) Science 264:418-420; Lederer T et al. (1995) Anal Biochem 232:190-196; Lederer T et al. (1996) Biochemistry 35:7439-7446). This interaction positions the VP16 domain of the tTA in close proximity to the Top10 promoter TATA box, enabling transgene transcription. However, in the presence of tetracycline, the TetR undergoes a conformational change (Hinrichs W et al. (1994) Science 264:418-420; Orth P et al. (1998) J Mol Biol 279: 439-447) that lowers its affinity for the Top10 promoter to non-specific binding levels (Lederer T et al. (1996) Biochemistry 35:7439-7446). Consequently, tTA binding to the Top10 promoter is inhibited, and transcription is switched off. Use of the Top10 promoter system is particularly advantageous in plants. First the Top10 promoter is not functional in the absence of the tTA. Second, transcriptional control is stringent, and tightly controlled by tetracycline. Third, tetracycline has no naturally occurring analogue in plant cells, which might otherwise interfere with promoter regulation. Fourth, the levels of tetracycline used to repress the Top10 promoter are extremely low, normally of the order of 1 µg/ml, and have no discernible secondary effect on plants (Weinmann P et al. (1994) Plant J 5:559-569). Finally, coupling the two transformations required for promoter function can be achieved by transforming the same plants first with the 35S::tTA plasmid construct and then with the Top10 promoter driving the gene of interest, or by mating transgenics which have independently been transformed with the appropriate constructs. The Top10 promoter has been successfully used in Nicotiana sp. (Weinmann P et al. (1994) Plant J 5:559-569) and in the moss *Physcomitrella patens* (Zeidler M et al. (1996) Plant Mol Biol 30:199-205). Alternatively, a positively regulated tetracyclin based inducible expression system can be employed. Especially preferred is the inducible reverse tetracycline system, which allows expression to be up-regulated only upon addition of tetracyclin or a lipid-soluble derivative of tetracycline, doxycyclin (dox, Gossen M. et al. (1995) Science 268:1766-1769; Jiang D M et al. (2001) J. Neurochem. 76(6); 1745-1755).

Inducible promoters that are directly responsive to physiologically active stimuli such as heat-shock (Prandl R et al. (1995) Plant Mol. Biol. 28:73-82; 1995; Severin K & Schoeffl F (1990) Plant Mol. Biol. 15:827-834), stress signalling molecules (Suchara K I et al. (1996) J. Ferm. Bioeng. 82, 51-55) or heavy metals (McKenzie, M J et al. (1998) Plant Physiol. 116, 969-977) may also be employed. However, chemically inducible promoter systems are preferred.

Inducib expression systems have been used in several plant species, including tobacco (Gatz C et al. (1991) Mol. Gen. Genet. 277:229-237), potato (Kumar A et al. (1996) Plant J. 9:147-158), tomato (Thompson A J & Myatt S C (1997) Plant Mol. Biol. 34:687-692) and *Arabidopsis thaliana* (Aoyarna T & Chua N H (1997) Plant J. 11:605-612).

An additional example includes the ecdysone responsive element (No et al., (1997) Proc. Natl. Acad. Sci. USA 93: 3346). Other examples of inducible promoters include the glutathione-S-transferase II promoter which is specifically induced upon treatment with chemical safeners such as N,N-diallyl-2,2-dichloroacetamide (PCT Application Nos. WO 90/08826 and WO 93/01294) and the alcA promoter from *Aspergillus*, which in the presence of the alcR gene product is induced with cyclohexanone (Lockington et al., (1985) Gene 33:137-149; Felenbok et al. (1988) Gene 73: 385-396; Gwynne et al. (1987) Gene 51:205-216) as well as ethanol. Chemical inducers of promoters can be combined with other active chemicals or inert carriers prior to application to an organism. For example, other agronomically useful chemical compositions such as pesticides or fertilizers as well as carriers and solvents can be combined with the inducer.

Further examples for inducible promoters include the PRP1 promoter (Ward et al., (1993) Plant. Mol. Biol. 22:361-366), a salicylic-acid-inducible promoter (WO 95/19443), a benzenesulfonamide-inducible promoter (EP-A-0388186), a tetracyclin-inducible promoter (Gatz et al., (1992) Plant J. 2:397-404), an abscisic acid-inducible promoter (EP-A 335528), a salicylic acid-inducible promoter (WO 95/19443) or an ethanol- (Salter M G et al. (1998) Plant J. 16:127-132) or cyclohexanone-inducible (WO 93/21334) promoter may likewise be used.

Other preferred promoters are promoters induced by biotic or abiotic stress, such as, for example, the pathogen-inducible promoter of the PRP1 gene (Ward et al., Plant Mol Biol 1993, 22:361-366), the tomato heat-inducible hsp80 promoter (U.S. Pat. No. 5,187,267), the potato chill-inducible alpha-amylase promoter (WO 96/12814) or the wound-induced pinII promoter (EP375091).

1.3 Additional Regulatory and Functional Elements for the Expression Cassette and Vectors of the Invention An expression cassette of the invention may comprise further regulatory elements. The term in this context is to be understood in a broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. Especially preferred is inducibility, described above in more detail. For example the expression may be made depending on certain stress factors such water stress, abscisin (Lam 1991) or heat stress (Schoffl 1989). Furthermore additional promoters or promoter elements may be employed, which may realize expression in other organisms (such as *E. coli* or *Agrobacterium*). Such regulatory elements can be found in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters, which are useful for plant transgene expression include those that are inducible, viral, synthetic, constitutive (Odell 1985), temporally regulated, spatially regulated, tissue-specific, and spatial-temporally regulated.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor 1 or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those, which include sequences, predicted to direct optimum expression of the attached gene, i.e., to include a preferred consensus leader sequence, which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes.

Such sequences that have been found to enhance gene expression in transgenic plants include intron sequences (see below for details) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as the TMV omega element (Gallie 1989), may further be included where desired. Additional examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

The cassette can also contain sequences that enhance translation and/or mRNA stability such as introns (e.g., from Adh1, bronze1, actin1, actin 2 (WO 00/760067), or the sucrose synthase intron; see: The Maize Handbook, Chapter 116, Freeling and Walbot, Eds., Springer, N.Y. (1994)). In one embodiment, the enhancer intron is a rice actin 1 intron 1 (U.S. Pat. No. 5,641,876, incorporated herein by reference in its entirety), a rice actin 2 intron 1 (U.S. Pat. No. 6,429,357, incorporated herein by reference in its entirety), an Adh intron 1 (Callis 1987), or a sucrose synthase intron (Vasil 1989).

However, intron sequences are not necessary to achieve the expression profile described herein. This is a surprising observation, keeping in mind the general expression modifying properties of introns. In another preferred embodiment the expression cassette of the invention does not comprise an intron with expression enhancing properties operably linked to said chimeric transcription regulating sequence (e.g., the super-promoter).

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Additionally, the expression cassettes may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

1.4 Assembly of the Chimeric Transcription Regulating Nucleic Acid Sequence, Expression Cassettes, and Vectors of the Invention An operable linkage in relation to any chimeric transcription regulating nucleic acid sequence, expression cassette or vector of the invention may be realized by various methods known in the art, comprising both in vitro and in vivo procedure. Thus, any chimeric transcription regulating nucleic acid sequence, expression cassette or vector of the invention may by realized using standard recombination and cloning techniques well known in the art (see e.g., Maniatis 1989; Silhavy 1984; Ausubel 1987). Many approaches or methods have been developed and used for gene cloning. Examples of these are cloning by restriction enzyme digestion and ligation of compatible ends, T-A cloning directly from PCR product, TOPO-attached unidirectional cloning, and recombination-based cloning. Recombination-based cloning is one of the most versatile cloning methods available due to its high cloning efficiency and its broad application for cloning a variety of genes regardless of available restriction enzyme sites. Recombination cloning uses the lambda recombination system to clone genes into vectors that contain recombination sequences for the lambda recombinase machinery. Recombination cloning uses site-specific recombinases, which along with associated proteins in some cases, recognize specific sequences of bases in a nucleic acid molecule and exchange the nucleic acid segments flanking those sequences. The recombinases and associated proteins are collectively referred to as "recombination proteins." Site-specific recombinases are proteins that are present in many organisms (e.g., viruses and bacteria) and have been characterized as having both endonuclease and ligase properties. Many of the known site-specific recombinases belong to the integrase family of recombinases including the Integrase/att system from bacteriophage lambda. An example of one application of the Integrase/att system from bacteriophage lambda is the LR cloning reaction as disclosed in U.S. Pat. No. 5,888,732 and U.S. Pat. No. 6,277,608 and U.S. published patent application 2002/0007051 A1 and International application WO 02/081711 A1, all of which are incorporated herein by reference. The LR cloning reaction is commercially available as the GATEWAY™ cloning technology (available from Invitrogen Corporation, Carlsbad, Calif.). The LR cloning reaction is catalyzed by the LR Clonase Enzyme mix, which comprises lambda recombination proteins Int, Xis, and the *E. coli*-encoded protein IHF.

An expression cassette may also be assembled by inserting a chimeric transcription regulating nucleic acid sequence of the invention (e.g., the super-promoter) into the plant genome. Such insertion will result in an operable linkage to a nucleic acid sequence of interest, which as such already existed in the genome. By the insertion the nucleic acid of interest is expressed in a starch-endosperm and germinating embryo-specific way due to the transcription regulating properties of the chimeric transcription regulating nucleotide sequence. The insertion may be directed or by chance. Preferably the insertion is directed and realized by for example homologous recombination. By this procedure a natural promoter may be exchanged against the chimeric transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

An operable linkage may—for example—comprise an sequential arrangement of the chimeric transcription regulating nucleotide sequence of the invention (for example the super-promoter) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. The term "appropriate conditions" mean preferably the presence of the expression cassette in a plant cell. Preferred are arrangements, in which the nucleic acid sequence of interest to be expressed is placed down-stream (i.e., in 3'-direction) of the chimeric transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

Virtually any DNA composition may be used for delivery to recipient monocotyledonous plants or plant cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors, which may be employed in conjunction with the present invention, will be known to those of skill of the art in light of the present disclosure (see, e.g., Sambrook 1989; Gelvin 1990).

The present invention further provides a recombinant vector or other DNA construct suitable for plant transformation (including but not limited to cosmids, YACs (yeast artificial chromosomes), BACs (bacterial artificial chromosomes), and plant artificial chromosomes) containing the expression cassette of the invention, and monocotyledonous host cells comprising the expression cassette or vector, e.g., comprising a plasmid. The expression cassette or vector may (preferably) augment the genome of a transformed monocotyledonous plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu.

The DNA construct according to the invention and any vectors derived therefrom may comprise further functional elements. The term "further functional elements" is to be understood in the broad sense. It preferably refers to all those elements which affect the generation, multiplication, function, use or value of said DNA construct or vectors comprising said DNA construct, or cells or organisms comprising the beforementioned. These further functional elements may include but shall not be limited to:

i) Origins of replication which ensure replication of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

ii) Multiple cloning sites (MCS) to enable and facilitate the insertion of one or more nucleic acid sequences.

iii) Sequences which make possible homologous recombination or insertion into the genome of a host organism.

iv) Elements, for example border sequences, which make possible the *Agrobacterium*-mediated transfer in plant cells for the transfer and integration into the plant genome, such as, for example, the right or left border of the T-DNA or the vir region.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences, which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof, which is introduced into the plant genome, is preferably preselected and defined, e.g., from one to about 5-10 such products of the introduced DNA may be formed.

The present invention also provides a monocotyledonous plant (preferably a transgenic plant), seed and parts from such a plant, and progeny plants from such a plant including hybrids and inbreds.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may is preferably a monocot (preferably as defined above). The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

2. Advantageous Traits or Properties to be Expressed by the Expression Cassette of the Invention The chimeric transcription regulating nucleotide sequences (e.g., the super-promoter) of the invention are useful to modify the phenotype of a plant. Various changes in the phenotype of a transgenic plant are desirable and can be achieved using the advantageous expression profile (i.e. starchy endosperm and germinating embryo-specific expression) of the transcription regulating nucleotide sequences disclosed herein. These results can be achieved by providing expression of heterologous products or increased expression of endogenous products in plants. Alternatively, the results can be achieved by providing for a reduction of expression of one or more endogenous products, particularly enzymes or cofactors in the plant. Generally, the chimeric transcription regulating nucleotide sequences may be employed to express a nucleic acid segment that is operably linked to said promoter such as, for example, an open reading frame, or a portion thereof, an anti-sense sequence, a sequence encoding for a sense or double-stranded RNA sequence, or a transgene in plants. These changes result in an alteration in the phenotype of the transformed plant.

The choice of a heterologous DNA for expression in a monocotyledonous plant host cell in accordance with the invention will depend on the purpose of the transformation. One of the major purposes of transformation of crop plants is to add commercially desirable, agronomically important or end-product traits to the plant.

Although numerous nucleic acid sequences are suitable to be expressed by the chimeric transcription regulating nucleic acid sequence of the invention (e.g., the super-promoter) most preferably the nucleic acid is conferring upon expression to the monocotyledonous plant a trait or property selected from the group consisting of
i) enhanced resistance against at least one stress factor,
ii) increased nutritional quality of a seed or a sprout,
iii) increased yield, and
iv) selection marker excision.

2.1 Basic Principles

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods, which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Thus, expression of the nucleic acid sequence under the chimeric transcription regulating sequence may result in expression of a protein, or expression of an antisense RNA, sense or double-stranded RNA.

Alternatively, an exogenous DNA sequence may be designed to down-regulate a specific nucleic acid sequence. This is typically accomplished by operably linking with the chimeric transcription regulating nucleic acid sequence (e.g., the super-promoter) of the invention, an exogenous DNA in an antisense orientation or a DNA designed such that a hairpin-forming RNA molecule is generated upon transcription. Gene suppression may be effective against a native plant gene associated with a trait, e.g. to provide plants with reduced levels of a protein encoded by the native gene or with enhanced or reduced levels of an affected metabolite. For example, the chimeric transcription regulating nucleic acid sequence (e.g., the super-promoter) of the invention may be operably linked to a heterologous DNA designed such that a hairpin-shaped RNA is formed for suppression of a native gene in maize embryos.

As used herein "gene suppression" means any of the well-known methods for suppressing an RNA transcript or production of protein translated from an RNA transcript, including post-transcriptional gene suppression and transcriptional suppression. Posttranscriptional gene suppression is mediated by double-stranded RNA having homology to a gene targeted for suppression. Gene suppression by RNA transcribed from an exogenous DNA construct comprising an inverted repeat of at least part of a transcription unit is a common feature of gene suppression methods known as anti-sense suppression, co-suppression and RNA interference. Transcriptional suppression can be mediated by a transcribed double-stranded RNA having homology to promoter DNA sequence to effect what is called promoter trans-suppression.

More particularly, post transcriptional gene suppression by inserting an exogenous DNA construct with anti-sense oriented DNA to regulate gene expression in plant cells is disclosed in U.S. Pat. Nos. 5,107,065 and 5,759,829, each of which is incorporated herein by reference in its entirety. Transgenic plants transformed using such anti-sense oriented DNA constructs for gene suppression can comprise DNA arranged as an inverted repeat, as disclosed by Redenbaugh et al. in "Safety Assessment of Genetically Engineered Flavr Savr™ Tomato", CRC Press, Inc. (1992). Inverted repeat insertions can comprises a part or all of a T-DNA construct, e.g. an inverted repeat of transcription terminator sequence.

Post transcriptional gene suppression by inserting an exogenous DNA construct with sense-oriented DNA to regulate gene expression in plants is disclosed in U.S. Pat. Nos. 5,283,184 and 5,231,020, each of which is incorporated herein by reference.

Different types of exogenous DNA arrangements resulting in gene suppression are known to those of skill in the art and include but are not limited to the following. International Publication WO 94/01550 discloses DNA constructs where the anti-sense RNA was stabilized with a self-complementary 3' segment. Other double-stranded hairpin-forming elements in transcribed RNA are disclosed in International Publication No. 98/05770 where the anti-sense RNA is stabilized by hairpin forming repeats of poly(CG) nucleotides and Patent Application Publication No. 2002/0048814 A1 describes sense or anti-sense RNA stabilized by a poly(T)-poly(A) tail. U.S. Patent Application Publication No. 2003/0018993 A1 discloses sense or anti-sense RNA that is stabilized by an inverted repeat of a subsequence of 3' untranslated region of the NOS gene. U.S. Patent Application Publication No. 2003/0036197 A1 describes an RNA stabilized by two complementary RNA regions having homology to a target sequence.

Gene silencing can also be effected by transcribing RNA from both a sense and an anti-sense oriented DNA, e.g. as disclosed in U.S. Pat. No. 5,107,065 and other examples as follows. U.S. Pat. No. 6,326,193 discloses gene targeted DNA which is operably linked to opposing promoters. Sijen et al., (Plant Cell, Vol. 8, 2277-2294 (1996)) disclose the use of constructs carrying inverted repeats of a cowpea mosaic virus gene in transgenic plants to mediate virus resistance. Such constructs for post transcriptional gene suppression in plants by double-stranded RNA are also disclosed in International Publication No. WO 99/53050, International Publication No. WO 99/49029, U.S. Patent Application Publication No. 2003/0175965 A1, U.S. patent application Ser. No. 10/465,800 and U.S. Pat. No. 6,506,559. See also U.S. application Ser. No. 10/393,347 which discloses constructs and methods for simultaneously expressing one or more recombinant genes while simultaneously suppressing one or more native genes in a transgenic plant. See also U.S. Pat. No. 6,448,473 which discloses multigene suppression vectors for use in plants. All of the above-described patents, applications and international publications disclosing materials and methods for post transcriptional gene suppression in plants are incorporated herein by reference.

Transcriptional suppression such as promoter trans suppression can be effected by a expressing a DNA construct comprising a promoter operably linked to inverted repeats of promoter DNA for a target gene. Constructs useful for such gene suppression mediated by promoter trans suppression are disclosed by Mette et al., (EMBO J. 18(1):241-148 (1999)) and by Mette et al., (EMBO J. 19(19):5194-5201 (2000)), both of which are incorporated herein by reference.

2.2 Agronomically Relevant Traits

The chimeric transcription regulating nucleotide sequences (e.g., the super-promoter) can be preferably employed to confer to the transformed monocotyledonous plant an agronomically relevant trait. Such traits include, but are not limited to, herbicide resistance, herbicide tolerance, insect resistance, insect tolerance, disease resistance, disease tolerance (viral, bacterial, fungal, nematode), stress tolerance, stress resistance, as exemplified by resistance or tolerance to drought, heat, chilling, freezing, excessive moisture, salt stress and oxidative stress, increased yield, food content and value, increased feed content and value, physical appearance, male sterility, female sterility, drydown, standability, prolificacy, starch quantity and quality, oil quantity and quality, protein quality and quantity, amino acid composition, and the like. Although numerous nucleic acid sequences are suitable to be expressed by the chimeric transcription regulating nucleic acid sequence of the invention (e.g., the super-promoter) most preferably the nucleic acid is conferring upon expression to the monocotyledonous plant an agronomically relevant trait selected from the group consisting of iv) enhanced resistance or tolerance against at least one stress factor,
v) increased nutritional quality of a seed or a sprout,
vi) increased yield.

One of the most economically relevant traits is yield. Yield is heavily affected by damage in any kind to the embryo and young seedling. Accordingly, any kind of trait which protects the young seedling and embryo or enhances its performance is advantageous with respect to yield. Thus, a trait resulting in stress resistance (see below) can also result in increased yield. Thus, another embodiment of the invention relates to a method for conferring increased yield to a monocotyledonous plant, said method comprising the steps of a) constructing an expression cassette by operably linking at least one chimeric transcription regulating nucleotide sequence comprising
  iii) at least one transcription regulating nucleotide sequence derived from the promoter of an *Agrobacterium* mannopine synthase gene, and
  iv) at least one upstream activating sequence derived from an *Agrobacterium* octopine synthase gene,
  to at least one nucleic acid sequence which is heterologous in relation to said chimeric transcription regulating nucleotide sequence and is suitable to confer to a plant increased yield, and
b) inserting said expression cassette into a monocotyledonous plant to provide a transgenic plant, wherein said plant expresses said heterologous nucleic acid sequence, and
c) selecting transgenic plants, which demonstrate increased yield in comparison to plants, which are not comprising said expression cassette but are otherwise identical to said transgenic plant.

The increased yield and the corresponding heterologous nucleic acid sequence to be expressed are defined as above. More specific examples are given herein below. Preferred chimeric transcription regulating nucleotide sequence are described above, most preferred is the super-promoter.

2.2.1 Increase Stress Resistance or Tolerance

The chimeric transcription regulating nucleotide sequences (e.g., the super-promoter) can be preferably employed to confer to the transformed monocotyledonous plant an increased (or enhanced) stress resistance (preferably to achieve a stress-resistant or stress tolerant plant). By "resistant" is meant a plant, which exhibits substantially no phenotypic changes as a consequence of agent administration, infection with a pathogen, or exposure to stress. By "tolerant" is meant a plant, which, although it may exhibit some phenotypic changes as a consequence of infection, does not have a substantially decreased reproductive capacity or substantially altered metabolism.

Accordingly another embodiment of the invention relates to a method for conferring enhanced stress resistance or tolerance to a monocotyledonous plant, said method comprising the steps of
a) constructing an expression cassette by operably linking at least one chimeric transcription regulating nucleotide sequence comprising
  i) at least one transcription regulating nucleotide sequence derived from the promoter of an *Agrobacterium* mannopine synthase gene,
  ii) at least one upstream activating sequence derived from an *Agrobacterium* octopine synthase gene,
  to at least one nucleic acid sequence which is heterologous in relation to said chimeric transcription regulating nucleotide sequence and is suitable to confer to a plant an enhanced resistance against stress, and
b) inserting said expression cassette into a monocotyledonous plant to provide a transgenic plant, wherein said plant expresses said heterologous nucleic acid sequence, and
c) selecting transgenic plants, which demonstrate enhanced resistance or tolerance against at least one stress factor in comparison to plants, which are not comprising said expression cassette but are otherwise identical to said transgenic plant.

Various nucleic acids sequences are known to the person skilled in the art to obtain such stress resistance. Said sequences may include but are not limited to polynucleotides encoding a polypeptide involved in phytohormone biosynthesis, phytohormone regulation, cell cycle regulation, or carbohydrate metabolism. The stress factor is preferably defined as above. The heterologous nucleic acid sequence to be expressed (e.g., either as a sense, antisense or double-stranded RNA) may encode a polypeptide (or a part thereof; preferably a part of at least 5, more preferably at least 10, most preferably at least 30 consecutive amino acids) as described by any of SEQ ID NO: 6, 8, 16, 18, 20, 43, 45, 47, 49, 50, 51, or 53, or a functional equivalent thereof, which is capable to bring about the same phenotype than any of said polypeptide. Preferred chimeric transcription regulating nucleotide sequence are described above, most preferred is the super-promoter.

Preferred chimeric transcription regulating nucleotide sequence are described above, most preferred is the super-promoter.

The stress factor and the heterologous nucleic acid sequence to be expressed are preferably defined as above. Preferred chimeric transcription regulating nucleotide sequence are described above, most preferred is the super-promoter.

The stress resistance, which can be advantageously obtained, is preferably against an abiotic or biotic stress factor. The biotic stress factor may be selected from the group consisting of fungal resistance, nematode resistance, insect resistance, virus resistance, and bacteria resistance. Preferably, the biotic stress factor is a seed-borne disease (mainly fungal diseases e.g. common bunt (*Tilletia tritici*) mainly in wheat; leaf stripe (*Pyrenophora graminea*), and loose smut (*Ustilago nuda*) mainly in barley).

The abiotic stress factor may be selected from the group consisting of water stress and excessive moisture resistance, drought and heat resistance, chilling, freezing and cold resistance, salt stress resistance, high plant population density, and UV light and oxidative stress resistance. Preferably, the stress resistance is achieved by inducing early vigor.

Various nucleic acids sequences are known to the person skilled in the art to obtain such stress resistance. Said sequences may include but are not limited to polynucleotides encoding a polypeptide involved in phytohormone biosynthesis, phytohormone regulation, cell cycle regulation, or carbohydrate metabolism. More specific examples are given below.

The invention is applicable to all monocotyledonous plants such as maize, wheat, rice, barley, oat, rye, sorghum, millet, tricalate, banana, ryegrass or coix, but is preferably applicable to kernel producing cereal plants of the Pooideae family such as maize, wheat, rice, barley, oat, rye, sorghum, millet, or tricalate, preferably to maize, barley and wheat, most preferably to maize.

Further embodiments of the invention relate to seeds, parts and cells of the monocotyledonous plant of the invention. Preferably, the plant parts are selected from the group consisting of: cells, protoplasts, cell tissue cultures, callus, cell clumps, embryos, pollen, ovules, seeds, flowers, kernels, ears, cobs, leaves, husks, stalks, roots, root tips, anthers, and silk.

Indirectly, the increased stress tolerance may cause one or more traits which promote aspects of enhanced grain agronomic characteristics, grain fill, decreased kernel abortion, increased transport of nutrients and the like.

2.2.1.1 Insect Resistance and Tolerance

An important aspect of the present invention concerns the introduction of insect resistance-conferring genes into plants. Potential insect resistance genes, which can be introduced, include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA (c) genes. Endotoxin genes from other species of *B. thuringiensis*, which affect insect growth or development, may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes, which encode inhibitors of the insects' digestive system, or those that encode enzymes or co-factors that facilitate the production of inhibitors, may also be useful. Cystatin and amylase inhibitors, such as those from wheat and barley, may exemplify this group.

Also, genes encoding lectins may confer additional or alternative insecticide properties. Lectins (originally termed phytohemagglutinins) are multivalent carbohydrate-binding proteins, which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes, which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn rootworm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

2.2.1.2 Environment or Stress Resistance and Tolerance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes, which are not sugars, include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or tissue-specific of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

One use for the chimeric transcription regulating sequences (e.g., the super-promoter) is to protect the embryo from cold damage during germination. One important factor is oxidative damage. The super-promoter could drive i.e. catalase, ascorbate peroxidase, superoxide dismutase and alike. The cold affects the COX enzyme activity also through a rigid membrane. For drought-stress expression of glutamine synthase and glycine betain synthase might be beneficial. For example sequences see above.

2.2.1.3 Disease Resistance and Tolerance

It is proposed that increased resistance to diseases may be realized through introduction of genes into plants. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences, which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, alpha-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164). Other nucleic acid sequences which may be advantageously used herein include traits for insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), and bacterial disease resistance (U.S. Pat. No. 5,516,671).

The heterologous nucleic acid sequence to be expressed may encode a polypeptide (or a part thereof; preferably a part of at least 5, more preferably at least 10, most preferably at least 30 consecutive amino acids) as described by any of SEQ ID NO: 6, 8, 16, 18, 20, 43, 45, 47, 49, 50, 51, or 53, or a functional equivalent thereof, which is capable to bring about the same phenotype than any of said polypeptide. Preferred chimeric transcription regulating nucleotide sequence are described above, most preferred is the super-promoter. Preferred are sequences which confer fungal resistance, as for example the sequences described by any of SEQ ID NO: 43, 45, 47, 49, 50, 51, or 53.

2.2.2 Increased Nutritional Quality of a Seed or a Sprout

The chimeric transcription regulating nucleotide sequences (e.g., the super-promoter) can be preferably employed to confer to the transformed monocotyledonous plant an increased (or enhanced) increased nutritional quality of a seed or a sprout. Accordingly another embodiment of the invention relates to a method for conferring increased nutritional quality of a seed or a sprout to a monocotyledonous plant, said method comprising the steps of a) constructing an expression cassette by operably linking at least one chimeric transcription regulating nucleotide sequence comprising
  i) at least one transcription regulating nucleotide sequence derived from the promoter of an *Agrobacterium* mannopine synthase gene, and
  ii) at least one upstream activating sequence derived from an *Agrobacterium* octopine synthase gene,
  to at least one nucleic acid sequence which is heterologous in relation to said chimeric transcription regulating nucleotide sequence and is suitable to confer to a plant increased nutritional quality of a seed or a sprout, and
b) inserting said expression cassette into a monocotyledonous plant to provide a transgenic plant, wherein said plant expresses said heterologous nucleic acid sequence, and
c) selecting transgenic plants, which demonstrate increased nutritional quality of a seed or a sprout in comparison to plants, which are not comprising said expression cassette but are otherwise identical to said transgenic plant.

The nutritional quality may comprise an increased content of at least one compound selected from the group consisting of vitamins, carotenoids, antioxidants, unsaturated fatty acids, and poly-unsaturated fatty acids. The heterologous nucleic acid sequence to be expressed (e.g., either as a sense, antisense or double-stranded RNA) may encode a polypeptide (or a part thereof; preferably a part of at least 5, more preferably at least 10, most preferably at least 30 consecutive amino acids) as described by any of SEQ ID NO: 10, 12, or 14, or a functional equivalent thereof, which is capable to bring about the same phenotype than any of said polypeptide.

Preferred chimeric transcription regulating nucleotide sequence are described above, most preferred is the super-promoter.

The nutritional quality and the corresponding heterologous nucleic acid sequence to be expressed are defined herein below. Preferred chimeric transcription regulating nucleotide sequence are described above, most preferred is the super-promoter. The monocotyledonous plant to which the methods of this invention are preferably applied to may be selected from the group consisting of maize, wheat, rice, barley, oat, rye, sorghum, banana, ryegrass or coix. Preferably the plant is a cereal plant selected from the group consisting of maize, wheat, barley, rice, oat, rye, and sorghum, even more preferably from maize, wheat, and rice, most preferably the plant is a maize plant.

An increased nutritional quality may—for example—result in one or more of the following properties: modifying the fatty acid composition in a plant, altering the amino acid content of a plant, increases the concentration of a plant metabolite.

Genes may be introduced into monocotyledonous plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes, which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well-known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA, which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase, which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as anti-sense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups, which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping, quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252; 6,437,217; 6,515,201; and 6,583,338 and PCT Publication WO 02/057471, each of which is specifically incorporated herein by reference in its entirety. Such traits include but are not limited to:

Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.

Expression of genes which bring about an accumulation of fine chemicals such as of tocopherols, tocotrienols or carotenoids. An example which may be mentioned is phytoene desaturase. Preferred are nucleic acids which encode the Narcissus pseudonarcissus photoene desaturase (GenBank Acc. No.: X78815) or functional equivalents thereof. Preferred tocopherol biosynthetic enzymes include tyrA, slr1736, ATPT2, dxs, dxr, GGPPS, HPPD, GMT, MT1, tMT2, AANT1, slr1737, and an antisense construct for homogentisic acid dioxygenase (Kridl et al. (1991) Seed Sci. Res., 1:209:219; Keegstra (1989) Cell, 56(2):247-53; Nawrath et al. (1994) Proc. Natl. Acad. Sci. USA, 91:12760-12764; Xia et al. (1992) J. Gen. Microbiol., 138:1309-1316; Lois et al. (1998) Proc. Natl. Acad. Sci. USA, 95 (5): 2105-2110; Takahashi et al. (1998) Proc. Natl. Acad. Sci. USA, 95(17):9879-9884; Norris et al. (1998) Plant Physiol., 117:1317-1323; Bartley and Scolnik (1994) Plant Physiol., 104:1469-1470; Smith et al. (1997) Plant J., 11:83-92; WO 00/32757; WO 00/10380; Saint Guily et al. (1992) Plant Physiol., 100(2):1069-1071; Sato et al. (2000) J. DNA Res., 7(1):31-63) all of which are incorporated herein by reference.

starch production (U.S. Pat. Nos. 5,750,876 and 6,476,295), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648), low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference. Preferred starch branching enzymes (for modification of starch properties) include those set forth in U.S. Pat. Nos. 6,232,122 and 6,147,279; and PCT Publication WO 97/22703, all of which are incorporated herein by reference.

Modified oils production (U.S. Pat. No. 6,444,876), high oil production (U.S. Pat. Nos. 5,608,149 and 6,476,295), or modified fatty acid content (U.S. Pat. No. 6,537,750). Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 20030115632A1 and 20030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Preferred amino acid biosynthetic enzymes include anthranilate synthase (U.S. Pat. No. 5,965,727 and PCT Publications WO 97/26366, WO 99/11800, WO 99/49058), tryptophan decarboxylase (PCT Publication WO 99/06581), threonine decarboxylase (U.S. Pat. Nos. 5,534,421 and 5,942,660; PCT Publication WO 95/19442), threonine deaminase (PCT Publications WO 99/02656 and WO 98/55601), dihydrodipicolinic acid synthase (U.S. Pat. No. 5,258,300), and aspartate kinase (U.S. Pat. Nos. 5,367,110; 5,858,749; and 6,040,160) all of which are incorporated herein by reference.

Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the *Bertholletia excelsa* high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella alpina* Δ6-desaturase (Sakuradani et al. (1999) Gene 238:445-453), the *Caenorhabditis elegans* Δ5-desaturase (Michaelson et al. (1998) FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.

Production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E and Jilka J M (1999) Curr Opin Biotechnol 10(4):382-6; Ma J K and Vine N D (1999) Curr Top Microbiol Immunol 236:275-92). For example, it has been possible to produce recombinant avidin from chicken albumen and bacterial β-glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those which encode the *Medicago sativa* acetyl-CoA carboxylase (ACCase) (GenBank Acc. No.: L25042), or functional equivalents thereof. Alternatively, in some scenarios an increased storage protein content might be advantageous for high-protewin product production. Preferred seed storage proteins include zeins (U.S. Pat. Nos. 4,886,878; 4,885,357; 5,215,912; 5,589,616; 5,508,468; 5,939,599; 5,633,436; and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (PCT Publication WO 96/17064), albumin (PCT Publication WO 97/35023), beta-conglycinin (PCT Publication WO 00/19839), 11S (U.S. Pat. No. 6,107,051), alpha-hordothionin (U.S. Pat. Nos. 5,885,802 and 5,88,5801), arcelin seed storage proteins (U.S. Pat. No. 5,270,200), lectins (U.S. Pat. No. 6,110,891), and glutenin (U.S. Pat. Nos. 5,990,389 and 5,914,450) all of which are incorporated herein by reference.

Reducing levels of α-glucan L-type tuber phosphorylase (GLTP) or α-glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an α-glucan phosphorylase selected from the group consisting of α-glucan L-type tuber phosphorylase (GLTP) and α-glucan H-type phosphorylase (GHTP).

Further examples of advantageous genes are mentioned for example in Dunwell J M, Transgenic approaches to crop improvement, J Exp Bot. 2000; 51 Spec No; pages 487-96. A discussion of exemplary heterologous DNAs useful for the modification of plant phenotypes may be found in, for example, U.S. Pat. No. 6,194,636;

Another aspect of the invention provides a DNA construct in which the promoter with starchy-endosperm and/or germinating embryo-specific or -preferential expression drives a gene suppression DNA element, e.g. to suppress an amino acid catabolizing enzyme.

Seed maturation: Seed maturation or grain development refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

The current invention provides novel methods and compositions for the efficient expression of transgenes in plants, especially in the germinating embryo. The promoter described herein represents a developmentally regulated promoter from which expression appears to be specific for the starchy endosperm for most of the seed development and increases in the embryo up to 16 hours after imbibition in water. The expression in the starchy endosperm "switches" to the embryo 24 hours until 7 days after germination.

Expression specific promoters of this invention may be useful in minimizing yield drag and other potential adverse physiological effects on maize growth and development that might be encountered by high-level, non-inducible, constitutive expression of a transgenic protein or other molecule in a plant. When each transgene is fused to a promoter of the invention, the risk of DNA sequence homology dependent transgene inactivation (co-suppression) can be minimized.

It may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences, which bind to a specific DNA sequence (the zinc finger) and amino acid sequences that activate (e.g., GAL 4 sequences) or repress the transcription of the sequences linked to the specific DNA sequence.

General categories of genes of interest for the purposes of the present invention include, for example, those genes involved in information, such as Zinc fingers, those involved in communication, such as kinases, and those involved in housekeeping, such as heat shock proteins. More specific categories of transgenes include genes encoding important traits for agronomic quality, insect resistance, disease resistance, herbicide resistance, and grain characteristics. Still other categories of transgenes include genes for inducing expression of exogenous products such as enzymes, cofactors, and hormones from plants and other eukaryotes as well as from prokaryotic organisms. It is recognized that any gene of interest can be operably linked to the promoter of the invention and expressed under stress.

In a more preferred embodiment, the promoter of the instant invention modulates genes encoding proteins which act as cell cycle regulators, or which control carbohydrate metabolism or phytohormone levels, as has been shown in tobacco and canola with other tissue-preferred promoters. (Ma, Q. H. et al., (1998) Australian Journal of Plant Physiology 25(1):53-59; Roeckel, P. et al., (1997) Transgenic Research 6(2):133-141) For example, genes encoding isopentenyl transferase or IAA-M may be useful in modulating development of the female florets. Other important genes encode growth factors and transcription factors. Expression of selected endogenous or heterologous nucleotides under the direction of the promoter may result in continued or improved development of the female florets under adverse conditions.

Seed production may be improved by altering expression of genes that affect the response of seed growth and development during environmental stress (Cheikh-N et al. (1994) Plant Physiol. 106(1):45-51) and genes controlling carbohydrate metabolism to reduce seed abortion in maize (Zinselmeier et al. (1995) Plant Physiol. 107(2):385-391).

2.3 Targeted Sequence Excision

The specificity of the chimeric transcription regulating nucleic acid sequences of the invention (e.g., the super-promoter) in monocotyledonous plants makes it especially useful for targeted excision or deletion of sequences (such as marker sequences) from the genome of said monocotyledonous plant. It is one known disadvantage of the methods known in the prior art that excision is not homogenous through the entire plants thereby leading to mosaic-like excision patterns, which require laborious additional rounds of selection and regeneration. The specificity of the promoters of the invention in the early embryo allows for homogenous excision throughout the entire embryo, which will then provide a plant homogenous target-sequence (e.g., marker) free plant.

Another embodiment of the invention relates to a method for excision of target sequences (e.g., marker sequences) from a monocotyledonous plant, said method comprising the steps of a) constructing an expression cassette by operably linking at least one chimeric transcription regulating nucleotide sequence comprising
   iii) at least one transcription regulating nucleotide sequence derived from the promoter of an *Agrobacterium* mannopine synthase gene, and
   iv) at least one upstream activating sequence derived from an *Agrobacterium* octopine synthase gene,
   to at least one nucleic acid sequence which is heterologous in relation to said chimeric transcription regulating nucleotide sequence and is suitable to induce excision of marker sequences from a monocotyledonous plant, and
b) inserting said expression cassette into a monocotyledonous plant comprising at least one marker sequence to provide a transgenic plant, wherein said plant expresses said heterologous nucleic acid sequence, and
c) selecting transgenic plants, which demonstrate excision of said marker.

The excision is realized by various mean, including but not limited to:
   induction of sequence deletion by side specific recombination using site-specific recombinases, wherein said site-specific recombinase is expressed by the chimeric transcription regulating nucleotide sequence of the invention,
   induction of sequence deletion by induced homologous recombination, wherein the sequences to be deleted are flanked by sequences, said sequences having an orientation, a sufficient length and a homology to each other to allow for homologous recombination between them, wherein homologous recombination is induced by a site-specific double-strand break made by a site-specific endonuclease (preferably a homing endonuclease, more preferably the homing endonuclease I-SceI), wherein said site-specific endonuclease is expressed by the chimeric transcription regulating nucleotide sequence of the invention.

Another embodiment of the invention relates to a monocotyledonous plant or plant cell comprising i) at least one target sequence, which is stably inserted into the plant genome, wherein said target sequence is flanked by excision-sequences which are capable to mediate upon interaction with a sequence specific excision-mediating enzyme excision of said target sequence from the plant genome, and ii) an expression cassette comprising at least one nucleic acid sequence encoding an excision-mediating enzyme, which is capable to interact with said excision-sequences of i), operably linked to a chimeric transcription regulating nucleotide sequence comprising
   a) at least one transcription regulating nucleotide sequence derived from the promoter of an *Agrobacterium tumefaciens* mannopine synthase gene,
   b) at least one upstream activating sequence derived from an octopine synthase gene of *Agrobacterium tumefaciens*.

Preferred chimeric transcription regulating nucleotide sequence are described above, most preferred is the super-promoter. Preferred heterologous nucleic acid sequence to be expressed to achieve sequence excision (e.g., encoding for a site-specific recombinase or endonuclease) are described herein below.

The monocotyledonous plant to which the methods of this invention are preferably applied to may be selected from the group consisting of maize, wheat, rice, barley, oat, rye, sorghum, banana, ryegrass or coix. Preferably the plant is a cereal plant selected from the group consisting of maize, wheat, barley, rice, oat, rye, and sorghum, even more preferably from maize, wheat, and rice, most preferably the plant is a maize plant.

The chimeric transcription regulating nucleotide sequence is preferably defined as above and is most preferably the super-promoter. The target sequence in the above defined monocotyledonous pant or plant cell will be excised as soon seeds of said plant are germinated and the embryo starts to grow. From this embryo a target-sequence free plant will result.

The target-sequence and the expression cassette for the excision-mediating enzyme may be combined on one DNA or on different construct. The different DNA constructs may be combined by other means in the genome of the monocotyledonous plant of plant cell such as—for example—crossing of distinct parental lines comprising said target sequence and said expression cassette for the excision-mediating enzyme, respectively, or co-transformation or subsequent transformation.

Accordingly, another embodiment of the invention relates to a method for excising at least one target sequence from the genome of a monocotyledonous plant or plant cell comprising the steps of i) stably inserting into the genome a nucleic acid construct at least one target sequence, which is stably inserted into the plant genome, wherein said target sequence is flanked by excision-sequences, which are capable to mediate upon interaction with a sequence specific excision-mediating enzyme excision of said target sequence from the plant genome, and ii) introducing into said monocotyledonous plants or plant cells an expression cassette comprising at least one nucleic acid sequence encoding an excision-mediating enzyme, which is capable to interact with said excision-sequences of i), operably linked to a chimeric transcription regulating nucleotide sequence comprising
   a) at least one transcription regulating nucleotide sequence derived from the promoter of an *Agrobacterium* mannopine synthase gene, and
   b) at least one upstream activating sequence derived from an *Agrobacterium* octopine synthase gene, iii) generating seeds of said monocotyledonous plant or plant cells comprising both said target sequence and said expression cassette, germinating said seeds and growing plants therefrom, and iv) selecting plants from which said target sequence has be excised.

In a preferred embodiment the method of the invention further comprises the step of regeneration of a fertile plant. The method may further include sexually or asexually propagating or growing off-spring or a descendant of the plant regenerated from said plant cell.

Preferably, excision (or deletion) of the target sequence can be realized by various means known as such in the art, including but not limited to one or more of the following methods:

a) recombination induced by a sequence specific recombinase, wherein said target sequence is flanked by corresponding recombination sites in a way that recombination between said flanking recombination sites results in deletion of the target-sequences in-between from the genome, b) homologous recombination between homology sequences A and A' flanking said target sequence, preferably induced by a sequence-specific double-strand break between said homology sequences caused by a sequence specific endonuclease, wherein said homology sequences A and A' have sufficient length and homology in order to ensure homologous recombination between A and A', and having an orientation which—upon recombination between A and A'—will lead to excision of said target sequence from the genome of said plant.

Preferred excision sequences and excision enzymes are specified below. In another preferred embodiment the mechanism of deletion/excision can be induced or activated in a way to prevent pre-mature deletion/excision of the dual-function marker. Preferably, thus expression and/or activity of an preferably employed sequence-specific recombinase or endonuclease can be induced and/or activated, preferably by a method selected from the group consisting of a) inducible expression by operably linking the sequence encoding said excision enzyme (e.g., recombinase or endonuclease) to the chimeric transcription regulating sequence combined with an inducible promoter or promoter element, b) inducible activation, by employing an inducible, modified excision enzyme (e.g., a recombinase or endonuclease) for example comprising a ligand-binding-domain, wherein activity of said modified excision enzyme can by modified by treatment of a compound having binding activity to said ligand-binding-domain.

Preferably, the target sequence is a marker, more preferably a selection marker (preferred marker sequences are specified below). Thus the method of the inventions results in a monocotyledonous plant cell or plant, which is selection marker-free.

2.3.1 Preferred Excision Sequences and Excision Enzymes

For ensuring target sequence deletion/excision the target sequence is flanked by excision sequences, which are capable to mediate upon interaction with a sequence specific excision-mediating enzyme excision of said target sequence from the plant genome. Preferably, deletion of the target sequence can be realized by various means known in the art, including but not limited to one or more of the following methods:

a) recombination induced by a sequence specific recombinase, wherein said target sequence is flanked by corresponding recombination sites in a way that recombination between said flanking recombination sites results in deletion of the target sequence in-between from the genome, b) homologous recombination between homology sequences A and A' flanking said target sequence, preferably induced by a sequence-specific double-strand break between said homology sequences caused by a sequence specific endonuclease, wherein said homology sequences A and A' have sufficient length and homology in order to ensure homologous recombination between A and A', and having an orientation which—upon recombination between A and A'—will lead to excision of said target sequence from the genome of said plant.

Accordingly, for ensuring target sequence deletion/excision the target sequence is flanked by sequences which allow for specific deletion of said expression cassette. Said sequences may be recombination sites for a sequence specific recombinase, which are placed in a way the recombination induced between said flanking recombination sites results in deletion of the said target sequence from the genome. There are various recombination sites and corresponding sequence specific recombinases known in the art (described herein below), which can be employed for the purpose of the invention.

In another preferred embodiment, deletion/excision of the target sequence is performed by intramolecular (preferably intrachromosomal) homologous recombination. Homologous recombination may occur spontaneous but is preferably induced by a sequence-specific double-strand break (e.g., between the homology sequences). The basic principals are disclosed in WO 03/004659. For this purpose the target sequence is flanked by homology sequences A and A', wherein said homology sequences have sufficient length and homology in order to ensure homologous recombination between A and A', and having an orientation which—upon recombination between A and A'—will lead to an excision said target sequence from the genome. Furthermore, the sequence flanked by said homology sequences further comprises at least one recognition sequence of at least 10 base pairs for the site-directed induction of DNA double-strand breaks by a sequence specific DNA double-strand break inducing enzyme, preferably a sequence-specific DNA-endonuclease, more preferably a homing-endonuclease, most preferably a endonuclease selected from the group consisting of I-SceI, I-CpaI, I-CpaII, I-CreI and I-ChuI or chimeras thereof with ligand-binding domains. Suitable endonucleases are described herein below.

2.3.1.1 Recombination Sites and Recombinases

Sequence-specific recombinases and their corresponding recombination sites suitable within the present invention may include but are not limited to the Cre/lox system of the bacteriophage P1 (Dale E C and Ow D W (1991) Proc Natl Acad Sci USA 88:10558-10562; Russell S H et al. (1992) Mol Gene Genet. 234: 49-59; Osborne B I et al. (1995) Plant J. 7, 687-701), the yeast FLP/FRT system (Kilby N J et al. (1995) Plant J 8:637-652; Lyznik L A et al. (1996) Nucleic Acids Res 24:3784-3789), the Mu phage Gin recombinase, the *E. coli* Pin recombinase or the R/RS system of the plasmid pSR1 (Onouchi H et al. (1995) Mol Gen Genet. 247:653-660; Sugita K et al. (2000) Plant J. 22:461-469). The recombinase (for example Cre or FLP) interacts specifically with its corresponding recombination sequences (34 bp lox sequence and 47 bp FRT sequence, respectively) in order to delete or invert the interposed sequences. Deletion of standard selection marker in plants which was flanked by two lox sequences by the Cre is described (Dale E C and Ow D W (1991) Proc Natl Acad Sci USA 88:10558-10562). The preferred recombination sites for suitable recombinases are described in Table 1 below:

TABLE 1

Suitable sequence-specific recombinases

| Recombinase | Organism of origin | Recombination Sites |
|---|---|---|
| CRE | *Bacteriophage* P1 | 5'-AACTCTCATCGCTTCGGATAACTTCC TGTTATCCGAAACATATCACTCACTTTGG TGATTTCACCGTAACTGTCTATGATTAAT G-3' (SEQ ID NO: 66) |
| FLP | *Saccharomyces cerevisiae* | 5'-GAAGTTCCTATTCCGAAGTTCCTATT CTCTAGAA AGTATAGGAACTTC-3' (SEQ ID NO: 67) |
| R | pSR1 Plasmids | 5'-CGAGATCATATCACTGTGGACGTTGA TGAAAGAATACGTTATTCTTTCATCAAAT CGT (SEQ ID NO: 68) |

2.3.1.2 The Homology Sequences

Referring to the homology sequences (e.g., A, A') "sufficient length" preferably refers to sequences with a length of at least 20 base pairs, preferably at least 50 base pairs, especially preferably at least 100 base pairs, very especially preferably at least 250 base pairs, most preferably at least 500 base pairs.

Referring to the homology sequences (e.g., A, A'), "sufficient homology" preferably refers to sequences with at least 70%, preferably 80%, by preference at least 90%, especially preferably at least 95%, very especially preferably at least 99%, most preferably 100%, homology within these homology sequences over a length of at least 20 base pairs, preferably at least 50 base pairs, especially preferably at least 100 base pairs, very especially preferably at least 250 base pairs, most preferably at least 500 base pairs.

The homology sequences A and A' are preferably organized in the form of a direct repeat. The term "direct repeat" means a subsequent localization of two sequences on the same strand of a DNA molecule in the same orientation, wherein these two sequences fulfill the above given requirements for homologous recombination between said two sequences.

In a preferred embodiment, the homology sequences may be a duplication of a sequence having additional use within the DNA construct. For example, the homology sequences may be two transcription terminator sequences. One of these terminator sequences may be operably linked to the agronomically valuable trait, while the other may be linked to the dual-function selection marker, which is localized in 3'-direction of the trait gene. Recombination between the two terminator sequences will excise the target sequence (e.g., a marker gene) but will reconstitute the terminator of the trait gene. In another example, the homology sequences may be two promoter sequences. One of these promoter sequences may be operably linked to the agronomically valuable trait, while the other may be linked to the target sequence (e.g., a selection marker), which is localized in 5'-direction of the trait gene. Recombination between the two promoter sequences will excise the target sequence (e.g., a marker gene) but will reconstitute the promoter of the trait gene. The person skilled in the art will know that the homology sequences do not need to be restricted to a single functional element (e.g. promoter or terminator), but may comprise or extent to other sequences (e.g. being part of the coding region of the trait gene and the respective terminator sequence of said trait gene.

2.3.1.3. Double-Strand Break Inducing Enzyme

Preferably, deletion/excision of the target sequence (e.g., a marker gene) is realized by homologous recombination between the above specified homology sequences induced by a sequence-specific double-strand break, preferably between the homology sequences which should recombine. General methods are disclosed for example in WO 03/004659, incorporated herein entirely by reference. Various enzyme suitable for induction of sequence-specific double-strand breaks (hereinafter together "endonuclease") are known in the art. The endonuclease may be for example selected from the group comprising:

1. Restriction endonucleases (type II), preferably homing endonucleases as described in detail hereinbelow.
2. Transposases, for example the P-element transposase (Kaufman P D and Rio D C (1992) Cell 69(1):27-39) or AcDs (Xiao Y L and Peterson T (2000) Mol Gen Genet. 263(1):22-29). In principle, all transposases or integrases are suitable as long as they have sequence specificity (Haren L et al. (1999) Annu Rev Microbiol. 1999; 53:245-281; Beall E L, Rio DC (1997) Genes Dev. 11(16):2137-2151).
3. Chimeric nucleases as described in detail hereinbelow.
4. Enzymes which induce double-strand breaks in the immune system, such as the RAG1/RAG2 system (Agrawal A et al. (1998) Nature 394(6695):744-451).
5. Group II intron endonucleases. Modifications of the intron sequence allows group II introns to be directed to virtually any sequence in a double-stranded DNA, where group II introns can subsequently insert by means of a reverse splice mechanism (Mohr et al. (2000) Genes & Development 14:559-573; Guo et al. (2000) Science 289:452-457). During this reverse splice mechanism, a double-strand break is introduced into the target DNA, the excised intron RNA cleaving the sense strand while the protein portion of the group II intron endonuclease hydrolyses the antisense strand (Guo et al. (1997) EMBO J. 16: 6835-6848). If it is only desired to induce the double-strand break without achieving complete reverse splicing, as is the case in the present invention, it is possible to resort to, for example, group II intron endonucleases which lack the reverse transcriptase activity. While this does not prevent the generation of the double-strand break, the reverse splicing mechanism cannot proceed to completion.

Suitable enzymes are not only natural enzymes, but also synthetic enzymes. Preferred enzymes are all those endonucleases whose recognition sequence is known and which can either be obtained in the form of their proteins (for example by purification) or expressed using their nucleic acid sequence.

In a preferred embodiment a sequence-specific endonuclease is employed for specific induction of double-strand breaks and subsequent induced homologous recombination. The term "sequence specific DNA-endonuclease" generally refers to all those enzymes, which are capable of generating double-strand breaks in double stranded DNA in a sequence-specific manner at one or more recognition sequences. Said DNA cleavage may result in blunt ends, or so-called "sticky" ends of the DNA (having a 5'- or 3'-overhang). The cleavage site may be localized within or outside the recognition sequence. Various kinds of endonucleases can be employed. Endonucleases can be, for example, of the Class II or Class IIs type. Class IIs R-M restriction endonucleases catalyze the DNA cleavage at sequences other than the recognition sequence, i.e. they cleave at a DNA sequence at a particular number of nucleotides away from the recognition sequence (Szybalski et al. (1991) Gene 100:13-26). The following may be mentioned by way of example, but not by limitation:

1. Restriction endonucleases (e.g., type II or IIs), preferably homing endonucleases as described in detail hereinbelow.
2. Chimeric or synthetic nucleases as described in detail hereinbelow.

Unlike recombinases, restriction enzymes typically do not ligate DNA, but only cleave DNA. Restriction enzymes are described, for instance, in the New England Biolabs online catalog (neb.com), Promega online catalog (promega.com) and Rao et al. (2000) Prog Nucleic Acid Res Mol Biol 64:1-63. Within this invention "ligation" of the DNA ends resulting from the cleavage by the endonuclease is realized by fusion by homologous recombination of the homology sequences.

Preferably, the endonuclease is chosen in a way that its corresponding recognition sequences are rarely, if ever, found in the unmodified genome of the target plant organism. Ideally, the only copy (or copies) of the recognition sequence in the genome is (or are) the one(s) introduced by the DNA construct of the invention, thereby eliminating the chance that other DNA in the genome is excised or rearranged when the sequence-specific endonuclease is expressed.

One criterion for selecting a suitable endonuclease is the length of its corresponding recognition sequence. Said recognition sequence has an appropriate length to allow for rare cleavage, more preferably cleavage only at the recognition sequence(s) comprised in the DNA construct of the invention. One factor determining the minimum length of said recognition sequence is—from a statistical point of view—the size of the genome of the host organism. In a preferred embodiment the recognition sequence has a length of at least 10 base pairs, preferably at least 14 base pairs, more preferably at least 16 base pairs, especially preferably at least 18 base pairs, most preferably at least 20 base pairs.

A restriction enzyme that cleaves a 10 base pair recognition sequence is described in Huang B et al. (1996) J Protein Chem 15(5):481-9.

Suitable enzymes are not only natural enzymes, but also synthetic enzymes. Preferred enzymes are all those sequence specific DNA-endonucleases whose recognition sequence is known and which can either be obtained in the form of their proteins (for example by purification) or expressed using their nucleic acid sequence.

Especially preferred are restriction endonucleases (restriction enzymes) which have no or only a few recognition sequences—besides the recognition sequences present in the transgenic recombination construct—in the chromosomal DNA sequence of a particular eukaryotic organism. This avoids further double-strand breaks at undesired loci in the genome. This is why homing endonucleases are very especially preferred (Review: (Belfort M and Roberts RJ (1997) Nucleic Acids Res 25: 3379-3388; Jasin M (1996) Trends Genet. 12:224-228; Internet: rebase.neb.com/rebase/rebase-.homing.html). Owing to their long recognition sequences, they have no, or only a few, further recognition sequences in the chromosomal DNA of eukaryotic organisms in most cases.

The sequences encoding for such homing endonucleases can be isolated for example from the chloroplast genome of *Chlamydomonas* (Turmel M et al. (1993) J Mol Biol 232: 446-467). They are small (18 to 26 kD) and their open reading frames (ORF) have a "codon usage" which is suitable directly for nuclear expression in eukaryotes (Monnat R J Jr et al. (1999) Biochem Biophys Res Com 255:88-93). Homing endonucleases which are very especially preferably isolated are the homing endonucleases I-SceI (WO96/14408), I-SceII (Sarguiel B et al. (1990) Nucleic Acids Res 18:5659-5665), I-SceIII (Sarguiel B et al. (1991) Mol Gen Genet. 255:340-341), I-CeuI (Marshall (1991) Gene 104:241-245), I-CreI (Wang J et al. (1997) Nucleic Acids Res 25: 3767-3776), I-ChuI (Cote V et al. (1993) Gene 129:69-76), I-TevI (Chu et al. (1990) Proc Natl Acad Sci USA 87:3574-3578; Bell-Pedersen et al. (1990) Nucleic Acids Res 18:3763-3770), I-TevII (Bell-Pedersen et al. (1990) Nucleic Acids Res18: 3763-3770), I-TevIII (Eddy et al. (1991) Genes Dev. 5:1032-1041), Endo SceI (Kawasaki et al. (1991) J Biol Chem 266: 5342-5347), I-CpaI (Turmel M et al. (1995a) Nucleic Acids Res 23:2519-2525) and I-CpaII (Turmel M et al. (1995b) Mol. Biol. Evol. 12, 533-545).

Further homing endonucleases are detailed in the above-mentioned Internet website, and examples which may be mentioned are homing endonucleases such as F-SceI, F-SceII, F-SuvI, F-TevI, F-TevII, I-AmaI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DdiII, I-DirI, I-DmoI, I-HmuI, I-HmuII, I-HspNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-PspI, PI-Rma43812IP, PI-SPBetaIP, PI-SceI, PI-TfuI, PI-TfuII, PI-ThyI, PI-TliI, PI-TliII, H-DreI, I-BasI, I-BmoI, I-PogI, I-TwoI, PI-MgaI, PI-PabI, PI-PabII.

Preferred in this context are the homing endonucleases whose gene sequences are already known, such as, for example, F-SceI, I-CeuI, I-ChuI, I-DmoI, I-CpaI, I-CpaII, I-CreI, I-CsmI, F-TevI, F-TevII, I-TevI, I-TevII, I-AniI, I-CvuI, I-DdiI, I-HmuI, I-HmuII, I-LlaI, I-NanI, I-MsoI, I-NitI, I-NjaI, I-PakI, I-PorI, I-PpoI, I-ScaI, I-Ssp6803I, PI-PkoI, PI-PkoII, PI-PspI, PI-TfuI, PI-TliI. Especially preferred are commercially available homing endonucleases such as I-CeuI, I-SceI, I-DmoI, I-PpoI, PI-PspI or PI-SceI. Endonucleases with particularly long recognition sequences, and which therefore only rarely (if ever) cleave within a genome include: I-CeuI (26 bp recognition sequence), PI-PspI (30 bp recognition sequence), PI-SceI (39 bp recognition sequence), I-SceI (18 bp recognition sequence) and I-PpoI (15 bp recognition sequence). The enzymes can be isolated from their organisms of origin in the manner with which the skilled worker is familiar, and/or their coding nucleic acid sequence can be cloned. The sequences of various enzymes are deposited in GenBank. Very especially preferred are the homing endonucleases I-SceI, I-CpaI, I-CpaII, I-CreI and I-ChuI. Sequences encoding said nucleases are known in the art and—for example—specified in WO 03/004659 (e.g., as SEQ ID NO: 2, 4, 6, 8, and 10 of WP 03/004659 hereby incorporated by reference).

The heterologous nucleic acid sequence to be expressed may preferably encode a polypeptide as described by any of SEQ ID NO: 22, or a functional equivalent thereof, which is capable to bring about the same phenotype than any of said polypeptide. Most preferably the nucleic acid sequence to be expressed is described by SEQ ID NO 21 or 23.

In a preferred embodiment, the sequences encoding said homing endonucleases can be modified by insertion of an intron sequence. This prevents expression of a functional enzyme in procaryotic host organisms and thereby facilitates cloning and transformations procedures (e.g., based on *E. coli* or *Agrobacterium*). In plant organisms, expression of a functional enzyme is realized, since plants are able to recognize and "splice" out introns. Preferably, introns are inserted in the homing endonucleases mentioned as preferred above (e.g., into I-SceI or I-CreI).

In some aspects of the invention, molecular evolution can be employed to create an improved endonuclease. Polynucleotides encoding a candidate endonuclease enzyme can, for example, be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer (1994) Proc Natl Acad Sci USA 91:10747-10751; Stemmer (1994) Nature 370:389-391; and U.S. Pat. Nos. 5,605,793, 5,837,458, 5,830,721 and 5,811,238.

Other synthetic endonucleases which may be mentioned by way of example are chimeric nucleases which are composed of an unspecific nuclease domain and a sequence-specific DNA binding domain consisting of zinc fingers (Bibikova M et al. (2001) Mol Cell Biol. 21:289-297). These DNA-binding zinc finger domains can be adapted to suit any DNA sequence. Suitable methods for preparing suitable zinc finger domains are described and known to the skilled worker (Beerli R R et al. (2000) Proc Natl Acad Sci USA. 97 (4): 1495-1500; Beerli R R et al. (2000) J Biol Chem 275(42): 32617-32627; Segal D J and Barbas C F 3rd., Curr Opin Chem Biol (2000) 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deli Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

The endonuclease is preferably expressed as a fusion protein with a nuclear localization sequence (NLS). This NLS sequence enables facilitated transport into the nucleus and increases the efficacy of the recombination system. A variety of NLS sequences are known to the skilled worker and described, inter alia, by Jicks G R and Raikhel N V (1995) Annu. Rev. Cell Biol. 11:155-188. Preferred for plant organisms is, for example, the NLS sequence of the SV40 large antigen. Examples are provided in WO 03/060133. However, owing to the small size of many DSBI enzymes (such as, for example, the homing endonucleases), an NLS sequence is not necessarily required. These enzymes are capable of passing through the nuclear pores even without any aid.

In a further preferred embodiment, the activity of the endonuclease can be induced. Suitable methods have been described for sequence-specific recombinases (Angrand P O et al. (1998) Nucl. Acids Res. 26(13):3263-3269; Logie C and Stewart A F (1995) Proc Natl Acad Sci USA 92(13):5940-5944; Imai T et al. (2001) Proc Natl Acad Sci USA 98(1): 224-228). These methods employ fusion proteins of the endonuclease and the ligand binding domain for steroid hormone receptor (for example the human androgen receptor, or mutated variants of the human estrogen receptor as described therein). Induction may be effected with ligands such as, for example, estradiol, dexamethasone, 4-hydroxytamoxifen or raloxifen. Some endonucleases are active as dimers (homo- or heterodimers; I-CreI forms a homodimer; I-SecIV forms a heterodimerk) (Wernette C M (1998) Biochemical & Biophysical Research Communications 248(1):127-333)). Dimerization can be designed as an inducible feature, for example by exchanging the natural dimerization domains for the binding domain of a low-molecular-weight ligand. Addition of a dimeric ligand then brings about dimerization of the fusion protein. Corresponding inducible dimerization methods, and the preparation of the dimeric ligands, have been described in (Amara J F et al. (1997) Proc Natl Acad Sci USA 94(20):10618-1623; Muthuswamy S K et al. (1999) Mol Cell Biol 19(10):6845-685; Schultz L W and Clardy J (1998) Bioorg Med Chem. Lett. 8(1):1-6; Keenan T et al. (1998) Bioorg Med. Chem. 6(8):1309-1335).

Recognition sequences for sequence specific DNA endonuclease (e.g., homing endonucleases) are described in the art. "Recognition sequence" refers to a DNA sequence that is recognized by a sequence-specific DNA endonuclease of the invention. The recognition sequence will typically be at least 10 base pairs long, is more usually 10 to 30 base pairs long, and in most embodiments, is less than 50 base pairs long.

"Recognition sequence" generally refers to those sequences which, under the conditions in a plant cell used within this invention, enable the recognition and cleavage by the sequence specific DNA-endonuclease. The recognition sequences for the respective sequence specific DNA-endonucleases are mentioned in Table 2 hereinbelow by way of example, but not by limitation.

Table 2. Recognition sequences and organisms of orgin for endonucleases (e.g., homimg endonucleases; "^" indicates the cleavage site of the sequence specific DNA-endonuclease within a recognition sequence).

TABLE 2

Recognition sequences and organisms of origin for endonucleases (e.g., homing endonucleases; "^" indicates the cleavage site of the sequence specific DNA-endonuclease within a recognition sequence).

| DSBI Enzyme | Organism of origin | Recognition sequence | SEQ ID NO: |
|---|---|---|---|
| P-Element Trans-Posase | Drosophila | 5'-CTAGATGAAATAACATAAGGT GG-3' | 69 |
| I-AniI | Aspergillus nidulans | 5'-TTGAGGAGGTT^TCTCTGTAA ATAANNNNNNNNNNNNNNNN 3'-AACTCCTCCAAAGAGACATTT ATTNNNNNNNNNNNNNNNN^ | 70 |
| I-DdiI | Dictyostelium discoideumAX3 | 5'-TTTTTTGGTCATCCAGAAGTA TAT 3'-AAAAAACCAG^TAGGTCTTCA TATA | 71 |
| I-CvuI | Chlorella vulgaris | 5'-CTGGGTTCAAAACGTCGTGA^ GACAGTTTGG | 72 |

TABLE 2-continued

Recognition sequences and organisms of origin for endonucleases (e.g., homing endonucleases; "^" indicates the cleavage site of the sequence specific DNA-endonuclease within a recognition sequence).

| DSBI Enzyme | Organism of origin | Recognition sequence | SEQ ID NO: |
|---|---|---|---|
| | | 3'-GACCCAAGTTTTGCAG^CACT CTGTCAAACC | |
| I-CsmI | Chlamydomonas smithii | 5'-GTACTAGCATGGGGTCAAATG TCTTTCTGG | 73 |
| I-CmoeI | Chlamydomonas moewusii | 5'-TCGTAGCAGCT^CACGGTT 3'-AGCATCG^TCGAGTGCCAA | 74 |
| I-CreI | Chlamydomonas reinhardtii | 5'-CTGGGTTCAAAACGTCGTGA^ GACAGTTTGG 3'-GACCCAAGTTTTGCAG^CACT CTGTCAAACC | 75 |
| I-ChuI | Chlamydomonas humicola | 5'-GAAGGTTTGGCACCTCG^ATG TCGGCTCATC 3'-CTTCCAAACCGTG^GAGCTAC AGCCGAGTAG | 76 |
| I-CpaI | Chlamydomonas pallidostigmatica | 5'-CGATCCTAAGGTAGCGAA^AT TCA 3'-GCTAGGATTCCATC^GCTTTA AGT | 77 |
| I-CpaIL | Chlamydomonas pallidostigmatica | 5'-CCCGGCTAACTC^TGTGCCAG 3'-GGGCCGAT^TGAGACACGGTC | 78 |
| I-CeuI | Chlamydomonas eugametos | 5'-CGTAACTATAACGGTCCTAA^ GGTAGCGAA 3'-GCATTGATATTGCCAG^GATT CCATCGCTT | 79 |
| I-DmoI | Desulfurococcus mobilis | 5'-ATGCCTTGCCGGGTAA^GTTC CGGCGCGCAT 3'-TACGGAACGGCC^CATTCAAG GCCGCGCGTA | 80 |
| I-SceI | Saccharomyces cerevisiae | 5'-AGTTACGCTAGGGATAA^CAG GGTAATATAG 3'-TCAATGCGATCCC^TATTGTC CCATTATATC | 81 |
| | | 5'-TAGGGATAA^CAGGGTAAT 3'-ATCCC^TATTGTCCCATTA ("Core"-Sequence) | 82 |
| I-SceII | S. cerevisiae | 5'-TTTTGATTCTTTGGTCACCC^ TGAAGTATA 3'-AAAACTAAGAAACCAG^TGGG ACTTCATAT | 83 |
| I-SceIII | S. cerevisiae | 5'-ATTGGAGGTTTTGGTAAC^TA TTTATTACC 3'-TAACCTCCAAAACC^ATTGAT AAATAATGG | 84 |
| I-SceIV | S. cerevisiae | 5'-TCTTTTCTCTTGATTA^GCCC TAATCTACG 3'-AGAAAAGAGAAC^TAATCGGG ATTAGATGC | 85 |
| I-SceV | S. cerevisiae | 5'-AATAATTTCT^TCTTAGTAA TGCC 3'-TTATTAAAGAAGAATCATTA ^CGG | 86 |
| I-SceVI | S. cerevisiae | 5'-GTTATTTAATG^TTTAGTAG TTGG 3'-CAATAAATTACAAAATCATCA ^ACC | 87 |

TABLE 2-continued

Recognition sequences and organisms of origin for endonucleases (e.g., homing endonucleases; "^" indicates the cleavage site of the sequence specific DNA-endonuclease within a recognition sequence).

| DSBI Enzyme | Organism of origin | Recognition sequence | SEQ ID NO: |
|---|---|---|---|
| I-SceVII | S.cerevisiae | 5'-TGTCACATTGAGGTGCACTAG TTATTAC | 88 |
| PI-SceI | S.cerevisiae | 5'-ATCTATGTCGGGTGC^GGAGA AAGAGGTAAT<br>3'-TAGATACAGCC^CACGCCTCT TTCTCCATTA | 89 |
| F-SceI | S.cerevisiae | 5'-GATGCTGTAGGC^ATAGGCTT GGTT<br>3'-CTACGACA^TCCGTATCCGAA CCAA | 90 |
| F-SceII | S.cerevisiae | 5'-CTTTCCGCAACA^GTAAATT<br>3'-GAAAGGCG^TTGTCATTTTAA | 91 |
| I-HmuI | Bacillus subtilis bacteriophage SPO1 | 5'-AGTAATGAGCCTAACGCTCAG CAA<br>3'-TCATTACTCGGATTGC^GAGT CGTT | 92 |
| I-HmuII | Bacillus subtilis bacteriophage SP82 | 5'-AGTAATGAGCCTAACGCTCAA CAANNNNNNNNNNNNNNN-NNN-NNN NNNNNNNNNNNNNNNNNNNNN | 93 |
| I-LlaI | Lactococcus lactis | 5'-CACATCCATAAC^CATATCAT TTTT<br>3'-GTGTAGGTATTGGTATAGTAA ^AAA | 94 |
| I-MsoI | Monomastix species | 5'-CTGGGTTCAAAACGTCGTGA^ GACAGTTTGG<br>3'-GACCCAAGTTTTGCAG^CACT CTGTCAAACC | 95 |
| I-NanI | Naegleria andersoni | 5'-AAGTCTGGTGCCA^GCACCCG C<br>3'-TTCAGACC^ACGGTCGTGGGC G | 96 |
| I-NitI | Naegleria italica | 5'-AAGTCTGGTGCCA^GCACCCG C<br>3'-TTCAGACC^ACGGTCGTGGGC G | 97 |
| I-NjaI | Naegleria jamiesoni | 5'-AAGTCTGGTGCCA^GCACCCG C<br>3'-TTCAGACC^ACGGTCGTGGGC G | 98 |
| I-PakI | Pseudendoclonium akinetum | 5'-CTGGGTTCAAAACGTCGTGA^ GACAGTTTGG<br>3'-GACCCAAGTTTTGCAG^CACT CTGTCAAACC | 99 |
| I-PorI | Pyrobaculum organotrophum | 5'-GCGAGCCCGTAAGGGT^GTGT ACGGG<br>3'-CGCTCGGGCATT^CCCACACA TGCCC | 100 |
| I-PpoI | Physarum polycephalum | 5'-TAACTATGACTCTCTTAA^GG TAGCCAAAT<br>3'-ATTGATACTGAGAG^AATTCC ATCGGTTTA | 101 |
| I-ScaI | Saccharomyces capensis | 5'-TGTCACATTGAGGTGCACT^A GTTATTAC<br>3'-ACAGTGTAACTCCAC^GTGAT CAATAATG | 102 |

TABLE 2-continued

Recognition sequences and organisms of origin for endonucleases (e.g., homing endonucleases; "^" indicates the cleavage site of the sequence specific DNA-endonuclease within a recognition sequence).

| DSBI Enzyme | Organism of origin | Recognition sequence | SEQ ID NO: |
|---|---|---|---|
| I-Ssp6803I | Synechocystis species | 5'-GTCGGGCT^CATAACCCGAA<br>3'-CAGCCCGAGTA^TTGGGCTT | 103 |
| PI-PfuI | Pyrococcus furiosus Vc1 | 5'-GAAGATGGGAGGAGGG^ACCG GACTCAACTT<br>3'-CTTCTACCCTCC^TCCCTGGC CTGAGTTGAA | 104 |
| PI-PfuII | Pyrococcus furiosus Vc1 | 5'-ACGAATCCATGTGGAGA^AGA GCCTCTATA<br>3'-TGCTTAGGTACAC^CTCTTCT CGGAGATAT | 105 |
| PI-PkoI | Pyrococcus koda-karaensis KOD1 | 5'-GATTTTAGAT^CCCTGTACC<br>3'-CTAAAA^TCTAGGGACATGG | 106 |
| PI-PkoII | Pyrococcus koda-karaensis KOD1 | 5'-CAGTACTACG^GTTAC<br>3'-GTCATG^ATGCCAATG | 107 |
| PI-PspI | Pyrococcus sp. | 5'-AAAATCCTGGCAAACAGCTAT TAT^GGGTAT<br>3'-TTTTAGGACCGTTTGTCGAT^ AATACCCATA | 108 |
| PI-TfuI | Thermococcus fumicolans ST557 | 5'-TAGATTTTAGGT^CGCTATAT CCTTCC<br>3'-ATCTAAAA^TCCAGCGATATA GGAAGG | 109 |
| PI-TfuII | Thermococcus fumicolans ST557 | 5'-TAYGCNGAYACN^GACGGYTT YT<br>3'-ATRCGNCT^RTGNCTGCCRAA RA | 110 |
| PI-ThyI | Thermococcus hydrothermalis | 5'-TAYGCNGAYACN^GACGGYTT YT<br>3'-ATRCGNCT^RTGNCTGCCRAA RA | 111 |
| PI-TliI | Thermococcus litoralis | 5'-TAYGCNGAYACNGACGG^YTT YT<br>3'-ATRCGNCTRTGNC^TGCCRAA RA | 112 |
| PI-TliII | Thermococcus litoralis | 5'-AAATTGCTTGCAAACAGCTAT TACGGCTAT | 113 |
| I-TevI | Bacteriophage T4 | 5'-AGTGGTATCAAC^GCTCAGTA GATG<br>3'-TCACCATAGT^TGCGAGTCAT CTAC | 114 |
| I-TevII | Bacteriophage T4 | 5'-GCTTATGAGTATGAAGTGAAC ACGT^TATTC<br>3'-CGAATACTCATACTTCACTTG TG^CAATAAG | 115 |
| F-TevI | Bacteriophage T4 | 5'-GAAACACAAGA^AATGTTTAG TAAANNNNNNNNNNNNNN<br>3'-CTTTGTGTTCTTTACAAATCA TTTNNNNNNNNNNNNNN^ | 116 |
| F-TevII | Bacteriophage T4 | 5'-TTTAATCCTCGCTTC^AGATA TGGCAACTG<br>3'-AAATTAGGAGCGA^AGTCTAT ACCGTTGAC | 117 |

TABLE 2-continued

Recognition sequences and organisms of origin for endonucleases (e.g., homing endonucleases; "^" indicates the cleavage site of the sequence specific DNA-endonuclease within a recognition sequence).

| DSBI Enzyme | Organism of origin | Recognition sequence | SEQ ID NO: |
|---|---|---|---|
| H-DreI | E. coli pI-DreI | 5'-CAAAACGTCGTAA^GTTCCGG CGCG<br>3'-GTTTTGCAG^CATTCAAGGCC GCGC | 118 |
| I-BasI | Bacillus thuringiensis phage Bastille | 5' AGTAATGAGCCTAACGCTCAG CAA<br>3'-TCATTACGAGTCGAACTCGGA TTG | 119<br>120 |
| I-BmoI | Bacillus mojavensis s87-18 | 5'-GAGTAAGAGCCCG^TAGTAAT GACATGGC<br>3'-CTCATTCTCG^GGCATCATTA CTGTACCG | 121 |
| I-PogI | Pyrobaculum oguniense | 5'-CTTCAGTAT^GCCCCGAAAC<br>3'-GAAGT^CATACGGGCTTTG | 122 |
| I-TwoI | Staphylococcus aureus phage Twort | 5'-TCTTGCACCTACACAATCCA<br>3'-AGAACGTGGATGTGTTAGGT | 123 |
| PI-MgaI | Mycobacterium gastri | 5'-CGTAGCTGCCCAGTATGAGTC A<br>3'-GCATCGACGGGTCATACTCAG T | 124 |
| PI-PabI | Pyrococcus abyssi | 5'-GGGGGCAGCCAGTGGTCCCGT T<br>3'-CCCCCGTCGGTCACCAGGGCA A | 125 |
| PI-PabII | Pyrococcus abyssi | 5'-ACCCCTGTGGAGAGGAGCCCC TC<br>3'-TGGGGACACCTCTCCTCGGGG AG | 126 |

Also encompassed are minor deviations (degenerations) of the recognition sequence which still enable recognition and cleavage by the sequence specific DNA-endonuclease in question. Such deviations—also in connection with different framework conditions such as, for example, calcium or magnesium concentration—have been described (Argast G M et al. (1998) J Mol Biol 280: 345-353). Also encompassed are core sequences of these recognition sequences and minor deviations (degenerations) in there. It is known that the inner portions of the recognition sequences suffice for an induced double-strand break and that the outer ones are not absolutely relevant, but can codetermine the cleavage efficacy. Thus, for example, an 18 bp core sequence can be defined for I-SceI.

2.3.2 Initiation of Deletion/Excision

There are various means to appropriately initiate deletion/excision of the target sequence. Preferably deletion is only initiated after successful integration of the target sequence into the plant genome. For example in cases, where the target sequence is a selection marker, excision is preferably initiated after the marker has successfully completed its function resulting in insertion of the DNA construct into the genome of the plant cell or organism to be transformed.

Various means are available for the person skilled in art to combine the excision enzyme with the target sequence flanked by the excision sequences. Preferably, an excision enzyme (e.g., a recombinase or endonuclease) can be expressed or combined with its corresponding excision sequence (e.g., a recombination or recognition site), respectively, by a method selected from the group consisting of:

a) incorporation of the expression cassette for the excision enzyme (e.g., the recombinase or sequence-specific endonuclease) into a DNA construct, preferably together with the target sequence (e.g., a marker gene) flanked by said excision sequences, b) incorporation of the expression cassette for the excision enzyme (e.g., the recombinase or sequence-specific endonuclease) into plant cells or plants, which are already comprising the target sequence (e.g., a marker gene) flanked by said excision sequences, c) incorporation of the expression cassette for the excision enzyme (e.g., the recombinase or sequence-specific endonuclease) into plant cells or plants, which are subsequently used for as master plants or cells for transformation with constructs comprising the target sequence (e.g., a marker gene) flanked by said excision sequences, d) incorporation of the expression cassette for the excision enzyme (e.g., the recombinase or sequence-specific endonuclease) into a separate DNA construct, which is transformed by way of co-transformation with a separate DNA construct comprising the target sequence (e.g., a marker gene) flanked by said excision sequences.

Accordingly the target sequence and the excision enzyme (e.g., the recombinase or endonuclease) can be combined in a plant organism, cell, cell compartment or tissue for example as follows:

1.) Plants comprising inserted into their genome the target sequence (e.g., a marker gene) flanked by excision sequences (preferably into the chromosomal DNA) are generated in the customary manner. A further expression cassette for the excision enzyme is then combined with said DNA constructs by
    a) a second transformation with said second expression cassette, or
    b) crossing of the plants comprising the target sequence with master plants comprising the expression cassette for the excision enzyme.
2.) The expression cassette encoding for the excision enzyme can be integrated into the DNA construct which already bears the target sequence. It is preferred to insert the sequence encoding the excision enzyme between the sequences allowing for deletion and thus to delete it from the genomic DNA after it has fulfilled its function. Very especially preferably, expression of the endonuclease is inducible in such a case (for example under the control of one of the inducible promoters described hereinbelow), in a development-dependent fashion using a development-dependent promoter, or else excision enzymes are employed whose activity is inducible in order to avoid premature deletion of the dual-function marker prior to its insertion into the genome.
3.) Relying on the co-transformation technique, the expression cassette for the excision enzyme can be transformed into the cells simultaneously with the DNA construct comprising the target sequence, but on a separate DNA molecule (e.g., vector). Co-transformation can be stable or transient. In such a case, expression of the excision enzyme is preferably inducible (for example under the control of one of the inducible chimeric transcription regulating sequence as described above), although the development-dependent expression pattern of the unmodified super-promoter is already preventing premature excision.
4.) Plants expressing the excision enzyme may also act as parent individuals. In the progeny from the crossing between plants expressing the excision enzyme on the one hand and plants bearing the target sequence on the other hand, the desired target sequence excision (e.g., by double-strand breaks and recombination between the homology sequences) are observed.

A preferred embodiment of the invention is related to DNA constructs comprising both the target sequence (e.g., an expression cassette a selection marker; the first expression cassette) and a second expression cassette for the excision enzyme (e.g., an endonuclease or recombinase encoding sequence linked to a plant promoter), preferably in a way that said second expression cassette is together with said first expression cassette flanked by said excision sequences, which allow for specific target sequence deletion.

In another preferred embodiment the mechanism of deletion/excision can be induced or activated in a way to prevent pre-mature deletion/excision of the dual-function marker. Preferably, thus expression and/or activity of an preferably employed excision enzyme can be induced, preferably by a method selected from the group consisting of
a) inducible expression by operably linking the sequence encoding said excision enzyme (e.g., a recombinase or endonuclease) to an inducible promoter,
b) inducible activation, by employing a modified excision enzyme (e.g., a recombinase or endonuclease) comprising a ligand-binding-domain, wherein activity of said modified excision enzyme can by modified by treatment of a compound having binding activity to said ligand-binding-domain.

Expression of the polynucleotide encoding the excision enzyme is preferably controlled by an excision promoter, which allows for expression in a timely manner so that the dual-function marker can perform its function as a negative selection marker before getting excised. Suitable promoters are for example described in the German Patent Application DE 03028884.9. Such promoters may have for example expression specificity for late developmental stages like e.g., reproductive tissue. The excision promoter may be selected from one of the following groups of promoters:

2.3.3 Optional Methods of Preventing Premature Excision of the Excision Construct It is useful to have a system to maintain the dual-function marker comprising construct of the invention especially during transformation and selection. In general, a control polynucleotide can be introduced into the DNA-construct encoding for the excision enzyme to achieve this goal. The control polynucleotide generally functions either to inhibit expression of the excision enzyme when inhibition is desired (e.g., during transformation and selection; for preferred time frames see above) or to release repression of the excision promoter, thus allowing for expression from the excision promoter. Those of skill will recognize that there are numerous variations for controlling or pre-venting expression of the excision enzyme in a particular cell or tissue or at a particular developmental stage.

In one aspect, expression from the first excision promoter (i.e. the promoter operably linked to the a first excision enzyme, which excises the dual-function marker) can be countered by a second no-excision promoter. For example, the second no-excision promoter can be operably linked to a repressor gene, which, when expressed, prevents expression of the first excision promoter. Examples of repressors include the tet and lac repressors (Gatz, et al. (1991) Mol Gen Genet. 227:229-237). The second no-excision promoter is preferably a promoter which has the highest activity in the tissue used for transformation/selection but has low activity in the reproductive cell (e.g., pollen or oocyte), a precursor cell or tissue of said reproductive cell, or an omnipotent cell (e.g. zygote) resulting from reproduction. Also an inducible promoter can be employed and induction is used during the transformation/selection phase. Such an inducible promoter can be for example a tetracycline (doxycycline)-inducible system, which is induced by tetracycline or doxycycline (see above). Antibiotics like this can be employed during transformation/selection.

Alternatively, the second no-excision promoter can be linked to the polynucleotide encoding the endonuclease in the opposite orientation of the first excision promoter (i.e., from the 3'-end of the coding sequence towards the 5'-end of the sequence), thereby interrupting expression of the DNA cleaving enzyme. In these embodiments, the transcriptional activity of the second no-excision promoter prevents completion of transcripts from the first excision promoter, thereby preventing expression of the excision enzyme.

In other embodiments, an antisense polynucleotide or a polynucleotide producing a double-stranded RNA molecule can be operably linked to the second no-excision promoter, thereby preventing the translation of the DNA cleaving enzyme mRNA. See, e.g., Sheehy et al. (1988) Proc Natl Acad Sci USA 85:8805-8809, and U.S. Pat. No. 4,801,340 for a description of antisense technology; and EP-A1 1 042 462, EP-A1 1 068 311 for a description of the double-stranded RNA interference technique. The antisense or double-stranded RNA molecule should have homology to the nucleotide encoding the excision enzyme to guarantee efficient suppression. In general, antisense technology involves the generation of RNA transcripts that hybridize to a target transcript (i.e., the transcript encoding the sequence-specific endonuclease). Alternatively, the second no-excision promoter can be operably linked to a DNA cleaving enzyme polynucleotide in the sense orientation to induce sense suppression of the gene (see, e.g., Napoli et al. (1990) Plant Cell 2:279-289, U.S. Pat. Nos. 5,034,323, 5,231,020, and 5,283,184 for a description of sense suppression technology).

In some embodiments, aptamer technology can be used to repress expression of the first excision promoter. See, e.g., Hermann et al. (2000) Science 287(5454):820-5; and Famulok et al. (1999) Curr Top Microbiol Immunol 243:123-36. For example, a small oligonucleotide could be developed that only binds and represses the first excision promoter when stabilized by a particular chemical which can be applied when transgenic seed are desired. For example, combinatorial library selections through the systematic evolution of ligands by exponential enrichment (SELEX) technique can be used to identify nucleic acid aptamers that bind with high affinity and specificity to a wide range of selected molecules. See, e.g., Conrad et al. (1995) Mol Divers 1(1):69-78; and Kusser (2000) J Biotechnol 74(1):27-38.

In some embodiments, a multi-tiered excision system is used. For example, the first excision promoter can be interrupted by a second recombination cassette. This second recombination cassette may again be flanked by a second set of homology sequences B and B' flanking a chemically-induced promoter operably linked to a polynucleotide encoding a second sequence-specific DNA cleaving enzyme. In general, this system allows for the transgenic construct to remain intact in the genome (e.g., during transformation and selection) as long as the chemical inducer is not provided. Once the chemical inducer is presented, the second DNA cleaving enzyme is induced and excises its own coding region, induces homologous recombination between B and B', thereby reconstituting the first excision promoter to an intact promoter. Since B remains after excision, B and B' are preferably a sub-sequence of said first excision promoter.

2.3.4 The Target Sequence to be Excised

Although various sequences are contemplated herein, where excision might be advantageous, the most preferred target sequence to be excised is a marker sequence. Various selectable and screenable marker sequences are comprised under the general term marker sequence. Thus, the methods of the invention results in a monocotyledonous plant cell or plant, which is marker-free. The terms "marker-free" or "selection marker free" as used herein with respect to a cell or an organism are intended to mean a cell or an organism which is not able to express a functional marker protein. The sequence encoding said marker protein may be absent in part or—preferably—entirely.

2.3.4.1 Marker Genes

Marker genes (e.g., selectable or screenable marker) are frequently used in order to improve the ability to identify transformants. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention. Included within the terms selectable or screenable marker genes are also genes which encode a "secretable marker" whose secretion can be detected as a means of identifying or selecting for transformed cells. Examples include markers, which encode a secretable antigen that can be identified by antibody interaction, or even secretable enzymes, which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements. One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

The marker sequence can be expressed by any transcription regulating sequence or promoter having expression capability in plant cells (suitable promoter sequences are described below). Most preferred are marker sequences, which are employed in plant transformation, screening and selection. Markers enable transgenic cells or organisms (e.g., plants or plant cells) to be identified after transformation. They can be divided into positive selection marker (conferring a selective advantage), negative selection marker (compensating a selection disadvantage), and counter-selection marker (conferring a selection disadvantage), respectively. Such markers may include but are not limited to:

2.3.4.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide), which suppresses growth of an untransformed wild type tissue. Especially preferred negative selection markers are those, which confer resistance to herbicides. Examples, which may be mentioned, are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A10 218 571).

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, X112, XA17, and/or Hra mutation (EP-A1154 204)

Bromoxynil® degrading nitrilases (bxn; Stalker 1988)

Kanamycin- or geneticin (G418) resistance genes (NPTII; NPT or neo; Potrykus 1985) coding e.g., for neomycin phosphotransferases (Fraley 1983; Nehra 1994)

2-Desoxyglucose-6-phosphate phosphatase ($DOG^R1$-Gene product; WO 98/45456; EP 0 807 836) conferring resistance against 2-desoxyglucose (Randez-Gil 1995).

hygromycin phosphotransferase (HPT), which mediates resistance to hygromycin (Vanden Elzen 1985).

altered dihydrofolate reductase (Eichholtz 1987) conferring resistance against methotrexat (Thillet 1988);

mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3.1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/L may be included in the medium. For example, with the dao1 gene as the selective marker, D-serine or D-alanine at a concentration of from about 3 to 100 mg/L may be included in the medium. Typical concentrations for selection are 20 to 40 mg/L. For example, with the mutated ahas genes as the selective marker, PURSUIT at a concentration of from about 3 to 100 mg/L may be included in the medium. Typical concentrations for selection are 20 to 40 mg/L.

2.3.4.1.2 Positive Selection Marker

Furthermore, positive selection marker can be employed. Positive selection marker are those, which do not result in detoxification of a biocidal compound, but confer an advantage by increased or improved regeneration, growth, propagation, multiplication as the like of the cell or organism comprising such kind of marker. Examples are isopentenyltransferase (a key enzyme of the cytokinin biosynthesis facilitating regeneration of transformed plant cells by selection on cytokinin-free medium; Ebinuma 2000a; Ebinuma 2000b; for example from strain:PO22; Genbank Acc.-No.: AB025109). Additional positive selection markers, which confer a growth advantage to a transformed plant cells in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.3.4.1.3 Counter-Selection Marker

The target sequence to be excised may not only comprise a negative selection marker or a positive selection marker (to facilitate selection and isolation of successfully transformed plants) but may also comprise a counter-selection marker to evaluate successful subsequent marker excision. In one preferred embodiment both the negative and/or positive selection marker and the counter selection marker are flanked be the excision sequences and are both deleted/excised by action of the excision enzyme. Counter-selection markers are especially suitable to select organisms with defined deleted sequences comprising said marker (Koprek 1999). Counter-selection markers are sequences encoding for enzymes which are able to convert a non-toxic compound into a toxic compound. In consequence, only cells will survive treatment with said non-toxic compound which are lacking said counter-selection marker, thereby allowing for selection of cells which have successfully undergone sequence (e.g., marker) deletion. Typical counter-selection markers known in the art are for example a) cytosine deaminases (CodA) in combination with 5-fluorocytosine (5-FC) (WO 93/01281; U.S. Pat. No. 5,358,866; Gleave A P et al. (1999) Plant Mol Biol 40(2):223-35; Perera R J et al. (1993) Plant Mol Biol 23(4):793-799; Stougaard J (1993) Plant J 3:755-761); EP-A1595 837; Mullen C A et al. (1992) Proc Natl Acad Sci USA 89(1): 33-37; Kobayashi T et al. (1995) Jpn J Genet. 70(3):409-422; Schlaman H R M & Hooykaas P F F (1997) Plant J 11:1377-1385; Xiaohui Wang H et al. (2001) Gene 272(1-2): 249-255; Koprek T et al. (1999) Plant J 19(6):719-726; Gleave A P et al. (1999) Plant Mol Biol 40(2):223-235; Gallego M E (1999) Plant Mol Biol 39(1):83-93; Salomon S & Puchta H (1998) EMBO J. 17(20):6086-6095; Thykjaer T et al. (1997) Plant Mol Biol 35(4):523-530; Serino G (1997) Plant J 12(3):697-701; Risseeuw E (1997) Plant J 11(4):717-728; Blanc V et al. (1996) Biochimie 78(6):511-517; Corneille S et al. (2001) Plant J 27:171-178).

b) Cytochrome P-450 enzymes in combination with the sulfonylurea pro-herbicide R7402 (2-methylethyl-2-3-dihydro-N-[(4,6-dimethoxypyrimidine-2-yl)aminocarbonyl]-1,2-benzoisothiazol-7-sulfonamid-1,1-dioxide) (O'Keefe D P et al. (1994) Plant Physiol 105:473-482; Tissier A F et al. (1999) Plant Cell 11:1841-1852; Koprek T et al. (1999) Plant J 19(6):719-726; O'Keefe D P (1991) Biochemistry 30(2):447-55).

c) Indoleacetic acid hydrolases like e.g., the tms2 gene product from *Agrobacterium tumefaciens* in combination with naphthalacetamide (NAM) (Fedoroff N V & Smith D L (1993) Plant J 3:273-289; Upadhyaya N M et al. (2000) Plant Mol Biol Rep 18:227-223; Depicker A G et al. (1988) Plant Cell rep 104:1067-1071; Karlin-Neumann G A et al. (1991) Plant Cell 3:573-582; Sundaresan V et al. (1995) Gene Develop 9:1797-1810; Cecchini E et al. (1998) Mutat Res 401(1-2):199-206; Zubko E et al. (2000) Nat Biotechnol 18:442-445).

d) Haloalkane dehalogenases (dhlA gene product) from *Xanthobacter autotropicus* GJ10 in combination with 1,2-dichloroethane (DCE) (Naested H et al. (1999) Plant J 18(5)571-576; Janssen D B et al. (1994) Annu Rev Microbiol 48:163-191; Janssen D B (1989) J Bacteriol 171(12): 6791-9).

e) Thymidine kinases (TK), e.g., from Type 1 Herpes Simplex virus (TK HSV-1), in combination with acyclovir, ganciclovir or 1,2-deoxy-2-fluoro-β-D-arabinofuranosil-5-iodouracile (FIAU) (Czako M & Marton L (1994) Plant Physiol 104:1067-1071; Wigler M et al. (1977) Cell 11(1): 223-232; McKnight S L et al. (1980) Nucl Acids Res 8(24):5949-5964; McKnight S L et al. (1980) Nucl Acids Res 8(24):5931-5948; Preston et al. (1981) J Virol 38(2): 593-605; Wagner et al. (1981) Proc Natl Acad Sci USA 78(3):1441-1445; St. Clair et al. (1987) Antimicrob Agents Chemother 31(6):844-849).

Several other counter-selection systems are known in the art (see for example international application WO 04/013333; p. 13 to 20 for a summary; hereby incorporated by reference).

2.3.4.1.4. Screenable Markers

Screenable markers (also named reporter genes or proteins; Schenborn E, Groskreutz D. (1999) Mol Biotechnol 13(1):29-44) that may be employed include, but are not limited to, a beta-glucuronidase (GUS; Jefferson et al. (1987) EMBO J. 6:3901-3907) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986; Millar et al. (1992) Plant Mol Biol Rep 10:324-414), which allows for bioluminescence detection; or even an aequorin gene (Prasher 1985), which may be employed in calcium-sensitive bioluminescence detection, or a green fluorescent protein gene (GFP) (Niedz 1995; Chui W L et al. (1996) Curr Biol 6:325-330; Leffel S M et al. (1997) Biotechniques 23(5):912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12): 5888-5893; Tian et al. (1997) Plant Cell Rep 16:267-271; WO 97/41228).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

2.3.4.1.5. Dual-Function Marker

In one preferred embodiment of the invention the target sequence is a dual-function marker. The term dual-function marker relates to a marker which combines in one sequence the opportunity to be employed as negative or counter selection marker. The choice, which effect is achieved, depends on the substrate employed in the screening process. Most preferably the dual-function marker is a D-amino acid oxidase. This enzyme is capable to convert D-amino acids. Some D-amino acids are toxic to plants and are detoxified by action of the enzyme. Other D-amino acids are harmless to plants but are converted to toxic compounds by the enzyme.

The term D-amino acid oxidase (abbreviated DAAO, DAMOX, or DAO) is referring to the enzyme coverting a D-amino acid into a 2-oxo acid, by—preferably—employing Oxygen ($O_2$) as a substrate and producing hydrogen peroxide ($H_2O_2$) as a co-product (Dixon M & Kleppe K. *Biochim. Biophys. Acta* 96 (1965) 357-367; Dixon M & Kleppe K *Biochim. Biophys. Acta* 96 (1965) 368-382; Dixon M & Kleppe *Biochim. Biophys. Acta* 96 (1965) 383-389; Massey V et al. *Biochim. Biophys. Acta* 48 (1961) 1-9. Meister A & Wellner D Flavoprotein amino acid oxidase. In: Boyer, P. D., Lardy, H. and Myrbäck, K. (Eds.), *The Enzymes*, 2nd ed., vol. 7, Academic Press, New York, 1963, p. 609-648.)

DAAO can be described by the Nomenclature Committee of the International Union of Biochemistry and Molecular Biology (IUBMB) with the EC (Enzyme Commission) number EC 1.4.3.3. Generally a DAAO enzyme of the EC 1.4.3.3. class is an FAD flavoenzyme that catalyzes the oxidation of neutral and basic D-amino acids into their corresponding keto acids. DAAOs have been characterized and sequenced in fungi and vertebrates where they are known to be located in the peroxisomes. The term D-amino oxidase further comprises D-aspartate oxidases (EC 1.4.3.1) (DASOX) (Negri A et al. (1992) J Biol. Chem. 267:11865-11871), which are enzymes structurally related to DAAO catalyzing the same reaction but active only toward dicarboxylic D-amino acids. Within this invention DAAO of the EC 1.4.3.3. class is preferred.

In DAAO, a conserved histidine has been shown (Miyano M et al. (1991) J Biochem 109:171-177) to be important for the enzyme's catalytic activity. In a preferred embodiment of the invention a DAAO is referring to a protein comprising the following consensus motive:

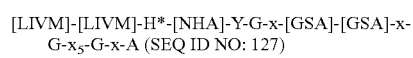
[LIVM]-[LIVM]-H*-[NHA]-Y-G-x-[GSA]-[GSA]-x-
G-$x_5$-G-x-A (SEQ ID NO: 127)

wherein amino acid residues given in brackets represent alternative residues for the respective position, x represents any amino acid residue, and indices numbers indicate the respective number of consecutive amino acid residues. The abbreviation for the individual amino acid residues have their standard IUPAC meaning as defined above. Further potential DAAO enzymes comprising said motif are described in Table 3.

TABLE 3

Suitable D-amino acid oxidases from various organism.

| Acc.-No. | Gene Name | Description | Source Organism | Length |
|---|---|---|---|---|
| Q19564 | F18E3.7 | Putative D-amino acid oxidase (EC 1.4.3.3) (DAMOX) (DAO) (DAAO) | *Caenorhabditis elegans* | 334 |
| P24552 | | D-amino acid oxidase (EC 1.4.3.3) (DAMOX) (DAO) (DAAO) | *Fusarium solani* (subsp. *pisi*) (*Nectria haematococca*) | 361 |
| P14920 | DAO, DAMOX | D-amino acid oxidase (EC 1.4.3.3) (DAMOX) (DAO) (DAAO) | *Homo sapiens* (Human) | 347 |
| P18894 | DAO, DAO1 | D-amino acid oxidase (EC 1.4.3.3) (DAMOX) (DAO) (DAAO) | *Mus musculus* (Mouse) | 346 |
| P00371 | DAO | D-amino acid oxidase (EC 1.4.3.3) (DAMOX) (DAO) (DAAO) | *Sus scrofa* (Pig) | 347 |
| P22942 | DAO | D-amino acid oxidase (EC 1.4.3.3) (DAMOX) (DAO) (DAAO) | *Oryctolagus cuniculus* (Rabbit) | 347 |
| O35078 | DAO | D-amino acid oxidase (EC 1.4.3.3) (DAMOX) (DAO) (DAAO) | *Rattus norvegicus* (Rat) | 346 |
| P80324 | DAO1 | D-amino acid oxidase (EC 1.4.3.3) (DAMOX) (DAO) (DAAO) | *Rhodosporidium toruloides* (Yeast) (*Rhodotorula gracilis*) | 368 |
| U60066 | DAO | D-amino acid oxidase (EC 1.4.3.3) (DAMOX) (DAO) (DAAO) | *Rhodosporidium toruloides*, strain TCC 26217 | 368 |
| Q99042 | DAO1 | D-amino acid oxidase (EC 1.4.3.3) (DAMOX) (DAO) (DAAO) | *Trigonopsis variabilis* (Yeast) | 356 |
| P31228 | DDO | D-aspartate oxidase (EC 1.4.3.1) (DASOX) (DDO) | *Bos taurus* (Bovine) | 341 |
| Q99489 | DDO | D-aspartate oxidase (EC 1.4.3.1) (DASOX) (DDO) | *Homo sapiens* (Human) | 341 |
| Q9C1L2 | NCU06558.1 | (AF309689) putative D-amino acid oxidase G6G8.6 (Hypothetical protein) | *Neurospora crassa* | 362 |

TABLE 3-continued

Suitable D-amino acid oxidases from various organism.

| Acc.-No. | Gene Name | Description | Source Organism | Length |
|---|---|---|---|---|
| Q7SFW4 | NCU03131.1 | Hypothetical protein | Neurospora crassa | 390 |
| Q8N552 | | Similar to D-aspartate oxidase | Homo sapiens (Human) | 369 |
| Q7Z312 | DKFZP686F04272 | Hypothetical protein DKFZp686F04272 | Homo sapiens (Human) | 330 |
| Q9VM80 | CG11236 | CG11236 protein (GH12548p) | Drosophila melanogaster (Fruit fly) | 341 |
| O01739 | F20H11.5 | F20H11.5 protein | Caenorhabditis elegans | 383 |
| O45307 | C47A10.5 | C47A10.5 protein | Caenorhabditis elegans | 343 |
| Q8SZN5 | CG12338 | RE73481p | Drosophila melanogaster (Fruit fly) | 335 |
| Q9V5P1 | CG12338 | CG12338 protein (RE49860p) | Drosophila melanogaster (Fruit fly) | 335 |
| Q86JV2 | | Similar to Bos taurus (Bovine). D-aspartate oxidase (EC 1.4.3.1) (DASOX) (DDO) | Dictyostelium discoideum (Slime mold) | 599 |
| Q95XG9 | Y69A2AR.5 | Hypothetical protein | Caenorhabditis elegans | 322 |
| Q7Q7G4 | AGCG53627 | AgCP5709 (Fragment) | Anopheles gambiae str. PEST | 344 |
| Q7PWY8 | AGCG53442 | AgCP12432 (Fragment) | Anopheles gambiae str. PEST | 355 |
| Q7PWX4 | AGCG45272 | AgCP12797 (Fragment) | Anopheles gambiae str. PEST | 373 |
| Q8PG95 | XAC3721 | D-amino acid oxidase | Xanthomonas axonopodis (pv. citri) | 404 |
| Q8P4M9 | XCC3678 | D-amino acid oxidase | Xanthomonas campestris (pv. campestris) | 405 |
| Q9X7P6 | SCO6740, SC5F2A.23C | Putative D-amino acid oxidase | Streptomyces coelicolor | 320 |
| Q82MI8 | DAO, SAV1672 | Putative D-amino acid oxidase | Streptomyces avermitilis | 317 |
| Q8VCW7 | DAO1 | D-amino acid oxidase | Mus musculus (Mouse) | 345 |
| Q9Z302 | | D-amino acid oxidase | Cricetulus griseus (Chinese hamster) | 346 |
| Q9Z1M5 | | D-amino acid oxidase | Cavia porcellus (Guinea pig) | 347 |
| Q922Z0 | | Similar to D-aspartate oxidase | Mus musculus (Mouse) | 341 |
| Q8R2R2 | | Hypothetical protein | Mus musculus (Mouse) | 341 |
| P31228 | | D-aspartate oxidase | B. taurus | 341 |

Acc.-No. refers to protein sequence from SwisProt database.

D-Amino acid oxidase (EC-number 1.4.3.3) can be isolated from various organisms, including but not limited to pig, human, rat, yeast, bacteria or fungi. Example organisms are *Candida tropicalis, Trigonopsis variabilis, Neurospora crassa, Chlorella vulgaris*, and *Rhodotorula gracilis*. A suitable D-amino acid metabolising polypeptide may be an eukaryotic enzyme, for example from a yeast (e.g. *Rhodotorula gracilis*), fungus, or animal or it may be a prokaryotic enzyme, for example, from a bacterium such as *Escherichia coli*. Examples of suitable polypeptides which metabolise D-amino acids are shown in Table 4.

TABLE 4

Suitable D-amino acid oxidases from various organism.

| GenBank Acc.-No, | Source Organism |
|---|---|
| Q19564 | Caenorhabditis elegans F18E3.7. |
| P24552 | Fusarii solani (subsp. pisi) (Nectria haematococca). |
| JX0152 | Fusarium solani |
| P14920 | Homo sapiens (Human) |
| P18894 | Mus musculus (mouse) |
| P00371 | Sus scrofa (pig) |
| P22942 | Oryctolagus cuniculus (Rabbit) |
| O35078 | Rattus norvegicus (Rat) |
| P80324 | Rhodosporidium toruloides (Yeast) (Rhodotorula gracilis) |
| Q99042 | Trigonopsis variabilis |
| Q9Y7N4 | Schizosaccharomyces pombe (Fission yeast) SPCC1450 |
| O01739 | Caenorhabditis elegans. F20H11.5 |
| Q28382 | Sus scrofa (Pig). |
| O33145 | Mycobacterium leprae |
| Q9X7P6 | Streptomyces coelicolor. SCSF2A.23C |
| Q9JXF8 | Neisseria meningitidis (serogroup B). |
| Q9Z302 | Cricetulus griseus (Chinese hamster) |
| Q921M5 | D-AMINO ACID OXIDASE. Cavia parcellus (Guinea pig) |

Acc.-No. refers to protein sequence from SwisProt database

Preferably the D-amino acid oxidase is selected from the enzymes encoded by a nucleic acid sequence or a corresponding amino acid sequences selected from the following Table 5:

TABLE 5

Suitable D-amino acid oxidases from various organism.

| GenBanc Acc.-No | Organism |
|---|---|
| U60066 | Rhodosporidium toruloides (Yeast) |
| Z71657 | Rhodotorula gracilis |
| A56901 | Rhodotorula gracilis |
| AF003339 | Rhodosporidium toruloides |
| AF003340 | Rhodosporidium toruloides |
| U53139 | Caenorhabditis elegans |

TABLE 5-continued

Suitable D-amino acid oxidases from various organism.

| GenBanc Acc.-No | Organism |
|---|---|
| D00809 | Nectria haematococca |
| Z50019. | Trigonopsis variabilis |
| NC_003421 | Schizosaccharomyces pombe (fission yeast) |
| AL939129. | Streptomyces coelicolor A3(2) |
| AB042032 | Candida boidinii |

Acc.-No. refers to protein sequence from GenBank database.

DAAO is a well-characterized enzyme, and both its crystal structure and its catalytic mechanism have been determined by high-resolution X-ray spectroscopy (Umhau S. et al. (2000) Proc. Natl. Acad. Sci. USA 97:12463-12468). It is a flavoenzyme located in the peroxisome, and its recognized function in animals is detoxification of D-amino acids (Pilone M S (2000) Cell. Mol. Life. Sci. 57:1732-174). In addition, it enables yeasts to use D-amino acids for growth (Yurimoto H et al. (2000) Yeast 16:1217-1227). As demonstrated above, DAAO from several different species have been characterized and shown to differ slightly in substrate affinities (Gabler M et al. (2000) Enzyme Microb. Techno. 27:605-611), but in general they display broad substrate specificity, oxidatively deaminating all D-amino acids (except D-glutamate and D-aspartate for EC 1.4.3.3. calss DAAO enzymes; Pilone M S (2000) Cell. Mol. Life. Sci. 57:1732-174).

DAAO activity is found in many eukaryotes (Pilone M S (2000) Cell. Mol. Life. Sci. 57:1732-174), but there is no report of DAAO activity in plants. The low capacity for D-amino acid metabolism in plants has major consequences for the way plants respond to D-amino acids.

In a preferred embodiment D-amino acid oxidase expressed form the DNA-construct of the invention has preferably enzymatic activity against at least one of the amino acids selected from the group consisting of D-alanine, D-serine, D-isoleucine, D-valine, and derivatives thereof.

Suitable D-amino acid oxidases also include fragments, mutants, derivatives, variants and alleles of the polypeptides exemplified above. Suitable fragments, mutants, derivatives, variants and alleles are those which retain the functional characteristics of the D-amino acid oxidase as defined above. Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included.

The D-amino acid oxidase of the invention may be expressed in the cytosol, peroxisome, or other intracellular compartment of the plant cell. Compartmentalisation of the D-amino acid metabolising polypeptide may be achieved by fusing the nucleic acid sequence encoding the DAAO polypeptide to a sequence encoding a transit peptide to generate a fusion protein. Gene products expressed without such transit peptides generally accumulate in the cytosol. The localisation of expressed DAAO in the peroxisome produces $H_2O_2$ that can be metabolised by the $H_2O_2$ degrading enzyme catalase. Higher levels of D-amino acids may therefore be required to produce damaging levels of $H_2O_2$. Expression of DAAO in the cytosol, where levels of catalase activity are lower, reduces the amount of D-amino acid required to produce damaging levels $H_2O_2$. Expression of DAAO in the cytosol may be achieved by removing peroxisome targeting signals or transit peptides from the encoding nucleic acid sequence. For example, the dao1 gene (EC: 1.4.3.3: GenBank Acc.-No.: U60066) from the yeast Rhodotorula gracilis (Rhodosporidium toruloides) was cloned as described (WO 03/060133). The last nine nucleotides encode the signal peptide SKL, which guides the protein to the peroxisome subcellular organelle. Although no significant differences were observed between cytosolic and peroxisomal expressed DAAO, the peroxisomal construction was found to be marginally more effective than the cytosolic version in respect of inhibiting the germination of the DAAO transgenic plants on 30 mM D-Asn. However, both constructs are inhibited significantly more than the wild-type and may thus be used for conditional counter-selection.

Additional modifications and use of dual-function marker are disclosed in EP Appl. No. 04006358.8 (SweTree Technologies AB & BASF; IMPROVED CONSTRUCTS FOR MARKER EXCISION BASED ON DUAL-FUNCTION SELECTION MARKER) and additional national and international applications claiming priority therefrom.

2.3.5. Expression of the Marker Gene and Other Sequences

The marker gene (or other sequences which can be expressed from one of the DNA constructs of the invention) may be expressed by any promoter functional in plants. These promoters include, but are not limited to, constitutive, inducible, temporally regulated, developmentally regulated, spatially-regulated, chemically regulated, stress-responsive, tissue-specific, viral and synthetic promoters. The promoter may be a gamma zein promoter, an oleosin ole16 promoter, a globulins promoter, an actin I promoter, an actin cl promoter, a sucrose synthetase promoter, an INOPS promoter, an EXM5 promoter, a globulin2 promoter, a β-32, ADPG-pyrophosphorylase promoter, an Ltpl promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapeturn-specific gene promoter, tapeturn-specific gene RAB24 promoter, a anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an α-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

2.4 Miscellaneous Traits

Numerous other advantageous traits can be successfully achieved with the invention disclosed herein. In fact any sequence and trait can be combined with the chimeric transcription nucleotide sequence of the invention for which a preferential expression in the embryo and early seedling is preferred. Thus, another embodiment of the invention relates to a method for starchy-endosperm and/or germinating embryo-specific or preferred expression of nucleic acid sequences in monocotyledonous plants, said method comprising the steps of a) constructing an expression cassette by operably linking at least one chimeric transcription regulating nucleotide sequence comprising
  iii) at least one transcription regulating nucleotide sequence derived from the promoter of an *Agrobacterium tumefaciens* mannopine synthase gene,
  iv) at least one upstream activating sequence derived from an octopine synthase gene of *Agrobacterium tumefaciens*,
  to at least one nucleic acid sequence which is heterologous in relation to said chimeric transcription regulating nucleotide sequence, and
b) inserting said expression cassette into a monocotyledonous plant to provide a transgenic plant, and
c) selecting transgenic plants, which demonstrate starchy-endosperm and/or germinating embryo-specific or -preferred expression of said heterologous nucleic acid sequence.

As described above, the method for starchy-endosperm and/or germinating embryo-specific or -preferred expression of the invention is resulting in expression a heterologous nucleic acid sequence which confers to a monocotyledonous plant at least one trait or property selected from the group consisting of v) enhanced resistance against at least one stress factor,
vi) increased nutritional quality of a seed or a sprout,
vii) increased yield, and
viii) selection marker excision.

Preferred specified traits and sequences to achieve them are specified herein below.

The monoteledonous plant to which the methods of this invention are preferrably applied to may be selected from the group consisting of maize, wheat, rice, barley, oat, rye, sorghum, banana, ryegress or coix. Preferably the plant is a cereal plant selected from the group consisting of maize, wheat, barley, rice, oat, rye, and sorghum, even more preferably from maize, wheat, and rice, most preferably the plant is a maize plant.

In one preferred embodiment of the invention the nucleotide sequence expressed from the chimeric transcription regulating sequence of the invention is not encoding a a beta-glucuronidase (GUS), or is not a method for expression GUS-gene for the purpose of achieving a GUS-mediating staining.

3. Assays of Transgene Expression

To confirm the presence of an exogenous DNA in regenerated plants, a variety of assays may be performed. Such assays include, for example, molecular biological assays such as Southern and Northern blotting and PCR; biochemical assays such as detecting the presence of a protein product, e.g., by immunological means (ELISAs and Western blots) or by enzymatic function; plant part assays such as leaf or root assays; and in some cases phenotype analysis of a whole regenerated plant. Additional assays useful for determining the efficiency of transgene expression and promoter function also include without limitation fluorescent in situ hybridization (FISH), direct DNA sequencing, pulsed field gel electrophoresis (PFGE) analysis, single-stranded conformation analysis (SSCA), RNase protection assay, allele-specific oligonucleotide (ASO), dot blot analysis, denaturing gradient gel electrophoresis, RT-PCR, quantitative RT-PCR, RFLP and PCR-SSCP. Such assays are known to those of skill in the art (see also above).

4. Transformed (Transgenic) Plants of the Invention and Methods of Preparation

Moocot plant species may be transformed with the DNA construct of the present invention by various methods known in the art. Any plant tissue capable of subsequent clonal propagation, whether by organogenesis or embryogenesis, may be transformed. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) monocotyledonous plants and monocotyledonous plant cell, in planta or ex planta, including a transformed plastid or other organelle, e.g., nucleus, mitochondria or chloroplast. The present invention may be used for transformation of any monocotyledonous plant species, including, but not limited to, cells from the plant species specified above in the DEFINITION section. Preferably, transgenic plants of the present invention are crop plants and in particular cereals (for example, corn, alfalfa, rice, barley, sorghum, wheat, millet etc.), and even more preferably corn, wheat and rice. Other embodiments of the invention are related to cells, cell cultures, tissues, parts (such as plants organs, leaves, roots, etc.) and propagation material (such as seeds) of such monocotyledonous plants.

Transformation of monocotyledonous plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (see, for example, EP 295959 and EP 138341). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cofton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art.

Those skilled in the art will appreciate that the choice of method might depend on the type of monocotyledonous plant targeted for transformation. Suitable methods of transforming plant cells include, but are not limited to, microinjection (Crossway 1986), electroporation (Riggs 1986), *Agrobacterium*-mediated transformation, direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Datta 1990; (rice); Klein 1988 (maize); Klein 1988 (maize); Klein 1988 (maize); Fromm 1990 (maize); and Gordon-Kamm 1990 (maize); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat), Li 1993 and Christou 1995 (rice); Osjoda 1996 (maize via *Agrobacterium tumefaciens*), rice (Hiei 1994), and corn (Gordon-Kamm 1990; Fromm 1990); all of which are herein incorporated by reference. *Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known. Various *Agrobacterium* strains can be employed, preferably disarmed *Agrobacterium tumefaciens* or rhizogenes strains. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105 [pEHA105] (Li 1992), LBA4404[pAL4404] (Hoekema 1983), C58C1[pMP90] (Koncz & Schell 1986), and C58C1 [pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Klapwijk 1980). In another preferred embodiment the soil-borne bacterium is a disarmed variant of *Agrobacterium rhizogenes* strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with super-virulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo & Hooykaas 1991).

*Agrobacterium* is grown and used in a manner similar to that described in Ishida (1996). The vector comprising *Agrobacterium* strain may, for example, be grown for 3 days on YP medium (5 g/L yeast extract, 10 g/L peptone, 5 g/L NaCl, 15 g/L agar, pH 6.8) supplemented with the appropriate antibiotic (e.g., 50 mg/L spectinomycin). Bacteria are collected with a loop from the solid medium and resuspended. In a preferred embodiment of the invention, *Agrobacterium* cultures are started by use of aliquots frozen at −80° C.

The transformation of the target tissue (e.g., an immature embryo) by the Agrobacterium may be carried out by merely contacting the target tissue with the *Agrobacterium*. The concentration of *Agrobacterium* used for infection and co-cultivation may need to be varied. For example, a cell suspension of the *Agrobacterium* having a population density of approximately from $10^5$-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the *Agrobacterium*.

Preferably, the bacterium is employed in concentration of $10^6$ to $10^{10}$ cfu/mL. In a preferred embodiment for the co-cultivation step about 1 to 10 µl of a suspension of the soil-borne bacterium (e.g., *Agrobacteria*) in the co-cultivation medium are directly applied to each target tissue explant and air-dried. This is saving labor and time and is reducing unintended *Agrobacterium*-mediated damage by excess *Agrobacterium* usage.

For *Agrobacterium* treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defense responses (like phenolic oxidation) may further improve the efficiency of *Agrobacterium*-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 µM to about 10 µM of silver nitrate and from about 50 mg/L to about 1,000 mg/L of L-Cysteine. This results in a highly reduced vulnerability of the target tissue against *Agrobacterium*-mediated damage (such as induced necrosis) and highly improves overall transformation efficiency.

Various vector systems can be used in combination with *Agrobacteria*. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or *Agrobacterium*-mediated transfer usually, but not necessarily, are undertaken with a selectable marker, which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells, which are then grown to callus. Shoots are grown from callus. Plantlets are generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA, which has been introduced. Components of DNA constructs including transcription cassettes of this invention may be prepared from sequences, which are native (endogenous) or foreign (exogenous) to the host. By "foreign" it is meant that the sequence is not found in the wild-type host into which the construct is introduced. Heterologous constructs will contain at least one region, which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR or TaqMan; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using these technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate trans-mission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays. Two or more generations can be grown to ensure that tissue-preferred expression of the desired phenotypic characteristic under conditions of interest is stably maintained and inherited.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant, which only differs in that the expression cassette is absent. The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding, which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross-pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, which for example increase the effectiveness of conventional methods such as herbicide or pesticide treatment or allow dispensing with said methods due to their modified genetic properties. Alternatively new crops with improved stress tolerance can be obtained which, due to their optimized genetic "equipment", yield harvested product of better quality than products, which were not able to tolerate comparable adverse developmental conditions.

| Sequences | |
|---|---|
| 1. SEQ ID NO: 1 | Nucleotide sequence encoding upstream activating sequence derived from an octopine synthase gene of *Agrobacterium tumefaciens* |
| 2. SEQ ID NO: 2 | Nucleotide sequence encoding transcription regulating nucleotide sequence derived from the promoter of an *Agrobacterium tumefaciens* mannopine synthase gene |
| 3. SEQ ID NO: 3 | Nucleotide sequence encoding transcription regulating nucleotide sequence derived from the promoter of an *Agrobacterium tumefaciens* mannopine synthase gene comprising some stuffer sequences |
| 4. SEQ ID NO: 4 | Nucleotide sequence encoding chimeric transcription regulating sequence (super-promoter) |

-continued

| Sequences | |
|---|---|
| 5. SEQ ID NO: 5 | Nucleotide sequence encoding *Physcomitrella patens*, EST217: 14-3-3 protein (gb AX281102) [pBPSSuP001] |
| 6. SEQ ID NO: 6 | Amino acid sequence encoding *Physcomitrella patens*, EST217: 14-3-3 protein (gb AX281102) [pBPSSuP001] |
| 7. SEQ ID NO: 7 | Nucleotide sequence encoding *Physcomitrella patens*, EST268: phosphoinositide-specific phospholipase C (gb AX281101) [pBPSSuP002] |
| 8. SEQ ID NO: 8 | Amino acid sequence encoding *Physcomitrella patens*, EST268: phosphoinositide-specific phospholipase C (gb AX281101) [pBPSSuP002] |
| 9. SEQ ID NO: 9 | Nucleotide sequence encoding *Arabidopsis thaliana*, putative tyrosine aminotransferase (At5g53970) gb BT000782 [pBPSSuP003] |
| 10. SEQ ID NO: 10 | Amino acid sequence encoding *Arabidopsis thaliana*, putative tyrosine aminotransferase (At5g53970) gb BT000782 [pBPSSuP003] |
| 11. SEQ ID NO: 11 | Nucleotide sequence encoding *Oryza sativa* putative porphobilinogen deaminase [gb XM_464262] (pBPSSuP004) |
| 12. SEQ ID NO: 12 | Amino acid sequence encoding *Oryza sativa* putative porphobilinogen deaminase [gb XM_464262] (pBPSSuP004) |
| 13. SEQ ID NO: 13 | Nucleotide sequence encoding *Oryza sativa* putative omega-3 fatty acid desaturase [gb NM_185577] (pBPSSuP005) |
| 14. SEQ ID NO: 14 | Amino acid sequence encoding *Oryza sativa* putative omega-3 fatty acid desaturase [gb NM_185577] (pBPSSuP005) |
| 15. SEQ ID NO: 15 | Nucleotide sequence encoding *Oryza sativa* Fusarium resistance protein I2C-5-like [gb NM_194161] (pBPSSuP006) |
| 16. SEQ ID NO: 16 | Amino acid sequence encoding *Oryza sativa* Fusarium resistance protein I2C-5-like [gb NM_194161] (pBPSSuP006) |
| 17. SEQ ID NO: 17 | Nucleotide sequence encoding *Arabidopsis thaliana*, constitutive expressor of pathogenesis related genes 5 (cpr5, At5g64930; gb AY033229) [pBPSSuP007] |
| 18. SEQ ID NO: 18 | Amino acid sequence encoding *Arabidopsis thaliana*, constitutive expressor of pathogenesis related genes 5 (cpr5, At5g64930; gb AY033229) [pBPSSuP007] |
| 19. SEQ ID NO: 19 | Nucleotide sequence encoding *Oryza sativa*, Plant disease resistance polyprotein-like [gb XM_465297] (pBPSSuP008) |
| 20. SEQ ID NO: 20 | Amino acid sequence encoding *Oryza sativa*, Plant disease resistance polyprotein-like [gb XM_465297] (pBPSSuP008) |
| 21. SEQ ID NO: 21 | Nucleotide sequence encoding *Saccharomyces cerevisiae* homing endonuclease I-SceI |
| 22. SEQ ID NO: 22 | Amino acid sequence encoding *Saccharomyces cerevisiae* homing endonuclease I-SceI |
| 23. SEQ ID NO: 23 | Nucleotide sequence encoding *Saccharomyces cerevisiae* himing endonuclease I-SceI comprising an intron (e.g., to supress functional protein expression in bacterial (e.g., *E. coli* or *Agrobacterium* cells) |
| 24. SEQ ID NO: 24-41 | Oligonucleotide primer sequences |
| 42. SEQ ID NO: 42 | Nucleotide sequence encoding HvRACB (RACB, a GTPase from barley. RACBV15 constitutive active form appears to show an increasd *fusarium* resistance) |
| 43. SEQ ID NO: 43 | Amino acid sequence encoding HvRACB (RACB, a GTPase from barley. RACBV15 constitutive active form appears to show an increased *fusarium* resistance) |
| 44. SEQ ID NO: 44 | Nucleotide sequence encoding BAX Inhibitor1 (Barley antiapoptotic gene, the overexpression of which results in an increased broad spectrum resistance) |
| 45. SEQ ID NO: 45 | Amino acid sequence encoding BAX INhibitor1 (Barley antiapoptotic gene, the overexpression of which results in an increased broad spectrum resistance) |

| | Sequences |
|---|---|
| 46. SEQ ID NO: 46 | Nucleotide sequence encoding HvADF3 (Actin Depolymerization Factor 3, overexpression results in an increased broad-spectrum resistance) |
| 47. SEQ ID NO: 47 | Amino acid sequence encoding HvADF3 (Actin Depolymerization Factor 3, overexpression results in an increased broad-spectrum resistance) |
| 48. SEQ ID NO: 48 | Nucleotide sequence encoding HvSNAP34 (t-SNARE interactor of ROR2, involved in vesicle transport. Overexpression increases fungal resistance) |
| 49. SEQ ID NO: 49 | Amino acid sequence encoding HvSNAP34 (t-SNARE interactor of ROR2, involved in vesicle transport. Overexpression increases fungal resistance) |
| 50. SEQ ID NO: 50 | Nucleotide sequence encoding HvROR2 (Syntaxin, interactor of SNAP34. Overexpression increases fungal resistance) |
| 51. SEQ ID NO: 51 | Amino acid sequence encoding HvROR2 (Syntaxin, interactor of SNAP34. Overexpression increases fungal resistance) |
| 52. SEQ ID NO: 52 | Nucleotide sequence encoding HvPOX8.1 (Peroxidase, the overexpression of which results in increased fungal resistance) |
| 53. SEQ ID NO: 53 | Amino acid sequence encoding HvPOX8.1 (Peroxidase, the overexpression of which results in increased fungal resistance) |
| 54. SEQ ID NO: 54-65 | Oligonucleotide primer sequences |

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of E. coli cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Vector Construction

The promoter fragment was isolated from p1bxSuperGUS by digesting with XbaI and XmaI enzymes and subcloned into the upstream of GUS gene in pBPSCER011 [GUS (potato invertase intron 2)::NOS in pUC], which generated pBPSMM188. GUS chimeric cassette driven by super-promoter was digested with AscI and SacI and cloned into pBPSMM146 by replacing existing GUS cassette with super-promoter::GUS (1)::NOS terminator. This transformation construct was named pBPSMM225.

Example 2

Agrobacterium-mediated Transformation in Monocotyledonous Plants

The Agrobacterium-mediated plant transformation using standard transformation and regeneration techniques may also be carried out for the purposes of transforming crop plants (Gelvin 1995; Glick 1993, U.S. Pat. No. 5,591,616). The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag New York).

The use of phytotoxic compounds (e.g., antibiotics, herbicides, etc.) for the selection of Agrobacteria and plants depends on the binary vector and the Agrobacterium strain used for the transformation. The selection of maize is generally carried out using phosphinotricin or D-serine or D-alanine as selective compounds.

Example 3

Detection of Reporter Gene Expression

To identify the characteristics of the promoter and the essential elements of the latter, which bring about its tissue specificity, it is necessary to place the promoter itself and various fragments thereof before what is known as a reporter gene, which allows the determination of the expression activity. An example which may be mentioned is the bacterial β-glucuronidase (Jefferson 1987a). The β-glucuronidase activity can be detected in-planta by means of a chromogenic substrate such as 5-bromo-4-chloro-3-indolyl-β-D-glucuronic acid in an activity staining (Jefferson 1987b). To study the tissue specificity, the plant tissue is cut, embedded, stained and analyzed as described (for example Bäumlein 1991b).

A second assay permits the quantitative determination of the GUS activity in the tissue studied. For the quantitative activity determination, MUG (4-methylumbelliferyl-β-D-glucuronide) is used as substrate for β-glucuronidase, and the MUG is cleaved into MU (methylumbelliferone) and glucuronic acid.

To do this, a protein extract of the desired tissue is first prepared and the substrate of GUS is then added to the extract. The substrate can be measured fluorimetrically only after the GUS has been reacted. Samples which are subsequently measured in a fluorimeter are taken at various points in time. This assay may be carried out for example with linseed embryos at various developmental stages (21, 24 or 30 days after flowering). To this end, in each case one embryo is ground into a powder in a 2 mL reaction vessel in liquid nitrogen with the aid of a vibration grinding mill (Type: Retsch M M 2000). After addition of 100 µL of EGL buffer (0.1 M $KPO_4$, pH 7.8; 1 mM EDTA; 5% glycerol; 1 M DTT), the mixture is centrifuged for 10 minutes at 25° C. and 14,000×g. The supernatant is removed and recentrifuged. Again, the supernatant is transferred to a new reaction vessel and kept on ice until further use. 25 µL of this protein extract are treated with 65 µL of EGL buffer (without DTT) and employed in the GUS assay. 10 µL of the substrate MUG (10 mM 4-methylumbelliferyl-β-D-glucuronide) are now added, the mixture is vortexed, and 30 µL are removed immediately as zero value and treated with 470 µL of Stop buffer (0.2 M $Na_2CO_3$). This procedure is repeated for all of the samples at an interval of 30 seconds. The samples taken were stored in the refrigerator until measured. Further readings were taken after 1 h and after 2 h. A calibration series which contained concentrations from 0.1 mM to 10 mM MU (4-methylumbelliferone) was established for the fluorimetric measurement. If the sample values were outside these concentrations, less protein extract was employed (10 µL, 1 µL, 1 µL from a 1:10 dilution), and shorter intervals were measured (0 h, 30 min, 1 h). The measurement was carried out at an excitation of 365 nm and an emission of 445 nm in a Fluoroscan II apparatus (Labsystem). As an alternative, the substrate cleavage can be monitored fluorimetrically under alkaline conditions (excitation at 365 nm, measurement of the emission at 455 nm; Spectro Fluorimeter BMG Polarstar+) as described in Bustos (1989). All the samples were subjected to a protein concentration determination by the method of Bradford (1976), thus allowing an identification of the promoter activity and promoter strength in various tissues and plants.

Example 4

Starch Endosperm and/or Germinating Embryo-Specific Expression in Maize

Super-promoter showed only sporadically low expression in roots of young seedling (up to 7 days after imbibition) but was in most plants undetectable. It was expressed in developing ears and T2 kernels at low levels. In kernels still on the cob expression was limited to the central endosperm. The same expression pattern was observed in dry seeds at lower levels. However, 24 hours after imbibition in water the super-promoter was highly expressed in the embryo while staining in the restricted region of the endosperm was weaker or almost undetectable. This strong embryo-specific expression was maintained during germination until 7 days after imbibition. After 7 days of imbibition, medium level of GUS expression was detected in radicle and a few very young roots. The expression in roots was undetectable in older plants.

TABLE 6

GUS expression controlled monocot potential constitutive promoter candidates

| Tissues/Developmental stages | Promoter (GUS expression levels) | |
|---|---|---|
| | Maize ubiquitin* | pBPSMM225 |
| 3 days after co-cultivation | +++++ | + |
| Callus | +++++ | + |
| In vitro leaves | +++++ | − |
| In vitro roots | +++++ | − |
| Stem | +++++ | − |
| Pre-pollination | +++++ | − |
| 5 days after pollination [DAP][1] | +++++ | + |
| 10 DAP[1] | +++++ | + |
| 20 DAP[1] | +++++ | + |
| Dry seeds[1] | ++++ | + |
| Imbibition | | |
| 0 h[1] | ++++ | + |
| 3 h[1] | +++++ | +++ |

TABLE 6-continued

GUS expression controlled monocot potential constitutive promoter candidates

| Tissues/Developmental stages | Promoter (GUS expression levels) | |
|---|---|---|
| | Maize ubiquitin* | pBPSMM225 |
| 5 h[1] | +++++ | +++ |
| 8 h[1] | +++++ | +++ |
| 16 h[1] | +++++ | ++++ |
| 24 h[2] | +++++ | +++++ |
| 4 d[2] | +++++ | +++++ |
| 7 d[2] | +++++ | ++++ |

*positive control as a constitutive promoter; a range of GUS expression levels measured by histochemical assay (− to +++++),
ND: not determined yet,
[1]starch endosperm region
[2]embryo Example 5

Utilization of Transgenic Crops

A reporter gene in pBPSMM225 can be replaced with a gene of interest to be expressed mostly in roots and kernel (e.g., by antisense or double-stranded RNA), thereby improving—for example—biomass and/or yield, tolerance to biotic and abiotic environmental stresses, or the nutritional value of seeds/sprouts. The chimeric constructs are transformed into monocotyledonous plants. Standard methods for transformation in the art can be used if required. Transformed plants are regenerated using known methods. Various phenotypes are measured to determine improvement of biomass, yield, fatty acid composition, high oil, disease tolerance, or any other phenotypes that indicate yield enhancement or yield stability. Gene expression levels are determined at different stages of development and in different generations ($T_0$ to $T_2$ plants or further generations). Results of the evaluation in plants lead to identification of appropriate genes that increase yield in combination with this promoter.

Example 6

Trait Gene Constructs Driven by the Super-Promoter 6.1 Isolation of the Gene Candidates Genomic DNA from plant species of interest is extracted using the Qiagen DNAeasy Plant Mini Kit (Qiagen). Genomic DNA regions containing genes of interest (GOI) are isolated using conventional PCR. Approximately 0.1 µg of digested genomic DNA is used for the regular PCR reaction (see below). The primers are designed based on the genomic sequences. One µL of the diluted digested genomic DNA is used as the DNA template in the primary PCR reaction. The reactions comprise the following primer sets (Table 7) in a mixture containing Buffer 3 following the protocol outlined by an Expand Long PCR kit (Cat #1681-842, Roche-Boehringer Mannheim). The isolated DNA is employed as template DNA in a PCR amplification reaction using the following primers:

TABLE 7

Primer sequences

| Primer name | Sequence | SEQ ID NO: |
|---|---|---|
| 14-3-3 protein | FP: 5'-ATCCCGGGCGGACTGTCGTGG-3' | 24 |
| | RP: 5'-GCGAGCTCGGCACGCAACTGC-3' | 25 |

TABLE 7-continued

Primer sequences

| Primer name | Sequence | SEQ ID NO: |
|---|---|---|
| phosphoinositide-specific phospholipase C | FP: 5'-ATCCCGGGCTTCGGGAGTTTA-3'<br>RP: 5'-GGCGTTAACCTTGGGTGCACA-3' | 26<br>27 |
| Tyrosin aminotransferase | FP: 5'-AAAATCAAAACCTTCTCTTCT-3'<br>RP: 5'-CAAGTTAACATTTTTCTGTTT-3' | 28<br>29 |
| Putative prophobilinogen deaminase | FP: 5'-ATGCCGCCGCCGCCGAGATGC-3'<br>RP: 5'-TCATTGCAAGCTATCAAAGAA-3' | 30<br>31 |
| Putative omega-3 faty acid desaturase | FP: 5'-ATGGCCCGGCTGCTACTCTCC-3'<br>RP: 5'-TTAGTTAGCAGGGTCGGTCTG-3' | 32<br>33 |
| Os.I2C-5-like | FP: 5'-ATGGATAACACGTTGGTGGCA-3'<br>RP: 5'-TCAGTTGTCATCGACTTCTGA-3' | 34<br>35 |
| Constitutive expressor of pathogenesis related genes 5 | FP: 5'-ATGGAAGCCCTCCTCCTCCCT-3'<br>RP: 5'-TCAAGCATAGTCAGACCCACC-3' | 36<br>37 |
| Plant disease resistance polyprotein-like | FP: 5'-ATGGGGAAGAAAAGGAAAGGGG-3'<br>RP: 5'-CTAGGCTCGCCGCCGCACCGCG-3' | 38<br>39 |
| Homing endonuclease I-SceI | FP: 5'-ATGCATATGAAAAACATCAAA-3'<br>RP: 5'-TTATTTCAGGAAAGTTTCGGA-3' | 40<br>41 |
| GTPase | FP: 5'-ATGAGCGCGTCCAGGTTCATA-3'<br>RP: 5'-TCACAAGATGGAGCAAGCCCC-3' | 54<br>55 |
| Barley antiapoptotic gene | FP: 5'-ATGCGCTTGAATATCGGTGGA-3'<br>RP: 5'-CTAAGTTTCTTCATTATTTCT-3' | 56<br>57 |
| Actin Depolymerization Factor 3 | FP: 5'-ATGGCTAATGCAGCATCAGGA-3'<br>RP: 5'-TCAATTGGCTCGGCTTTTGAA-3' | 58<br>59 |
| t-SNARE interactor of ROR2 | FP: 5'-ATGAGCGCCACCAGGCCCTCC-3'<br>RP: 5'-CTATCTGCCAAGCAGGCGACG-3' | 60<br>61 |
| Syntaxin, interactor of SNAP34 | FP: 5'-ATGAACAACCTCTTCTCGAGCTCG-3'<br>RP: 5'-CTACTGCTGGCTGTTGTTGTT-3' | 62<br>63 |
| Peroxidase | FP: 5'-ATGGCCTCTACTTCGTCCCTA-3'<br>RP: 5'-TTAATTCACCTTGGAGCAGCT-3' | 64<br>65 |

The sequences indicated in this table show only the part homologous to the target sequence to be amplified. The complete primer comprises a SmaI restriction site linker 5' end of forward primer (5-CCCGGG-3') and a SacI restriction site linker (5-GAGCTC-3') at the 5' end reverse primer.

Forward and reverse primers include SmaI and SacI restriction enzyme site overhang at the 5' end of the primers. Amplification is carried out in the PCR reaction (5 µL 10× Advantage PCR Mix [Eppendorf], 5 µL genomic DNA [corresponds to approximately 80 ng], 2.5 mM of each dATP, dCTP, dGTP and dTTP [Invitrogen: dNTP mix], 1 µL of 20 µM 5'-intron specific primer 20 µM, 1 µL of 20 µM 3' intron specific primer, 1 µL TripleMaster DNA Polymerase mix [Eppendorf], in a final volume of 50 µL) under the optimized PCR program (1 cycle with 15 sec at 94° C. and 1 min at 80° C. 35 cycles with 15 sec at 94° C., 1 min at 58° C. and 1 min at 72° C.) provided by Thermocycler (T3 Thermocycler Biometra).

The PCR product is applied to an 1% (w/v) agarose gel and separated at 80V. The PCR products are excised from the gel and purified with the aid of the Qiagen Gel Extraction Kit (Qiagen, Hilden, Germany). The PCR product can be cloned directly into vector pCR4-TOPO (Invitrogen) following the manufacturer's instructions, i.e. the PCR product obtained is inserted into a vector having T overhangs with its A overhangs and a topoisomerase.

4.2 Vector Construction

The base vector to which the gene candidates are clone in is pBPSMM225. This vector comprises the super-promoter followed by the GUSint ORF (including the potato invertase [PIV]2 intron to prevent bacterial expression), followed by nopaline synthase (NOS) terminator.

The chimeric constructs containing super-promoter::gene of interest::NOS terminator are generated by ligation of SmaI-SacI digested gene of interest PCR products into SmaI-SacI linearized pBPSMM225, thereby resulting in the following vectors (Table 8).

TABLE 8

Trait gene chimeric constructs driven by the super-promoter

| | Binary vector | Target/Trait | Gene of interest candidates [GenBank Accession No] |
|---|---|---|---|
| 1 | pBPSSuP001 pBPSSuP002 | Abiotic stress$^R$ [cold, chilling, early vigor, and high yield] | 14-3-3 protein & phosphoinositide-specific phospholipase C [WO0177355 and U.S. Pat. No. 6,720,477] |
| 2 | pBPSSuP003 | Nutritious sprouts [vitamin, fatty acids, etc.] | Tyrosin aminotransferase (Vit E) [BT000782; WO02072848] |
| | pBPSSuP004 | | putative prophobilinogen deaminase (Vit B12) [XM464262] |
| | pBPSSuP005 | | putative omega-3 fatty acid desaturase [NM185577] |
| 3 | pBPSSuP006 | Seed-borne disease$^R$ | *Oryza sativa Fusarium* resistance protein I2C-5-like [NM194161] |
| | pBPSSuP007 | | Constitutive expressor of pathogenesis related genes 5 (cpr5) [NM125892.2] |
| | pBPSSuP008 | | Plant disease resistance polyprotein-like [XM465297] |
| 5 | pBPSSuP009 | Marker excision | Homing endonuclease I-SceI |
| 6 | pBPSSuP010 | Fungal resistance | GTPase [WO03020939] |
| | pBPSSuP011 | | Barley antiapoptotic gene [WO03020939] |
| | pBPSSuP012 | | Actin Depolymerization Factor 3 [WO2004035798] |
| | pBPSSuP013 | | t-SNARE interactor of ROR2 [WO2004081217] |
| | pBPSSuP014 | | Syntaxin, interactor of SNAP34 [WO2004081217] |
| | pBPSSuP015 | | Peroxidase |

4.3 Enhanced Resistance Against at Least One Stress Factor, Nutritional Quality of a Seed or a Sprout, Yield, or Frequency of Selection Marker Excision A reporter gene in pBPSMM225 can be replaced with
(1) abiotic stress resistance genes (14-3-3 protein & phosphoinositide-specific phospholipase C: WO0177355 and U.S. Pat. No. 6,720,477),
(2) genes involved in vitamin E biosynthesis (tyrosin aminotransferase (BT000782: WO02072848), putative porphobilinogen deaminase, putative omega-3 fatty acid desaturase [NM185577])
(3) biotic stress resistance genes (*Oryza sativa Fusarium* resistance protein I2C-5-like [NM194161], constitutive expressor of pathogenesis related genes 5 (cpr5: NM185577)), GTPase [WO03020939], Actin Depolymerization Factor 3 [WO2004035798], t-SNARE interactor of ROR2 and Syntaxin, interactor of SNAP34 [WO2004081217],
(4) homing endonuclease gene (for example a sequence encoding the homing endonuclease I-SceI)
to be expressed in embryo during germination, thereby improving—for example tolerance to abiotic environmental stresses, early vigor resulting in potential yield enhancement, the amount of vitamin E, tolerance to biotic stresses and the frequency of marker excision. The chimeric constructs are transformed into monocotyledonous plants. Standard methods for transformation in the art can be used if required. Transformed plants are regenerated using known methods. Various phenotypes are measured to determine improvement of biomass, yield, fatty acid composition, high oil, disease tolerance, or any other phenotypes that indicate yield enhancement or yield stability. Gene expression levels are determined at different stages of development and in different generations ($T_0$ to T2 plants or further generations). Results of the evaluation in plants lead to identification of appropriate genes in combination with this promoter that increase yield, improve disease tolerance, improve abiotic stress tolerance and/or increase nutritional quality of seed or sprout.

Example 5

Deletion Analysis

The cloning method is described by Rouster (1997) and Sambrook (1989). Detailed mapping of the promoter (i.e., narrowing down of the nucleic acid segments relevant for its specificity) is performed by generating various reporter gene expression vectors which firstly contain the entire promoter region and secondly various fragments thereof. Firstly, the entire promoter region or fragments thereof are cloned into a binary vector containing GUS or other reporter gene. To this end, fragments are employed firstly, which are obtained by using restriction enzymes for the internal restriction cleavage sites in the full-length promoter sequence. Secondly, PCR fragments are employed which are provided with cleavage sites introduced by primers. The chimeric GUS constructs containing various deleted promoters are transformed into maize and other plant species using transformation methods in the current art. Promoter activity is analyzed by using GUS histochemical assays or other appropriate methods in various tissues and organs at the different developmental stages.

Example 6

In Vivo Mutagenesis

The skilled worker is familiar with a variety of methods for the modification of the promoter activity or identification of important promoter elements. One of these methods is based on random mutation followed by testing with reporter genes as described above. The in vivo mutagenesis of microorganisms can be achieved by passage of the plasmid (or of another vector) DNA through *E. coli* or other microorganisms (for example *Bacillus* spp. or yeasts such as *Saccharomyces cerevisiae*) in which the ability of maintaining the integrity of the genetic information is disrupted. Conventional mutator strains have mutations in the genes for the DNA repair system (for example mutHLS, mutD, mutT and the like; for reference, see Rupp 1996). The skilled worker is familiar with these strains. The use of these strains is illustrated for example by Greener (1994). The transfer of mutated DNA molecules into plants is preferably effected after selection and testing of the microorganisms. Transgenic plants are generated and analyzed as described above.

Example 7

PLACE Analysis for Super-promoter (SEQ ID NO: 4)

Based on the below given PLACE results indicates that no TATA box consensus sequences are available in the 1,112 base pairs of SEQ ID NO: 4. The following clusters of promoter elements were identified in the super-promoter as described by SEQ ID NO: 4:

Table 9. Regulatory protein binding DNA motifs located in the super-promoter

TABLE 9

Regulatory protein binding DNA motifs located in the super-promoter

| IUPAC | Position from-to | Str. | Sequence | SEQ ID NO: |
|---|---|---|---|---|
| CGACGOSAMY3 | 14-18 | (+) | CGACG | 128 |
| NONAMERMOTIFTAH3H4 | 17-25 | (−) | CATCCAACG | 129 |
| PYRIMIDINEBOXOSRAM | 43-48 | (+) | CCTTTT | 130 |
| IBOXCORENT | 48-54 | (−) | GATAAGA | 131 |
| ACGTABOX | 62-67 | (+) | TACGTA | 132 |
| ACGTABOX | 62-67 | (−) | TACGTA | 132 |
| OCSENHANMOTIFAT | 63-78 | (+) | ACGTAAGCGCTTACGT | 133 |
| OCSENHANMOTIFAT | 63-78 | (−) | ACGTAAGCGCTTACGT | 133 |
| RAV1AAT | 109-113 | (−) | CAACA | 134 |
| CGACGOSAMY3 | 233-237 | (+) | CGACG | 128 |
| NONAMERMOTIFTAH3H4 | 236-244 | (−) | CATCCAACG | 129 |
| PYRIMIDINEBOXOSRAM | 262-267 | (+) | CCTTTT | 130 |
| IBOXCORENT | 267-273 | (−) | GATAAGA | 131 |
| ACGTABOX | 281-286 | (+) | TACGTA | 132 |
| ACGTABOX | 281-286 | (−) | TACGTA | 132 |
| OCSENHANMOTIFAT | 282-297 | (+) | ACGTAAGCGCTTACGT | 133 |
| OCSENHANMOTIFAT | 282-297 | (−) | ACGTAAGCGCTTACGT | 133 |
| RAV1AAT | 328-332 | (−) | CAACA | 134 |
| CGACGOSAMY3 | 452-456 | (+) | CGACG | 128 |
| NONAMERMOTIFTAH3H4 | 455-463 | (−) | CATCCAACG | 129 |
| PYRIMIDINEBOXOSRAM | 481-486 | (+) | CCTTTT | 130 |
| IBOXCORENT | 486-492 | (−) | GATAAGA | 131 |
| ACGTABOX | 500-505 | (+) | TACGTA | 132 |
| ACGTABOX | 500-505 | (−) | TACGTA | 132 |
| OCSENHANMOTIFAT | 501-516 | (+) | ACGTAAGCGCTTACGT | 133 |
| OCSENHANMOTIFAT | 501-516 | (−) | ACGTAAGCGCTTACGT | 133 |
| P$FAM270/P$RAV1AAT | 547-551 | (−) | CAACA | 134 |
| OCTAMERMOTIFTAH3H4 | 659-666 | (−) | CGCGGATC | 135 |
| ELRECOREPCRP1 | 663-677 | (−) | ATTGACCAGCTCGCG | 136 |
| RAV1AAT | 699-703 | (+) | CAACA | 134 |

TABLE 9-continued

Regulatory protein binding DNA motifs located in the super-promoter

| IUPAC | Position from-to | Str. | Sequence | SEQ ID NO: |
|---|---|---|---|---|
| CCA1ATLHCB1 | 727-734 | (-) | AAAAATCT | 137 |
| -300ELEMENT | 728-736 | (-) | TGAAAAATC | 138 |
| ABRELATERD1 | 747-759 | (+) | CAAGACGTGACGT | 139 |
| TGACGTVMAMY | 749-761 | (+) | AGACGTGACGTAA | 140 |
| HEXMOTIFTAH3H4 | 751-763 | (-) | ACTTACGTCACGT | 141 |
| AUXRETGA1GMGH3 | 752-764 | (+) | CGTGACGTAAGTA | 142 |
| WBOXHVISO1 | 761-775 | (-) | ACTGACTCGGATACT | 143 |
| REBETALGLHCB21 | 762-768 | (-) | CGGATAC | 144 |
| LTRE1HVBLT49 | 805-810 | (-) | CCGAAA | 145 |
| -10PEHVPSBD | 848-853 | (+) | TATTCT | 146 |
| BOXIINTPATPB | 856-861 | (-) | ATAGAA | 147 |
| WUSATAg | 885-891 | (-) | TTAATGG | 148 |
| WBBOXPCWRKY1 | 923-937 | (-) | TTTGACTAGCGAGGC | 149 |
| -300CORE | 954-960 | (-) | TGTAAAG | 150 |
| TAAAGSTKST1 | 954-960 | (-) | TGTAAAG | 150 |
| ASF1MOTIFCAMV | 974-986 | (+) | GCGCGTGACGCTC | 151 |
| ASF1MOTIFCAMV | 986-998 | (+) | CGCGGTGACGCCA | 152 |
| -300ELEMENT | 1003-1011 | (-) | TGAAAAGGC | 153 |
| PYRIMIDINEBOXOSRAM | 1004-1009 | (+) | CCTTTT | 130 |
| AMYBOX2 | 1015-1021 | (-) | TATCCAT | 154 |
| TATCCAOSAMY | 1015-1021 | (-) | TATCCAT | 154 |
| MYBST1 | 1016-1022 | (+) | TGGATAA | 155 |
| IBOXCORE | 1018-1024 | (+) | GATAAAT | 156 |
| CCAATBOX1 | 1057-1061 | (+) | CCAAT | 157 |
| DPBFCOREDCDC3 | 1067-1073 | (+) | ACACTAG | 158 |
| MYB1AT | 1087-1092 | (+) | TAACCA | 159 |
| REALPHALGLHCB21 | 1088-1098 | (+) | AACCAATCTCG | 160 |
| CCAATBOX1 | 1090-1094 | (+) | CCAAT | 157 |

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience (1987).
7. Ballas et al., Nucleic Acids Res., 17:7891 (1989).
8. Barkai-Golan et al., Arch. Microbiol., 116:119 (1978).
9. Barker et al., (1983) Plant Molec. Biol. 2: 335-50.
10. Batzer et al., Nucleic Acid Res., 19:5081 (1991).
11. Bäumlein et al. Mol Gen Genet. 225:121-128 (1991)
12. Becker et al. (1994) Plant J., 5:299-307,
13. Bernal-Lugo and Leopold, Plant Physiol., 98:1207 (1992).
14. Bevan et al., Nature, 304:184 (1983).
15. Bevan et al., Nucl. Acids Res., 11:369 (1983).
16. Bevan, Nucl. Acids Res., 12:8711 (1984).
17. Blackman et al., Plant Physiol., 100:225 (1992).
18. Blochlinger & Diggelmann, Mol Cell Biol, 4:2929 (1984).
19. Bol et al., Ann. Rev. Phytopath., 28:113 (1990).
20. Bouchez et al., EMBO J., 8:4197 (1989).

21. Bourouis et al., EMBO J., 2:1099 (1983).
22. Bowler et al., Ann. Rev. Plant Physiol., 43:83 (1992).
23. Bradford, Anal. Biochem. 72:248-254 (1976)
24. Branson and Guss, Proc. North Central Branch Entomological Society of America (1972).
25. Broakgert et al., Science, 245:110 (1989).
26. Bustos et al. (1989) Plant Gell 1:839-853
27. Byrne et al. Plant Cell Tissue and Organ Culture, 8:3 (1987).
28. Callis et al., Genes and Develop., 1:1183 (1987).
29. Campbell and Gowri, Plant Physiol., 92:1 (1990).
30. Campbell, ed. Ivermectin and Abamectin, Springer-Verlag, New York, (1989).
31. Chee et al. Plant Physiol., 91:1212 (1989).
32. Chen et al., (1988) EMBO J., 6:3559-3564
33. Chen and Winans J. Bacteriol. 173: 1139-1144 (1991).
34. Christou et al. Proc. Natl. Acad. Sci. USA, 86:7500 (1989).
35. Christou et al., Biotechnology, 9:957 (1991).
36. Christou et al., Plant Physiol., 87:671 (1988).
37. Christou et al. (1995) Annals of Botany 75:407-413
38. Chui et al. Curr Biol 6:325-330 (1996).
39. Coe et al., In: Corn and Corn Improvement, Sprague et al. (eds.) pp. 81-258 (1988).
40. Corpet et al. Nucleic Acids Res., 16:10881 (1988).
41. Coxson et al., Biotropica, 24:121 (1992).
42. Crameri et al., Nature Biotech., 15:436 (1997).
43. Crameri et al., Nature, 391:288 (1998).
44. Crossway et al., BioTechniques, 4:320-334 (1986).
45. Cuozzo et al., Bio/Technology, 6:549 (1988).
46. Cutler et al., J. Plant Physiol., 135:351 (1989).
47. Czapla and Lang, J. Econ. Entomol., 83:2480 (1990).
48. Dale E C and Ow D W (1991) Proc Natl Acad Sci USA 88:10558-10562
49. Datta et al., Bio/Technology, 8:736-740 (1990).
50. Davies et al., Plant Physiol., 93:588 (1990).
51. Dayhoff et al., Atlas of Protein Sequence and Structure, Natl. Biomed. Res. Found., Washington, C. D. (1978).
52. De Blaere et al., Meth. Enzymol., 143:277 (1987).
53. De Block et al. Plant Physiol., 91:694 (1989).
54. De Block et al., EMBO Journal, 6:2513 (1987).
55. Deblaere et al. Nucl Acids Res 13:4777-4788 (1985)
56. Della-Cioppa et al. Bio/Technology 5:579-584 (1987)
57. Della-Cioppa et al., Plant Physiology, 84:965-968 (1987).
58. Dellaporta et al., in Chromosome Structure and Function, Plenum Press, 263-282 (1988).
59. Depicker et al., Plant Cell Reports, 7:63 (1988).
60. DiRita and Gelvin (1987) Mol. Gen. Genet. 207:233-4
61. Dunn et al., Can. J. Plant Sci., 61:583 (1981).
62. Dure et al., Plant Mol. Biol., 12:475 (1989).
63. Ebinuma et al. Proc Natl Acad Sci USA 94:2117-2121 (2000a).
64. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b).
65. Eichholtz et al. Somatic Cell and Molecular Genetics 13, 67-76 (1987).
66. Ellis et al., EMBO Journal, 6:3203 (1987).
67. Ellis et al., (1984) Mol. Gen. Genet. 195:466-73
68. Elroy-Stein et al., Proc. Natl. Acad. Sci. U.S.A., 86:6126 (1989).
69. English et al., Plant Cell, 8:179 (1996).
70. Erdmann et al., J. Gen. Microbiol., 138:363 (1992).
71. Erikson et al. Nat. Biotechnol. 22(4):455-8 (2004).
72. Everett et al., Bio/Technology, 5:1201 (1987).
73. Fedoroff & Smith Plant J 3:273-289 (1993).
74. Fire et al. Nature 391:806-811 (1998).
75. Fitzpatrick, Gen. Engineering News, 22:7 (1993).
76. Fox et al. (1992) Plant Mol. Biol. 20:219-33
77. Fraley et al. Proc Natl Acad Sci USA 80:4803 (1983).
78. Fromm et al., Bio/Technology, 8:833-839 (1990).
79. Fromm et al., Nature (London), 319:791 (1986).
80. Galbiati et al. Funct. Integr Genozides, 20 1:25-34 (2000).
81. Gallie et al. Nucl Acids Res 15:8693-8711 (1987).
82. Gallie et al., Nucleic Acids Res., 15:3257 (1987).
83. Gallie et al., The Plant Cell, 1:301 (1989).
84. Gan et al., Science, 270:1986 (1995).
85. Gatehouse et al., J. Sci. Food Agric., 35:373 (1984).
86. Gelfand, eds., PCR Strategies Academic Press, New York (1995).
87. Gelvin et al., Plant Molecular Biology Manual, (1990).
88. Gleave et al. Plant Mol. Biol. 40(2):223-35 (1999)
89. Gordon-Kamm et al., Plant Cell, 2:603 (1990).
90. Goring et al, PNAS, 88:1770 (1991).
91. Gruber, et al., Vectors for Plant Transformation, in: "Methods in Plant Molecular Biology & Biotechnology" in Glich et al., (Eds. pp. 89-119, CRC Press, 1993).
92. Guerineau et al., Mol. Gen. Genet., 262:141 (1991).
93. Guerrero et al., Plant Mol. Biol., 15:11 (1990).
94. Guevara-Garcia et al., (1993) Plant J. 4:495-505.
95. Gupta et al., PNAS, 90:1629 (1993).
96. Haines and Higgins (eds.), Nucleic Acid Hybridization, IRL Press, Oxford, U.K.
97. Hajdukiewicz et al., Plant Mol Biol 25:989-994 (1994).
98. Hammock et al., Nature, 344:458 (1990).
99. Hansen et al. Proc. Natl. Acad. Sci. USA 91:7603-7607 (1994).
100. Hare P & Chua N H (2002) Nat. Biotechnol. 20, 575-580
101. Harpster et al., (1988) Mol. Gen. Genet. 212:182-90
102. Hayford et al. Plant Physiol. 86:1216 (1988)
103. Hemenway et al., EMBO Journal, 7:1273 (1988).
104. Henikoff & Henikoff, Proc. Natl. Acad. Sci. USA, 89:10915 (1989).
105. Hiei et al. Plant J 6: 271-282 (1994)
106. Higgins et al., Gene, 73:237 (1988).
107. Higo et al. (1999) Nucl Acids Res 27(1): 297-300
108. Hilder et al., Nature, 330:160 (1987).
109. Hille et al. Plant Mol. Biol. 7:171 (1986)
110. Hinchee et al. Bio/Technology 6:915 (1988).
111. Hoekema et al. Nature 303:179-181 (1983).
112. Hoekema, In: The Binary Plant Vector System. Offsetdrukkerij Kanters B.V.; Alblasserdam (1985).
113. Hood et al. J Bacteriol 168:1291-1301 (1986).
114. Huang et al., CABIOS, 8:155 (1992).
115. Ikeda et al., J. Bacteriol., 169:5612 (1987).
116. Ikuta et al., Biotech., 8:241 (1990).
117. Ingelbrecht et al., Plant Cell, 1:671 (1989).
118. Innis and Gelfand, eds., PCR Methods Manual (Academic Press, New York) (1999).
119. Innis et al., eds., PCR Protocols: A Guide to Methods and Applications (Academic Press, New York 1995).
120. Innis et al., PCR Protocols: A Guide to Methods and Applications, Academic Press, Inc., San Diego, Calif. (1990).
121. Ishida et al. Nature Biotech 745-750 (1996).
122. Jefferson et al. EMBO J. 6:3901-3907 (1987).
123. Jefferson et al. Plant Mol Biol Rep 5:387-405 (1987).
124. Jenes et al. Techniques for Gene Transfer, in: Recombinant Plants, Vol. 1, Engineering and Utilization, edited by SD Kung and R Wu, Academic Press, pp. 128-143 (1993)
125. Jobling et al., Nature, 325:622 (1987).
126. Johnson et al., PNAS USA, 86:9871 (1989).
127. Jones et al. Mol. Gen. Genet., 210:86 (1987).

127. Joshi et al., Nucleic Acid Res., 15:9627 (1987).
128. Kaasen et al., J. Bacteriol., 174:889 (1992).
129. Karlin and Altschul, Proc. Natl. Acad. Sci. USA, 87:2264 (1990).
130. Karlin and Altschul, Proc. Natl. Acad. Sci. USA, 90:5873 (1993).
131. Karsten et al., Botanica Marina, 35:11 (1992).
132. Kasuga et al., (1999) Nature Biotechnology 17(3):287-291
133. Katz et al., J. Gen. Microbiol., 129:2703 (1983).
134. Keller et al., EMBO Journal, 8:1309 (1989).
135. Keller et al., Genes Dev., 3:1639 (1989)
136. Kilby N J et al. (1995) Plant J 8:637-652
137. Klapwijk et al. J. Bacteriol., 141, 128-136 (1980).
138. Klein et al., Bio/Technology, 6:559-563 (1988).
139. Klein et al., Plant Physiol., 91:440-444 (1988).
140. Klein et al., Proc. Natl. Acad. Sci. USA, 85:4305-4309 (1988).
141. Knauf, et al., Genetic Analysis of Host Range Expression by *Agrobacterium* In: Molecular Genetics of the Bacteria-Plant Interaction, Puhler, A. ed., Springer-Verlag, New York, 1983.
142. Komro et al., (1985) Plant Mol. Biol. 4:253-63
143. Koncz & Schell Mol Gen Genet. 204:383-396 (1986).
144. Kononowicz et al., (1992) Plant Cell 4:17-27
145. Koprek et al. Plant J 19(6): 719-726 (1999).
146. Koster and Leopold, Plant Physiol., 88:829 (1988).
147. Koziel et al., Biotechnology, 11:194 (1993).
148. Kridl et al., (1991) Seed Sci. Res., 1:209-219
149. Kuiper H A et al. (2001) Plant J. 27, 503-528
150. Kunkel et al., Methods in Enzymol., 154:367 (1987).
151. Kunkel, Proc. Natl. Acad. Sci. USA, 82:488 (1985).
152. Lam and Chua, J Biol Chem; 266(26):17131-17135 (1991).
153. Langridge et al., (1989) Proc. Nat'l Acad. Sci. 86:7890-94
154. Laufs et al., PNAS, 87:7752 (1990).
155. Lawton et al., Mol. Cell. Biol., 7:335 (1987).
156. Lee and Saier, J. Bacteriol., 153 (1982).
157. Leffel et al. Biotechniques 23(5):912-8 (1997).
158. Lescot et al. Nucleic Acids Res 30(1):325-7 (2002).
159. Leung et al., (1991) Mol. Gen. Genet. 230:463-74
160. Levings, Science, 250:942 (1990).
161. Li et al. Plant Mol Biol 20:1037-1048 (1992).
162. Li et al. (1993) Plant Cell Reports 12:250-255
163. Lindsey et al., Transgenic Research, 2:3347 (1993).
164. Liu et al., Plant J. 8, 457-463 (1995)
165. Lommel et al., Virology, 181:382 (1991).
166. Loomis et al., J. Expt. Zool., 252:9 (1989).
167. Lorz et al., Mol. Gen. Genet., 199:178 (1985).
168. Lyznik L A et al. (1996) Nucleic Acids Res 24:3784-3789
169. Ma et al., Nature, 334:631 (1988).
170. Macejak et al., Nature, 353:90 (1991).
171. Maki et al., Methods in Plant Mol. Biol. & Biotechnol, Glich et al., 67-88 CRC Press, (1993).
172. Maniatis et al., Molecular Cloning: A Laboratory Manual, Cold Spring Harbor Laboratory, Cold Spring Harbor (NY), (1989).
173. Mariani et al., Nature, 347:737 (1990).
174. Matzke et al. (2000) Plant Mol Biol 43:401-415 (2000).
175. McBride et al., PNAS USA, 91:7301 (1994).
176. McCabe et al., Bio/Technology, 6:923 (1988).
177. Meinkoth and Wahl, Anal. Biochem., 138:267 (1984).
178. Messing and Vierra, Gene, 19:259 (1982).
179. Michael et al., J. Mol. Biol., 26:585 (1990)
180. Millar et al. Plant Mol Biol Rep 10:324-414 (1992).
181. Mogen et al., Plant Cell, 2:1261 (1990).
182. Moore et al., J. Mol. Biol., 272:336 (1997).
183. Mozo and Hooykaas, Plant Mol. Biol. 16:917-918 (1991).
184. Mundy and Chua, EMBO J., 7:2279 (1988).
185. Munroe et al., Gene, 91:151 (1990).
186. Murakami et al., Mol. Gen. Genet., 205:42 (1986).
187. Murata et al., FEBS Lett., 296:187 (1992).
188. Murdock et al., Phytochemistry, 29:85 (1990).
189. Murray et al., Nucleic Acids Res., 17:477 (1989).
190. Myers and Miller, CABIOS, 4:11 (1988).
191. Naested, Plant J 18:571-576 (1999).
192. Napoli et al., Plant Cell, 2:279 (1990).
193. Needleman and Wunsch, J. Mol. Biol., 48:443-453 (1970).
194. Nehra et al. Plant J. 5:285-297 (1994)
195. Ni M et al. (1995) Plant J 7(4):661-676
196. Niedz et al., Plant Cell Reports, 14:403 (1995).
197. Odell et al., Mol. Gen. Genet., 113:369 (1990).
198. Odell et al., Nature, 313:810 (1985).
199. Ohtsuka et al., J. Biol. Chem., 260:2605 (1985).
200. Olhoft et al. Plant Cell Rep 20: 706-711 (2001).
201. Onouchi H et al., (1995) Mol Gen Genet. 247:653-660
202. Osborne B I et al. (1995) Plant J. 7:687-701
203. Osjoda et al. (1996) Nature Biotechnology 14:745-750
204. Ow et al., Science, 234:856 (1986).
205. Ow D W and Medberry S L (1995) Crit. Rev in Plant Sci 14:239-261
206. Pacciotti et al., Bio/Technology, 3:241 (1985).
207. Park et al., J. Plant Biol., 38:365 (1985).
208. Paszkowski et al., EMBO J., 3:2717-2722 (1984).
209. Pearson and Lipman, Proc. Natl. Acad. Sci., 85:2444 (1988).
210. Pearson et al., Meth. Mol. Biol., 24:307 (1994).
211. Perera et al. Plant Mol. Biol. 23(4): 793-799 (1993).
212. Perlak et al., Proc. Natl. Acad. Sci. USA, 88:3324 (1991).
213. Phillips et al., In Corn & Corn Improvement, 3rd Edition 10 Sprague et al. (Eds. pp. 345-387)(1988).
214. Phi-Van et al., Mol. Cell. Biol., 10:2302 (1990).
215. Piatkowski et al., Plant Physiol., 94:1682 (1990).
216. Potrykus et al., Mol. Gen. Genet., 199:183 (1985).
217. Potrykus, Trends Biotech., 7:269 (1989).
218. Prasher et al., Biochem. Biophys. Res. Comm., 126: 1259 (1985).
219. Proudfoot, Cell, 64:671 (1991).
220. Reed et al., J. Gen. Microbiol., 130:1 (1984).
221. Riggs et al., Proc. Natl. Acad. Sci. USA, 83:5602-5606 (1986).
222. Rossolini et al., Mol. Cell. Probes, 8:91 (1994).
223. Ruiz, Plant Cell, 10:937 (1998).
224. Russell S H et al. (1992) Mol Gene Genet. 234:49-59
225. Saito et al., (1991) Planta 184:40-46
226. Sambrook et al., Molecular Cloning: A Laboratory Manual (2d ed., Cold Spring Harbor Laboratory Press, Plainview, N.Y.) (1989).
227. Sanfacon et al., Genes Dev., 5:141 (1991).
228. Sanford et al., Particulate Science and Technology, 5:27 (1987).
229. Sanger et al., (1990) Plant Mol. Biol. 14: 433-43
230. Scheeren-Groot et al., J. Bacteriol 176: 6418-6426 (1994).
231. Schenborn and Groskreutz, Mol Biotechnol 13(1): 29-44 (1999).
232. Schlaman and Hooykaas, Plant J 11:1377-1385 (1997).
233. Schoffl et al. Mol Gen Genetics 217(2-3):246-53 (1989).
234. Shagan et al., Plant Physiol., 101:1397 (1993).

235. Shah et al. Science 233: 478 (1986).
236. Shapiro, Mobile Genetic Elements, Academic Press, N.Y. (1983).
237. Shimamoto et al., Nature, 338:274 (1989).
238. Silhavy et al., Experiments with Gene Fusions, Cold Spring Harbor Laboratory Press, Cold Spring Harbor (NY), (1984).
239. Skuzeski et al., Plant Molec. Biol. 15: 65-79 (1990).
240. Smith et al., Adv. Appl. Math., 2:482. (1981).
241. Smith et al., Mol. Gen. Genet., 224:447 (1990).
242. Spencer et al., Theor. Appl. Genet, 79:625 (1990).
243. Stalker et al., Science, 242:419 (1988).
244. Staub et al., EMBO J., 12:601 (1993).
245. Staub et al., Plant Cell, 4:39 (1992).
246. Steifel et al., The Plant Cell, 2:785 (1990).
247. Stemmer, Nature, 370:389 (1994).
248. Stemmer, Proc. Natl. Acad. Sci. USA, 91:10747 (1994).
249. Stief et al., Nature, 341:343 (1989).
250. Stougaard, Plant J 3:755-761 (1993)
251. Sugita Ket et al. (2000) Plant J. 22:461-469
252. Sukhapinda et al., Plant Mol. Biol., 8:209 (1987).
253. Sundaresan et al. Gene Develop 9: 1797-1810 (1995).
254. Sutcliffe, PNAS USA, 75:3737 (1978).
255. Svab et al., Plant Mol. Biol. 14:197 (1990).
256. Svab et al., Proc. Natl. Acad. Sci. USA, 87:8526 (1990).
257. Svab et al., Proc. Natl. Acad. Sci. USA, 90:913 (1993).
258. Tarczynski et al., PNAS USA, 89:2600 (1992).
259. Teeri et al., (1989) EMBO J., 8: 343-50
260. Thillet et al., J. Biol. Chem., 263:12500 (1988).
261. Tijssen, Laboratory Techniques in Biochemistry and Molecular Biology-Hybridization with Nucleic Acid Probes, Elsevier, N.Y. (1993).
262. Tomes et al., Plant Cell, Tissue and Organ Culture: Fundamental Methods, Springer Verlag, Berlin (1995).
263. Tomic et al., NAR, 12:1656 (1990).
264. Thompson et al., NAR 22(22):4673-4680 (1994).
265. Turner et al., Molecular Biotechnology, 3:225 (1995).
266. Twell et al., Plant Physiol., 91:1270 (1989).
267. Ugaki et al., Nucl. Acids Res., 19:371 (1991).
268. Ulmasov et al., Plant Mol. Biol., 35:417 (1997).
269. Upender et al., Biotechniques, 18:29 (1995).
270. van der Krol et al., Plant Cell, 2:291 (1990).
271. Vanden Elzen et al. Plant Mol. Biol. 5:299 (1985).
272. Vasil et al. Bio/Technology, 10:667-674 (1992).
273. Vasil et al. Bio/Technology, 11:1153-1158 (1993).
274. Vasil et al., Mol. Microbiol., 3:371 (1989).
275. Vasil et al., Plant Physiol., 91:1575 (1989).
276. Vernon and Bohnert, EMBO J., 11:2077 (1992).
277. Walker and Gaastra, eds., Techniques in Molecular Biology, MacMillan Publishing Company, New York (1983).
278. Wan & Lemaux Plant Physiol., 104:3748 (1994).
279. Wang et al., Mol. Cell. Biol., 12:3399 (1992).
280. Waterman, Introduction to Computational Biology: Maps, sequences and genomes. Chapman & Hall. London (1995).
281. Watrud et al., in Engineered Organisms and the Environment (1985).
282. Watson et al. J. Bacteriol 123, 255-264 (1975)
283. Watson et al., Corn: Chemistry and Technology (1987).
284. Weeks et al. Plant Physiol 102:1077-1084 (1993)
285. Weissinger et al., Annual Rev. Genet., 22:421 (1988).
286. White et al., Nucl Acids Res, 18, 1062 (1990).
287. Wingender et al. Nucleic Acids Res 29(1):281-3 (2001).
288. Wolter et al., EMBO Journal, 11:4685 (1992).
289. Wyn-Jones and Storey, Physiology and Biochemistry of Drought Resistance in Plants, Paleg et al. (eds.), pp. 171-204 (1981).
290. Yamaguchi-Shinozaki et al., Plant Cell Physiol., 33:217 (1992).
291. Zhang et al., Proc. Natl. Acad. Sci. USA, 94:4504 (1997).
292. Zubko et al. (2000) Nature Biotech 18(4):442-445
293. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method for starchy-endosperm- and/or germinating embryo-specific expression of a nucleic acid sequence in a monocotyledonous plant, comprising:
   (a) constructing an expression cassette by operably linking at least one transcription regulating nucleotide sequence to at least one nucleic acid sequence which is heterologous to said at least one transcription regulating nucleotide sequence,
   (b) transforming said expression cassette into a monocotyledonous plant, and
   (c) selecting a transgenic plant demonstrating starchy-endosperm- and/or germinating embryo-specific expression of said at least one nucleic acid sequence, wherein the at least one transcription regulating nucleotide sequence comprises a nucleotide sequence selected from the group consisting of:
   (i) the sequence of SEQ ID NO: 4;
   (ii) a fragment of the sequence of SEQ ID NO: 4, wherein the fragment directs starchy-endosperm- and/or germinating embryo-specific expression of said at least one nucleic acid sequence;
   (iii) a nucleotide sequence having at least 95% sequence identity to the sequence SEQ ID NO: 4, wherein the nucleotide sequence comprises the DNA motifs provided in Table 9 and directs starchy-endosperm- and/or germinating embryo-specific expression of said at least one nucleic acid sequence;
   (iv) a nucleotide sequence having at least 95% sequence identity to the sequence of SEQ ID NO: 4, wherein the nucleotide sequence further comprises the sequences of SEQ ID NO: 1 and SEQ ID NO: 2 and directs starchy-endosperm- and/or germinating embryo-specific expression of said at least one nucleic acid sequence; and
   (v) a nucleotide sequence which is complement or reverse complement of any of the nucleotide sequence of (i) to (iv).

2. The method of claim 1, wherein the expression of said at least one nucleic acid sequence confers to the transgenic plant at least one trait or property selected from the group consisting of:
   (a) enhanced resistance against at least one stress factor,
   (b) increased nutritional quality of a seed or a sprout,
   (c) increased yield, and
   (d) excision of selection marker.

3. The method of claim 1, wherein said transcription regulating nucleotide sequence comprises a nucleotide sequence having at least 95% sequence identity to the sequence of SEQ ID NO: 4, wherein the nucleotide sequence further comprises at least three copies of the sequence of SEQ ID NO: 1, and wherein the nucleotide sequence directs starchy-endosperm- and/or germinating embryo-specific expression of said at least one nucleic acid sequence.

4. The method of claim 1, wherein said transcription regulating nucleotide sequence comprises a nucleotide sequence having at least 95% sequence identity to the sequence of SEQ ID NO: 4, wherein the nucleotide sequence further comprises the sequence of SEQ ID NO: 3 and directs starchy-endosperm- and/or germinating embryo-specific expression of said at least one nucleic acid sequence.

5. The method of claim 1, wherein the at least one transcription regulating nucleotide sequence comprises a nucleotide sequence
   having at least 98% sequence identity to the sequence of SEQ ID NO: 4, and
   wherein the nucleotide sequence comprises the DNA motifs provided in Table 9 and directs starchy-endosperm- and/or germinating embryo-specific expression of said at least one nucleic acid sequence.

6. The method of claim 1, wherein said expression cassette does not comprise an intron with expression enhancing properties operably linked to said transcription regulating sequence.

7. The method of claim 2, wherein the enhanced resistance is against an abiotic or biotic stress factor.

8. The method of claim 7, wherein the enhanced resistance against a biotic stress factor is selected from the group consisting of fungal resistance, nematode resistance, insect resistance, viral resistance, and bacteria resistance.

9. The method of claim 7, wherein the enhanced resistance against an abiotic stress factor is selected from the group consisting of water stress resistance, drought resistance, cold resistance, salt resistance, high plant population density, and UV light resistance.

10. The method of claim 7, wherein the enhanced resistance is achieved by inducing early vigor.

11. The method of claim 1, wherein said at least one nucleic acid sequence encodes a polypeptide involved in phytohormone biosynthesis, phytohormone regulation, cell cycle regulation, or carbohydrate metabolism.

12. The method of claim 1, wherein said at least one nucleic acid sequence encodes a polypeptide comprising the amino acid sequence of SEQ ID NO: 6, 8, 10, 12, 14, 16, 18, 20, 22, 43, 45, 47, 49, 50, 51, or 53.

13. The method of claim 1, wherein said monocotyledonous plant is a maize, wheat, rice, barley, oat, rye, sorghum, banana, ryegrass or coix plant.

14. The method of claim 2, wherein the excision of selection marker is realized by:
   (a) inducing sequence deletion by side specific recombination using a site-specific recombinase, wherein said site-specific recombinase is expressed by said transcription regulating nucleotide sequence, or
   (b) inducing sequence deletion by induced homologous recombination, wherein the sequences to be deleted are flanked by sequences having an orientation, a sufficient length and a homology to each other to allow for homologous recombination between them, wherein homologous recombination is induced by a site-specific double-strand break made by a site-specific endonuclease, wherein said site-specific endonuclease is expressed by said transcription regulating nucleotide sequence.

15. The method of claim 1, wherein the expression of said at least one nucleic acid sequence results in expression of a protein, or expression of an antisense RNA, sense or double-stranded RNA.

* * * * *